US008461415B2

(12) United States Patent
Sampson et al.

(10) Patent No.: US 8,461,415 B2
(45) Date of Patent: Jun. 11, 2013

(54) AXMI-192 FAMILY OF PESTICIDAL GENES AND METHODS FOR THEIR USE

(75) Inventors: Kimberly S. Sampson, Durham, NC (US); Daniel John Tomso, Bahama, NC (US); Rong Guo, Cary, NC (US)

(73) Assignee: Athenix Corp., Morrisville, NC (US)

( * ) Notice: Subject to any disclaimer, the term of this patent is extended or adjusted under 35 U.S.C. 154(b) by 250 days.

(21) Appl. No.: 12/846,900

(22) Filed: Jul. 30, 2010

(65) Prior Publication Data

US 2011/0030096 A1 Feb. 3, 2011

Related U.S. Application Data

(60) Provisional application No. 61/230,659, filed on Jul. 31, 2009.

(51) Int. Cl.

| | |
|---|---|
| ***C12N 15/32*** | (2006.01) |
| ***C12N 15/82*** | (2006.01) |
| ***C12N 5/10*** | (2006.01) |
| ***C12N 1/21*** | (2006.01) |
| ***A01H 5/00*** | (2006.01) |
| ***A01H 5/10*** | (2006.01) |

(52) U.S. Cl.

USPC ..... 800/279; 800/320.1; 800/302; 536/23.71; 435/252.3; 435/320.1; 435/468; 435/418; 435/419; 435/69.1

(58) Field of Classification Search

None

See application file for complete search history.

(56) References Cited

U.S. PATENT DOCUMENTS

| | | | | |
|---|---|---|---|---|
| 5,262,158 | A | 11/1993 | Payne et al. | |
| 6,632,792 | B2 * | 10/2003 | Schnepf et al. | 514/21.2 |
| 2004/0014091 | A1 | 1/2004 | Duck et al. | |
| 2008/0070829 | A1 | 3/2008 | Carozzi et al. | |
| 2010/0004176 | A1 | 1/2010 | Sampson et al. | |
| 2010/0162439 | A1 | 6/2010 | Sampson et al. | |

FOREIGN PATENT DOCUMENTS

| | | |
|---|---|---|
| WO | 2004074462 | 9/2004 |
| WO | 2006083891 | 8/2006 |
| WO | 2007147096 | 12/2007 |

OTHER PUBLICATIONS

Tounsi et al (2003) J. Appl Microbiol 95:23-28.* de Maagd et al (1999) Appl Environ. Microbiol 65:4369-4374.*

Aronson et al (2001) FEMS Microbiol. Lett. 195:1-8.*

Invitation to Pay Additional Fees and Partial International Search Report for PCT/US2010/043871 filed Jul. 30, 2010.

* cited by examiner

*Primary Examiner* — David T Fox

*Assistant Examiner* — Steven Bernacki

(57) ABSTRACT

Compositions and methods for conferring pesticidal activity to bacteria, plants, plant cells, tissues and seeds are provided. Compositions comprising a coding sequence for a toxin polypeptide are provided. The coding sequences can be used in DNA constructs or expression cassettes for transformation and expression in plants and bacteria. Compositions also comprise transformed bacteria, plants, plant cells, tissues, and seeds. In particular, isolated toxin nucleic acid molecules are provided. Additionally, amino acid sequences corresponding to the polynucleotides are encompassed, and antibodies specifically binding to those amino acid sequences. In particular, the present invention provides for isolated nucleic acid molecules comprising nucleotide sequences encoding the amino acid sequence shown in SEQ ID NO:28-62, or the nucleotide sequence set forth in SEQ ID NO:1-27, as well as variants and fragments thereof.

16 Claims, No Drawings

AXMI-192 FAMILY OF PESTICIDAL GENES AND METHODS FOR THEIR USE

CROSS REFERENCE TO RELATED APPLICATIONS

This application claims the benefit of U.S. Provisional Application Ser. No. 61/230,659, filed Jul. 31, 2009, the contents of which are herein incorporated by reference in their entirety.

REFERENCE TO SEQUENCE LISTING SUBMITTED ELECTRONICALLY

The official copy of the sequence listing is submitted electronically via EFS-Web as an ASCII formatted sequence listing with a file named "APA067US01_SEQLIST.txt", created on Jul. 27, 2010, and having a size of 273 kilobytes and is filed concurrently with the specification. The sequence listing contained in this ASCII formatted document is part of the specification and is herein incorporated by reference in its entirety.

FIELD OF THE INVENTION

This invention relates to the field of molecular biology. Provided are novel genes that encode pesticidal proteins. These proteins and the nucleic acid sequences that encode them are useful in preparing pesticidal formulations and in the production of transgenic pest-resistant plants.

BACKGROUND OF THE INVENTION

*Bacillus thuringiensis* is a Gram-positive spore forming soil bacterium characterized by its ability to produce crystalline inclusions that are specifically toxic to certain orders and species of insects, but are harmless to plants and other non-targeted organisms. For this reason, compositions including *Bacillus thuringiensis* strains or their insecticidal proteins can be used as environmentally-acceptable insecticides to control agricultural insect pests or insect vectors for a variety of human or animal diseases.

Crystal (Cry) proteins (delta-endotoxins) from *Bacillus thuringiensis* have potent insecticidal activity against predominantly Lepidopteran, Dipteran, and Coleopteran larvae. These proteins also have shown activity against Hymenoptera, Homoptera, Phthiraptera, Mallophaga, and Acari pest orders, as well as other invertebrate orders such as Nemathelminthes, Platyhelminthes, and Sarcomastigorphora (Feitelson (1993) The *Bacillus Thuringiensis* family tree. In *Advanced Engineered Pesticides*, Marcel Dekker, Inc., New York, N.Y.) These proteins were originally classified as CryI to CryV based primarily on their insecticidal activity. The major classes were Lepidoptera-specific (I), Lepidoptera- and Diptera-specific (II), Coleoptera-specific (III), Diptera-specific (IV), and nematode-specific (V) and (VI). The proteins were further classified into subfamilies; more highly related proteins within each family were assigned divisional letters such as Cry1A, Cry1B, Cry1C, etc. Even more closely related proteins within each division were given names such as Cry1C1, Cry1C2, etc.

A new nomenclature was recently described for the Cry genes based upon amino acid sequence homology rather than insect target specificity (Crickmore et al. (1998) *Microbiol. Mol. Biol. Rev.* 62:807-813). In the new classification, each toxin is assigned a unique name incorporating a primary rank (an Arabic number), a secondary rank (an uppercase letter), a tertiary rank (a lowercase letter), and a quaternary rank (another Arabic number). In the new classification, Roman numerals have been exchanged for Arabic numerals in the primary rank. Proteins with less than 45% sequence identity have different primary ranks, and the criteria for secondary and tertiary ranks are 78% and 95%, respectively.

The crystal protein does not exhibit insecticidal activity until it has been ingested and solubilized in the insect midgut. The ingested protoxin is hydrolyzed by proteases in the insect digestive tract to an active toxic molecule. (Höfte and Whiteley (1989) *Microbiol. Rev.* 53:242-255). This toxin binds to apical brush border receptors in the midgut of the target larvae and inserts into the apical membrane creating ion channels or pores, resulting in larval death.

Delta-endotoxins generally have five conserved sequence domains, and three conserved structural domains (see, for example, de Maagd et al. (2001) *Trends Genetics* 17:193-199). The first conserved structural domain consists of seven alpha helices and is involved in membrane insertion and pore formation. Domain II consists of three beta-sheets arranged in a Greek key configuration, and domain III consists of two antiparallel beta-sheets in "jelly-roll" formation (de Maagd et al., 2001, supra). Domains II and III are involved in receptor recognition and binding, and are therefore considered determinants of toxin specificity.

Aside from delta-endotoxins, there are several other known classes of pesticidal protein toxins. The VIP1/VIP2 toxins (see, for example, U.S. Pat. No. 5,770,696) are binary pesticidal toxins that exhibit strong activity on insects by a mechanism believed to involve receptor-mediated endocytosis followed by cellular toxification, similar to the mode of action of other binary ("A/B") toxins. A/B toxins such as VIP, C2, CDT, CST, or the *B. anthracis* edema and lethal toxins initially interact with target cells via a specific, receptor-mediated binding of "B" components as monomers. These monomers then form homoheptamers. The "B" heptamer-receptor complex then acts as a docking platform that subsequently binds and allows the translocation of an enzymatic "A" component(s) into the cytosol via receptor-mediated endocytosis. Once inside the cell's cytosol, "A" components inhibit normal cell function by, for example, ADP-ribosylation of G-actin, or increasing intracellular levels of cyclic AMP (cAMP). See Barth et al. (2004) *Microbiol Mol Biol Rev* 68:373-402.

The intensive use of *B. thuringiensis*-based insecticides has already given rise to resistance in field populations of the diamondback moth, *Plutella xylostella* (Ferré and Van Rie (2002) Annu. Rev. Entomol. 47:501-533). The most common mechanism of resistance is the reduction of binding of the toxin to its specific midgut receptor(s). This may also confer cross-resistance to other toxins that share the same receptor (Ferré and Van Rie (2002)).

SUMMARY OF INVENTION

Compositions and methods for conferring pest resistance to bacteria, plants, plant cells, tissues and seeds are provided. Compositions include nucleic acid molecules encoding sequences for toxin polypeptides, vectors comprising those nucleic acid molecules, and host cells comprising the vectors. Compositions also include the polypeptide sequences of the toxin, and antibodies to those polypeptides. The nucleotide sequences can be used in DNA constructs or expression cassettes for transformation and expression in organisms, including microorganisms and plants. The nucleotide or amino acid sequences may be synthetic sequences that have been designed for expression in an organism including, but not limited to, a microorganism or a plant. Compositions also comprise transformed bacteria, plants, plant cells, tissues, and seeds.

In particular, isolated or recombinant nucleic acid molecules corresponding to toxin nucleic acid sequences are provided. Additionally, amino acid sequences corresponding to the polynucleotides are encompassed. In particular, the present invention provides for an isolated nucleic acid molecule comprising a nucleotide sequence encoding the amino acid sequence shown in any of SEQ ID NO:28-62, or a nucleotide sequence set forth in any of SEQ ID NO:1-27, as well as variants and fragments thereof. Nucleotide sequences that are complementary to a nucleotide sequence of the invention, or that hybridize to a sequence of the invention are also encompassed.

The compositions and methods of the invention are useful for the production of organisms with pesticide resistance, specifically bacteria and plants. These organisms and compositions derived from them are desirable for agricultural purposes. The compositions of the invention are also useful for generating altered or improved toxin proteins that have pesticidal activity, or for detecting the presence of toxin proteins or nucleic acids in products or organisms.

DETAILED DESCRIPTION

The present invention is drawn to compositions and methods for regulating pest resistance or tolerance in organisms, particularly plants or plant cells. By "resistance" is intended that the pest (e.g., insect) is killed upon ingestion or other contact with the polypeptides of the invention. By "tolerance" is intended an impairment or reduction in the movement, feeding, reproduction, or other functions of the pest. The methods involve transforming organisms with a nucleotide sequence encoding a pesticidal protein of the invention. In particular, the nucleotide sequences of the invention are useful for preparing plants and microorganisms that possess pesticidal activity. Thus, transformed bacteria, plants, plant cells, plant tissues and seeds are provided. Compositions are pesticidal nucleic acids and proteins of bacterial species. The sequences find use in the construction of expression vectors for subsequent transformation into organisms of interest, as probes for the isolation of other homologous (or partially homologous) genes, and for the generation of altered pesticidal proteins by methods known in the art, such as domain swapping or DNA shuffling. The proteins find use in controlling or killing lepidopteran, coleopteran, dipteran, and nematode pest populations and for producing compositions with pesticidal activity.

By "pesticidal toxin" or "pesticidal protein" is intended a toxin that has toxic activity against one or more pests, including, but not limited to, members of the Lepidoptera, Diptera, and Coleoptera orders, or the Nematoda phylum, or a protein that has homology to such a protein. Pesticidal proteins have been isolated from organisms including, for example, *Bacillus* sp., *Clostridium bifermentans* and *Paenibacillus popilliae*. Pesticidal proteins include amino acid sequences deduced from the full-length nucleotide sequences disclosed herein, and amino acid sequences that are shorter than the full-length sequences, either due to the use of an alternate downstream start site, or due to processing that produces a shorter protein having pesticidal activity. Processing may occur in the organism the protein is expressed in, or in the pest after ingestion of the protein.

In various embodiments, the sequences disclosed herein have homology to delta-endotoxin proteins. Delta-endotoxins include proteins identified as cry1 through cry53, cyt1 and cyt2, and Cyt-like toxin. There are currently over 250 known species of delta-endotoxins with a wide range of specificities and toxicities. For an expansive list see Crickmore et al. (1998), *Microbiol. Mol. Biol. Rev.* 62:807-813, and for regular updates see Crickmore et al. (2003) "*Bacillus thuringiensis* toxin nomenclature," at www.biols.susx.ac.uk/Home/Neil_Crickmore/Bt/index. In some embodiments, the delta-endotoxin sequences disclosed herein include the nucleotide sequences set forth in any of SEQ ID NO:1-27, the amino acid sequences set forth in any of SEQ ID NO:28-62, as well as variants and fragments thereof.

Thus, provided herein are novel isolated or recombinant nucleotide sequences that confer pesticidal activity. Also provided are the amino acid sequences of the pesticidal proteins. The protein resulting from translation of this gene allows cells to control or kill pests that ingest it.

Isolated Nucleic Acid Molecules, and Variants and Fragments Thereof

One aspect of the invention pertains to isolated or recombinant nucleic acid molecules comprising nucleotide sequences encoding pesticidal proteins and polypeptides or biologically active portions thereof, as well as nucleic acid molecules sufficient for use as hybridization probes to identify nucleic acid molecules encoding proteins with regions of sequence homology. As used herein, the term "nucleic acid molecule" is intended to include DNA molecules (e.g., recombinant DNA, cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid sequence (or DNA) is used herein to refer to a nucleic acid sequence (or DNA) that is no longer in its natural environment, for example in an in vitro or in a recombinant bacterial or plant host cell. In some embodiments, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the invention, "isolated" when used to refer to nucleic acid molecules excludes isolated chromosomes. For example, in various embodiments, the isolated nucleic acid molecule encoding a pesticidal protein can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A pesticidal protein that is substantially free of cellular material includes preparations of protein having less than about 30%, 20%, 10%, or 5% (by dry weight) of non-pesticidal protein (also referred to herein as a "contaminating protein").

Nucleotide sequences encoding the proteins of the present invention include the sequence set forth in SEQ ID NO:1-27, and variants, fragments, and complements thereof. By "complement" is intended a nucleotide sequence that is sufficiently complementary to a given nucleotide sequence such that it can hybridize to the given nucleotide sequence to thereby form a stable duplex. The corresponding amino acid sequence for the toxin protein encoded by this nucleotide sequence are set forth in SEQ ID NO:28-62.

Nucleic acid molecules that are fragments of these nucleotide sequences encoding pesticidal proteins are also encompassed by the present invention. By "fragment" is intended a portion of the nucleotide sequence encoding a pesticidal protein. A fragment of a nucleotide sequence may encode a biologically active portion of a pesticidal protein, or it may be a fragment that can be used as a hybridization probe or PCR primer using methods disclosed below. Nucleic acid molecules that are fragments of a nucleotide sequence encoding a pesticidal protein comprise at least about 50, 100, 200, 300, 400, 500, 600, 700, 800, 900, 1000, 1100, 1200, 1300, 1350, 1400, 1500, 1600, 1700, 1800, 1900, 2000, 2500, 3000, 3500, 4000, 4500, 5000 contiguous nucleotides, or up to the number of nucleotides present in a full-length nucleotide sequence encoding a pesticidal protein disclosed herein, depending upon the intended use. By "contiguous" nucleotides is intended nucleotide residues that are immediately adjacent to one another. Fragments of the nucleotide sequences of the present invention will encode protein fragments that retain the biological activity of the pesticidal protein and, hence, retain pesticidal activity. By "retains activity" is intended that the fragment will have at least about 30%, at least about 50%, at least about 70%, 80%, 90%, 95% or higher of the pesticidal activity of the pesticidal protein. In one embodiment, the pesticidal activity is coleoptericidal activity. In another embodiment, the pesticidal activity is lepidoptericidal activity. In another embodiment, the pesticidal activity is nematocidal activity. In another embodiment, the pesticidal activity is diptericidal activity. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

A fragment of a nucleotide sequence that encodes a biologically active portion of a pesticidal protein of the invention will encode at least about 15, 25, 30, 50, 75, 100, 125, 150, 175, 200, 250, 300, 350, 400, 450, 500, 550, 600, 650, 700, 750, 800, 850, 900, 950, 1000, 1050, 1100 contiguous amino acids, or up to the total number of amino acids present in a full-length pesticidal protein of the invention. In some embodiments, the fragment is a C-terminal truncation of at least about 10, 20, 30, 40, 50, 60, 70, 80, 90, 100, 110, 120, 130, 140, 150, 160, 170, 180, 190, 200, 250, 300, 350, 400, 450, 500, 650, 600 or more amino acids relative to the amino acid sequences of the invention.

Preferred pesticidal proteins of the present invention are encoded by a nucleotide sequence sufficiently identical to the nucleotide sequence of SEQ ID NO:1-27. By "sufficiently identical" is intended an amino acid or nucleotide sequence that has at least about 60% or 65% sequence identity, about 70% or 75% sequence identity, about 80% or 85% sequence identity, about 90%, 91%, 92%, 93%, 94%, 95%, 96%, 97%, 98%, 99% or greater sequence identity compared to a reference sequence using one of the alignment programs described herein using standard parameters. One of skill in the art will recognize that these values can be appropriately adjusted to determine corresponding identity of proteins encoded by two nucleotide sequences by taking into account codon degeneracy, amino acid similarity, reading frame positioning, and the like.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In another embodiment, the comparison is across the entirety of the reference sequence (i.e., across the entirety of any of SEQ ID NO:1-61) The percent identity between two sequences can be determined using techniques similar to those described below, with or without allowing gaps. In calculating percent identity, typically exact matches are counted.

The determination of percent identity between two sequences can be accomplished using a mathematical algorithm. A nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the BLASTN and BLASTX programs of Altschul et al. (1990) *J. Mol. Biol.* 215:403. BLAST nucleotide searches can be performed with the BLASTN program, score=100, wordlength=12, to obtain nucleotide sequences homologous to pesticidal-like nucleic acid molecules of the invention. BLAST protein searches can be performed with the BLASTX program, score=50, wordlength=3, to obtain amino acid sequences homologous to pesticidal protein molecules of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., BLASTX and BLASTN) can be used. Alignment may also be performed manually by inspection.

Another non-limiting example of a mathematical algorithm utilized for the comparison of sequences is the ClustalW algorithm (Higgins et al. (1994) *Nucleic Acids Res.* 22:4673-4680). ClustalW compares sequences and aligns the entirety of the amino acid or DNA sequence, and thus can provide data about the sequence conservation of the entire amino acid sequence. The ClustalW algorithm is used in several commercially available DNA/amino acid analysis software packages, such as the ALIGNX module of the Vector NTI Program Suite (Invitrogen Corporation, Carlsbad, Calif.). After alignment of amino acid sequences with ClustalW, the percent amino acid identity can be assessed. A non-limiting example of a software program useful for analysis of ClustalW alignments is GENEDOC™. GENEDOC™ (Karl Nicholas) allows assessment of amino acid (or DNA) similarity and identity between multiple proteins. Another non-limiting example of a mathematical algorithm utilized for the comparison of sequences is the algorithm of Myers and Miller (1988) *CABIOS* 4:11-17. Such an algorithm is incorporated into the ALIGN program (version 2.0), which is part of the GCG Wisconsin Genetics Software Package, Version 10 (available from Accelrys, Inc., 9685 Scranton Rd., San Diego, Calif., USA). When utilizing the ALIGN program for comparing amino acid sequences, a PAM120 weight residue table, a gap length penalty of 12, and a gap penalty of 4 can be used.

Unless otherwise stated, GAP Version 10, which uses the algorithm of Needleman and Wunsch (1970) *J. Mol. Biol.* 48(3):443-453, will be used to determine sequence identity or similarity using the following parameters: % identity and % similarity for a nucleotide sequence using GAP Weight of 50 and Length Weight of 3, and the nwsgapdna.cmp scoring matrix; % identity or % similarity for an amino acid sequence using GAP weight of 8 and length weight of 2, and the BLOSUM62 scoring program. Equivalent programs may also be used. By "equivalent program" is intended any sequence comparison program that, for any two sequences in question, generates an alignment having identical nucleotide residue matches and an identical percent sequence identity when compared to the corresponding alignment generated by GAP Version 10. The invention also encompasses variant nucleic acid molecules. "Variants" of the pesticidal protein encoding nucleotide sequences include those sequences that encode the pesticidal proteins disclosed herein but that differ conservatively because of the degeneracy of the genetic code as well as those that are sufficiently identical as discussed above. Naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the pesticidal proteins disclosed in the present invention as discussed below. Variant proteins encompassed by the present invention are biologically active, that is they continue to possess the desired biological activity of the native protein, that is, retaining pesticidal activity. By "retains activity" is intended that the variant will have at least about 30%, at least about 50%, at least about 70%, or at least about 80% of the pesticidal activity of the native protein. Methods for measuring pesticidal activity are well known in the art. See, for example, Czapla and Lang (1990) *J. Econ. Entomol.* 83: 2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

The skilled artisan will further appreciate that changes can be introduced by mutation of the nucleotide sequences of the invention thereby leading to changes in the amino acid sequence of the encoded pesticidal proteins, without altering the biological activity of the proteins. Thus, variant isolated nucleic acid molecules can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, conservative amino acid substitutions may be made at one or more, predicted, nonessential amino acid residues. A "nonessential" amino acid residue is a residue that can be altered from the wild-type sequence of a pesticidal protein without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Delta-endotoxins generally have five conserved sequence domains, and three conserved structural domains (see, for example, de Maagd et al. (2001) *Trends Genetics* 17:193-199). The first conserved structural domain consists of seven alpha helices and is involved in membrane insertion and pore formation. Domain II consists of three beta-sheets arranged in a Greek key configuration, and domain III consists of two antiparallel beta-sheets in "jelly-roll" formation (de Maagd et al., 2001, supra). Domains II and III are involved in receptor recognition and binding, and are therefore considered determinants of toxin specificity.

Amino acid substitutions may be made in nonconserved regions that retain function. In general, such substitutions would not be made for conserved amino acid residues, or for amino acid residues residing within a conserved motif, where such residues are essential for protein activity. Examples of residues that are conserved and that may be essential for protein activity include, for example, residues that are identical between all proteins contained in an alignment of similar or related toxins to the sequences of the invention (e.g., residues that are identical in an alignment of homologous proteins). Examples of residues that are conserved but that may allow conservative amino acid substitutions and still retain activity include, for example, residues that have only conservative substitutions between all proteins contained in an alignment of similar or related toxins to the sequences of the invention (e.g., residues that have only conservative substitutions between all proteins contained in the alignment homologous proteins). However, one of skill in the art would understand that functional variants may have minor conserved or nonconserved alterations in the conserved residues.

Alternatively, variant nucleotide sequences can be made by introducing mutations randomly along all or part of the coding sequence, such as by saturation mutagenesis, and the resultant mutants can be screened for ability to confer pesticidal activity to identify mutants that retain activity. Following mutagenesis, the encoded protein can be expressed recombinantly, and the activity of the protein can be determined using standard assay techniques.

Using methods such as PCR, hybridization, and the like corresponding pesticidal sequences can be identified, isolated, or recovered from a sample (e.g., a sample containing nucleic acid sequences, such as a biological sample), such sequences having substantial identity to the sequences of the invention (e.g., at least about 70%, at least about 75%, 80%, 85%, 90%, 95% or more sequence identity across the entirety of the reference sequence) and having or conferring pesticidal activity. See, for example, Sambrook and Russell (2001) *Molecular Cloning: A Laboratory Manual.* (Cold Spring Harbor Laboratory Press, Cold Spring Harbor, N.Y.) and Innis, et al. (1990) *PCR Protocols: A Guide to Methods and Applications* (Academic Press, NY).

In a hybridization method, all or part of the pesticidal nucleotide sequence can be used to screen cDNA or genomic libraries. Methods for construction of such cDNA and genomic libraries are generally known in the art and are disclosed in Sambrook and Russell, 2001, supra. The so-called hybridization probes may be genomic DNA fragments, cDNA fragments, RNA fragments, or other oligonucleotides, and may be labeled with a detectable group such as $^{32}P$, or any other detectable marker, such as other radioisotopes, a fluorescent compound, an enzyme, or an enzyme co-factor. Probes for hybridization can be made by labeling synthetic oligonucleotides based on the known pesticidal protein-encoding nucleotide sequence disclosed herein. Degenerate primers designed on the basis of conserved nucleotides or amino acid residues in the nucleotide sequence or encoded amino acid sequence can additionally be used. The probe typically comprises a region of nucleotide sequence that hybridizes under stringent conditions to at least about 12, at least about 25, at least about 50, 75, 100, 125, 150, 175, or 200 consecutive nucleotides of nucleotide sequence encoding a pesticidal protein of the invention or a fragment or variant thereof. Methods for the preparation of probes for hybridization are generally known in the art and are disclosed in Sambrook and Russell, 2001, supra herein incorporated by reference.

For example, an entire pesticidal protein sequence disclosed herein, or one or more portions thereof, may be used as a probe capable of specifically hybridizing to corresponding pesticidal protein-like sequences and messenger RNAs. To achieve specific hybridization under a variety of conditions, such probes include sequences that are unique and are preferably at least about 10 nucleotides in length, or at least about 20 nucleotides in length. Such probes may be used to amplify corresponding pesticidal sequences from a chosen organism or sample by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Cold Spring Harbor, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Cold Spring Harbor, N.Y.).

Isolated Proteins and Variants and Fragments Thereof

Pesticidal proteins are also encompassed within the present invention. By "pesticidal protein" is intended a protein having the amino acid sequence set forth in SEQ ID NO:28-62. Fragments, biologically active portions, and variants thereof are also provided, and may be used to practice the methods of the present invention. An "isolated protein" is used to refer to a protein that is no longer in its natural environment, for example in vitro or in a recombinant bacterial or plant host cell.

"Fragments" or "biologically active portions" include polypeptide fragments comprising amino acid sequences sufficiently identical to the amino acid sequence set forth in any of SEQ ID NO:28-62 and that exhibit pesticidal activity. A biologically active portion of a pesticidal protein can be a polypeptide that is, for example, 10, 25, 50, 100 or more amino acids in length. Such biologically active portions can be prepared by recombinant techniques and evaluated for pesticidal activity. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety. As used here, a fragment comprises at least 8 contiguous amino acids of SEQ ID NO:28-62. The invention encompasses other fragments, however, such as any fragment in the protein greater than about 10, 20, 30, 50, 100, 150, 200, 250, 300, 350, 400, 400, 450, 500, 550, 600, 650, 700, 750, 800, 850, 900, 950, 1000, 1050, 1100, 1150, 1200, 1250, or 1300 amino acids.

By "variants" is intended proteins or polypeptides having an amino acid sequence that is at least about 60%, 65%, about 70%, 75%, about 80%, 85%, about 90%, 91%, 92%, 93%, 94%, 95%, 96%, 97%, 98% or 99% identical to the amino acid sequence of any of SEQ ID NO:28-62. Variants also include polypeptides encoded by a nucleic acid molecule that hybridizes to the nucleic acid molecule of SEQ ID NO:1-27, or a complement thereof, under stringent conditions. Variants include polypeptides that differ in amino acid sequence due to mutagenesis. Variant proteins encompassed by the present invention are biologically active, that is they continue to possess the desired biological activity of the native protein, that is, retaining pesticidal activity. In some embodiments, the variants have improved activity. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

Bacterial genes, such as the axmi genes of this invention, quite often possess multiple methionine initiation codons in proximity to the start of the open reading frame. Often, translation initiation at one or more of these start codons will lead to generation of a functional protein. These start codons can include ATG codons. However, bacteria such as *Bacillus* sp. also recognize the codon GTG as a start codon, and proteins that initiate translation at GTG codons contain a methionine at the first amino acid. On rare occasions, translation in bacterial systems can initiate at a TTG codon, though in this event the TTG encodes a methionine. Furthermore, it is not often determined a priori which of these codons are used naturally in the bacterium. Thus, it is understood that use of one of the alternate methionine codons may also lead to generation of pesticidal proteins. These pesticidal proteins are encompassed in the present invention and may be used in the methods of the present invention. It will be understood that, when expressed in plants, it will be necessary to alter the alternate start codon to ATG for proper translation.

Antibodies to the polypeptides of the present invention, or to variants or fragments thereof, are also encompassed. Methods for producing antibodies are well known in the art (see, for example, Harlow and Lane (1988) *Antibodies: A Laboratory Manual*, Cold Spring Harbor Laboratory, Cold Spring Harbor, N.Y.; U.S. Pat. No. 4,196,265).

Altered or Improved Variants

It is recognized that DNA sequences of a pesticidal protein may be altered by various methods, and that these alterations may result in DNA sequences encoding proteins with amino acid sequences different than that encoded by a pesticidal protein of the present invention. This protein may be altered in various ways including amino acid substitutions, deletions, truncations, and insertions of one or more amino acids of SEQ ID NO:28-62, including up to about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 100, about 105, about 110, about 115, about 120, about 125, about 130 or more amino acid substitutions, deletions or insertions.

Methods for such manipulations are generally known in the art. For example, amino acid sequence variants of a pesticidal protein can be prepared by mutations in the DNA. This may also be accomplished by one of several forms of mutagenesis and/or in directed evolution. In some aspects, the changes encoded in the amino acid sequence will not substantially affect the function of the protein. Such variants will possess the desired pesticidal activity. However, it is understood that the ability of a pesticidal protein to confer pesticidal activity may be improved by the use of such techniques upon the compositions of this invention. For example, one may express a pesticidal protein in host cells that exhibit high rates of base misincorporation during DNA replication, such as XL-1 Red (Stratagene). After propagation in such strains, one can isolate the toxin DNA (for example by preparing plasmid DNA, or by amplifying by PCR and cloning the resulting PCR fragment into a vector), culture the toxin mutations in a non-mutagenic strain, and identify mutated toxin genes with pesticidal activity, for example by performing an assay to test for pesticidal activity. Generally, the protein is mixed and used in feeding assays. See, for example Marrone et al. (1985) *J. of Economic Entomology* 78:290-293. Such assays can include contacting plants with one or more pests and determining the plant's ability to survive and/or cause the death of the pests. Examples of mutations that result in increased toxicity are found in Schnepf et al. (1998) *Microbiol. Mol. Biol. Rev.* 62:775-806.

Alternatively, alterations may be made to the protein sequence of many proteins at the amino or carboxy terminus without substantially affecting activity. This can include insertions, deletions, or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest (2) introduce a binding domain, enzymatic activity, or epitope to facilitate either protein purification, protein detection, or other experimental uses known in the art (3) target secretion or translation of a protein to a subcellular organelle, such as the periplasmic space of Gram-negative bacteria, or the endoplasmic reticulum of eukaryotic cells, the latter of which often results in glycosylation of the protein.

Variant nucleotide and amino acid sequences of the present invention also encompass sequences derived from mutagenic and recombinogenic procedures such as DNA shuffling. With such a procedure, one or more different pesticidal protein coding regions can be used to create a new pesticidal protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between a pesticidal gene of the invention and other known pesticidal genes to obtain a new gene coding for a protein with an improved property of interest, such as an increased insecticidal activity. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

Domain swapping or shuffling is another mechanism for generating altered delta-endotoxin proteins. Domains may be swapped between delta-endotoxin proteins, resulting in hybrid or chimeric toxins with improved pesticidal activity or target spectrum. Methods for generating recombinant proteins and testing them for pesticidal activity are well known in the art (see, for example, Naimov et al. (2001) *Appl. Environ. Microbiol.* 67:5328-5330; de Maagd et al. (1996) *Appl. Environ. Microbiol.* 62:1537-1543; Ge et al. (1991) *J. Biol. Chem.*

266:17954-17958; Schnepf et al. (1990) *J. Biol. Chem.* 265: 20923-20930; Rang et al. 91999) *Appl. Environ. Microbiol.* 65:2918-2925).

In yet another embodiment, variant nucleotide and/or amino acid sequences can be obtained using one or more of error-prone PCR, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, gene site saturation mutagenesis, permutational mutagenesis, synthetic ligation reassembly (SLR), recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation, and the like.

Vectors

A pesticidal sequence of the invention may be provided in an expression cassette for expression in a plant of interest. By "plant expression cassette" is intended a DNA construct that is capable of resulting in the expression of a protein from an open reading frame in a plant cell. Typically these contain a promoter and a coding sequence. Often, such constructs will also contain a 3' untranslated region. Such constructs may contain a "signal sequence" or "leader sequence" to facilitate co-translational or post-translational transport of the peptide to certain intracellular structures such as the chloroplast (or other plastid), endoplasmic reticulum, or Golgi apparatus.

By "signal sequence" is intended a sequence that is known or suspected to result in cotranslational or post-translational peptide transport across the cell membrane. In eukaryotes, this typically involves secretion into the Golgi apparatus, with some resulting glycosylation. Insecticidal toxins of bacteria are often synthesized as protoxins, which are protolytically activated in the gut of the target pest (Chang (1987) *Methods Enzymol.* 153:507-516). In some embodiments of the present invention, the signal sequence is located in the native sequence, or may be derived from a sequence of the invention. By "leader sequence" is intended any sequence that when translated, results in an amino acid sequence sufficient to trigger co-translational transport of the peptide chain to a sub-cellular organelle. Thus, this includes leader sequences targeting transport and/or glycosylation by passage into the endoplasmic reticulum, passage to vacuoles, plastids including chloroplasts, mitochondria, and the like.

By "plant transformation vector" is intended a DNA molecule that is necessary for efficient transformation of a plant cell. Such a molecule may consist of one or more plant expression cassettes, and may be organized into more than one "vector" DNA molecule. For example, binary vectors are plant transformation vectors that utilize two non-contiguous DNA vectors to encode all requisite cis- and trans-acting functions for transformation of plant cells (Hellens and Mullineaux (2000) *Trends in Plant Science* 5:446-451). "Vector" refers to a nucleic acid construct designed for transfer between different host cells. "Expression vector" refers to a vector that has the ability to incorporate, integrate and express heterologous DNA sequences or fragments in a foreign cell. The cassette will include 5' and 3' regulatory sequences operably linked to a sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

"Promoter" refers to a nucleic acid sequence that functions to direct transcription of a downstream coding sequence. The promoter together with other transcriptional and translational regulatory nucleic acid sequences (also termed "control sequences") are necessary for the expression of a DNA sequence of interest.

Such an expression cassette is provided with a plurality of restriction sites for insertion of the pesticidal sequence to be under the transcriptional regulation of the regulatory regions.

The expression cassette will include in the 5'-3' direction of transcription, a transcriptional and translational initiation region (i.e., a promoter), a DNA sequence of the invention, and a translational and transcriptional termination region (i.e., termination region) functional in plants. The promoter may be native or analogous, or foreign or heterologous, to the plant host and/or to the DNA sequence of the invention. Additionally, the promoter may be the natural sequence or alternatively a synthetic sequence. Where the promoter is "native" or "homologous" to the plant host, it is intended that the promoter is found in the native plant into which the promoter is introduced. Where the promoter is "foreign" or "heterologous" to the DNA sequence of the invention, it is intended that the promoter is not the native or naturally occurring promoter for the operably linked DNA sequence of the invention.

The termination region may be native with the transcriptional initiation region, may be native with the operably linked DNA sequence of interest, may be native with the plant host, or may be derived from another source (i.e., foreign or heterologous to the promoter, the DNA sequence of interest, the plant host, or any combination thereof). Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) may be optimized for increased expression in the transformed host cell. That is, the genes can be synthesized using host cell-preferred codons for improved expression, or may be synthesized using codons at a host-preferred codon usage frequency. Generally, the GC content of the gene will be increased. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

In one embodiment, the pesticidal sequence is targeted to the chloroplast for expression. In this manner, where the pesticidal sequence is not directly inserted into the chloroplast, the expression cassette will additionally contain a nucleic acid encoding a transit peptide to direct the pesticidal sequence to the chloroplasts. Such transit peptides are known in the art. See, for example, Von Heijne et al. (1991) *Plant*

*Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

The pesticidal gene to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

Plant Transformation

Methods of the invention involve introducing a nucleotide construct into a plant. By "introducing" is intended to present to the plant the nucleotide construct in such a manner that the construct gains access to the interior of a cell of the plant. The methods of the invention do not require that a particular method for introducing a nucleotide construct to a plant is used, only that the nucleotide construct gains access to the interior of at least one cell of the plant. Methods for introducing nucleotide constructs into plants are known in the art including, but not limited to, stable transformation methods, transient transformation methods, and virus-mediated methods.

By "plant" is intended whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells, pollen).

"Transgenic plants" or "transformed plants" or "stably transformed" plants or cells or tissues refers to plants that have incorporated or integrated exogenous nucleic acid sequences or DNA fragments into the plant cell. These nucleic acid sequences include those that are exogenous, or not present in the untransformed plant cell, as well as those that may be endogenous, or present in the untransformed plant cell. "Heterologous" generally refers to the nucleic acid sequences that are not endogenous to the cell or part of the native genome in which they are present, and have been added to the cell by infection, transfection, microinjection, electroporation, microprojection, or the like.

The transgenic plants of the invention express one or more of the pesticidal sequences disclosed herein. In various embodiments, the transgenic plant further comprises one or more additional genes for insect resistance, for example, one or more additional genes for controlling coleopteran, lepidopteran, heteropteran, or nematode pests. It will be understood by one of skill in the art that the transgenic plant may comprise any gene imparting an agronomic trait of interest.

Transformation of plant cells can be accomplished by one of several techniques known in the art. The pesticidal gene of the invention may be modified to obtain or enhance expression in plant cells. Typically a construct that expresses such a protein would contain a promoter to drive transcription of the gene, as well as a 3' untranslated region to allow transcription termination and polyadenylation. The organization of such constructs is well known in the art. In some instances, it may be useful to engineer the gene such that the resulting peptide is secreted, or otherwise targeted within the plant cell. For example, the gene can be engineered to contain a signal peptide to facilitate transfer of the peptide to the endoplasmic reticulum. It may also be preferable to engineer the plant expression cassette to contain an intron, such that mRNA processing of the intron is required for expression.

Typically this "plant expression cassette" will be inserted into a "plant transformation vector". This plant transformation vector may be comprised of one or more DNA vectors needed for achieving plant transformation. For example, it is a common practice in the art to utilize plant transformation vectors that are comprised of more than one contiguous DNA segment. These vectors are often referred to in the art as "binary vectors". Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "gene of interest" (a gene engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the pesticidal sequence are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as is understood in the art (Hellens and Mullineaux (2000) *Trends in Plant Science* 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethylene glycol, etc.

In general, plant transformation methods involve transferring heterologous DNA into target plant cells (e.g. immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Explants are typically transferred to a fresh supply of the same medium and cultured routinely. Subsequently, the transformed cells are differentiated into shoots after placing on regeneration medium supplemented with a maximum threshold level of selecting agent. The shoots are then transferred to a selective rooting medium for recovering rooted shoot or plantlet. The transgenic plantlet then grows into a mature plant and produces fertile seeds (e.g. Hiei et al. (1994) *The Plant Journal* 6:271-282; Ishida et al. (1996) *Nature Biotechnology* 14:745-750). Explants are typically transferred to a fresh supply of the same medium and cultured routinely. A general description of the techniques and methods for generating transgenic plants are found in Ayres and Park (1994) *Critical Reviews in Plant Science* 13:219-239 and Bommineni and Jauhar (1997) *Maydica* 42:107-120. Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants.

Transformation protocols as well as protocols for introducing nucleotide sequences into plants may vary depending on the type of plant or plant cell, i.e., monocot or dicot, targeted for transformation. Generation of transgenic plants may be performed by one of several methods, including, but not limited to, microinjection, electroporation, direct gene transfer, introduction of heterologous DNA by *Agrobacterium* into plant cells (*Agrobacterium*-mediated transformation), bombardment of plant cells with heterologous foreign DNA adhered to particles, ballistic particle acceleration, aerosol beam transformation (U.S. Published Application No. 20010026941; U.S. Pat. No. 4,945,050; International Publication No. WO 91/00915; U.S. Published Application No. 2002015066), Lec1 transformation, and various other non-particle direct-mediated methods to transfer DNA.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

Following integration of heterologous foreign DNA into plant cells, one then applies a maximum threshold level of appropriate selection in the medium to kill the untransformed cells and separate and proliferate the putatively transformed cells that survive from this selection treatment by transferring regularly to a fresh medium. By continuous passage and challenge with appropriate selection, one identifies and proliferates the cells that are transformed with the plasmid vector. Molecular and biochemical methods can then be used to confirm the presence of the integrated heterologous gene of interest into the genome of the transgenic plant.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

Evaluation of Plant Transformation

Following introduction of heterologous foreign DNA into plant cells, the transformation or integration of heterologous gene in the plant genome is confirmed by various methods such as analysis of nucleic acids, proteins and metabolites associated with the integrated gene.

PCR analysis is a rapid method to screen transformed cells, tissue or shoots for the presence of incorporated gene at the earlier stage before transplanting into the soil (Sambrook and Russell (2001) *Molecular Cloning: A Laboratory Manual*. Cold Spring Harbor Laboratory Press, Cold Spring Harbor, N.Y.). PCR is carried out using oligonucleotide primers specific to the gene of interest or *Agrobacterium* vector background, etc.

Plant transformation may be confirmed by Southern blot analysis of genomic DNA (Sambrook and Russell, 2001, supra). In general, total DNA is extracted from the transformant, digested with appropriate restriction enzymes, fractionated in an agarose gel and transferred to a nitrocellulose or nylon membrane. The membrane or "blot" is then probed with, for example, radiolabeled $^{32}P$ target DNA fragment to confirm the integration of introduced gene into the plant genome according to standard techniques (Sambrook and Russell, 2001, supra).

In Northern blot analysis, RNA is isolated from specific tissues of transformant, fractionated in a formaldehyde agarose gel, and blotted onto a nylon filter according to standard procedures that are routinely used in the art (Sambrook and Russell, 2001, supra). Expression of RNA encoded by the pesticidal sequence is then tested by hybridizing the filter to a radioactive probe derived from a toxin, by methods known in the art (Sambrook and Russell, 2001, supra).

Western blot, biochemical assays and the like may be carried out on the transgenic plants to confirm the presence of protein encoded by the pesticidal gene by standard procedures (Sambrook and Russell, 2001, supra) using antibodies that bind to one or more epitopes present on the pesticidal protein.

Pesticidal Activity in Plants

In another aspect of the invention, one may generate transgenic plants expressing a toxin that has pesticidal activity. Methods described above by way of example may be utilized to generate transgenic plants, but the manner in which the transgenic plant cells are generated is not critical to this invention. Methods known or described in the art such as *Agrobacterium*-mediated transformation, biolistic transformation, and non-particle-mediated methods may be used at the discretion of the experimenter. Plants expressing a pesticidal sequence may be isolated by common methods described in the art, for example by transformation of callus, selection of transformed callus, and regeneration of fertile plants from such transgenic callus. In such process, one may use any gene as a selectable marker so long as its expression in plant cells confers ability to identify or select for transformed cells.

A number of markers have been developed for use with plant cells, such as resistance to chloramphenicol, the aminoglycoside G418, hygromycin, or the like. Other genes that encode a product involved in chloroplast metabolism may also be used as selectable markers. For example, genes that provide resistance to plant herbicides such as glyphosate, bromoxynil, or imidazolinone may find particular use. Such genes have been reported (Stalker et al. (1985) *J. Biol. Chem.* 263:6310-6314 (bromoxynil resistance nitrilase gene); and Sathasivan et al. (1990) *Nucl. Acids Res.* 18:2188 (AHAS imidazolinone resistance gene). Additionally, the genes disclosed herein are useful as markers to assess transformation of bacterial or plant cells. Methods for detecting the presence of a transgene in a plant, plant organ (e.g., leaves, stems, roots, etc.), seed, plant cell, propagule, embryo or progeny of the same are well known in the art. In one embodiment, the presence of the transgene is detected by testing for pesticidal activity.

Fertile plants expressing a pesticidal sequence may be tested for pesticidal activity, and the plants showing optimal activity selected for further breeding. Methods are available in the art to assay for pest activity. Generally, the protein is mixed and used in feeding assays. See, for example Marrone et al. (1985) *J. of Economic Entomology* 78:290-293.

The present invention may be used for transformation of any plant species, including, but not limited to, monocots and dicots. Examples of plants of interest include, but are not limited to, corn (maize), sorghum, wheat, sunflower, tomato, crucifers, peppers, potato, cotton, rice, soybean, sugarbeet, sugarcane, tobacco, barley, and oilseed rape, *Brassica* sp., alfalfa, rye, millet, safflower, peanuts, sweet potato, cassava, coffee, coconut, pineapple, citrus trees, cocoa, tea, banana, avocado, fig, guava, mango, olive, papaya, cashew, macadamia, almond, oats, vegetables, ornamentals, and conifers.

Vegetables include, but are not limited to, tomatoes, lettuce, green beans, lima beans, peas, and members of the genus *Curcumis* such as cucumber, cantaloupe, and musk melon. Ornamentals include, but are not limited to, azalea, hydrangea, hibiscus, roses, tulips, daffodils, petunias, carnation, poinsettia, and chrysanthemum. Preferably, plants of the present invention are crop plants (for example, maize, sorghum, wheat, sunflower, tomato, crucifers, peppers, potato, cotton, rice, soybean, sugarbeet, sugarcane, tobacco, barley, oilseed rape., etc.).

Use in Pesticidal Control

General methods for employing strains comprising a nucleotide sequence of the present invention, or a variant thereof, in pesticide control or in engineering other organisms as pesticidal agents are known in the art. See, for example U.S. Pat. No. 5,039,523 and EP 0480762A2.

The *Bacillus* strains containing a nucleotide sequence of the present invention, or a variant thereof, or the microorganisms that have been genetically altered to contain a pesticidal gene and protein may be used for protecting agricultural crops and products from pests. In one aspect of the invention, whole, i.e., unlysed, cells of a toxin (pesticide)-producing organism are treated with reagents that prolong the activity of the pesticidal protein produced in the cell when the cell is applied to the environment of target pest(s).

Alternatively, the pesticide is produced by introducing a pesticidal gene into a cellular host. Expression of the pesticidal gene results, directly or indirectly, in the intracellular production and maintenance of the pesticide. In one aspect of this invention, these cells are then treated under conditions that prolong the activity of the pesticidal produced in the cell when the cell is applied to the environment of target pest(s). The resulting product retains the toxicity of the pesticidal protein. These naturally encapsulated pesticides may then be formulated in accordance with conventional techniques for application to the environment hosting a target pest, e.g., soil, water, and foliage of plants. See, for example EPA 0192319, and the references cited therein. Alternatively, one may formulate the cells expressing a gene of this invention such as to allow application of the resulting material as a pesticide.

Pesticidal Compositions

The active ingredients of the present invention are normally applied in the form of compositions and can be applied to the crop area or plant to be treated, simultaneously or in succession, with other compounds. These compounds can be fertilizers, weed killers, cryoprotectants, surfactants, detergents, pesticidal soaps, dormant oils, polymers, and/or time-release or biodegradable carrier formulations that permit long-term dosing of a target area following a single application of the formulation. They can also be selective herbicides, chemical insecticides, virucides, microbicides, amoebicides, pesticides, fungicides, bacteriocides, nematocides, molluscicides or mixtures of several of these preparations, if desired, together with further agriculturally acceptable carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers. Likewise the formulations may be prepared into edible "baits" or fashioned into pest "traps" to permit feeding or ingestion by a target pest of the pesticidal formulation.

Methods of applying an active ingredient of the present invention or an agrochemical composition of the present invention that contains at least one of the pesticidal proteins produced by the bacterial strains of the present invention include leaf application, seed coating and soil application. The number of applications and the rate of application depend on the intensity of infestation by the corresponding pest.

The composition may be formulated as a powder, dust, pellet, granule, spray, emulsion, colloid, solution, or such like, and may be prepared by such conventional means as desiccation, lyophilization, homogenation, extraction, filtration, centrifugation, sedimentation, or concentration of a culture of cells comprising the polypeptide. In all such compositions that contain at least one such pesticidal polypeptide, the polypeptide may be present in a concentration of from about 1% to about 99% by weight.

Lepidopteran, dipteran, heteropteran, coleopteran, or nematode pests may be killed or reduced in numbers in a given area by the methods of the invention, or may be prophylactically applied to an environmental area to prevent infestation by a susceptible pest. Preferably the pest ingests, or is contacted with, a pesticidally-effective amount of the polypeptide. By "pesticidally-effective amount" is intended an amount of the pesticide that is able to bring about death to at least one pest, or to noticeably reduce pest growth, feeding, or normal physiological development. This amount will vary depending on such factors as, for example, the specific target pests to be controlled, the specific environment, location, plant, crop, or agricultural site to be treated, the environmental conditions, and the method, rate, concentration, stability, and quantity of application of the pesticidally-effective polypeptide composition. The formulations may also vary with respect to climatic conditions, environmental considerations, and/or frequency of application and/or severity of pest infestation.

The pesticide compositions described may be made by formulating either the bacterial cell, crystal and/or spore suspension, or isolated protein component with the desired agriculturally-acceptable carrier. The compositions may be formulated prior to administration in an appropriate means such as lyophilized, freeze-dried, desiccated, or in an aqueous carrier, medium or suitable diluent, such as saline or other buffer. The formulated compositions may be in the form of a dust or granular material, or a suspension in oil (vegetable or mineral), or water or oil/water emulsions, or as a wettable powder, or in combination with any other carrier material suitable for agricultural application. Suitable agricultural carriers can be solid or liquid and are well known in the art. The term "agriculturally-acceptable carrier" covers all adjuvants, inert components, dispersants, surfactants, tackifiers, binders, etc. that are ordinarily used in pesticide formulation technology; these are well known to those skilled in pesticide formulation. The formulations may be mixed with one or more solid or liquid adjuvants and prepared by various means, e.g., by homogeneously mixing, blending and/or grinding the pesticidal composition with suitable adjuvants using conventional formulation techniques. Suitable formulations and application methods are described in U.S. Pat. No. 6,468,523, herein incorporated by reference.

The plants can also be treated with one or more chemical compositions, including one or more herbicide, insecticides, or fungicides. Exemplary chemical compositions include: Fruits/Vegetables Herbicides: Atrazine, Bromacil, Diuron, Glyphosate, Linuron, Metribuzin, Simazine, Trifluralin, Fluazifop, Glufosinate, Halo sulfuron Gowan, Paraquat, Propyzamide, Sethoxydim, Butafenacil, Halosulfuron, Indaziflam; Fruits/Vegetables Insecticides: Aldicarb, *Bacillus thuriengiensis*, Carbaryl, Carbofuran, Chlorpyrifos, Cypermethrin, Deltamethrin, Diazinon, Malathion, Abamectin, Cyfluthrin/beta-cyfluthrin, Esfenvalerate, Lambda-cyhalothrin, Acequinocyl, Bifenazate, Methoxyfenozide, Novaluron, Chromafenozide, Thiacloprid, Dinotefuran, Fluacrypyrim, Tolfenpyrad, Clothianidin, Spirodiclofen, Gamma-cyhalothrin, Spiromesifen, Spinosad, Rynaxypyr, Cyazypyr, Spinoteram, Triflumuron, Spirotetramat, Imidacloprid, Flubendiamide, Thiodicarb, Metaflumizone, Sulfoxaflor, Cyflumetofen, Cyanopyrafen, Imidacloprid, Clothianidin, Thiamethoxam, Spinotoram, Thiodicarb, Flonicamid, Methiocarb, Emamectin-benzoate, Indoxacarb, Forthiazate, Fenamiphos, Cadusaphos, Pyriproxifen, Fenbutatin-oxid, Hexthiazox, Methomyl, 4-[[(6-Chlorpyridin-3-yl)methyl](2,2-difluorethyl)amino]furan-2(5H)-on; Fruits/Vegetables Fungicides:
Carbendazim, Chlorothalonil, EBDCs, Sulphur, Thiophanate-methyl, Azoxystrobin, Cymoxanil, Fluazinam, Fosetyl, Iprodione, Kresoxim-methyl, Metalaxyl/mefenoxam, Trifloxystrobin, Ethaboxam, Iprovalicarb, Trifloxystrobin, Fenhexamid, Oxpoconazole fumarate, Cyazofamid, Fenamidone, Zoxamide, Picoxystrobin, Pyraclostrobin, Cyflufenamid, Boscalid; Cereals Herbicides: Isoproturon, Bromoxynil, Ioxynil, Phenoxies, Chlorsulfuron, Clodinafop, Diclofop, Diflufenican, Fenoxaprop, Florasulam, Fluoroxypyr, Metsulfuron, Triasulfuron, Flucarbazone, Iodosulfuron, Propoxycarbazone, Picolinafen, Mesosulfuron, Beflubutamid, Pinoxaden, Amidosulfuron, Thifensulfuron, Tribenuron, Flupyrsulfuron, Sulfosulfuron, Pyrasulfotole, Pyroxsulam, Flufenacet, Tralkoxydim, Pyroxasulfon; Cereals Fungicides: Carbendazim, Chlorothalonil, Azoxystrobin, Cyproconazole, Cyprodinil, Fenpropimorph, Epoxiconazole, Kresoxim-methyl, Quinoxyfen, Tebuconazole, Trifloxystrobin, Simeconazole, Picoxystrobin, Pyraclostrobin, Dimoxystrobin, Prothioconazole, Fluoxastrobin; Cereals Insecticides: Dimethoate, Lambda-cyhalthrin, Deltamethrin, alpha-Cypermethrin, β-cyfluthrin, Bifenthrin, Imidacloprid, Clothianidin, Thiamethoxam, Thiacloprid, Acetamiprid, Dinetofuran, Clorphyriphos, Metamidophos, Oxidemethon-methyl, Pirimicarb, Methiocarb; Maize Herbicides: Atrazine, Alachlor, Bromoxynil, Acetochlor, Dicamba, Clopyralid, (S-)Dimethenamid, Glufosinate, Glyphosate, Isoxaflutole, (S-)Metolachlor, Mesotrione, Nicosulfuron, Primisulfuron, Rimsulfuron, Sulcotrione, Foramsulfuron, Topramezone, Tembotrione, Saflufenacil, Thiencarbazone, Flufenacet, Pyroxasulfon; Maize Insecticides: Carbofuran, Chlorpyrifos, Bifenthrin, Cyazypyr, Fipronil, Imidacloprid, Lambda-Cyhalothrin, Tefluthrin, Terbufos, Thiamethoxam, Clothianidin, Spiromesifen, Flubendiamide, Triflumuron, Rynaxypyr, Deltamethrin, Thiodicarb, β-Cyfluthrin, Cypermethrin, Bifenthrin, Lufenuron, Triflumoron, Tefluthrin, Tebupirimphos, Ethiprole, Cyazypyr, Thiacloprid, Acetamiprid, Dinetofuran, Avermectin, Methiocarb, Spirodiclofen, Spirotetramat; Maize Fungicides: Fenitropan, Thiram, Prothioconazole, Tebuconazole, Trifloxystrobin; Rice Herbicides: Butachlor, Propanil, Azimsulfuron, Bensulfuron, Cyhalofop, Daimuron, Fentrazamide, Imazosulfuron, Mefenacet, Oxaziclomefone, Pyrazosulfuron, Pyributicarb, Quinclorac, Thiobencarb, Indanofan, Flufenacet, Fentrazamide, Halosulfuron, Oxaziclomefone, Benzobicyclon, Pyriftalid, Penoxsulam, Bispyribac, Oxadiargyl, Ethoxysulfuron, Pretilachlor, Mesotrione, Tefuryltrione, Oxadiazone, Fenoxaprop, Pyrimisulfan; Rice Insecticides: Diazinon, Fenitrothion, Fenobucarb, Monocrotophos, Benfuracarb, Buprofezin, Dinotefuran, Fipronil, Imidacloprid, Isoprocarb, Thiacloprid, Chromafenozide, Thiacloprid, Dinotefuran, Clothianidin, Ethiprole, Flubendiamide, Rynaxypyr, Deltamethrin, Acetamiprid, Thiamethoxam, Cyazypyr, Spinosad, Spinotoram, Emamectin-Benzoate, Cypermethrin, Chlorpyriphos, Cartap, Methamidophos, Etofenprox, Triazophos, 4-[[(6-Chlorpyridin-3-yl)methyl](2,2-difluorethyl)amino]furan-2(5H)-on, Carbofuran, Benfuracarb; Rice Fungicides: Thiophanate-methyl, Azoxystrobin, Carpropamid, Edifenphos, Ferimzone, Iprobenfos, Isoprothiolane, Pencycuron, Probenazole, Pyroquilon, Tricyclazole, Trifloxystrobin, Diclocymet, Fenoxanil, Simeconazole, Tiadinil; Cotton Herbicides: Diuron, Fluometuron, MSMA, Oxyfluorfen, Prometryn, Trifluralin, Carfentrazone, Clethodim, Fluazifop-butyl, Glyphosate, Norflurazon, Pendimethalin, Pyrithiobac-sodium, Trifloxysulfuron, Tepraloxydim, Glufosinate, Flumioxazin, Thidiazuron; Cotton Insecticides: Acephate, Aldicarb, Chlorpyrifos, Cypermethrin, Deltamethrin, Malathion, Monocrotophos, Abamectin, Acetamiprid, Emamectin Benzoate, Imidacloprid, Indoxacarb, Lambda-Cyhalothrin, Spinosad, Thiodicarb, Gamma-Cyhalothrin, Spiromesifen, Pyridalyl, Flonicamid, Flubendiamide, Triflumuron, Rynaxypyr, Beta-Cyfluthrin, Spirotetramat, Clothianidin, Thiamethoxam, Thiacloprid, Dinetofuran, Flubendiamide, Cyazypyr, Spinosad, Spinotoram, gamma Cyhalothrin, 4-[[(6-Chlorpyridin-3-yl)methyl](2,2-difluorethyl)amino]furan-2(5H)-on, Thiodicarb, Avermectin, Flonicamid, Pyridalyl, Spiromesifen, Sulfoxaflor, Profenophos, Thriazophos, Endosulfan; Cotton Fungicides: Etridiazole, Metalaxyl, Quintozene; Soybean Herbicides: Alachlor, Bentazone, Trifluralin, Chlorimuron-Ethyl, Cloransulam-Methyl, Fenoxaprop, Fomesafen, Fluazifop, Glyphosate, Imazamox, Imazaquin, Imazethapyr, (S-)Metolachlor, Metribuzin, Pendimethalin, Tepraloxydim, Glufosinate; Soybean Insecticides: Lambda-cyhalothrin, Methomyl, Parathion, Thiocarb, Imidacloprid, Clothianidin, Thiamethoxam, Thiacloprid, Acetamiprid, Dinetofuran, Flubendiamide, Rynaxypyr, Cyazypyr, Spinosad, Spinotoram, Emamectin-Benzoate, Fipronil, Ethiprole, Deltamethrin, β-Cyfluthrin, gamma and lambda Cyhalothrin, 4-[[(6-Chlorpyridin-3-yl)methyl](2,2-difluorethyl)amino]furan-2(5H)-on, Spirotetramat, Spinodiclofen, Triflumuron, Flonicamid, Thiodicarb, beta-Cyfluthrin; Soybean Fungicides: Azoxystrobin, Cyproconazole, Epoxiconazole, Flutriafol, Pyraclostrobin, Tebuconazole, Trifloxystrobin, Prothioconazole, Tetraconazole; Sugarbeet Herbicides: Chloridazon, Desmedipham, Ethofumesate, Phenmedipham, Triallate, Clopyralid, Fluazifop, Lenacil, Metamitron, Quinmerac, Cycloxydim, Triflusulfuron, Tepraloxydim, Quizalofop; Sugarbeet Insecticides: Imidacloprid, Clothianidin, Thiamethoxam, Thiacloprid, Acetamiprid, Dinetofuran, Deltamethrin, β-Cyfluthrin, gamma/lambda Cyhalothrin, 4-[[(6-Chlorpyridin-3-yl)methyl](2,2-difluorethyl)amino]furan-2(5H)-on, Tefluthrin, Rynaxypyr, Cyaxypyr, Fipronil, Carbofuran; Canola Herbicides: Clopyralid, Diclofop, Fluazifop, Glufosinate, Glyphosate, Metazachlor, Trifluralin Ethametsulfuron, Quinmerac, Quizalofop, Clethodim, Tepraloxydim; Canola Fungicides: Azoxystrobin, Carbendazim, Fludioxonil, Iprodione, Prochloraz, Vinclozolin; Canola Insecticides:
Carbofuran, Organophosphates, Pyrethroids, Thiacloprid, Deltamethrin, Imidacloprid, Clothianidin, Thiamethoxam, Acetamiprid, Dinetofuran, β-Cyfluthrin, gamma and lambda Cyhalothrin, tau-Fluvaleriate, Ethiprole, Spinosad, Spinotoram, Flubendiamide, Rynaxypyr, Cyazypyr, 4-[[(6-Chlorpyridin-3-yl)methyl](2,2-difluorethyl)amino]furan-2(5H)-on.

"Pest" includes but is not limited to, insects, fungi, bacteria, nematodes, mites, ticks, and the like. Insect pests include insects selected from the orders Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, etc., particularly Coleoptera, Lepidoptera, and Diptera.

The order Coleoptera includes the suborders Adephaga and Polyphaga. Suborder Adephaga includes the superfamilies Caraboidea and Gyrinoidea, while suborder Polyphaga includes the superfamilies Hydrophiloidea, Staphylinoidea, Cantharoidea, Cleroidea, Elateroidea, Dascilloidea, Dryopoidea, Byrrhoidea, Cucujoidea, Meloidea, Mordelloidea, Tenebrionoidea, Bostrichoidea, Scarabaeoidea, Cerambycoidea, Chrysomeloidea, and Curculionoidea. Superfamily Caraboidea includes the families Cicindelidae, Carabidae, and Dytiscidae. Superfamily Gyrinoidea includes the family Gyrimidae. Superfamily Hydrophiloidea includes the family Hydrophilidae. Superfamily Staphylinoidea includes the families Silphidae and Staphylimidae. Superfamily Cantharoidea includes the families Cantharidae and Lampyridae. Superfamily Cleroidea includes the families Cleridae and Dermestidae. Superfamily Elateroidea includes the families Elateridae and Buprestidae. Superfamily Cucujoidea includes the family Coccinellidae. Superfamily Meloidea includes the family Meloidae. Superfamily Tenebrionoidea includes the family Tenebrionidae. Superfamily Scarabaeoidea includes the families Passalidae and Scarabaeidae. Superfamily Cerambycoidea includes the family Cerambycidae. Superfamily Chrysomeloidea includes the family Chrysomelidae. Superfamily Curculionoidea includes the families Curculionidae and Scolytidae.

The order Diptera includes the Suborders Nematocera, Brachycera, and Cyclorrhapha. Suborder Nematocera includes the families Tipulidae, Psychodidae, Culicidae, Ceratopogonidae, Chironomidae, Simuliidae, Bibionidae, and Cecidomyiidae. Suborder Brachycera includes the families Stratiomyidae, Tabanidae, Therevidae, Asilidae, Mydidae, Bombyliidae, and Dolichopodidae. Suborder Cyclorrhapha includes the Divisions Aschiza and Aschiza. Division Aschiza includes the families Phoridae, Syrphidae, and Conopidae. Division Aschiza includes the Sections Acalyptratae and Calyptratae. Section Acalyptratae includes the families Otitidae, Tephritidae, Agromyzidae, and Drosophilidae. Section Calyptratae includes the families Hippoboscidae, Oestridae, Tachinidae, Anthomyiidae, Muscidae, Calliphoridae, and Sarcophagidae.

The order Lepidoptera includes the families Papilionidae, Pieridae, Lycaenidae, Nymphalidae, Danaidae, Satyridae, Hesperiidae, Sphingidae, Saturniidae, Geometridae, Arctiidae, Noctuidae, Lymantriidae, Sesiidae, and Tineidae.

Nematodes include parasitic nematodes such as root-knot, cyst, and lesion nematodes, including *Heterodera* spp., *Meloidogyne* spp., and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode); and *Globodera rostochiensis* and *Globodera pailida* (potato cyst nematodes). Lesion nematodes include *Pratylenchus* spp., e.g. *Pratylenchus penetrans.*

Insect pests of the invention for the major crops include: Maize: *Ostrinia nubilalis*, European corn borer; *Agrotis ipsilon*, black cutworm; *Helicoverpa zea*, corn earworm; *Spodoptera frugiperda*, fall armyworm; *Diatraea grandiosella*, southwestern corn borer; *Elasmopalpus lignosellus*, lesser cornstalk borer; *Diatraea saccharalis*, sugarcane borer; *Diabrotica virgifera*, western corn rootworm; *Diabrotica longicornis barberi*, northern corn rootworm; *Diabrotica undecimpunctata howardi*, southern corn rootworm; *Melanotus* spp., wireworms; *Cyclocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Blissus leucopterus* leucopterus, chinch bug; *Melanoplus femurrubrum*, redlegged grasshopper; *Melanoplus sanguinipes*, migratory grasshopper; *Hylemya platura*, seedcorn maggot; *Agromyza parvicornis*, corn blot leafminer; *Anaphothrips obscrurus*, grass *thrips; Solenopsis milesta*, thief ant; *Tetranychus urticae*, twospotted spider mite; *Sorghum: Chilo partellus*, sorghum borer; *Spodoptera frugiperda*, fall armyworm; *Helicoverpa zea*, corn earworm; *Elasmopalpus lignosellus*, lesser cornstalk borer; *Feltia subterranea*, granulate cutworm; *Phyllophaga crinita*, white grub; *Eleodes, Conoderus*, and *Aeolus* spp., wireworms; *Oulema melanopus*, cereal leaf beetle; *Chaetocnema pulicaria*, corn flea beetle; *Sphenophorus maidis*, maize billbug; *Rhopalosiphum maidis*; corn leaf aphid; *Sipha flava*, yellow sugarcane aphid; *Blissus leucopterus leucopterus*, chinch bug; *Contarinia sorghicola*, sorghum midge; *Tetranychus cinnabarinus*, carmine spider mite; *Tetranychus urticae*, twospotted spider mite; Wheat: *Pseudaletia unipunctata*, army worm; *Spodoptera frugiperda*, fall armyworm; *Elasmopalpus lignosellus*, lesser cornstalk borer; *Agrotis orthogonia*, western cutworm; *Elasmopalpus lignosellus*, lesser cornstalk borer; *Oulema melanopus*, cereal leaf beetle; *Hypera punctata*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco *thrips; Cephus cinctus*, wheat stem sawfly; *Aceria tulipae*, wheat curl mite; Sunflower: *Suleima helianthana*, sunflower bud moth; *Homoeosoma electellum*, sunflower moth; *zygogramma exclamationis*, sunflower beetle; *Bothyrus gibbosus*, carrot beetle; *Neolasioptera murtfeldtiana*, sunflower seed midge; Cotton: *Heliothis virescens*, cotton budworm; *Helicoverpa zea*, cotton bollworm; *Spodoptera exigua*, beet armyworm; *Pectinophora gossypiella*, pink bollworm; *Anthonomus grandis*, boll weevil; *Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion *thrips; Franklinkiella fusca*, tobacco *thrips; Tetranychus cinnabarinus*, carmine spider mite; *Tetranychus urticae*, twospotted spider mite; Rice: *Diatraea saccharalis*, sugarcane borer; *Spodoptera frugiperda*, fall armyworm; *Helicoverpa zea*, corn earworm; *Colaspis brunnea*, grape *colaspis; Lissorhoptrus oryzophilus*, rice water weevil; *Sitophilus oryzae*, rice weevil; *Nephotettix nigropictus*, rice leafhopper; *Blissus leucopterus* leucopterus, chinch bug; *Acrosternum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet armyworm; *Heliothis virescens*, cotton budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean *thrips; Thrips tabaci*, onion *thrips; Tetranychus turkestani*, strawberry spider mite; *Tetranychus urticae*, twospotted spider mite; Barley: *Ostrinia nubilalis*, European corn borer; *Agrotis ipsilon*, black cutworm; *Schizaphis graminum*, greenbug; *Blissus leucopterus* leucopterus, chinch bug; *Acrosternum hilare*, green stink bug; *Euschistus servus*, brown stink bug; *Delia platura*, seedcorn maggot; *Mayetiola destructor*, Hessian fly; *Petrobia latens*, brown wheat mite; Oil Seed Rape: *Brevicoryne brassicae*, cabbage aphid; *Phyllotreta cruciferae*, Flea beetle; *Mamestra configurata*, Bertha armyworm; *Plutella xylostella*, Diamond-back moth; *Delia* ssp., Root maggots.

Methods for Increasing Plant Yield

Methods for increasing plant yield are provided. The methods comprise providing a plant or plant cell expressing a polynucleotide encoding the pesticidal polypeptide sequence disclosed herein and growing the plant or a seed thereof in a field infested with a pest against which said polypeptide has pesticidal activity. In some embodiments, the polypeptide has pesticidal activity against a lepidopteran, coleopteran, dipteran, hemipteran, or nematode pest, and said field is infested with a lepidopteran, hemipteran, coleopteran, dipteran, or nematode pest.

As defined herein, the "yield" of the plant refers to the quality and/or quantity of biomass produced by the plant. By "biomass" is intended any measured plant product. An increase in biomass production is any improvement in the yield of the measured plant product. Increasing plant yield has several commercial applications. For example, increasing plant leaf biomass may increase the yield of leafy vegetables for human or animal consumption. Additionally, increasing leaf biomass can be used to increase production of plant-derived pharmaceutical or industrial products. An increase in yield can comprise any statistically significant increase including, but not limited to, at least a 1% increase, at least a 3% increase, at least a 5% increase, at least a 10% increase, at least a 20% increase, at least a 30%, at least a 50%, at least a 70%, at least a 100% or a greater increase in yield compared to a plant not expressing the pesticidal sequence.

In specific methods, plant yield is increased as a result of improved pest resistance of a plant expressing a pesticidal protein disclosed herein. Expression of the pesticidal protein results in a reduced ability of a pest to infest or feed on the plant, thus improving plant yield.

The following examples are offered by way of illustration and not by way of limitation.

EXPERIMENTAL

Example 1

Discovery of Novel Pesticidal Genes from *Bacillus thuringiensis* Having Homology to Pesticidal Genes Novel pesticidal genes were identified from the bacterial strains listed in Table 1 using the following steps:

- Preparation of extrachromosomal DNA from the strain, which includes plasmids that typically harbor delta-endotoxin genes
- Mechanical shearing of extrachromosomal DNA to generate size-distributed fragments
- Cloning of ~2 Kb to ~10 Kb fragments of extrachromosomal DNA
- Outgrowth of ~1500 clones of the extrachromosomal DNA
- Partial sequencing of the 1500 clones using primers specific to the cloning vector (end reads)
- Identification of putative toxin genes via homology analysis via the MiDAS approach (as described in U.S. Patent Publication No. 20040014091, which is herein incorporated by reference in its entirety)
- Sequence finishing (walking) of clones containing fragments of the putative toxin genes of interest

TABLE 1

| Gene name | Strain | Molecular weight (Da) | Closest homolog | Nucleotide SEQ ID NO | Amino acid SEQ ID NO |
|---|---|---|---|---|---|
| axmi190 | ATX12995 | 73761 | 37.9% Axmi143 | 1 | 28 |
| axmi191 | ATX12995 | 58498 | 27.7% Cry36Aa1 | 2 | 29 |
| axmi192 | ATX12995 | 90190 | 64.9% Cry20Aa1 | 3 | 30 |
| axmi193 | ATX12995 | 35179 | 43.7% Mtx2 | 4 | 31 |
| axmi194 | ATX24031 | 34428.86 | 22% Cry55Aa | 5 | 32 |
| axmi195 | ATX24031 | 27107 | 45.6% Axmi194 | 6 | 33 |
| axmi196[5] | ATX24031 | 161013 | 46.2% Cry5Aa1 | 7 | 34 |
| axmi196 (truncated) | ATX24031 | | 35% Cry13Aa1_trunc | | 35 |
| axmi197 | ATX28233 | 40196.37 | 38.2% Axmi019 | 8 | 36 |
| axmi198 | ATX28233 | 43908 | 74.9% Axmi072 | 9 | 37 |
| axmi199 | ATX28233 | 40145 | 60.3% Axmi197 | 10 | 38 |
| axmi200[1] | ATX15076 | 77098 | 40.8% Axmi134_trunc | 11 | 39 |
| axmi201[2] | ATX15076 | 64361 | 85.9% Axmi084 | 12 | 40 |
| axmi202 | ATX12978 | 72115 | 17.3% Mtx2 | 13 | 41 |
| axmi203 | ATX27776 | 110587 | 21.5% Axmi148 | 14 | 42 |
| axmi203 (truncated) | | | | | 43 |
| axmi204 | ATX13053 | 65491 | 34.5% Axmi191 | 15 | 44 |
| axmi206 | ATX27753 | 63317 | 28.7% Axmi182 | 16 | 45 |
| axmi207 | ATX4846 | 146032 | 86.8% Axmi134 | 17 | 46 |
| axmi207 (truncated) | ATX4846 | | 83.6% Axmi134_trunc | | 47 |
| axmi208 | ATX4846 | 142602 | 92.1% Axmi134 | 18 | 48 |
| axmi208 (truncated) | | | 92.8% Axmi134_trunc | | 49 |
| axmi209 | ATX4846 | 34633 | 25.3% Axmi180 | 19 | 50 |
| axmi210 | ATX13028 | 131083 | 85.4% Axmi043 | 20 | 51 |

TABLE 1-continued

| Gene name | Strain | Molecular weight (Da) | Closest homolog | Nucleotide SEQ ID NO | Amino acid SEQ ID NO |
|---|---|---|---|---|---|
| axmi210 (truncated) | | | 80.5% Axmi043_trunc | | 52 |
| axmi211[6] | ATX13048 | 137085 | 74.1% Cry7Ca | 21 | 53 |
| axmi211 (truncated) | | | 59.1% Cry7Ca_trunc | | 54 |
| axmi212[7] | ATX13003 | 86972 | 33.2% Axmi035 | 22 | 55 |
| axmi213[3] | ATX13003 | 31570 | 27% Cry15Aa(Bti) | 23 | 56 |
| axmi214[4] | ATX13003 | 32786 | 48.3% Axmi213 | 24 | 57 |
| axmi215 | ATX13020 | 148168 | 60.3% Axmi155 | 25 | 58 |
| axmi215 (truncated) | | | 39.7% Axmi155_trunc | | 59 |
| axmi216 | ATX13020 | 41897 | 28.5% Axmi194 | 26 | 60 |
| axmi217 | ATX13020 | 43043 | 24% Axmi185 | 27 | 61 |

[1]pairs with axmi201

[2]pairs with axmi200

[3]pairs with axmi214

[4]pairs with axmi213

[5]Upon examination of the sequence of ATX24031, two overlapping open reading frames (ORFs) were identified, each with homology to endotoxin-like genes. After inspection of these ORFs and their encoded proteins, it was apparent that these two ORFs likely originated from a single ORF that had suffered a single nucleotide insertion (or larger insertion creating a single nucleotide frame-shift) in the region from nucleotide 224 to 309 from the start of the first ORF. These orfs are designated herein as ATX24031_contig4_orf1 (SEQ ID NO: 63) and ATX424031_contig4_orf2 (SEQ ID NO: 64). The full-length sequence is set forth in SEQ ID NO: 65. A composite ORF that has homology to endotoxins over its entirely can be assembled by "fixing" the insertion to create a single ORF. While it is understood that multiple solutions can be created to yield such an ORF and these solutions will differ in the region of overlap between the ORFs, one solution is provided herein, which is designated as axmi196 (SEQ ID NO: 7).

[6]A p19/CryBP1-like gene was identified immediately upstream of axmi211. The nucleotide sequence for this gene is set forth in SEQ ID NO: 66, and the amino acid sequence is set forth in SEQ ID NO: 67.

[6]An p19-like gene was identified immediately upstream of axmi212. The nucleotide sequence for this gene is set forth in SEQ ID NO: 68, and the amino acid sequence is set forth in SEQ ID NO: 69.

Example 2

Expression in *Bacillus*

The pesticidal gene disclosed herein is amplified by PCR from pAX980, and the PCR product is cloned into the *Bacillus* expression vector pAX916, or another suitable vector, by methods well known in the art. The resulting *Bacillus* strain, containing the vector with axmi gene is cultured on a conventional growth media, such as CYS media (10 g/l Bacto-casitone; 3 g/l yeast extract; 6 g/l $KH_2PO_4$; 14 g/l $K_2HPO_4$; 0.5 mM $MgSO_4$; 0.05 mM $MnCl_2$; 0.05 mM $FeSO_4$), until sporulation is evident by microscopic examination. Samples are prepared and tested for activity in bioassays.

Example 3

Insecticidal Activity of Axmi-191 and Axmi-192

Gene Expression and Purification

The DNA regions encoding the toxin domains of axmi-191 and axmi-192 were separately cloned into an *E. coli* expression vector pMAL-C4x behind the malE gene coding for Maltose binding protein (MBP). These in-frame fusions resulted in MBP-Axmi fusion proteins expression in *E. coli.*

For expression in *E. coli*, BL21*DE3 was transformed with individual plasmids. Single colony was inoculated in LB supplemented with carbenicillin and glucose, and grown overnight at 37° C. The following day, fresh medium was inoculated with 1% of overnight culture and grown at 37° C. to logarithmic phase. Subsequently, cultures were induced with 0.3 mM IPTG for overnight at 20° C. Each cell pellet was suspended in 20 mM Tris-Cl buffer, pH 7.4+200 mM NaCl+1 mM DTT+ protease inhibitors and sonicated. Analysis by SDS-PAGE confirmed expression of fusion proteins.

Total cell free extracts were run over amylose column attached to FPLC for affinity purification of MBP-axmi fusion proteins. Bound fusion protein was eluted from the resin with 10 mM maltose solution. Purified fusion proteins were then cleaved with Factor Xa to remove the amino terminal MBP tag from the Axmi protein. Cleavage and solubility of the proteins was determined by SDS-PAGE.

Insect Bioassays

Cleaved proteins were tested in insect assays with appropriate controls. A 5-day read of the plates showed that Axmi191 and Axmi192 had activity against diamondback moth species. Axmi191 showed stunting and Axmi192 showed severe stunting and 100% mortality.

Example 4

Construction of Synthetic Sequences

In one aspect of the invention, synthetic toxin sequences were generated. These synthetic sequences have an altered DNA sequence relative to the parent toxin sequence, and encode a protein that is collinear with the parent toxin protein to which it corresponds, but lacks the C-terminal "crystal domain" present in many delta-endotoxin proteins.

In another aspect of the invention, modified versions of synthetic genes are designed such that the resulting peptide is targeted to a plant organelle, such as the endoplasmic reticulum or the apoplast. Peptide sequences known to result in targeting of fusion proteins to plant organelles are known in the art. For example, the N-terminal region of the acid phosphatase gene from the White Lupin *Lupinus albus* (Genebank ID GI:14276838; Miller et al. (2001) Plant Physiology 127: 594-606) is known in the art to result in endoplasmic reticulum targeting of heterologous proteins. If the resulting fusion protein also contains an endoplasmic retention sequence comprising the peptide N-terminus-lysine-aspartic acid-glutamic acid-leucine (i.e. the "KDEL" motif (SEQ ID NO: 70) at the C-terminus, the fusion protein will be targeted to the endoplasmic reticulum. If the fusion protein lacks an endoplasmic reticulum targeting sequence at the C-terminus, the protein will be targeted to the endoplasmic reticulum, but will ultimately be sequestered in the apoplast.

Example 5

Assays for Pesticidal Activity

The ability of a pesticidal protein to act as a pesticide upon a pest is often assessed in a number of ways. One way well known in the art is to perform a feeding assay. In such a feeding assay, one exposes the pest to a sample containing either compounds to be tested, or control samples. Often this is performed by placing the material to be tested, or a suitable dilution of such material, onto a material that the pest will ingest, such as an artificial diet. The material to be tested may be composed of a liquid, solid, or slurry. The material to be tested may be placed upon the surface and then allowed to dry. Alternatively, the material to be tested may be mixed with a molten artificial diet, then dispensed into the assay chamber. The assay chamber may be, for example, a cup, a dish, or a well of a microtiter plate.

Assays for sucking pests (for example aphids) may involve separating the test material from the insect by a partition, ideally a portion that can be pierced by the sucking mouth parts of the sucking insect, to allow ingestion of the test material. Often the test material is mixed with a feeding stimulant, such as sucrose, to promote ingestion of the test compound.

Other types of assays can include microinjection of the test material into the mouth, or gut of the pest, as well as development of transgenic plants, followed by test of the ability of the pest to feed upon the transgenic plant. Plant testing may involve isolation of the plant parts normally consumed, for example, small cages attached to a leaf, or isolation of entire plants in cages containing insects.

Other methods and approaches to assay pests are known in the art, and can be found, for example in Robertson, J. L. & H. K. Preisler. 1992. *Pesticide bioassays with arthropods*. CRC, Boca Raton, Fla. Alternatively, assays are commonly described in the journals "Arthropod Management Tests" and "Journal of Economic Entomology" or by discussion with members of the Entomological Society of America (ESA).

Example 6

Expression of pMal Fusion Proteins

For expression in *E. coli*, select genes of the invention were cloned into a pMal expression vector (New England Biolabs) such that the protein was expressed in *E. coli* with an N-terminal fusion to maltose binding protein (MBP). A nucleotide sequence encoding a truncated variant of Axmi207 (corresponding to positions 15 through 647 of SEQ ID NO:47) was used to test for bioactivity. The truncated variant Axmi207 sequence is set forth in SEQ ID NO:62. For Axmi196, Axmi204, and Axmi209, the full length native sequence was used.

These fusion proteins were then purified by affinity chromatography as known in the art. The purified proteins were then cleaved with protease as known in the art to separate the MBP from the protein of the invention. The resulting proteins were then tested in bioassays against selected pests. The results are shown in Table 2.

TABLE 2

| Pest | axmi196 | axmi204 | axmi207 (truncated variant) | axmi209 |
|---|---|---|---|---|
| DBM | | Severe stunt 100% mortality | Severe stunt, 100% mortality | Severe stunt, 100% mortality |
| CPB | | | 100% mortality | |
| SWCB | | Moderate stunt, 50% mortality | Severe stunt, 100% mortality | Strong stunt, 50% mortality |
| VBC | Stunted | | Stunted | |
| ECB | | | Moderate stunt, 50% mortality | |
| Hz | Stunted | | | Stunted |
| FAW | | | | Stunted |
| SCB | | | Strong stunt | Stunted |
| SCN | 100% mortality | | | |
| *C. elegans* | 100% mortality | | | |
| *Pratylenchus Penetrans* | 40% mortality | | | |

DBM—Diamondback moth
CPB—Colorado potato beetle
SWCB—Southwestern corn borer
VBC—Velvetbean caterpillar
ECB—European corn borer
Hz—*Helicoverpa zea*
FAW—Fall armyworm
SCB—Sugarcane borer
SCN—Soybean cyst nematode Example 7

Vectoring of the Toxin Genes of the Invention for Plant Expression

Each of the coding regions of the genes of the invention is connected independently with appropriate promoter and terminator sequences for expression in plants. Such sequences are well known in the art and may include the rice actin promoter or maize ubiquitin promoter for expression in monocots, the *Arabidopsis* UBQ3 promoter or CaMV 35S promoter for expression in dicots, and the nos or PinII terminators. Techniques for producing and confirming promoter-gene-terminator constructs also are well known in the art.

Example 8

Transformation of the Genes of the Invention into Plant Cells by *Agrobacterium*-Mediated Transformation Ears are collected 8-12 days after pollination. Embryos are isolated from the ears, and those embryos 0.8-1.5 mm in size are used for transformation. Embryos are plated scutellum side-up on a suitable incubation media, and incubated overnight at 25° C. in the dark. However, it is not necessary per se to incubate the embryos overnight. Embryos are contacted with an *Agrobacterium* strain containing the appropriate vectors for Ti plasmid mediated transfer for 5-10 min, and then plated onto co-cultivation media for 3 days (25° C. in the dark). After co-cultivation, explants are transferred to recovery period media for five days (at 25° C. in the dark). Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated as known in the art. The resulting shoots are allowed to root on rooting media, and the resulting plants are transferred to nursery pots and propagated as transgenic plants.

Example 9

Transformation of Maize Cells with the Toxin Genes of the Invention

Maize ears are collected 8-12 days after pollination. Embryos are isolated from the ears, and those embryos 0.8-1.5 mm in size are used for transformation. Embryos are plated scutellum side-up on a suitable incubation media, such as DN62A5S media (3.98 g/L N6 Salts; 1 mL/L (of 1000× Stock) N6 Vitamins; 800 mg/L L-Asparagine; 100 mg/L Myo-inositol; 1.4 g/L L-Proline; 100 mg/L Casaminoacids; 50 g/L sucrose; 1 mL/L (of 1 mg/mL Stock) 2,4-D), and incubated overnight at 25° C. in the dark.

The resulting explants are transferred to mesh squares (30-40 per plate), transferred onto osmotic media for 30-45 minutes, then transferred to a beaming plate (see, for example, PCT Publication No. WO/0138514 and U.S. Pat. No. 5,240, 842).

DNA constructs designed to express the genes of the invention in plant cells are accelerated into plant tissue using an aerosol beam accelerator, using conditions essentially as described in PCT Publication No. WO/0138514 After beaming, embryos are incubated for 30 min on osmotic media, then placed onto incubation media overnight at 25° C. in the dark. To avoid unduly damaging beamed explants, they are incubated for at least 24 hours prior to transfer to recovery media. Embryos are then spread onto recovery period media, for 5 days, 25° C. in the dark, then transferred to a selection media. Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated by methods known in the art. The resulting shoots are allowed to root on rooting media, and the resulting plants are transferred to nursery pots and propagated as transgenic plants.

Materials

DN62A5S Media

| Components | per liter | Source |
|---|---|---|
| Chu'S N6 Basal Salt Mixture (Prod. No. C 416) | 3.98 g/L | Phytotechnology Labs |
| Chu's N6 Vitamin Solution (Prod. No. C 149) | 1 mL/L (of 1000x Stock) | Phytotechnology Labs |
| L-Asparagine | 800 mg/L | Phytotechnology Labs |
| Myo-inositol | 100 mg/L | Sigma |
| L-Proline | 1.4 g/L | Phytotechnology Labs |
| Casaminoacids | 100 mg/L | Fisher Scientific |
| Sucrose | 50 g/L | Phytotechnology Labs |
| 2,4-D (Prod. No. D-7299) | 1 mL/L (of 1 mg/mL Stock) | Sigma |

Adjust the pH of the solution to pH to 5.8 with 1N KOH/1N KCl, add Gelrite (Sigma) to 3 g/L, and autoclave. After cooling to 50° C., add 2 ml/L of a 5 mg/ml stock solution of Silver Nitrate (Phytotechnology Labs). Recipe yields about 20 plates.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A recombinant nucleic acid molecule comprising a nucleotide sequence selected from the group consisting of:

a) the nucleotide sequence of SEQ ID NO:7, or the complement thereof;

b) a nucleotide sequence that encodes a polypeptide comprising the amino acid sequence of SEQ ID NO:34 or 35;

c) a nucleotide sequence that encodes a polypeptide comprising an amino acid sequence having at least 95% sequence identity to the amino acid sequence of SEQ ID NO:34 or 35, wherein said amino acid sequence has pesticidal activity against a lepidopteran or nematode pest.

2. The recombinant nucleic acid molecule of claim 1, wherein said nucleotide sequence is a synthetic sequence that has been designed for expression in a plant.

3. The recombinant nucleic acid molecule of claim 1, wherein said nucleotide sequence is operably linked to a promoter capable of directing expression of said nucleotide sequence in a plant cell.

4. An expression cassette comprising the recombinant nucleic acid molecule of claim 3.

5. The expression cassette of claim 4, further comprising a nucleic acid molecule encoding a heterologous polypeptide.

6. A host cell that contains the expression cassette of claim 4.

7. The host cell of claim 5 that is a bacterial host cell.

8. The host cell of claim 7 that is a plant cell.

9. A transgenic plant comprising the host cell of claim 8.

10. The transgenic plant of claim 9, wherein said plant is selected from the group consisting of maize, sorghum, wheat, cabbage, sunflower, tomato, crucifers, peppers, potato, cotton, rice, soybean, sugarbeet, sugarcane, tobacco, barley, and oilseed rape.

11. A method for producing a polypeptide with pesticidal activity, comprising culturing the host cell of claim 6 under conditions in which the nucleic acid molecule encoding the polypeptide is expressed.

12. A plant or plant cell having stably incorporated into its genome a DNA construct comprising a nucleotide sequence that encodes a protein having pesticidal activity, wherein said nucleotide sequence is selected from the group consisting of:

a) the nucleotide sequence of SEQ ID NO:7;

b) a nucleotide sequence that encodes a polypeptide comprising the amino acid sequence of SEQ ID NO:34 or 35; and c) a nucleotide sequence that encodes a polypeptide comprising an amino acid sequence having at least 95% sequence identity to the amino acid sequence of SEQ ID NO:34 or 35, wherein said amino acid sequence has pesticidal activity against a lepidopteran or nematode pest;

wherein said nucleotide sequence is operably linked to a promoter that drives expression of a coding sequence in a plant cell.

13. A transgenic seed of the plant of claim 12 which comprises the DNA construct.

14. A method for protecting a plant from a lepidopteran or nematode pest, comprising expressing in a plant or cell thereof at least one expression vector comprising a nucleotide sequence that encodes a pesticidal polypeptide, wherein said nucleotide sequence is selected from the group consisting of:

a) the nucleotide sequence of SEQ ID NO:7;

b) a nucleotide sequence that encodes a polypeptide comprising the amino acid sequence of SEQ ID NO:34 or 35; and c) a nucleotide sequence that encodes a polypeptide comprising an amino acid sequence having at least 95% sequence identity to the amino acid sequence of SEQ ID NO:34 or 35, wherein said amino acid sequence has pesticidal activity against a lepidopteran or nematode pest.

15. The method of claim 14, wherein said plant produces a polypeptide having pesticidal activity against a lepidopteran or nematode pest.

16. A method for increasing yield in a plant comprising growing in a field a plant of or a seed thereof having stably incorporated into its genome a DNA construct comprising a nucleotide sequence that encodes a protein having pesticidal activity, wherein said nucleotide sequence is selected from the group consisting of:

a) the nucleotide sequence of SEQ ID NO:7;

b) a nucleotide sequence that encodes a polypeptide comprising the amino acid sequence of SEQ ID NO:34 or 35; and c) a nucleotide sequence that encodes a polypeptide comprising an amino acid sequence having at least 95% sequence identity to the amino acid sequence of SEQ ID NO:34 or 35, wherein said amino acid sequence has pesticidal activity against a lepidopteran or nematode pest;

wherein said field is infested with a pest against which said polypeptide has pesticidal activity.

* * * * *

SEQUENCE LISTING

```
<160> NUMBER OF SEQ ID NOS: 70

<210> SEQ ID NO 1
<211> LENGTH: 1922
<212> TYPE: DNA
<213> ORGANISM: Bacillus thuringiensis

<400> SEQUENCE: 1

ttggaaatta aaattggaag cggaggaaca tatatgaatc catataacaa cgaaagctat      60

gaaattattg atttaaatac ttcaccttat ccttctaaca gaaataattc taggtatcct     120

tatgcaaatg cttgcggttt tccagaaaac gtagattgga cagcaggcgc aagtgcaatg     180

ataattgtag ctggtacttt attaagtgct ataggttcag gaggagtagg tatagttgct     240

gcaggtatta tatcagttgg tacactattc cctttttttt ggcctcaaga taagcctact     300

gcacaagtat ggaaagattt tattaaacaa ggggatacta taactaataa aacaatatca     360
```

```
gcagccgtag aatctctagt actcgcagaa ttaaatggtt taaaatctat acttgatgtt    420
tatactgatg ctttagaact ttggaaaaaa gataaaaata atatagtcaa tagagacaat    480
gtaaaaagta tttttacaaa tttacatcta caatttgtag ccgctatgcc aaaatttgca    540
acaaatggtt atgaagtaat attattatct acttacacag cagctgcact tcttcatatt    600
actttttac atgaagctct tcaatatgca aatgaatgga atttagctcg aagtgaagga    660
accttctatc gtggacaatt aattcaagca atagaaaact acattaatta ttgtgaaaaa    720
tggtatcgtg aaggtttaga gatacttaaa aattctactt gggatatata tgctgcgtat    780
caaaatgaat acactctaag tatattaaat gttatttcaa tttttccaag atttgatata    840
cgtaatttcc ctacaaatat agcaactcga ttagaatcta cacaaaaact ttatacaaca    900
acaccaaata tgaaagcatt aaaaacaaat aactcaattg attatataaa agataaactt    960
atacctcctt tagatttatt taaaaaatta aaaagtttaa ctttttatac atttttagat   1020
agcaataacc aatatgatca tttacaaggt attgtaaata atagttatta tactaatatt   1080
tccactaaca aaatcttttc ttctggaact accgaaggta gttcatatca actaggtttg   1140
gcttctgatc aagttattta ctacactgac atcttccatc atctaaatca aagtaatttt   1200
aaggatggtt cccttggaat taaaataatt aattttaata ttataaataa atataatgag   1260
gtttctcaaa aatcttatga ttctaatgca acaagtaatc taatactaga agttatatta   1320
ccttttctaa aaacaactga gaaagattat aaatatattt tatcttatat tacaataact   1380
ccacagcaga tagtaggatg tctaagtcct agttatatat atggatttat ttggacacat   1440
agtagtgtta atcttaacaa tactattcat tatacaaata aaaataattt ttctcaaatt   1500
acacaaattt ctgcagtaaa agcatatctg aaaaaagatc gagtttcagt tatagaagga   1560
ccaggtcata caggcggaga tttagttaaa tttacacaat gggatgattc aatttcaact   1620
cattatcaat ttactagcag tggtgaatat aaaatacgtg tccgatatgc ttctactgct   1680
caagttaatc aaaccagcgg acttagtatg acgatatacc ataaaggaaa tcctacagaa   1740
acatgggatt taaacataaa taacaaatca gatacaatac ttaatttaaa tgaaccaaaa   1800
tacaatcatt ttcaatacac agaatttcca aataaaactc ttataataaa taaagaccca   1860
aattctccat acttagaact aagaatagac ttaagctata aaggaaatac tgcaacaact   1920
ct                                                                  1922
```

<210> SEQ ID NO 2
<211> LENGTH: 1518
<212> TYPE: DNA
<213> ORGANISM: Bacillus thuringiensis

<400> SEQUENCE: 2

```
atgaatggaa atggaaaaca tgataactgg aatcacaatc aacaaatatc aaatgtccaa     60
atgaaccaca atcatggtag atcatatgat tgcagttgtc aacaaaatca gtatgggtat    120
gagcaacaaa aacagcagta tgaacagaat aacagccaat atatgcagaa taatctggga    180
aacgaaaata ggaatggatt gtatccttat caagaaaatc aatatgaaca aaataagaat    240
tattatgcat caaacaattt aacatataat cagtctgatt tgtataattc taatcctcaa    300
aatatgtata aacatcaaac atattctaat gatttttatt gttctcctag ctatacagca    360
ggtgaaaata atatattaga tctattaggt acagaaagta aacaattcca aaaaatttca    420
aatataaata ctaaagattt acatcgaagt ataactgcga gcaatactca aattggttat    480
caaattgata ctcgtgttcc aggaccatgt aaaggtgtag attatcaaaa cacagtaacc    540
```

```
tatgaacaaa attcaatagg tggcgattcc caatacttga ttttttataa aacggattat    600
actgatgcat ttattattgc gaatagagca aatggtcgag ttttagaagt aatacctagt    660
tcagttaatg gttttgtaac aatttctaat atgtttactt ataatcaaaa tcaacttttt    720
attcgtacta aaatatcaaa taatgataat tcagatgatg ttccattttc tttaacaaca    780
gaaaacaatc aaacattaaa catatgccat catgaatttc aatataatac taaaattaca    840
gctcttgata atgcatatcg tttggatgat aaggttttat ttaaaccaac tagagataaa    900
atcaacatat catttccaaa tatggtagtg aatgcgaagg agaaattacc agaacccgag    960
gaattaacaa atatggataa gaatactctt tttataccga aagtgattat aagtaaaacg   1020
ttaattccag gtataattgt aaacgatgta actttattaa aggagcaaca aatagcaaaa   1080
agtccatatt atgtattaga atatgttcaa tcttgggaag aagtgtataa tgaaatagta   1140
cctgcttata gaccttcgta tacttggact tcaacagatg gaattagaca cgttaatcta   1200
ttagatataa agaatactat aaatatatca ataggtggaa ctagtcaagg ctggggatta   1260
agatttagtg ataaatcaga tctttttaaa aacataatta catcagcatt cattataaaa   1320
tcaacacaag ctccagatat gggattcagt gagaatgata tagatcagta ctatggtaag   1380
aatattgaca gtagagttaa aatatatata aaaacccata atttaatatt aagacgttta   1440
gatcaattga acaattcaat agctacatgg acaatatttg agaatacaaa acctgttata   1500
agaacgtttc caattagt                                                 1518
```

<210> SEQ ID NO 3
<211> LENGTH: 2337
<212> TYPE: DNA
<213> ORGANISM: Bacillus thuringiensis

<400> SEQUENCE: 3

```
atgaaggata aaaaatactg gaaatacgag ggaggaacca aaatgaatcc ttatcagaat     60
aagaatgaat atgaaatagt aaataatccg caaaattata atactgtttc caatagatat    120
ccttacacga atgatccaaa tgttgcaata caaaatacga attataaaga ttggatgaat    180
gggtatgaag aaattaatcc ttcttcaata tcgttaattt tagcttcaat aggaattctt    240
aatcaagcaa ttgctttaac tggagtatta ggtaagacac cagaaattat taacatagta    300
caagaaatgg tgggattaat tagcgggagt acaggcaatg atttattagt acatacagaa    360
caacttattc aacaaacttt agcacaacag tatagaaacg cagcaaccgg agcggtgaat    420
gctatatcta aatcatacaa tgattatttg atgtttttta ggcaatggga acgtaataga    480
acttctcaaa atggactaca agtagagagt gcttttaata ctgttaatac tttatgtctt    540
cgtactttaa ctcctcagga agcactttct cgcagaggat ttgaaactct tttattacca    600
aactatgcac tagcggcaaa tttccatttg ttattattaa gagatgctgt tctttataga    660
actcagtggt tacctaattt tatttcaact acaaatgcga atattgaaat attggaaagg    720
tccataaatc aatatcgtaa tcattgtaat cattggtaca atgacggctt aaatagattt    780
gcacgtacat cttttgatga ttgggttcgg tttaatgctt atcgtagaga tatgacgtta    840
tcggtattag attttgttac agtatttcca acttataatc ctataaactt tccaacacca    900
acaaatgttg aattgactag aatcgtttat accgatccaa taagtccacc tagaggatat    960
gcaagaactg gctcacctag ttttcgtcaa atggaagatc taattatttc cggtagccct   1020
agtttcttga atcaattaag tatatttaca acttattatc atgatcctcg taatgtaaat   1080
agagactttt gggccgggaa tcggaattat ttaagcaatg ggacttctcg acagtctgga   1140
```

gctaccacac cttggcgaac taatatacct atgcaaaaca ttgatatttt cagagtaaat 1200
ctaactactc atgacattga tgatatatca cgaagttatg gaggagttca tagatctgat 1260
ttcattggtg taaatacaat aaataatcaa agaacaacat tgttctatca ccaaaatgtg 1320
gatacttccc gttttctaat aaggaatgaa acagtatttt taccagggga ttccggctta 1380
gcaccaaatg aacgtaatta tactcacagg ttatttcaag tgatgaccac atatcgtact 1440
aacccgaatg ctcgtagggc agctttttta catgcatgga cgcatagaag tttaagacgt 1500
agaaatggat ttaggacgga tcagattatg caaatacctg ctgtgaagag cataagtaat 1560
ggtggtgatc gtgcagtcat atcctatact ggagaaaata tgatgaaatt agataactta 1620
actgcaagtt tatcctataa attaacagcg gaggattccg aagcatcgaa tacacgtttt 1680
atagtgcgta ttcgttatgc tagtatgaac aataatagat tgaatcttat tttaaatggt 1740
actcagatag catcgctgaa tgtggaaggt acaatgcaaa atggcggatc attaacaaat 1800
cttcaatctg aaaattttaa atatgctaca ttttcaggta atttcaagat gggttctcag 1860
tctatagtag gtatttttaa agagatatct aatgcagact ttattttaga taaaattgaa 1920
ttgattccaa ttcattttat gccattatta gaacaaaaac aaagctacaa caattacgac 1980
caaaacatgg atactacata tcaaccaaac tatgacactt ataatcaaaa tgccaatggt 2040
atgtatgacg atacatacta tccaaataat aatgatagtt ataatcaaaa taataccgat 2100
atgtatgatt caggctacaa taacaaccaa aatactaact ataattatga tcaagaatat 2160
aatacttaca atcaaaatat ggaaaatacg tatgaccaat cgtatgaaaa ttacaatcca 2220
gaaaccaaca attacaacca ataccctaat gatatgtaca atcaagagta tactaacgac 2280
tacaaccaaa actccggctg caggtgtaac caagggtata ataataatta ccctaaa 2337

<210> SEQ ID NO 4
<211> LENGTH: 966
<212> TYPE: DNA
<213> ORGANISM: Bacillus thuringiensis

<400> SEQUENCE: 4
atgaatttct tgtacaattt tgtgacatta gatatgctaa tattaaatag attagaagga 60
agtgatttta aaatgaagaa aaaagcaata gtgtgtggct tactagctag tactttatta 120
ggcggcggta cttttgtaga tgctgtgagt gcggctgaaa ttcaaaaaac taatcattta 180
aacaagtatg atagtgcaca agagaaagct ctacaagata ttaaccaaga agcgttacaa 240
gatattgatc aaaaagtcaa taagatgatt gattctatcc cacccatttt tggatcaaaa 300
tatacacgta cagatcgcta cggtgaaagt cttacttatt caggaataaa tctaaaagaa 360
aataatagta caaatgttga accgatgtac tttggttcaa atacatttta taacgataca 420
gagctagaac aatcctataa cactacttct tttagtgaag ctgttactaa atcaactact 480
actcaaacac aaaatggatt taaatcaggt gtaactacag gaggaaaggt tgggatacct 540
tttgtagctg aaggtgaagt gaaaatcaat cttgaatata attttacaca caccaattca 600
aatactacta gcaagactac aactttaaca gcccctccac aacctgttaa ggttcctgca 660
ggtaaagttt ataaagcaga cgtttatttt gaaaagaaat ctacttcggg tacggttgaa 720
ctttatggag atctccttac aggtgtagta gccgagggaa ggacatcatt tgtaggtaac 780
gtattacata aggcaactga tacacaaggg ctaattcaat ctcctgagga ttcaaataaa 840
gttcgtgcgg ttggaaaagg aacgttcacc actgaacatg gctcaaactt tatcgtcaaa 900
acatatgatg taacatcagg gcaaaaatcc gcaaaattgg tagatactag agtaatacct 960

-continued

```
ataaaa                                                              966

<210> SEQ ID NO 5
<211> LENGTH: 969
<212> TYPE: DNA
<213> ORGANISM: Bacillus thuringiensis

<400> SEQUENCE: 5

atgaatttaa ggaggatttc tatgagagtt tataaaaaat tagcaacgtt ggcacctatt     60

gctgcattaa gtacatccat tttatgttct cctgcaatga catttgcagc agaaaaagaa    120

tcaacagtga aacaaaccac acaacaaagt gcggttcaac aaggtcgtat cattcaaggg    180

tatcttatta aaaatggtgt gaaaatacca gtttatacag gtggattagt aacaaataag    240

gctgaacaag gtgcagcagc atttccacaa ttgtcttcca atcctaatga tcctatccct    300

caaaaaggtt ctatttcatc tgaagatgga aatattggag atattttata tttttctaaa    360

actccaatgg gagataatgt ttatataaaa aaacttgaga ataacaacat tgaaattgga    420

aaatataatc gaggcacttt agaattatcg aaatttgtga cagttaatgg agatccacag    480

ggacctataa tgttatttga tgctacggta aaacgtgaaa cggcatttga aaaaattggt    540

ggtgctgtac aaccaaaggc aacacaatat acttttagtc aagcggtaac atccggttta    600

tcaacatcag atgcgattgg cggttcatta acattaggat ataaaatatc gcttaaagaa    660

ggtggcggag tagtaccagc cgaagcaaca caggaattta gtacacaatt aagtgctaca    720

tataatcata caattacagt gacaaaccaa acaacgaata cacaaacaca aacctttaaa    780

cctatagaca gttatggaca atcaacctat gcagctgctg tgtatcaatt aaaatctcat    840

tatacggtga ttccaggagc aggattacag aagggattaa atagtggata tgtgttagat    900

caaacagcgt tttcatatag cgattctgat ttatatctag ctgtaacacc aggagcaggt    960

tcaaatgta                                                           969

<210> SEQ ID NO 6
<211> LENGTH: 756
<212> TYPE: DNA
<213> ORGANISM: Bacillus thuringiensis

<400> SEQUENCE: 6

ttgatcacta atcaagcagc acaagcaagt gatgcaccct atccagaatt accatcgaat     60

ccgaatgatg cgattccaaa tgccggggcc actcatgctg aaaatggaag tgtaggttcg    120

gttttatatt ttaaacagat agatttaaat aatctgggag ctggcatagg aaatagtcaa    180

aaagattatg tttacgtaga aaaaaaaggt gattctggat atgaattagg aaattacaat    240

ccgttaactt tacaaagaac taaaattaaa gattatgata aatccagtga acttgcagaa    300

aagatggatg gctattttaa aagtacaatt acacgagata ctttttttag taaaatcgga    360

tctggtgtcg taccaaaaaa tgcagcgtat acctttagtc aagcagttac atccggttta    420

actacatcag atgcgattgg gggtgcgcta acactcggat ataaagtaag tgttacagaa    480

ggcggaggaa tattcccagc tgcagcgtca gaagaattta gtgcacaatt aacagcaact    540

tataatcata cgattactgt ttccagccaa gtaacaaata ctcaaacatt gggcattaca    600

aaagctgcag atggctatca atatgataaa tatgtaggcg ctgtatatca attgcattcc    660

aagtatacat ttaaacctag tgatgaatta caatttgcaa tgaattcacc ttttggatat    720

aaggtaattc ttaatcaacg agcacaatca ttccaa                             756
```

<210> SEQ ID NO 7
<211> LENGTH: 4323
<212> TYPE: DNA
<213> ORGANISM: Bacillus thuringiensis

<400> SEQUENCE: 7
atgacaacaa taaatgaatt atatccggct gtaccttata atgtactggc atatgctcca 60
ccacttaatt tagctgattc gacaccatgg ggtcaaatag ttgttgctga tgcaattaaa 120
gaagcttggg ataattttca aaaatatggt gtattagatt taacagctat aaatcaaggg 180
tttgatgatg caaatacagg ttcttttagt tatcaagctt taatacaaac tgttttgggt 240
attataggta caattggtat gacagttcct gtggctgctc catttgcagc tacagcgcct 300
attattagtt tatttgtagg attttttgg cctaaaaaag ataagggacc acaattaatc 360
gatataattg ataaagaaat taaaaaatta ttagataagg aattaggaga gcaaaaacgt 420
aatgatttag ttagtgcttt aaatgagatg caagagggag caaatgagtt aagtgatatt 480
atgactaatg cactttttga aggtactata cagggaaatg ttgttactaa tgataaccct 540
caaggtaaaa ggcgaactcc taaagctcca acagttagtg attatgagaa tgtttattcg 600
gcatattttg tggaacatgt ggattttaga aacaaaatat ctacgtttct tactggttct 660
tatgatctta tagcactccc attatatgca ttagcaaaaa caatggagct ttcattgtat 720
caatcattta ttaattttgc taataaatgg atggattttg tatatacaaa agcaattaat 780
gaatcagcaa ctgatgatat gaaaagagat tatcaagcga gatacaatac tcaaaaaagt 840
aatttagctg tacaaaaaac acaattgatt aacaaaatta aagatggtac agatgctgtt 900
atgaaagttt ttaaagatac caataattta ccttcaatag gtactaataa attagcagta 960
aatgctcgta ataagtatat tagggcctta caaataaatt gtttagattt agttgctttg 1020
tggcctggct tatatccaga tgaatatctt ttaccattac aattagataa aacacgtgtt 1080
gtattttctg atacaatggg acctgatgaa acacatgatg gtcaaatgaa agttttaaat 1140
atattagact caactacaag ttataaccat caagatatag gaataagtac aactcaagat 1200
gtaaattctt tattatttta tccaagaaaa gaactgttag aattagattt tgctaaatat 1260
atttcatcta gtagtcgttt ttgggtttat ggatttggct taaaatattc agatgataac 1320
ttttatagat atggtgataa cgatccaagc agtgatttta aacctgcata taagtggttt 1380
acgaaaaatt cccagttcga aaaccttcct acttatggaa atcctactcc tattactaat 1440
ttaaatgcta aaactcaagt aacttcttat cttgatgcat taatatatta tatagacgga 1500
ggaactaatc tatataataa tgcgattctt catgatacag ggggttatat tccgggatat 1560
ccaggtgtag aaggatatgg tatgagtaat aatgaacctt tagcaggaca aaaattaaat 1620
gctttatatc ctataaaagt ggaaaatgta agtggttcac aaggaaaatt aggaacaata 1680
gcagcttatg ttcctttaaa tttacaacca gaaaatatta ttggtgatgc tgatccgaat 1740
acaggttttc cccttaatgt aattaaagga tttccatttg aaaaatatgg acctgattat 1800
gagggacgag gaatttcggt tgtaaaagaa tggataaatg gtgcaaatgc tgtaaaattg 1860
tctccaggtc aatcagttgg ggtacaaatt aaaaatataa caaaacaaaa ttatcaaatt 1920
cgtactcgtt atgcaagtaa taacagtaat caagtatatt ttaatgtaga tccaggtgga 1980
tcaccattat ttgcacaatc agtaacattt gaatctacaa caaatgttac aagtggccaa 2040
caaggcgaaa atggtagata tacattaaaa actatttttt ctggtaatga tctacttaca 2100
gtagaaatcc ctgttggaaa tttttatgtg catgttacga ataaaggatc ttctgatatc 2160
tttttagatc gtcttgagtt ttctacagtt ccttcatatg ttatatattc aggtgattat 2220

-continued

```
gatgctacag gtacagatga tgtcttattg tcagatccac atgagtattt ttatgatgtc   2280

atagtgaatg gtactgctag tcattctagt gcagctactt ctatgaattt gctcaataaa   2340

ggaaccgtag taagaagcat tgatattcca ggtcactcaa cgtcttattc tgtacagtat   2400

tcagttccag aaggatttga tgaagttaga attctcagtt ctcttccgga tattagtgga   2460

actataagag tagaatctag taaaccacct gtatttaaga atgatggtaa tagtggtgat   2520

ggtggtaata ctgaatataa ttttaatttt gatttatcag gattgcaaga tactgggctt   2580

tattctggta aacttaaatc tggtattcgt gtgcaaggta attacactta cacaggtgct   2640

ccatctttaa atctggttgt ttacagaaat aatagtgttg tatccacttt tccagtaggt   2700

tctccttttg atatcactat aacaacagaa actgataagg ttatcctttc attacaacct   2760

caacatgggt tggcaacagt tactggtact ggcacaataa caattcctaa tgataaatta   2820

gcaattgttt atgataagtt atttaaatta ccacatgatt tagaaaatat aagaatacaa   2880

gtaaatgcat tattcatatc gagtacacaa aatgaattag ctaaagaagt aaatgaccat   2940

gatattgaag aagttgcatt gaaagtagat gcattatcgg atgaagtatt tggaaaagag   3000

aaaaaagaat tacgtaaact ggtcaatcaa gcgaaacgtt taagtaaagc acgaaacctt   3060

ctggtaggag gcaattttga taattgggaa gcttggtata aaggaaaaga agttgcaaga   3120

gtatctgatc atgaattatt gaagagtgat catgtattat taccgcctcc aactatgtat   3180

ccatcctata tatatcaaaa agtagaagaa acaaaattaa agccaaatac tcgttatatg   3240

atttctggtt tcatcgcaca tgcggaagat ttagaaattg tggtttctcg ttatgggcaa   3300

gaagtaagga aaatagtgca agttccatat ggagaagctt tcccattaac atccaatgga   3360

tcaatttgtt gtacaccaag ttttagacgt gatggaaaac tatcagatcc acatttcttt   3420

agttatagta ttgatgtagg tgaactggat atgacggcag gtccaggtat tgaattggga   3480

cttcgtattg tagatcgatt aggaatggcc cgtgtaagta atttagaaat tcgtgaagat   3540

cgttctttaa cagcaaatga aatacgaaaa gtgcaacgta tggcaagaaa ttggagaacc   3600

gaatatgaga aagaacgtgc agaagtaaca gcattaattg aacctgtatt aaaccaaatc   3660

aatgcgttat atgaaaatgg agattggaat ggttctattc gttcagatat ttcgtactac   3720

gatatagaat ctattgtatt accaacatta ccaagattac gtcattggtt tgttcctgat   3780

atgttaactg aacatggaaa tatcatgaat cgattcgaag aagcattaaa tcgtgcttat   3840

acacagctgg aaggaaatac actattgcat aacggtcatt ttacaacaga tgcggtaaat   3900

tggatgatac aaggagatgc acatcaggta atattagaag atggtagacg tgtattacga   3960

ttaccagact ggtcttcgag tgtatcccaa acaattgaaa tcgagaaatt tgatccagat   4020

aaagaataca acttagtatt tcatgcgcaa ggagaaggaa cggttacgtt ggagcatgga   4080

gaaaaaacaa aatatataga aacgcataca catcattttg cgaattttac aacatcacaa   4140

agtcaaggaa ttacgtttga atcgaataag gtgaccgtgg aaatttcttc agaagatggg   4200

gaattattgg tagatcatat cgcacttgtg gaagttccta tgtttaacaa gaatcaaatg   4260

gtcaatgaaa atagagatgt aaatataaat agcaatacaa atatgaataa tagcaataat   4320

caa                                                                  4323
```

<210> SEQ ID NO 8
<211> LENGTH: 1092
<212> TYPE: DNA
<213> ORGANISM: Bacillus thuringiensis

<400> SEQUENCE: 8
atgttaataa aggagatgca atatatgcat tctattaaaa aatataaaaa ggttctatta 60
attgcaccac ttgcttgtat gttaacaggt gctattttac ctacagctac tacagttcat 120
gcacaagagg tagaaaataa aaaagctgta tcaatgatga agccgggagg agagtttgga 180
gcaactaaat attcaaaaga aaatttagta aaggaaatca atcttagatt attaacagcg 240
cttgatcgtt caacaagttt gcgtgaaaaa tttcatataa agggcaacga agttttagat 300
gttagtcagc ttgatgacac atctaaacaa ttaatggaga aattacaatt aacagctgaa 360
ggatcaattg atgtgaaacc acatgtcgat agctataaag atcttggtca aaccaatatt 420
gttacatata acaatgataa cggagtggtt ggacagacat ataacacacc agaaacaaca 480
gtaaaagaat ctgaaactca tacctactcg aatacagaag ggtgaaatt aggactcgag 540
gtaggaacaa aaattacagt tggaattcca tttatcggaa aagatgaaac agaaataaaa 600
gcaacatccg aattttctta tgaacataat gattcacaaa caaaaacgaa agaaactgat 660
gttacgttta aatcccaacc agtagttgcc gctccaggtg gaacaaccac ttattatggt 720
gatattaaaa cagcaacatt ttctggatca tttcaaagtg atgcttatgt agcaggcggt 780
ttcgaattga aagttcctat cgcacatgat atggcttcgc caaaaataga tcgttatgaa 840
acggctacgc tgacagctgc agatatatat gaaattttta atgcttctaa tgcgatagca 900
gcaccaaatt acttaaaact tgataacgca ggtaaaaaag ttcttcttac agacaaagca 960
acttttgata taaatggaca aggtggtttt tatacaacat tacaggttaa atttgttcct 1020
aaagattcta ataaaaagcc tcaaatgatg tcttataaag aatatgtaca aaaaatgaac 1080
aataatgaat ta 1092

<210> SEQ ID NO 9
<211> LENGTH: 1182
<212> TYPE: DNA
<213> ORGANISM: Bacillus thuringiensis

<400> SEQUENCE: 9
atgtattcta ttaaaagata taaaaaggta gcaatagtag ccccacttgt ttgtttattg 60
ggaacgggac taacatttgt taataaacca ataccagctg ctgcggcagt aactacaaat 120
tattctacag cagattctgc atcaaatttc caacccatta gtaaatatac tttagccgga 180
gatctatatg aacgatatat gagagctcta gtaagacatc ctgaattact ttcttcaggt 240
ggtttaaaac cagtaactaa tcaaacggat ctagaacaaa tcgacggata ctacaaggta 300
atggctcaat tcataagaga caataatcag aattttccat ctccttttaa tagaccaagt 360
atgaaattga tgactggagt taatccgttt tttaattggg ctcctcaata tactaatctt 420
tctactcaaa atgtaattaa cttagataat ccaaaagtag atgattataa agaagataat 480
attgaactag ctacttatac taataacaca acatcagaac aaactttttc gacgccttca 540
aaatcagaaa aagtaacaga ttctttcaca tattctaatt cagaaggtgg aaaattagga 600
gtttcttcca cgactacaat tagagcggga attccaatag cgcaagctca agaaactctt 660
acaatgtcat ttgaagcaac ttataatcat acaagctcga atacatcttc tactgaaaag 720
acagttacat atccatctca agtactaaag tgcctaccag gatatagaac ttctttaatt 780
gtaaaagtat ctcaagcgaa tttttctggt acaatggatt ttgacgttga accaactgtg 840
agttcattaa tagatggtat agaaaaaaat tggaaagaca taaaagacga taagacaata 900
aaaggagata aaagtggaga ttacacagtc ccaaatcgac aagaattttt atataatgtg 960
tataaatatt cagatttacc aattccatct tatgttaaat tagatgataa aaagaaaact 1020
gtatcatttg gaaaagttac aactccatat acaggtgtag caggtcattt atcagaagca 1080
aatgcaacac aagtaaaact ggaatcactt gataaagcac agaaaccaat tattatgcct 1140
ttaaaacaat atcaacaaaa aattcaaaat catgaatctt tt 1182

<210> SEQ ID NO 10
<211> LENGTH: 1080
<212> TYPE: DNA
<213> ORGANISM: Bacillus thuringiensis

<400> SEQUENCE: 10
atgcattcta ttaaaaaata taaaaaaatt ctattagttg caccacttgc ttgtatgtta 60
acaggtgcta ttttacctac agctactaca gttcatgcac aagaaatcaa gggaccgggg 120
gtaatgaaac ctgacgttcc gtggaatcaa gaacattata cgaaagaaaa tttagcatgg 180
cgtgcagcag atagactttc ctatgctgcg gatagaattc ctagtttacg tgagaaattt 240
aaattaaaac caaacgaaca tttttattgt agcaatgaca cgaggtacta tatggaagaa 300
accttattaa aaaacttgca attatcagct gaaggtccaa taaatgttac accacatgta 360
gatagttata ctgatttagg acaaacaaat ttattaacat ataacaatga tgatggaatt 420
gtagagcaaa aggcttctac accagaaact accattaaag aatcagaaac atcttcttat 480
tctaataaag aaggagttac attgggagca gaggtggaat ctaaagtaac attcaatata 540
ccatttatag tagctggaga aacaaaggta atagcgaaat ccgaattttc ttatgaacat 600
gatgatactc aaactaagac ccatgaaaaa gaggtaacat ttaaatcaca agagatcgtt 660
gctgctccag agggaacaac tacttattat ggttcaatca aaactgccaa tttttctgga 720
tcgttccaaa gtgatgctgt agtaggtggt ggtgtaacgt taacccttcc tataggagta 780
atggataagg atggtgggca gaaaaaaact catacggaaa cagctacttt aactgcagaa 840
gatatgtatg agattttcaa agcaccaatg ccttgggaca tgaataaatt accaccatat 900
ctaaaattag atgattctgg caaaagggtg ctactggcag aaaaagcaac ctttgatata 960
aagggacaag gtggttttta tacagaaata caggcaaaat ttgttccaaa agacaaaaat 1020
aagaaaacac aaattatgcc atacgcagag tatgtacaga aagtaaaaca gaatgctctt 1080

<210> SEQ ID NO 11
<211> LENGTH: 2028
<212> TYPE: DNA
<213> ORGANISM: Bacillus thuringiensis

<400> SEQUENCE: 11
gtgaaaagta tgaattcata tcaaaataaa aatgaatatg aaatattgga tgcttcacaa 60
aataactcta ctatgtctac tcgttatcca aggtatccac tagcaaagga tccacaagct 120
tctatgcaga ctacgaatta taaagattgg ctaaatctat gcgatactcc aaatatggaa 180
aatccagagt ttcaatcagt aggaagaagc gcactttcta ttctcattaa ccttagctct 240
agaatattat ccttattagg tattcctttc gcagcacaaa tcgggcaact ctggagctat 300
acactcaacc tactatggcc tgtggcaaat aatgctactc aatgggaaat ttttatgcgc 360
accatagaag aattaattaa tgcacgcata gagacttcgg taagaaatag agcccttgca 420
gagctggcag gcttaggaaa catattagag gactataagg tggttttaca acgatggaat 480
ctaaatccta ctaatccaac attgcaacgc gatgtggtac gccaatttga aatcgttcat 540 gcctttttttc gctttcaaat gccggtcttt gctgtagatg gttttgaagt accattattg 600
ccagtatatg cttcggcagc taatcttcat ttgcttttac taagggatgt tgtaattaac 660
ggagctcgtt ggggcttgga atctgatgta attaacgatt atcatgacct tcaattacgt 720
cttacatcaa catatgtaga ccattgcgta acttggtaca acactggatt aaacaggtta 780
attggcacaa atgctagaca atgggtaact tacaatcagt tccgtaggga gatgactata 840
tccgtactag atattatttc attattttct aactatgatg ttcgtagata cccaacaaaa 900
acacagagcg agctaacaag gatgatttat acagatccaa taggtaccga agggaatcaa 960
tttattcctg ggtgggtaga taatgcacct tctttctcgg ttatagagaa tagtgtagtt 1020
cgaagcccag gagctttcac ttttctggaa agggttggta ttttcacagg gttcttacat 1080
ggatggagta gccggtctga gttttggtca gcccatagat tattttctag accggttttg 1140
ggttggatat gggagagtgt tatttttggc aatccccaaa ataatattgg gtatcaagaa 1200
gtggatttta cgaattttga tgtatttagc attaattcta gggccacttc tcatatgttc 1260
ccaaatggca gtgctagatt atttggagtt ccacgagtta catttgattt atcgaatgta 1320
actaataata atctagcaca aagaacttat aacagaccat ttacttttgg cggccaggat 1380
atagtgtcga gattacctgg cgaaacaaca gagataccga atagtagtaa ctttagtcac 1440
agactagccc atatttcatc ttttccagta ggtaacaatg gatcagtcct ctcatatggg 1500
tggacacacc gtaatgtgaa tcgtcataat agactgaatc cgaacagtat tacacagatt 1560
ccagctataa agtttgctag tggttctgca cggagaggtc ctgggcatac aggtggagat 1620
cttgcaattg ctcaacaaca cagtggttat cagctgttta tgcaatcgcc ttcagcacaa 1680
aggtaccgtc tccgtttgcg ttatgccggt atttcgggag gtagtatttc tgtttcgcat 1740
cgggacgaaa ataatcaaaa catccttcat agtgctacat tcaatgttag ggctacatca 1800
ggtcagctaa gatacgccga tttcatttat acagacctag aggagaacac aacgttgttt 1860
gaaactcgaa atggagtgaa tctatataga ctaatgattt ttgtttcaag tggctctata 1920
ttaattgacc gaattgagta tatccctgaa aatacaacaa ctatagaata tgaggaagaa 1980
cgaaatctag aaaaagaaaa gaaagcggtg gacgatttgt ttaccaat 2028

<210> SEQ ID NO 12
<211> LENGTH: 1701
<212> TYPE: DNA
<213> ORGANISM: Bacillus thuringiensis

<400> SEQUENCE: 12
gtgaataata tgtataccaa taatatgaaa actacattaa aacttgagac gacagattat 60
gaaatagatc aagcggcaat ttcaatagaa tgtatgtcag atgaacaaga tctacaggaa 120
aaaatgatgt tatgggatga agtaaaactt gcaaaacaac tcagtcaatc tcgtaattta 180
ctctacaatg gtgattttga agattcatcc aacggctgga aaacaagtaa taatattacg 240
attcaattgg agaatcctat tttaaaaggg aaatacctca atatgcctgg agcacgagac 300
atatatggaa ccatatttcc aacatatgtt tatcaaaaaa tagatgaatc taaattaaaa 360
cccaatacac gttatcgagt aagaggtttt gtgggaagta gtaaagatct aaaattagtg 420
gtaacacgtt atgagaaaga aattgatgct agtatggatg ttccaaatga tttgtcctat 480
atgcagccta gcccttcatg tggggattat ggctgtgact catcatccca gccaatgatg 540
aatcaaggat atcctacacc atatacagac gactatgctt ccgatatgta tgcatgctcg 600
tcaaacctag gtaaaaaaca tgtgaagtgt cacgatcgtc atccatttga ttttcatatt 660
gacaccggag aattagatac aaatacaaac ttaggtattt gtatcttatt taaaatttcc 720
aatccagatg gatatgctac attaggaaat ctagaagtaa ttgaagaagg accactaaca 780

-continued

```
agcgaagcgt tagcacatgt gaatcaaaag gaaaagaaat ggaatcaaca aatggagaaa    840

aagcgatcgg aaacacaaca agcctatgat ccggcaaaac aagcagtaga tgcattattc    900

acaaattcac aaggagaaga gttacactat catattactt tagatcatat tcagaacgcc    960

aatcagttgg tacagtcgat tccttatgta caccatgctt ggttaccgga tgccccagga   1020

atgaactatg atttatataa caatttaaag gtacgtatag aacaagcacg ttatttatac   1080

gatgcacgaa atgtcataac aaatggcgac tttgcacagg ggctaacggg gtggcacgca   1140

acaggtaaag tagacgtaca acaaatggat ggagcttctg tattagttct atcaaactgg   1200

agtgcggggg tatctcagaa tctgcatgcc caagatcatc atggatatat gttacgtgtg   1260

attgccaaaa aagaaggtcc tggaaaaggc tatgtaacga tgatggattg taatggacat   1320

caggaaacac tgaagttcac ttcttgtgaa gaggggtata tgacaaaaac agtagaggta   1380

ttcccagaaa gtgatcgtgt acggattgaa ataggagaaa ccgaaggtac attttatata   1440

gatagcatcg agttgctttg tatgcaagga tatgctagca ataatacccc acacacaggt   1500

aatatgtatg agcaaagtta taatggaatt tataatcaga atacgagcga tctgtatcac   1560

caagggtata caaacaacta taaccaagaa tctagtagta tgtataatca aaattatact   1620

aacaatgatg accagcattc cggttgcaca tgtaaccaag ggcataattc tggctgtaca   1680

tgtaatcaag gatataaccg t                                             1701
```

<210> SEQ ID NO 13
<211> LENGTH: 1920
<212> TYPE: DNA
<213> ORGANISM: Bacillus thuringiensis

<400> SEQUENCE: 13

```
atggaagaat tagagttaaa aagaacaaac acactatctt ctgaggatgt gaatatttta     60

caaattgaaa atttagtaaa agaatatgtt aagcaaacat atggtaattc agctgaaatc    120

aaaaaacttt cattagatgg gttagatgtt ttgtataatt tagatattcc ttctatttta    180

aagggtactt cttcttcttc tgctattaaa gttggtactg acaatttgaa taacccaaca    240

gatacagcga aaaccattaa acttccagtt aaaaatgtac gaaaaaaaga atttaaggtt    300

aaacctattc aagctttaaa ttttgaaaat ggtgcaacaa tcactaaaaa aagtataact    360

tcaattccta gtattaatgc tacttttata gctttggctg aacagaattt tcaaaatgca    420

cattttcata tagtaaacga tagtcaatct tatgaaaatg aaatacccat ctatgtacct    480

ccacattcaa aagttgaaat aacatactac gtgaaagaaa tccaatttga tgcaattatt    540

cagtccactg ccacaatagg tggatccata agttttgaat atattgttca tgataatggc    600

catgaaggaa tagattttct tactattttc gaattagtaa atagccttaa tctaaatgac    660

tttgaaattc aggaggcatc tgatgtacat ggtaaggtag tttataaagg gaaatcccaa    720

tttcagggaa ctgtaggttt aaatttattc atgcaaatca aaggaacgcc attggatgaa    780

agtaaaaata actatgaatt taccaaagta ctatcagagg acgttgaaat gagtctatct    840

ccgtcggagg gagaatatta tattgatttc gggtcatctc ctaaattaac aaataaagaa    900

gaagtaatag ttaaatttac aagagattac cttttgtcaa atgaccgcaa aaacgcatac    960

gtacaacaac taccacgtct tgaatatgga gaagaagtta ctacattaaa atctattgat   1020

actgctcatg aaaggaaaga aatcatagct tctacaatta atacttttca aaatccttct   1080

gatacagaga ttaccagaaa tacaataaaa gagacattta gtacaacgga tacaattact   1140

accactgcta caactgataa gtttcttgaa ctgggaggaa gtatagaaac ctctgcaaaa   1200
```

ggaaaagttc cactagtcgc agaagcatct ataaaagtta cacagagtat aaaaggtggt 1260
tggaaatggg taagtacaaa aactaataca agaacaaacg tccatacaat tgaaatacca 1320
tcgcaatcta ttaaaatacc tccacacaaa atgtggaaat accagtatat tctaacaaaa 1380
ttcgaatcaa gtggttattt aagctcagct tgggaaataa atactaaaga atctatgtca 1440
gctccggagg ttcacatagg ttactataat aaagatcttc agaatccaag aaatataacg 1500
gggctatcgg caaatgttga atctggaaat gtagttggac gtgtatttga attcaataaa 1560
ttccagccag gaggacttca ttacaaaata ctgaatagtg aaaatatatt aaatgcaact 1620
ccttatcaat tttttaaaga attagccaaa cgtgttaatc aatacccatt aatacaaaat 1680
aatcctcgct atagacgatt aggaattctt ttgggatttg gaaaggacat atctcaaatc 1740
acttgggaac ctcagataca ctataatgaa catgtgttat ttgatgctga agaactatta 1800
aatgttttac gttttgatga tattgccaat aaagtatatg cacttgatgg aggcacacct 1860
tttacagttg ctgtaggtca tgagctacta ccaaaagagt caatagaacc attaaataat 1920

<210> SEQ ID NO 14
<211> LENGTH: 2898
<212> TYPE: DNA
<213> ORGANISM: Bacillus thuringiensis

<400> SEQUENCE: 14
gtgatgaata tgagtaatac cttagcacct tataatgttt tgagaagtat ggatatgccg 60
aacatatcag gaaccaagtg ggataaagga atgtttatca atgcacttga taatacttct 120
tttcttttag agcttataga aaaaggaatt aatgatgatg atgatgtgtt aggtctgtta 180
agttttattg gattaacagc cttagaggca attccaattg tgggtggagt tatgtccaaa 240
cttgtttcta tgatattttt ccctacaaaa tcaagcatta atttccagaa gatatgggag 300
caattagaaa aagctattga acaaatagtt gacaaaaaaa taactgaagc tatgatgtct 360
cagctaatgc aagaaatagc cggtttagcc gatgtattag aagaatatag gaatgcttat 420
gatttatata atggtaaaaa attatttaat ataccagata agatgacacc tggggattat 480
ctgatcaatg tatttactac tgcaaatttg caattcattc agagaatacc gacatttcag 540
aactctatat atgatgtagt gtttcttcca ttctttgttc acgctgctga aatgcatatt 600
cttctgatta gggatgcagc aatacatggt caagaatggg ggatggatga aactgtacac 660
caaaaattta aaagggattt aaaaacttta attaataaat attctagtta tttattagct 720
acatataaaa aaggattaaa agaagcatcc gaaaaaaaac ttgaaaataa tgattttcca 780
acatctaaca accaacatca ttatattaat acagttagat ggaatgtaat caatcaatat 840
aaaagaggga tggctttaac tgtttttgat tttgcttaca aatggaagta ttaccaagaa 900
gtttatcaaa ataatataac gttaaatcct gctagaacaa tttattcaga tattgcaggt 960
tcggtatatc cttatgaaaa aactacaaat gaaattgata atattatcaa agagcagaat 1020
cttaaatatc gcggactctt aaaagaactg ctaattaatc atggggatag aatcgatagt 1080
attcaaagta agtatataag gaacaatgaa ataattgata gtaacagaac tggggggggct 1140 ggtggaaggg caaccttttt cgatttaaaa tctccaataa ataacccttt catacaagta 1200
aatatgtggt ctgaattagt accattctct ttaggattca aatattataa tggggaggag 1260
tcaaaactta tatggggagg agggacccct gggaaacata agtttggttc ttatcattat 1320
gtagggaata aagtgtcttc tattatagga tttggtaaaa atggaaccgg tggattcaac 1380
tctttagatg caatggtagt tggttttaaa cgagatgatt atatacctga aaatagattt 1440
gttggtgtaa acaaaaatgg tgaacctgta actaaagtaa tagatgcaga gaatttctac 1500
caagagaagt ttcaatcaaa tataaaaatg atagatgagc ctatgtttgg agaggcggtt 1560
ttacaattcg aaaattattc taataatctt aataaggata gttatgtgac atatcaaatt 1620
gatgcaaaga tagagggtac ttacgaatta catgtaatta taggtgcaaa aaaacaaaaa 1680
gataaaatag cttttaaaat ggctcttaat gaaaaacagc cagaaaagtt tataactgaa 1740
ccctttaatg ccggtgatat ttgggaagga atatcattga gcgaaggctt agtttataag 1800
agaatattat taggaaattt ccaacttaag aaaggtatga atcgtattac tattcacaat 1860
ggggtcctcc aaacatcagc aaatataaaa acatggaatt tagctaaact agagttaaca 1920
ctcacttctg atagcttaaa agaccctgat attacaactt tatatgataa agataattat 1980
tcaggaacaa aaaagtttat tttcgagaat acgagtcgtt taaaagactt taatgataaa 2040
acatcatcaa taaaagtcga gtctcattta gctggcatta ggatttatca agattacaat 2100
tataaaggta agtctatgga ccttgtaggt ggagaaaaaa taagtttaaa aaatcattca 2160
tttaataaca gagcttcttc agttaaattt gctaatatcg ttttatataa ccaagataac 2220
tatcagggtt caagaaaact agtttttgaa gatattcctg atttaggaaa acaaagcttt 2280
aacgataaaa cctcttcaat tgttgttagt tctaatgtat ctggtgctag actatatgaa 2340
catgcttatt ataaaggtaa gtatgtggat gttgttggtg gacagaaact taatttaaaa 2400
aatcatgtat taaataaaaa gatttcatcc attaaatttt ttaaagaggg tgaagtactt 2460
aatggtgtat atcaaattat tactgcaata aataacacga gtgtaataga taaacatcta 2520
gaaaattcta acgttcattt atgggagaat gcagaaaaca aaaatcaaaa atggcgaatt 2580
gagtatgatg tggctaaaaa agcttatcaa attaagaata tgttggatga gaagttagta 2640
ttatcaacgc atgagttatt tccaattttc tcagcactat attgtttacc taacaaaggt 2700
tatgtttcgc aatactggat ttttgagtat gtaggaaatg gttattatat tattaaaaat 2760
aaagcgtatc ctgattgggt attagatgta gatggtttga attctgataa tggtacttta 2820
attaaattac attcacagca tgatttaact gatccactta ttaatgcgca aaaatttaaa 2880
cttaaggata taaataat 2898

<210> SEQ ID NO 15
<211> LENGTH: 1725
<212> TYPE: DNA
<213> ORGANISM: Bacillus thuringiensis

<400> SEQUENCE: 15
atgaatggaa atggaagaca tgatggatgg aatcagaatc aacacataga aaatggacag 60
atgaacccaa atcatagtgg atcttgtaag tgcgggtgtc aacaaaataa taatggatcg 120
tatccttcga atgagtataa ttcaaataat aatggatcgt atccttcgaa tgagtataat 180
tcaaataata atggatcgta tccttcgaat gagtataatt caaataataa tggatcgtat 240
ccttcgaatg agtataattc aaataataat ggatcgtatc cttcgaatga gtataattca 300
aataataatg gatcgtatcc ttcgaatgag tataattcaa ataataatgg atcgtatcct 360
tcgaatgagt ataattcaaa taataatgga tcgtatcctt cgaatgagta taattcaaat 420
aataatggat cgtattcttc gaatgagtat aattcaaata ataatggatc gtatccttcg 480
aatgagtata attcaaataa taatggatcg tatccttcga atgagtataa ttcaaataat 540
aatggatcgt atccttcgaa tgagtatgta ggaggatata gtatacaaga tggtttacct 600
caagaaagta aacagtttca aaaaatttca aatatgaata ctagagataa tcatcgtgtt 660

```
ttagacgcac aagatactta ttttggtcaa ttgattgata atcgtgtagg tgacacatgt    720
aaatatgtag agcataaaaa ttcagtaatt tatgaactta gtaggcaacc tgtatatact    780
cctgattccc aatatttcat tttttatcaa atggataatg ggaattttat aattgcgaat    840
aaagaaaata gtcgagtttt agaagttata tttagttcag taaatggatt tgtaacaata    900
tcaaatgagt ttaatgcaac ttcagatcaa cgttttaagg ttgttagatc aaagaatgat    960
acattccgct tagtaacaga aggaaataaa acattaaata tatgtggtca ttcatttcaa   1020
tataatacta aaattacagc tgtaaatgcg gatattgatg gtgataatta tttatttcaa   1080
aaatctatgg ataaggatac aagggattta tatttcggaa caatatctaa taaaaatcca   1140
gaaatattaa atgacccaag aaatttaaaa agtttagatg atcttggtga tgagccgaga   1200
gcatttaaag gagccgcatt acttcctgct ctatttgtaa atgaccctag atattcagtg   1260
catcgaagag tatcaaatag tccatattat tacttagagt atacacagta ttggcataga   1320
atatggactg atgttttgcc tattgatggt tatggcgcat ggatagaaat gatagggggta   1380
acaaatgata cacaagtaaa tatgaaaaac ataatgaata ttacaataac tggaaaagat   1440
ttaggtgtag atttgggtat agatttggga ttaagatttg gtgataagtc atttcttttt   1500
gaacaaaaaa tcctttcagg attatctata cggaaaactg attatccaaa tctcggaata   1560
gatgaaagag caatgtatca aagaaacaat agtaatttaa aaaccagatt tgtaagatac   1620
gtgaaaaaac atgaatttgt attaagagat ttgaatggga gtaaggtagc tgaaccatgg   1680
attatcacgg aagatagatc gattacgaaa gaatactctt caaat                   1725
```

```
<210> SEQ ID NO 16
<211> LENGTH: 1677
<212> TYPE: DNA
<213> ORGANISM: Bacillus thuringiensis

<400> SEQUENCE: 16

atgaagtaca aaaatcgaac acgtgcaaaa tgcaaataca aacaagcgct tcttgtaaca     60
gtagcaacaa tgacactagg agtaagtaca ttaggaagca atgcctcagc attcgctgat    120
gaaaaagaaa agaatgttat tcagcaaaaa agtcctggca cttattatga agatgcgcaa    180
aaaaatctgg gctccctagc acgatttgat acatgggcac aagatcttgg aaaaacaaca    240
ggtgcaggga attataaaac tacacttggt atggcagaaa agctactacc aacaatttat    300
aatgatttaa atagtggaaa tttcaacaat actgcaaggt ccattacgat gttatctaca    360
gcgttgattc catatggagg agcattcatt tctccgataa ttgggatact ttggccagaa    420
aacgggccaa atataaaaga aatgctgcag gaaatggaaa acaaacttgt tggtataatg    480
gatgaaaaaa ttgaagccaa agatttagat gatcttgagg ctgcagtaaa aggattgatg    540
gtaagtctaa aagaatttga aaactcattg aatggtaata taggtggtga atattattct    600
gccctagctg atgtagactc acttaaccga ggtcgtataa cagccattca aaagggtttt    660
aacgacctta ttagtgctac tagtaaaccg aagttcaaaa taacagaact tcctctatat    720
acaattattg caactgctca cttgaatttc ttgaatactg tggaaaaaca gggaacttca    780
cctaaaataa actacacaga agcagcctta aaagatcttc tacaaaatat gaagaagaat    840
cacaaggatt atgcagatta tatagaaaaa acgtatacag aaggagaagc tagaatcaat    900
agcaaactag aagataaaca aaaaatagaa caagatttag ctgccgtaaa ccaaaagcta    960
tcggaaatgc ctcgtaaacc taagaatcac acccacgagg aagagaataa atttataatt   1020
caaaaagaga agctttacgc gcaacaagac tctcttgaga aaaagttgtc tgaatacaat   1080
```

gacttgatgt atcaaaagag tgatttttat agcaagacaa agggtagcga agcattccaa 1140
atagcatcaa caggaaaaac gataccaact ccaagttggg ttaaaacaga aggaacgtgg 1200
gtttgcgagg ctggtttttg gttttatatt gacgcaaaag ggcaaaagaa aagtgattgg 1260
ttcaatgata agacacctga tggtaaggat agatggtatt accttagcac tgaaacacca 1320
cgtctcgaca atgtaagggg gaatgcttat gttggaaaag gaacaatgct gactggttgg 1380
ttccacgata cgcgtaaaga taagcagatc atcggtgtga atacgaagac tacttatgaa 1440
tactggtatt acctcagccc agaaaaaaat cttaaaaact ctgccggaga actatttaag 1500
cagggacaga tgatgacgaa atgggttgaa attaaggata caaagactgg tgaaccacac 1560
tggtattatt tcaatcctga cgacggtagt atgacacatg ataaaaaagc ggtacaaatt 1620
ggtgacaaaa aatatgattt tggttccaat ggtgtatgta caacgcctaa cggttac 1677

<210> SEQ ID NO 17
<211> LENGTH: 3879
<212> TYPE: DNA
<213> ORGANISM: Brevibacillus laterosporus

<400> SEQUENCE: 17
atgaatcaga atcaaaataa aaatgaaatg caaattatag aaccttcaag tgattctttt 60
ctttatagtc acaacaatta tccgtatgcc actgatccaa atacagtatt agaaggtagg 120
aattataaag agtggctaaa taagtgtaca gataattata cagacgcttt acagagtccc 180
gaagctactg ctatttcaaa aggagctgtt tctgctgcga tttctataag caccaaagtt 240
cttggtttat taggtgttcc atttgcagct caaatcgggc aactttggac cttcatatta 300
aatgcgttat ggccttcaga caatactcaa tgggaagagt tcatgagaca tgtagaagaa 360
ctcataaacc aacgaatagc cgattatgca agaaataagg cacttgcaga attaacgggt 420
ttaggtaata atctagattt atatatagag gctcttgatg attggaaacg aaatcctact 480
agtcaagaag ctaaaacccg tgtaatagat agattccgta tagtagatgg attatttgaa 540
gcatatatac cttcatttgc agtatcaggt tatcaagtac aattattaac ggtgtatgca 600
gccgctgcaa atctccactt acttttatta agagattcca ctatttacgg aattgattgg 660
ggattaagtc aaactaatgt taatgataat tacaatcgcc aaataagact caccgcaacg 720
tatgcaaatc attgtacaac ttggtatcaa actggtttag aaagattgag gggttccaat 780
gcttccagtt gggtcactta taataggttt cgaagggaaa tgacgttaac cgtattggat 840
atttgttcct tattttcaaa ttatgattat cgtagttacc cagcagaggt aaggggagag 900
attacgagag aaatttatac agacccagta ggtgtaggct gggtggatag tgcaccatca 960
ttcggagaaa tagaaaatct agcaattagg gcaccaagaa ccgttacttg gttaaattca 1020
acaagaattt ttacagggag attgcagggc tggagtggta ctaacaatta ttgggcagct 1080
cacatgcaaa acttctcaga aaccaattca ggaaatatac aatttgaagg tcctctctat 1140
gggtcgacgg taggtactat tcatcgtact gatgattacg atatggggaa tcgagatatt 1200
tacaccatta cttcacaagc tgttttaggc ctttgggcaa ctggtcaaag ggtgttgggg 1260
gtcgcttcgg ctagatttac tttaagaaat cttttcaata atcttacaca ggtgctggtg 1320
tatgagaacc caataagttc aacttttgga agttcaactt taactcatga attatctgga 1380
gaaaactcag ataggccaac ttctagcgac tatagtcata gactaacgag tatcacaggt 1440
tttcgagctg gagctaatgg aacggtccca gtgtttggtt ggacatctgc aactgttgat 1500
cgtaacaata taattgagcg aaacaaaata acacaattcc caggtgttaa gtcacacact 1560

```
ctcaacaatt gtcaagtagt taggggtact ggatttacag gaggagactg gttgagacca   1620
aataataatg gtacatttag actaactatt acttcattct ccagccaatc ttaccgaatt   1680
cgcttacgtt atgctacttc agtagggaat acttctttag ttatatcttc ttctgatgca   1740
ggtatttctt ccacaacaat tccgcttacc tcaacaataa catcactgcc acaaactgta   1800
ccataccaag cttttagggt tgtagattta cctattactt ttacaacacc tactacccaa   1860
agaaattata cgtttgattt ccgtctccaa aatccatcaa acgcaaatgt attcattgat   1920
agatttgaat ttgttccaat tggggggttct ttgtctgagt atgaaaccaa acatcagcta   1980
gaaaaagcaa ggaaagcggt gaacgatttg tttaccaatg aatcgaaaaa tgtgttaaaa   2040
aaagacacga ccgattatga tatagatcaa gctgcaaact tggtagaatg tgtatctgat   2100
gaatgtgcaa atgctaaaat gatcctatta gatgaagtaa aatatgcgaa acaacttagc   2160
gaagcccgca atctacttct aaatggtaat tttgaatacc aagatagaga tggggagaat   2220
ccatggaaaa caagtcccaa tgttaccatc caagagaata accccatttt taaaggccgc   2280
tatctcagta tgtcaggtgc gaacaatatc gaggcaacca atgagatatt tcccacttat   2340
gtataccaaa aaattgatga atccaaatta aaaccttata cccgttataa agttcgaggt   2400
tttgttggaa atagtaaaga tttagaatta ttggttacac ggtatgatga agaagtagat   2460
gcgattttaa atgtaccaaa tgatatacca catgctccgc cacctttctg cggtgaattt   2520
gatcgatgca agccgcattc ttatcctcct attaatccag aatgtcacca tgatgtaata   2580
aataacattg aaatatcctc tccttgccaa cacaataaga tggtagataa cgctgatata   2640
tcttatcgcc atagccgatt aagtaaaaaa catggcattt gtcatgaatc tcatcatttt   2700
gaattccata ttgatacagg gaaaatcgat ttggtcgaaa atttgggaat ttgggttgta   2760
tttaaaatat gttccacaga tggttacgca acattagata atttggaagt tattgaagag   2820
ggtcctttag gagccgaatc cttagaacgt gtgaaaagaa gagaaaagaa atggaaacat   2880
cacatggaac acaaatgttc agaaactaaa catgcatatc atgccgcaaa acaagcggtg   2940
gtggcgttat tcaccaactc taaatatgat agattaaagt tcgaaacaac catatccaat   3000
attcttttg ctgattatct cgtgcagtca attccgtatg tatataataa atggttacca   3060
ggtgttccag gtatgaatta cgatatctat acagaattaa aaatctgtt tacgggagct   3120
ttcaatctat atgatcagcg aaatattata aaaaatggag actttaatcg tgggctcatg   3180
cattggcatg cgacacctca tgcaagagta gagcaaataa tagataatag gtctgtgcta   3240
gtgcttccaa attatgctgc caatgtttca caagaggttt gtttagaaca caatcgtggt   3300
tatgtattac gtgtaacggc gaaaaaagaa ggccctggaa ttggatatgt tacattcagt   3360
gattgtgcaa atcatataga aaagcttaca tttacttctt gcgattatgg tacaaacgta   3420
gtgccatatg aacaatctaa ttatcctaca gacggagtac catatggaca acatggttgt   3480
aatatagacg gagtaccgta tgaacaatcc ggttatcgta cagacggagt accgtatgaa   3540
caatccggtt atcgtacaga cggagtaccg tacgaacaat ctggtcatcg tacagatgga   3600
gtaccgtacg aacaatctgg ttatcgtaca gacggagtac catgcgaaca acatggttgt   3660
catacagacg gactaccaca catacaacat ggttgtcgta cagacggact accacacata   3720
caacatggtt gtcgtacaga cagatcaaga gatgaactac ttggttatgt gacaaaaacg   3780
attgatgtat tccctaatac agataaagta cgtatcgaca ttggagaaac cgaaggtact   3840
tttaaagtag aaagtgtaga actgatttgt atggaagag                          3879
```

-continued

<210> SEQ ID NO 18
<211> LENGTH: 3768
<212> TYPE: DNA
<213> ORGANISM: Brevibacillus laterosporus

<400> SEQUENCE: 18
atgaatcaaa atcaaaatca gaatcaaaat aaaaatgaac tgcaaatcat agaaccttca 60
agcgattctt ttctttatag tcacaacaat tatccgtatg ccactgatcc aaatacagta 120
ttacaaggta ggaattacaa agagtggcta aacatgtgta caggtacaga cgattcacga 180
agtcccgaag ctgcttctac tgcaaaatca gctatttcag ttgcgattac tataagcacc 240
acaattcttg gcttactagg tgttccgttt gcatctcaaa tcggggcatt ttataacttc 300
gtattgaata cggtttggcc tcagggaaat aaccaatggg aagagttcat gagacatgta 360
gaagatctca taaacgaacg aatagctgat tatgcaagaa gtaaggcact tgcagaatta 420
gcgggtttag gtaataactt agatttatat agagaggctt ttgaagattg gagacgaaat 480
cctactagtc aacaagctaa aacccgtgta atagaaagat ttcgtatact agatggtctt 540
tttgaacaat atatgccatc atttgcagta caaggttttc aagtacaatt attaacagtg 600
tatgcatccg ctgcaaatat ccatttattt ttattaagag atagctctat ttacggtttg 660
gattggggat taagtcaaac taatgttaac gaaaattaca atcgccaaat aaggcacgcc 720
gcaacgtatg caaatcattg tacaacttgg tatcaaactg gtttacaaag attgcaaggt 780
accaatgcta ccagttgggt cgcttataat agatttagaa gggaaatgac attaacagta 840
ttagatatta gttcattatt ttcaaattat gattatcgta gttatccaac agaggtaagg 900
ggagagctta cgagagaaat ttatacggac ccagtaggta gaaactggca gaatagtgca 960
ccatcattcg ctcaaataga aaatctagca attagggcac caagaaccgt tacttggtta 1020
aattcaacaa gaatttctac agggaccttg cagggctgga gtggttctaa cagatattgg 1080
gcagctcaca tgcaaaactt ttcagaaacc aattcaggaa atatacgatt tgacggtcct 1140
ctatatgggt cgacggtagg tactattcat cgtactgatg attacgatat ggggaatcga 1200
gatatttaca ccattacttc agaagttgtt gcctcccttt gggcaactgg tcaaactgtg 1260
ttgggagtcg cttcggctag atttacttta agaaatcttt tcaataatct tacacaggcg 1320
ctggtgtatg agaacccaat aagttcaagt tttaataggt caactttaac tcatgaatta 1380
cctggagaaa actcagatag gccaacttct agcgactata gtcatagact atcgagtatc 1440
acaggttttc gagctggagc taatggaacg gtcccagtgt ttggttggac atctgcaact 1500
gttgatcgta acaatataat tgagcgaaac aaaataacac aattcccagg tgttaagtca 1560
cacactctca acaattgtca agtagttagg ggtactggat ttacaggagg agactggttg 1620
agaccaaata ataatggtac atttagacta actattactt cattctccag tcaatcttac 1680
cgaattcgct tacgttatgc tacttcagta gggaatactt ctttagttat atcttcttct 1740
gatggaggta tttcttccac aacaattccg cttacctcaa caataacatc actgccacaa 1800
actgtaccat accaggcttt tagggttgta gatttaccta ttacttttac aacacctact 1860
acccaaagaa attatacgtt tgatttccgt ctccaaaatc catcaaacgc aaatgtattc 1920
attgatagaa ttgaatttgt tccaattggg ggttctttgt ctgagtatga aaccaaacat 1980
cagctagaaa aagcaaggaa agcggtgaac gatttgttta ccaatgaatc gaaaaatgtg 2040
ttaaaaaaag acacgaccga ttatgatata gatcaagctg caaacttggt agaatgtgta 2100
tctgatgaat gtgcaaatgc taaaatgatc ctattagatg aagtaaaata tgcgaaacaa 2160
cttagcgaag cccgcaatct acttctaaat ggtaattttg ataacataga tagagatggt 2220

```
gagaatccat ggaaaacaag tcccaatgtt accatccaag agaataaccc catttttaaa   2280
ggccgctatc ttagtatgtc aggtgcgaac aatatcgagg caaccaatga gatatttccc   2340
acttatgcat accaaaaaat agatgaagca aaattaaaac cctatacgcg ttataaagtt   2400
cgagggtttg ttggaaatag taaagattta gagttgttgg ttacacggta tgatgaagaa   2460
gtagatgcaa ttttaaatgt accaaatgat ataccacatg ctccgccacc tttttgcggt   2520
gaatttgatc gatgcaaccc gcattcttat cctcctatga atccagaatg tcaccatgat   2580
gtaataaata acattgaaat atcctctcct tgccaacaca ataagatggt agataacgct   2640
gatatatctt atcgccatag ccataaaaaa catggcattt gtcatgaatc tcatcatttc   2700
gaattccata ttgatacagg gaaaatcgat ttggtcgaaa atttgggaat ttgggttata   2760
tttaaaatat gttccacaga tggttacgca acattagata atttggaagt tattgaagag   2820
cgtcctttag gagccgaatc attagaacgt gtgaaaagaa gagaaaagaa atggaaacat   2880
cacatggaac acaagtgttc agaaactaaa cttgcatatc atgctgcaaa acaagcgctg   2940
gtggggttat tcacaaacac tgaatatgat agattaaagt tcgaaacaac catatccaat   3000
attctttttg ctgattatct cgtgcagtca attccgtatg tatataataa atggttacca   3060
gatgttccag gtatgaattt cgagatctat acagaattaa aaaatctgta tacgggagct   3120
ttcaatttat atgatcagcg aaatattata aaaaatggag actttaatcg cgggctcatg   3180
cattggcatg cgacacctca tgcaagagta gagcaaatag ataataggtc tgtgctggtg   3240
cttccaaatt atgctgccaa tgtttcacaa gaggtttgtt tagaacacaa tcgtggttat   3300
gtattacgtg taacggcgaa aaaagaaggc cctggaattg gatatattac attcagtgat   3360
tgtgcaaata atatagaaaa gctgacattt acttcttgcg attatggtac aaacgaagtg   3420
ccgtatgagc aatctaatta tcctacagac ggagtttcat acggacacca tggttgtaat   3480
atagacagag taaggtacga agaatctggt tatcgtacag acggtgtacc gtacgaacaa   3540
tctggttatc gtgcagacgg agtatcgtac gaacaacatg gttgtcatac cgacggagta   3600
ccatacaaac aacatggttg tcgtacggac agatcaagag atgaacaact tggttacgtg   3660
acaaaaacga ttgatgtatt ccctgatact gataaagtac gtatcgacat tggagaaacc   3720
gaaggtacct ttaaagtaga aagtgtggaa ctgatttgta tggaagag                3768
```

<210> SEQ ID NO 19
<211> LENGTH: 951
<212> TYPE: DNA
<213> ORGANISM: Brevibacillus laterosporus

<400> SEQUENCE: 19

```
atgaaaaaat ttgcaagttt aattcttata agtgtgttcc ttttttcgag tacgcaattt     60
gttcatgcgt catccacaga tgttcaagaa agattacggg acttggcaag agaaaatgaa    120
gctggaaccc ttaatgaagc atggaatact aacttcaaac ccagtgatga acaacaattc    180
tcttatagtc caactgaagg tattgttttc ttaacaccac ctaaaaatgt tattggcgaa    240
agaagaattt cacagtataa agtaaataat gcatgggcta cattagaagg aagtccaacc    300
gaagtatcgg ggacaccttt atatgtggga aaaaacgtat tagataactc aaaaggaaca    360
agcgatcaag agctgttaac acccgagttt aactatacct atacggaaag cacttcaaat    420
acaacaactc atggattaaa attaggagtc aaaaccactg ctaccatgaa attcccgatt    480
gctcagggta gcatggaagc ttctactgaa tataactttc aagattcttc cactgatact    540
acaactaaaa cagtatcata taaaagccca tcacaaaaga ttaaagtacc agcaggtaaa    600
```

acctttagag ttttagcata cctaaatact ggatctattt caggtgaagc taacctttac 660
gcaaatgttg ggggtatagc ttggggggtt ttaccaggtt atcccaatgg cggaggagta 720
aatataggtg ctgtacttac caaatgccaa caaaaaggat ggggagattt cagaaacttt 780
caacctagtg gaagagatgt aatcgttaaa ggccaaggta ctttcaaatc taattatgga 840
acggacttca ttttaaaaat tgaagacatc acagattcaa agttacgaaa caataacggg 900
agtggaactg tcgttcaaga gattaaagtt ccactaatta gaactgaaat a 951

<210> SEQ ID NO 20
<211> LENGTH: 3462
<212> TYPE: DNA
<213> ORGANISM: Bacillus thuringiensis

<400> SEQUENCE: 20
gtgaattttt tatttttagt taattatgaa aaaaataagt ttaaatataa tatacaagga 60
gacttgaata tgaatcaaaa aaactatgat attataggtt cttcgacaaa cggcacaacg 120
aaattacctg aagattataa cattataatt agtcctgatg cagccccaga ggctgttact 180
attgcgattt caattacagg agaagtactg tctctttttg gtgttccagg tgcaacatta 240
ggaagtactc ttcttaatac acttgttgat aaattatggc caaccaatac aaatactgta 300
tggggtacat ttacagagga aactgcaaaa cttataaatg aagtatataa tccatcagat 360
ccagtagtaa aagatgcaga tgctcgacta acatcgttac atgaatcgtt aaaattatat 420
caattagcct ttggaaattg gtttaaatca caagataatt caaaactcaa agaagaggta 480
cgacgccagt ttgatattac tcataataga tttgtaacta gtatgccttt ttttaaggta 540
tcggactacg aaattagatt gttaacaaat tatgctcaag ctgctaatct tcatttaact 600
tttttaagag atgcgtccat ttatgggctt gattggggtt tcagtgacga gcatagtaat 660
gatttgtatg aacaacaaaa gaatcgtaca ggagaataca cagatcattg tgtaaagtgg 720
tataacgcag gattagaaaa attaaaagga aatttaactg ggaaaaattg gtacacttat 780
aatagatttc gtagagaaat gacgttaatg gtgttagacg tagttgcatt atttccaaac 840
tatgatacac gaatgtaccc gatcgcaacg tcatcagaac ttacaagaat gatttataca 900
gatccaatcg cttatacaca aagcgatcca tggtacaaga taacatctct ttctttttcg 960
aatattgaaa acagcgcgat tccaagtcct tctttcttca ggtggctaaa atccgtttca 1020
attaatagcc agtggtgggg cagtggtcct aatcaaacct actattgggt tggacatgaa 1080
ttggtatatt ctaattcaaa ttataatcaa tcacttaagg ttaaatacgg ggatcccaat 1140
tcttatattg agcccccctga ttctttcagt ttttcttcta cggatgttta cagaaccatc 1200
tctgtcgtta gaaattcaat tagtaattat atagtaagtg aagttcaatt caattcaatt 1260
agtaatacaa atcaaattag tgaagaaatt tataaacatc aatcaaattg gaatagaaga 1320
gaaaccaaag attcaattac tgaactatcc ttagctgcta atcccccaac aacatttgga 1380
aacgtagcag aatacagtca tagattagca tatatttcag aggcatacca aagtaacaac 1440
ccatcaaaat acccagccta cattcctgta ttcggttgga cgcatacaag cgtacgttac 1500
gataataaaa ttttcccgga caaaatcact caaattccag ctgttaaaag ttcctcagct 1560
gaaggtggaa catggaaaaa tatagcgaaa ggtcctggat ttactggagg cgatgtgaca 1620
acagctgttt cgccagcatt tataacagat gtaataaaaa tacacgttac tctagatcca 1680
aattcacttt cacaaaaata tcgtgcacga cttcgctacg cttccaatgc atatgtagca 1740
gctacattgt atacaaattc aagtagtaat tataattttg aacttacaaa aggtacaacg 1800
gaacagttta caacatataa ttcataccag tatgtagata ttccaggttc aatacaattt 1860
aatactactt ctgatacagt gtctgtttat ttgcatatgg attcaacaac taatgcaaac 1920
gttcatgtag atagaattga attcattcca gtagatgaaa attacgataa cagagtaaca 1980
ctagaaaaag cacagaaagc cgtgaatgcc ttgtttacag cgggaagaca tgcactccaa 2040
acagatgtga cagattttaa agtagatcag gtttcaattt tagtggattg tgtatcaggg 2100
gaattatatc ccaatgagaa acgcgaacta ctcagtttag tcaaatacgc aaaacgtttg 2160
agttattccc gtaatttact cctagatcca acattcgatt ctattaattc atctgaggag 2220
aatggctggc acggaagtaa tggtattgca attggcaatg ggaactttgt attcaaagga 2280
aactatttaa ttttctcagg taccaatgat acacaatacc caacgtatct ctatcaaaaa 2340
attgatgaat ccaagctcaa agaatataca cgctataaac tgagaggatt tatcgagagt 2400
agtcaagatt tagaagcata tgtgattcgc tatgatgcaa aatatgaaac attggatgta 2460
tccaataatc tatacccaga tatttctcct gtaaatgcat gcggagaacc caatcgttgt 2520
gcggcactac catacctgga tgaaaatccg aggttagaat gtagttcgat acaagatggc 2580
attttatctg attcgcattc attttctctc aatatagata caggttctat tgattccaat 2640
gagaacgtag gaatttgggt gttgtttaaa atttccacac cggaagggta tgcgaaattt 2700
ggaaacctag aagtgattga agatggccca gtcattggag aagcattagc ccgtgtgaaa 2760
cgtcaagaaa cgaagtggag aaacaagttg acacaactgc gaacggaaac acaagcgatt 2820
tatacacgcg caaaacaagc cattgataat ttattcacaa atgcacagga ctctcactta 2880
aaaataggtg ctacattcgc gtcaattgtg gctgcgcgaa agattgtcca atccatacgt 2940
gaagcgtata tgccatggtt atctatcgtc ccaggtgtaa attaccctat tttcacagag 3000
ttgaatgaga gagtacagca agcatttcaa ttatatgatg tacggaatgt cgtgcgtaat 3060
ggccgattcc tgaatggagt atcggattgg attgtgacat ctgatgtaac ggtacaagaa 3120
gaaaatggga acaatgtatt agttctttcc aattgggatg cgcaagtatt acaatgtctg 3180
aagctctatc aagatcgcgg atatatcttg cgtgtaacgg cacgtaaaga aggattggga 3240
gaaggatata ttacaattac ggatgaagaa gggtatacag atcaattgac atttggcaca 3300
tgtgaggaga tagatgcatc taacacgttc gtatccacag gttatattac aaaagaactg 3360
gaattcttcc cagatacaga gaaagtgcgt atagaagtag gagaaacaga aggaaccttc 3420
cgggtagaaa gtgtagaatt attcttgatg gaagaacact gt 3462

<210> SEQ ID NO 21
<211> LENGTH: 3618
<212> TYPE: DNA
<213> ORGANISM: Bacillus thuringiensis

<400> SEQUENCE: 21
atgcggttaa aaaaattact tgtatgtaat ataagaattg gaggaacaaa tatgaatttg 60
ggaaactata atgaattcga tatcatagat attactgaaa acaatcagac taaaacatca 120
cgatataata atgtgaatag acaagagaat ccatctaata tgattatttc aaatccttct 180
tctaactatc ctctagcaaa caatccaaat acacccttcc aaaatataaa ttataaagat 240
tttttgaata tgaatgagga gattgcaccg tatgcaagtt cgaaagatgt aatttttagt 300
tcaatgaata tcattagaac cttcatgggt tttgcaggac atgggactgc tggaggtatt 360
gttgcattat ttacggaagt attaagatta ctatggccta ataagcaaga tgagctttgg 420
gaatcgttta tgaaagaagt agagaaactt attgaacaag aaataacaga tgcggtagta 480

-continued agtaaagctt tggcagaatt agagggttta agaaacgctt tgcaaggata tacagatgca 540
ctggaagcat ggcaaaataa tcgtagtgat aaacttaagc aattactagt gtatgataga 600
tttgtttcta cagaaaattt atttaaattt gcaatgccgt cttttagagt gggaggtttt 660
gaagttccat tattaacagt atatgcacaa gccgcaaatc ttcacttatt attattaaaa 720
aattccgaat tattcggggc agaatgggga atgcagcaat acgaaataga cctattttat 780
aatgaacaaa aggattacgt agtagaatat acagatcatt gtgttaaatg gtatactgaa 840
gggttaaata ggttgaagaa tgcaagcgga gtaaaaggta aggtatggga ggaatataat 900
cgttttcgca gagaaatgac gattatggtg ttagatcttc ttccattatt tccaatctat 960
gatgtacgca catatcctac ggaaacagta acagagttga caagacaaat tttcacagat 1020
ccaataggtc ttagaggaat taatgagtcg aaatatcctg attggtatgg agctgcaagt 1080
gatagtttca gtcttataga aaatagggca gtaccacaac ctagcttatt tcaatggtta 1140
actgaattta aagtatatac taaatatgtt gaaccgaatg ataagcttac aattttggct 1200
ggacacagtg taactactca atatactagc tattataaaa agagcacatt tacttatgga 1260
gatacttcaa gtgctaattc atctagaact tttgacctac ttgctaaaga tgtatatcag 1320
gttgattctg tagctgcagc aagtaaaagt gctacttggt atttggctgt tcctgaaatg 1380
cgattatata gcattaatac taacaatata ttatctgaag attatttttc tttgagtact 1440
aatataccat ccagtaagat gagacgtatg tattctagtg aggaattacc gataggaatc 1500
tcggatacac ctatttatgg agatcttgag gaatatagtc ataggttaag ttttatttct 1560
gaaattatgc ataactctgg aagtgtaaca ggttcaaata acatcaaagg aataattcca 1620
gtattaggat ggacacatac aagtgtatct cctgaaaatt atattcacag ggataaaatt 1680
tcacaattat atgctgttaa agcatacacc actagtaatg tttctgttgt aggaggacct 1740
ggatttttag gaggaaatat aattaaaggt aataatgatc ctgctagcta taccggaagc 1800
gtgagctggg caattagatt ggatggttca acagtaagtc gattccgtct tagaattccc 1860
tatgctgctg aaacagatgg cacattttct attactgttc gagacgattt aggccctttt 1920
actataaaga aggactttat agcaacaatg aaaccaggag atcctttatc atatggtaaa 1980
tttgaatatt tagaatttga acaaacaatg agtcttaata ataagcatgg tcaatttttc 2040
gttcatacag aaaatttaaa agatagaaat tctagtgtat attggaatag agttgaaatt 2100
atcccggtgg atgaaaatta cgataacaga gtaagattag aaaaagcaca gaaagccgtg 2160
aatgctttgt ttacagcggg aagacatgca ctccaaacaa atgtgacgga ttacaaagtg 2220
gatcaggttt caatcttagt ggattctgta tcaggggaat tatatccaaa tgagaaacgc 2280
gaactacaaa gtttagttaa atatgcaaaa cgtttgagct attcccgtaa tttacttcta 2340
gatccaacat tcgattctat taattcatct gaggagaatg gctggtacgg aagtaatggt 2400
attgcaattg gaaatgggaa ctttgtattc aaaggaaact atttaaattt ctcaggtacc 2460
aatgatacac aatacccaac gtatctctat caaaaaattg atgaatccaa gctcaaagaa 2520
tatacacgct ataaactgag aggatttatc gagagtagtc aagatttaga agcatatgtg 2580
gttcgctatg atgcaaaaca tgaaacattg gatgtatcca ataatctatt cccagatatt 2640
tctcctgtga atgcatgcgg agaacccaat cgttgtgcgg cactaccata cctggataaa 2700
aatccgaggt tagaatgtag tttgatacaa gatggtattt tatctgattc gcattcattt 2760
tctctcaata tagatacagg ttctattgat tccactgaga acgtaggaat ttgggtgttg 2820
tttaaaattt ccacaccgga agggtatgcg aaatttggaa acctagaagt gattgaatat 2880

-continued ggcccagtca ttggagaagc attagcccgt gtgaaacgtc aagaaacgaa gtggagaaac 2940
aagttgacac aactgcgaac ggaaacacaa gcgatttata cacgagcaaa acaagccatt 3000
gataatttat tcacaaatac acaggactct tacctaaaaa taggtgctac attcgcgtca 3060
attgtggctg cacgaaagat tgtccaatcc atacgtgaag cgtatatgtc atggttatct 3120
atcgtcccag gtgtaaatta tcctattttc acagagttga atgagagagt acagcgagca 3180
tttcaattat atgatgtacg gaatgtcgtg cgtaatggcc gattcctgag tggagtatca 3240
gattggattg tgacatctga tgtaaaggta caagaagaaa atgggaacaa tgtattagtt 3300
ctttccaatt gggatgcaca agtattacaa tgtctgaagc tctatcaaga tcgcggatat 3360
atcttgcgtg taacggcacg taaggaagga ctcggagaag gatatattac aattacggat 3420
gaagaagggc atacagatca attgacattt ggcacatgtg aggaaataga tgcatctaac 3480
acgttcgtat ccacaggtta tattacaaaa gaactggaat tcttcccaga tacagagaaa 3540
gtgcgcatag aaattggaga aacagaggga atattcaagg tggaaagtgt agaattattt 3600
ttgatggaag atctatgt 3618

<210> SEQ ID NO 22
<211> LENGTH: 2316
<212> TYPE: DNA
<213> ORGANISM: Bacillus thuringiensis

<400> SEQUENCE: 22
atggtgaatg aaaatatgga tatgtataat aacaacggta gtatgaacgg aaatccagat 60
atgtacaata aaaacggaag tatgaacgga aatacggatg tgtataataa caacggtagt 120
atgaacggaa atccagatat gtacaataac aacggaagca tgaacggaaa tacagatgtg 180
tataataaca acggaagcat gaacggaaat ccagatgtgt ataataaaaa cggaagcatg 240
gacggaaatc cagatatgta caataacaac ggaagcatga acggaaatac agatgtgtat 300
aataaaaacg gaagcatgaa cggaaatcca gatatgtaca ataacaacgg aagtatgaac 360
ggaaatacgg atgtgtacaa taacaacgga agtatgaacg gaaatacgga taatcaagtg 420
ccggcttata acattctttc tgcggaaaac ccttctaata ttttagaaag tgatactaga 480
tgcacactaa atgttaaaaa tgtgcaagat gaggctatct gtacaggtag taatttaacc 540
aacgaaatag gtccacttgt tgttcccatt gcttttactc ctattattct aacgcctgca 600
cttattgaag taggtaaatg gttaggagtt caaattggta aatgggctct aagtacagct 660
ttaaaagaat taaaatcttt tctctttcca aattctgatc cccaaaggga aatggagaaa 720
ttacgcatag aattagaaaa ttcatttaat aagaaattaa cagaagataa attgaatttt 780
ttaactgccg cgtatactgg ttttaataat ttatctaatt cttttatttc tgcaaccgag 840
cgtgtaaaag cagcagaaat tacattagct acagctcctt ctcaagaaaa tcaagatatt 900
ttagatgaag ctagaacatt agcaagagac tattttgtga gtttacactc acaaatgata 960
gtgtggcttc cccagtttga aattagtgga tatgaagaaa tttccttacc attatttact 1020
cagatgtgca ctttacatct cactcatcta aaagatggag tattaatggg gcagaattgg 1080
gggctttcta cagatgatat taaacatttt aaaggtgaat tttacagatt aagcaatgat 1140
tacacttcta gagctttcga ttcatttcat agaggtttta atcgtttacg aacacaacaa 1200
ggaacagctg gagtcataaa atttagaaca gccatgaatg catatgcttt tgacaatata 1260
tataaatggt cattgttgcg ttatgagggt attaatccta ggataacaag aagtttatgg 1320
cattatattg gatataattc atctttagga tctaatgatt ttaatacact atacaaactt 1380
atggtgggta taccgcatga aagatttaga acagttgcaa taggatatcg tgctaaaaca 1440
ggtgaggatt ggaaagttac aggggctaaa tcaacttttt attctggtgg tggtgaatgg 1500
gttggaaacg tctccaaagc aacaagaatc cctgtttaca ctactaaaac ggattggagg 1560
caatttgaaa gaagaataca tggcagatta ggaactgagc aatatactag atggcatctt 1620
acaattcaag atacgaatat cattggtaat tcatatttaa ccggtttacc ctttgatatt 1680
tcatatcctg attattttat ccgaacaatt tcagcaaaac cagaagccta ccctatttat 1740
aaatcgctta gtctgggga taatccagga tacgtagtag acaatcctgg aaataacctt 1800
attataggtt tttctcctga taatttaaaa acatttatga ctgatggaaa cagatatcat 1860
tcaatagaat caggatatcc aacaaaccca tcttgtacta taccagcggt actttataat 1920
agtgtaagta acccattcca agcttatttt aatgatgaat taggtaatgg ttcagatggg 1980
agtataactt taatccgtcg aggtggtgca cattatcttg ttgattcaag atctgcttct 2040
tatgacagaa gctttcgtct tataattaga attcaggcag ggagttctgc attcaaggta 2100
acagtaagat caaggcacac atctgagagc tttgaattaa atttcacact tctttcagat 2160
caagatatta attattatta tgattatata tcccaacctt ttaatctaag ctctacttac 2220
tattatatag atgtagaacg tgttgttagt gatgacataa gagcgttaac ttttaatcaa 2280
atgattatag ttccaactac agaattccag atatta 2316

<210> SEQ ID NO 23
<211> LENGTH: 867
<212> TYPE: DNA
<213> ORGANISM: Bacillus thuringiensis

<400> SEQUENCE: 23
atggcaattt acgatatagc agcagatttg ttcgatctta ccagatggta cgccgaacaa 60
aattataatg caaatccaac aacatttaga ggggctaaag tatatgatcg aatcgtatca 120
gatgttcaat ctataccgga aaaagtagat tttaatttga taccaggctt agcttatacg 180
gtgaaaaatg aaatcgtaaa tgatactaat acagaacaat ctatgagtac aaaactcatg 240
catacattaa ttgaatcaaa ttctgttaca accacaaaag gatataaaat tggaagtagt 300
atcaaaaata cgtttagcgt aaacattgag ggaagttttt ttgttggtgg tgggtctaca 360
gagcattcca ttgaagtatc agtaagtggg gaatataatc atagttcttc agaaactaaa 420
acaaatacct cacagaaaac atgggaatat aacagcccta ttcttgtccc agcaaaaaca 480
aaagttacag caactttaga tatttatgca ggaccagttg tagtcccagt aactttaaaa 540
agtacagtta ctggaacggg tattgtgaat aattttccta acgtattaac gagtttaagt 600
tacattgata gaaacaataa gttgtggaca gactctcttc caactgcttt gttatatgat 660
tatcgaaatc agtggccagg aagtcagtct atttatgttg ggaagaatgg gggaggtgta 720
caggtagaag gtaaagctga aatacaatta gaactaggtc tatactccat tgcaaccttc 780
gactctcagc cactgtcagg gaacacaaca ggtaaagaag cagtgtattc taaggctata 840
ctccgagatg gatctattat tgatatt 867

<210> SEQ ID NO 24
<211> LENGTH: 318
<212> TYPE: DNA
<213> ORGANISM: Bacillus thuringiensis

<400> SEQUENCE: 24
taaattcaat tatgattcgt aattaaaatg tgaaaattaa caatctccga atttcatgtt 60
aatttatggg tgtcaaataa aattatataa ggcctactta tattttcgag attactatat 120
gaggcctaaa atatttaaca aattgctatg tcttgcatat aaacaaattt aagtatggtg 180
aatttctcaa gatatatgta taaaaatgat aattatatcc tttgttgttt tttgtgaata 240
gatgaatgct aactattctt acctatgaaa aatagattaa tttgcctata aagtattttt 300
taaaaggagg aatgtatt 318

<210> SEQ ID NO 25
<211> LENGTH: 3999
<212> TYPE: DNA
<213> ORGANISM: Bacillus thuringiensis

<400> SEQUENCE: 25
ttggcacaat taaatgaaat ttatccaagt tattacaatg ttttagcata tccccctcta 60
attctcgacg ataagagcct atatgatcag tatacagagt ggaagaaaaa aattgataag 120
acttggaaac aatatgacaa agacttttta ccaaagcctt taatggattt aggaaaatct 180
ctggcagagg cctataaggg tgatcctgat ggttaccttc atatcgcaaa cacagcaata 240
agaatagctt tcttattgat accaggaggg caaactgctg cttttggtgt aaatcttgtg 300
ctgaataaag caatagggat cttttatcct cctcaaaata aatctctatt tgatcaaatt 360
aaggacgctg tatccaacct ggtggatcaa aaattgatag accaagaaat ctctggagta 420
ctgattaaac ttaacagcct acagcagccc ctatcacgtt tcagcaattc catacagcga 480
gctgttggaa aaccacagga cttcgacgac caaactacat catccaacgc aattattctt 540
gatgagacac aggactgcag taaggacgat tcgtgttctt gttccaatac tcaacctcgt 600
ccttctgatg cgcctctttg taccccatgt atttgtcgta tgaaggaagt tcaacaaaca 660
ttcaacaact caagtactga tgttaaccga gcattaactg acatgaaaac aacgttaaag 720
gacgtagtgg gtgcggatca actgagaagc tacatgcaaa tatatttacc gttatatgtg 780
acggctgcta caatggagtt acaaatgtat aaaacctata ttgactttac acaaaaattc 840
gatttcgatg taactggcac gacaaaggaa catgtaaacg agttacgtca aaaaatcaaa 900
acgcatagtg agtacatcat gggcttattt aagaaatctt taccagaaat tagtaataat 960
acaaaagaac aactaaatgc atatattaaa tatacacgta atataacttt gaatgctctt 1020
gatatggtaa gtacatggaa atttttagac cctgttgact accctacgac tgctacattc 1080
aatccgacta gaattatatt taacgatctt gcaggacctg ttgagtgtct gaatagcact 1140
caggacagca ataaactaca ttttaatttc tttgatatga acggacagtc tatgcctaat 1200
aatgatattt tcaattattt ttatagaggt atgcaagtaa aaggtctgca gatccaaacc 1260
tatactagct ctgacaccaa aaatccacag cattttcctg taggattcct atcctcttat 1320
tatggtagta acggtgattt tccatttgac aagagagtag atcctaacaa atttacaggg 1380
ggaagcaaat ccgtcaaact gggagacgat gtatatgaga gccgttcagc tttaagtgta 1440
ataaatgcag tgagtaatca gctacaagtt tttctaaact atattgatac agaagatttg 1500
tattttgacc aatctgtatc ccctggtggc actgcatgtg ggtcaggtaa ttccacaatt 1560
tggccagacc aaaaaattca agctatatac cctatacaac ctgataattc tcaaacatat 1620
ccaagttatt attcaacaag taaaatagga tttgttacta cacttgtccc taatgatacc 1680
actccatgga tcacttttac cgataacggc aataacagca tttatacgtt ttctgcagaa 1740
aatacacgaa ctcttacagg ttcagcggga ccggttcgtg aatttataac tggttcagct 1800
cctcttggac tgtctcctgg aggcggtgca caatattcta ttaatactag tgatgctcct 1860

-continued

```
agcggagatt atcaggttcg cgttcatgta gccacacctg gctctggtgg gtcccttgct   1920
atctcagttg atggaaaaac gcaaacttta caactaccgg atacaaatgt gaacgataca   1980
aaccatatag cgggattcgc gggaacatat acgcttgctc ctgcaaccca agtagacgct   2040
gcaaccctta aaccaaaggc acctactgaa aatattttcc cagtgcgtca aacatcttct   2100
ctacctgtga gcataaccaa taattcttca acagttatta atatagaccg cattgaattt   2160
gttcctgttt ctgctcctgc tcctgatcct agtcctgact ctggtaagcc aatacacaaa   2220
tcagtgccta agacagtgac acaactaagc acaacgaaag agatttggtc atctactagc   2280
gagtatgcta caactatatc ttttacaggg aatgtttata acgatgcttc cattacattt   2340
cagttattaa gttcaggtca ggtagtgaaa gaatttccat ttaccggaaa cggggtcgcg   2400
agtaaaccag gttttcatgg cagttcaccg tcctgctatg acacgcctta tccattttcc   2460
caaccggacc tatcagtgcc taaatataat aaattgcagg tggtaatgaa gagcgatggt   2520
tactcaaaac cttgtgatct tggcgactca ttccctaata cttttgatgc ggaaatagac   2580
ataaagttta atttgagtga taccgcagac ttagcacaaa tcactgcaca agtgcaggga   2640
ttattcacat cttcttcatc tacagaatta tctccaaacg tttccggcta tcaaattgat   2700
caaatcgcac tgaaagtgaa tgcactatcc gatgaagtat tttgtaaaga aaaaatagta   2760
ttacgcaaat tagtcaacaa agccaagcaa ttcatgaaga cacgtaatct gctgataggc   2820
ggggattttg aaatacttga taaatgggca ttaggaacac aagctactat aaaagataat   2880
tcatctttat ttaaagggaa tcacttattt ttacaaccga ctaatggcat atcttcatct   2940
tatgcttatc aaaaaataga tgaatccaag ttaaaaccct acacacgcta taacgtttct   3000
ggttttgtag cgcaaagtga acacttagaa attgtcgttt ctcgctatgg gaaagaaatc   3060
gataaaatat taaatgtccc atatgaagaa gcattaccgg tttcttctgg gaatcagtcc   3120
acttgttgca aaccatcttc ttgctcatgt tcagcttgta ctggtggacc acatccacat   3180
ttctttagct atagcattga tgtcggtaag ctatatccag acttaaatcc aggaatagaa   3240
tttggactgc gtcttgcaca cccaagtgga tatgcaaaag tcggcaatct cgaaattgta   3300
gaagaacgcc ctcttacaaa cacagaaatt cgaaaaatcc aaagaaaaga agagaaatgg   3360
aaaaaagcat gggatacaga acgggcagaa attaatgcca tccttcagcc agtcattaac   3420
cagatcaatg ctttctatac aaatggagat tggaacggtt ctattcttcc tcatgtcaca   3480
tatcaagacc tatataatat cgtattacca gaattatcaa aattaagaca ttggtttatg   3540
aaagatcgtc caggtgaaca ctatactatc ctccaacaat tcaagcaagc tttagaacgc   3600
gtattcaatc aattagaaga aagaaactta atccacaatg gtagttttac aaatggatta   3660
gcaaattggc tggtagacgg agatacccaa ataactacct tagaaaatgg aaatctcgca   3720
ttacaactct cagactggga tgcaagcgca tcacaatcca ttgatatctc ggactttgat   3780
gaagataaag aatatacagt tcgcgtatat gcaaaaggaa aaggaaccat tagaactgta   3840
aactgtgaaa atgagcccct atcctttaat acaaacacat tcacaatcct agaacaacga   3900
ttatatttcg acaacccatc cgttctcctg cacatacaat cagaaggttc tgaattcgtc   3960
ataggcagtg tggaactcat tgaattgtca gacgacgaa                          3999
```

<210> SEQ ID NO 26
<211> LENGTH: 1134
<212> TYPE: DNA
<213> ORGANISM: Bacillus thuringiensis

<400> SEQUENCE: 26

```
ttgtattgta atacaatatt gcgaaaacgt tataaaaagt tagctacgat tataccgctt      60

acaagtatgt cagccgttgc gattgcacct gctacgtctt ttgcagttga aacacaaaaa     120

gcagatgttt catcacaaga agggccgatt caaggttacc agatggaaaa tggaaaaatt     180

actcctgtgt acaaaaataa acttacccag tttaatacgg cggatgatat cgatcctggc     240

cttccactac tcccagagaa tccatataat ccaattcctg atcatggaac tgcatatgtt     300

gaatcaactg atataggaga tactgtatat ttcaaaccat ttgaaccccc taaaaataat     360

gtattagagt taggtgactg tgatgataat acttatcagt ggtccgtatt tgtagattca     420

cagaaatata aaagtgtagg atactttgtt caaaaacaag ccgatggtca aattagagtt     480

ggatattata atccagaaga tttatctctg attacagatt caaaccatgc tttcgcagga     540

gtgccaggtt tcaaactgac agcagaagag aaagctgaga tgcaacgaga tttaaatcga     600

gaatatggcg atatatggga tggcacaagt aaactaaaac gagaaacaaa ctataaactt     660

ctgccaaatg cctcaggtct acaggatgac gcatcgggat ttggttataa tcaaacatta     720

acttcgggtg tatcaactac aaatatgttt ggaatagcga caacagttgg gtggaaaatg     780

gggataaaag tatcggttgt tcctcttgtt gcagacgtta cgtcagagat tagtgcaagt     840

ttaacagcta gttatcagca tactgtaaac gttacaaacc aaacgagttc gcaagtgaaa     900

tttgacgtat caagagtaga taaccctgac tataagtata atgactatgc ggcagctgta     960

tacaaaatat acacagacta tacattagaa ccgggtaaag gattatctcg tttttttagca    1020

aagcaagatc ttaaagatcc tgtgcgtaca gctgcattag caaatacgaa ttatgcatat    1080

gaaggttcaa aatactactt tacagtaaca cctggatcac acaagaaaat tgtg           1134
```

<210> SEQ ID NO 27
<211> LENGTH: 1149
<212> TYPE: DNA
<213> ORGANISM: Bacillus thuringiensis

<400> SEQUENCE: 27

```
atggattttt taaattatta taataaatta aaaaatgaat tggatgatgt aaattctaaa      60

aaatattctt tagaatatac atcagatgga ttaatggttc aacctactga tgatccatta     120

aacacaatgc ctttgcctga tagacctgta ttatctggaa acccaaatga ccctatccct     180

tcagaaggaa caacacgtac agatattcaa aaacaaaatc caccctttttt tacatttaaa    240

gtagtagcta aattagctta ttctggaaaa ggtgaaaatt gtcaaaaggc tcgtgcagca     300

tcagtttatg gtgcagttct tgaacttgaa aaagttaaac aattaccaga atattctaat     360

gtatatttat actcggaaac aggaataaaa acagatcgta gtaatataag atacaacacg     420

gacggtataa tacaattttt gaatcctagt tttataaaca cattttcttc aaatcctata     480

aaatatgggg atacagtagg ttatatttct tatccatatg atacattaaa atttccttct     540

acaacacaat tagaacgttt ggtgtacttt aatttactag atagtaatat tcttgataaa     600

cacattggtt ttgattggtc aaaaagtgtt acaaatggaa cagaagatac agaaatgtgg     660

actcatagtt ccactgttgg cgctgaatta aatcttaaag atatactaca gatcaatgca     720

agttatgagc atacattttc aacgtctcat atggagaaaa aagagaatac tgtatcaaaa     780

actgctcatt ttaatagtcc tttacctcct tataactatg ctacatgggt agcagctata     840

tatcaattat ccattcgata tcaacgtaca aatgcacaac cgatactaga tacgataaat     900

gctgttaatt caggattaac agcatctgaa acagatattt atctgaaggc attatacggt     960

gctgggaaga atggtaagcc tgctgtgggt gatccatcaa tattacacaa gttaagtaat    1020
```

```
gtcatagaag atgcttatga atatttatat tattcggata ctctttattt tactcaaact   1080

ccttctggaa acagcccaac accaaattct ccaaatcgca ttcaatttat tgccacagat   1140

cctcaaagt                                                           1149


<210> SEQ ID NO 28
<211> LENGTH: 651
<212> TYPE: PRT
<213> ORGANISM: Bacillus thuringiensis

<400> SEQUENCE: 28

Met Glu Ile Lys Ile Gly Ser Gly Gly Thr Tyr Met Asn Pro Tyr Asn
 1               5                  10                  15

Asn Glu Ser Tyr Glu Ile Ile Asp Leu Asn Thr Ser Pro Tyr Pro Ser
            20                  25                  30

Asn Arg Asn Asn Ser Arg Tyr Pro Tyr Ala Asn Ala Cys Gly Phe Pro
        35                  40                  45

Glu Asn Val Asp Trp Thr Ala Gly Ala Ser Ala Met Ile Ile Val Ala
    50                  55                  60

Gly Thr Leu Leu Ser Ala Ile Gly Ser Gly Gly Val Gly Ile Val Ala
65                  70                  75                  80

Ala Gly Ile Ile Ser Val Gly Thr Leu Phe Pro Phe Phe Trp Pro Gln
                85                  90                  95

Asp Lys Pro Thr Ala Gln Val Trp Lys Asp Phe Ile Lys Gln Gly Asp
            100                 105                 110

Thr Ile Thr Asn Lys Thr Ile Ser Ala Ala Val Glu Ser Leu Val Leu
        115                 120                 125

Ala Glu Leu Asn Gly Leu Lys Ser Ile Leu Asp Val Tyr Thr Asp Ala
    130                 135                 140

Leu Glu Leu Trp Lys Lys Asp Lys Asn Asn Ile Val Asn Arg Asp Asn
145                 150                 155                 160

Val Lys Ser Ile Phe Thr Asn Leu His Leu Gln Phe Val Ala Ala Met
                165                 170                 175

Pro Lys Phe Ala Thr Asn Gly Tyr Glu Val Ile Leu Leu Ser Thr Tyr
            180                 185                 190

Thr Ala Ala Ala Leu Leu His Ile Thr Phe Leu His Glu Ala Leu Gln
        195                 200                 205

Tyr Ala Asn Glu Trp Asn Leu Ala Arg Ser Glu Gly Thr Phe Tyr Arg
    210                 215                 220

Gly Gln Leu Ile Gln Ala Ile Glu Asn Tyr Ile Asn Tyr Cys Glu Lys
225                 230                 235                 240

Trp Tyr Arg Glu Gly Leu Glu Ile Leu Lys Asn Ser Thr Trp Asp Ile
                245                 250                 255

Tyr Ala Ala Tyr Gln Asn Glu Tyr Thr Leu Ser Ile Leu Asn Val Ile
            260                 265                 270

Ser Ile Phe Pro Arg Phe Asp Ile Arg Asn Phe Pro Thr Asn Ile Ala
        275                 280                 285

Thr Arg Leu Glu Ser Thr Gln Lys Leu Tyr Thr Thr Thr Pro Asn Met
    290                 295                 300

Lys Ala Leu Lys Thr Asn Asn Ser Ile Asp Tyr Ile Lys Asp Lys Leu
305                 310                 315                 320

Ile Pro Pro Leu Asp Leu Phe Lys Lys Leu Lys Ser Leu Thr Phe Tyr
                325                 330                 335

Thr Phe Leu Asp Ser Asn Asn Gln Tyr Asp His Leu Gln Gly Ile Val
            340                 345                 350
```

```
Asn Asn Ser Tyr Tyr Thr Asn Ile Ser Thr Asn Lys Ile Phe Ser Ser
        355                 360                 365

Gly Thr Thr Glu Gly Ser Ser Tyr Gln Leu Gly Leu Ala Ser Asp Gln
    370                 375                 380

Val Ile Tyr Tyr Thr Asp Ile Phe His His Leu Asn Gln Ser Asn Phe
385                 390                 395                 400

Lys Asp Gly Ser Leu Gly Ile Lys Ile Ile Asn Phe Asn Ile Ile Asn
                405                 410                 415

Lys Tyr Asn Glu Val Ser Gln Lys Ser Tyr Asp Ser Asn Ala Thr Ser
            420                 425                 430

Asn Leu Ile Leu Glu Val Ile Leu Pro Phe Leu Lys Thr Thr Glu Lys
        435                 440                 445

Asp Tyr Lys Tyr Ile Leu Ser Tyr Ile Thr Ile Thr Pro Gln Gln Ile
    450                 455                 460

Val Gly Cys Leu Ser Pro Ser Tyr Ile Tyr Gly Phe Ile Trp Thr His
465                 470                 475                 480

Ser Ser Val Asn Leu Asn Asn Thr Ile His Tyr Thr Asn Lys Asn Asn
                485                 490                 495

Phe Ser Gln Ile Thr Gln Ile Ser Ala Val Lys Ala Tyr Leu Lys Lys
            500                 505                 510

Asp Arg Val Ser Val Ile Glu Gly Pro Gly His Thr Gly Gly Asp Leu
        515                 520                 525

Val Lys Phe Thr Gln Trp Asp Asp Ser Ile Ser Thr His Tyr Gln Phe
    530                 535                 540

Thr Ser Ser Gly Glu Tyr Lys Ile Arg Val Arg Tyr Ala Ser Thr Ala
545                 550                 555                 560

Gln Val Asn Gln Thr Ser Gly Leu Ser Met Thr Ile Tyr His Lys Gly
                565                 570                 575

Asn Pro Thr Glu Thr Trp Asp Leu Asn Ile Asn Asn Lys Ser Asp Thr
            580                 585                 590

Ile Leu Asn Leu Asn Glu Pro Lys Tyr Asn His Phe Gln Tyr Thr Glu
        595                 600                 605

Phe Pro Asn Lys Thr Leu Ile Ile Asn Lys Asp Pro Asn Ser Pro Tyr
    610                 615                 620

Leu Glu Leu Arg Ile Asp Leu Ser Tyr Lys Gly Asn Thr Ala Thr Thr
625                 630                 635                 640

Leu Ile Asp Lys Ile Glu Phe Ile Pro Val Ser
                645                 650


<210> SEQ ID NO 29
<211> LENGTH: 506
<212> TYPE: PRT
<213> ORGANISM: Bacillus thuringiensis

<400> SEQUENCE: 29

Met Asn Gly Asn Gly Lys His Asp Asn Trp Asn His Asn Gln Gln Ile
 1               5                  10                  15

Ser Asn Val Gln Met Asn His Asn His Gly Arg Ser Tyr Asp Cys Ser
            20                  25                  30

Cys Gln Gln Asn Gln Tyr Gly Tyr Glu Gln Gln Lys Gln Gln Tyr Glu
        35                  40                  45

Gln Asn Asn Ser Gln Tyr Met Gln Asn Asn Leu Gly Asn Glu Asn Arg
    50                  55                  60

Asn Gly Leu Tyr Pro Tyr Gln Glu Asn Gln Tyr Glu Gln Asn Lys Asn
65                  70                  75                  80
```

-continued

```
Tyr Tyr Ala Ser Asn Asn Leu Thr Tyr Asn Gln Ser Asp Leu Tyr Asn
                85                  90                  95

Ser Asn Pro Gln Asn Met Tyr Lys His Gln Thr Tyr Ser Asn Asp Phe
            100                 105                 110

Tyr Cys Ser Pro Ser Tyr Thr Ala Gly Glu Asn Asn Ile Leu Asp Leu
        115                 120                 125

Leu Gly Thr Glu Ser Lys Gln Phe Gln Lys Ile Ser Asn Ile Asn Thr
    130                 135                 140

Lys Asp Leu His Arg Ser Ile Thr Ala Ser Asn Thr Gln Ile Gly Tyr
145                 150                 155                 160

Gln Ile Asp Thr Arg Val Pro Gly Pro Cys Lys Gly Val Asp Tyr Gln
                165                 170                 175

Asn Thr Val Thr Tyr Glu Gln Asn Ser Ile Gly Gly Asp Ser Gln Tyr
            180                 185                 190

Leu Ile Phe Tyr Lys Thr Asp Tyr Thr Asp Ala Phe Ile Ile Ala Asn
        195                 200                 205

Arg Ala Asn Gly Arg Val Leu Glu Val Ile Pro Ser Ser Val Asn Gly
    210                 215                 220

Phe Val Thr Ile Ser Asn Met Phe Thr Tyr Asn Gln Asn Gln Leu Phe
225                 230                 235                 240

Ile Arg Thr Lys Ile Ser Asn Asn Asp Asn Ser Asp Asp Val Pro Phe
                245                 250                 255

Ser Leu Thr Thr Glu Asn Asn Gln Thr Leu Asn Ile Cys His His Glu
            260                 265                 270

Phe Gln Tyr Asn Thr Lys Ile Thr Ala Leu Asp Asn Ala Tyr Arg Leu
        275                 280                 285

Asp Asp Lys Val Leu Phe Lys Pro Thr Arg Asp Lys Ile Asn Ile Ser
    290                 295                 300

Phe Pro Asn Met Val Val Asn Ala Lys Glu Lys Leu Pro Glu Pro Glu
305                 310                 315                 320

Glu Leu Thr Asn Met Asp Lys Asn Thr Leu Phe Ile Pro Lys Val Ile
                325                 330                 335

Ile Ser Lys Thr Leu Ile Pro Gly Ile Ile Val Asn Asp Val Thr Leu
            340                 345                 350

Leu Lys Glu Gln Gln Ile Ala Lys Ser Pro Tyr Tyr Val Leu Glu Tyr
        355                 360                 365

Val Gln Ser Trp Glu Glu Val Tyr Asn Glu Ile Val Pro Ala Tyr Arg
    370                 375                 380

Pro Ser Tyr Thr Trp Thr Ser Thr Asp Gly Ile Arg His Val Asn Leu
385                 390                 395                 400

Leu Asp Ile Lys Asn Thr Ile Asn Ile Ser Ile Gly Gly Thr Ser Gln
                405                 410                 415

Gly Trp Gly Leu Arg Phe Ser Asp Lys Ser Asp Leu Phe Lys Asn Ile
            420                 425                 430

Ile Thr Ser Ala Phe Ile Ile Lys Ser Thr Gln Ala Pro Asp Met Gly
        435                 440                 445

Phe Ser Glu Asn Asp Ile Asp Gln Tyr Tyr Gly Lys Asn Ile Asp Ser
    450                 455                 460

Arg Val Lys Ile Tyr Ile Lys Thr His Asn Leu Ile Leu Arg Arg Leu
465                 470                 475                 480

Asp Gln Leu Asn Asn Ser Ile Ala Thr Trp Thr Ile Phe Glu Asn Thr
                485                 490                 495

Lys Pro Val Ile Arg Thr Phe Pro Ile Ser
```

500 505

<210> SEQ ID NO 30
<211> LENGTH: 779
<212> TYPE: PRT
<213> ORGANISM: Bacillus thuringiensis

<400> SEQUENCE: 30

```
Met Lys Asp Lys Lys Tyr Trp Lys Tyr Glu Gly Gly Thr Lys Met Asn
 1               5                  10                  15

Pro Tyr Gln Asn Lys Asn Glu Tyr Glu Ile Val Asn Asn Pro Gln Asn
            20                  25                  30

Tyr Asn Thr Val Ser Asn Arg Tyr Pro Tyr Thr Asn Asp Pro Asn Val
        35                  40                  45

Ala Ile Gln Asn Thr Asn Tyr Lys Asp Trp Met Asn Gly Tyr Glu Glu
    50                  55                  60

Ile Asn Pro Ser Ser Ile Ser Leu Ile Leu Ala Ser Ile Gly Ile Leu
65                  70                  75                  80

Asn Gln Ala Ile Ala Leu Thr Gly Val Leu Gly Lys Thr Pro Glu Ile
                85                  90                  95

Ile Asn Ile Val Gln Glu Met Val Gly Leu Ile Ser Gly Ser Thr Gly
            100                 105                 110

Asn Asp Leu Leu Val His Thr Glu Gln Leu Ile Gln Gln Thr Leu Ala
        115                 120                 125

Gln Gln Tyr Arg Asn Ala Ala Thr Gly Ala Val Asn Ala Ile Ser Lys
    130                 135                 140

Ser Tyr Asn Asp Tyr Leu Met Phe Phe Arg Gln Trp Glu Arg Asn Arg
145                 150                 155                 160

Thr Ser Gln Asn Gly Leu Gln Val Glu Ser Ala Phe Asn Thr Val Asn
                165                 170                 175

Thr Leu Cys Leu Arg Thr Leu Thr Pro Gln Glu Ala Leu Ser Arg Arg
            180                 185                 190

Gly Phe Glu Thr Leu Leu Leu Pro Asn Tyr Ala Leu Ala Ala Asn Phe
        195                 200                 205

His Leu Leu Leu Leu Arg Asp Ala Val Leu Tyr Arg Thr Gln Trp Leu
    210                 215                 220

Pro Asn Phe Ile Ser Thr Thr Asn Ala Asn Ile Glu Ile Leu Glu Arg
225                 230                 235                 240

Ser Ile Asn Gln Tyr Arg Asn His Cys Asn His Trp Tyr Asn Asp Gly
                245                 250                 255

Leu Asn Arg Phe Ala Arg Thr Ser Phe Asp Asp Trp Val Arg Phe Asn
            260                 265                 270

Ala Tyr Arg Arg Asp Met Thr Leu Ser Val Leu Asp Phe Val Thr Val
        275                 280                 285

Phe Pro Thr Tyr Asn Pro Ile Asn Phe Pro Thr Pro Thr Asn Val Glu
    290                 295                 300

Leu Thr Arg Ile Val Tyr Thr Asp Pro Ile Ser Pro Pro Arg Gly Tyr
305                 310                 315                 320

Ala Arg Thr Gly Ser Pro Ser Phe Arg Gln Met Glu Asp Leu Ile Ile
                325                 330                 335

Ser Gly Ser Pro Ser Phe Leu Asn Gln Leu Ser Ile Phe Thr Thr Tyr
            340                 345                 350

Tyr His Asp Pro Arg Asn Val Asn Arg Asp Phe Trp Ala Gly Asn Arg
        355                 360                 365

Asn Tyr Leu Ser Asn Gly Thr Ser Arg Gln Ser Gly Ala Thr Thr Pro
```

```
    370                 375                 380

Trp Arg Thr Asn Ile Pro Met Gln Asn Ile Asp Ile Phe Arg Val Asn
385                 390                 395                 400

Leu Thr Thr His Asp Ile Asp Asp Ile Ser Arg Ser Tyr Gly Gly Val
                405                 410                 415

His Arg Ser Asp Phe Ile Gly Val Asn Thr Ile Asn Asn Gln Arg Thr
            420                 425                 430

Thr Leu Phe Tyr His Gln Asn Val Asp Thr Ser Arg Phe Leu Ile Arg
        435                 440                 445

Asn Glu Thr Val Phe Leu Pro Gly Asp Ser Gly Leu Ala Pro Asn Glu
    450                 455                 460

Arg Asn Tyr Thr His Arg Leu Phe Gln Val Met Thr Thr Tyr Arg Thr
465                 470                 475                 480

Asn Pro Asn Ala Arg Arg Ala Ala Phe Leu His Ala Trp Thr His Arg
                485                 490                 495

Ser Leu Arg Arg Arg Asn Gly Phe Arg Thr Asp Gln Ile Met Gln Ile
            500                 505                 510

Pro Ala Val Lys Ser Ile Ser Asn Gly Gly Asp Arg Ala Val Ile Ser
        515                 520                 525

Tyr Thr Gly Glu Asn Met Met Lys Leu Asp Asn Leu Thr Ala Ser Leu
    530                 535                 540

Ser Tyr Lys Leu Thr Ala Glu Asp Ser Glu Ala Ser Asn Thr Arg Phe
545                 550                 555                 560

Ile Val Arg Ile Arg Tyr Ala Ser Met Asn Asn Asn Arg Leu Asn Leu
                565                 570                 575

Ile Leu Asn Gly Thr Gln Ile Ala Ser Leu Asn Val Glu Gly Thr Met
            580                 585                 590

Gln Asn Gly Gly Ser Leu Thr Asn Leu Gln Ser Glu Asn Phe Lys Tyr
        595                 600                 605

Ala Thr Phe Ser Gly Asn Phe Lys Met Gly Ser Gln Ser Ile Val Gly
    610                 615                 620

Ile Phe Lys Glu Ile Ser Asn Ala Asp Phe Ile Leu Asp Lys Ile Glu
625                 630                 635                 640

Leu Ile Pro Ile His Phe Met Pro Leu Leu Glu Gln Lys Gln Ser Tyr
                645                 650                 655

Asn Asn Tyr Asp Gln Asn Met Asp Thr Thr Tyr Gln Pro Asn Tyr Asp
            660                 665                 670

Thr Tyr Asn Gln Asn Ala Asn Gly Met Tyr Asp Asp Thr Tyr Tyr Pro
        675                 680                 685

Asn Asn Asn Asp Ser Tyr Asn Gln Asn Asn Thr Asp Met Tyr Asp Ser
    690                 695                 700

Gly Tyr Asn Asn Asn Gln Asn Thr Asn Tyr Asn Tyr Asp Gln Glu Tyr
705                 710                 715                 720

Asn Thr Tyr Asn Gln Asn Met Glu Asn Thr Tyr Asp Gln Ser Tyr Glu
                725                 730                 735

Asn Tyr Asn Pro Glu Thr Asn Asn Tyr Asn Gln Tyr Pro Asn Asp Met
            740                 745                 750

Tyr Asn Gln Glu Tyr Thr Asn Asp Tyr Asn Gln Asn Ser Gly Cys Arg
        755                 760                 765

Cys Asn Gln Gly Tyr Asn Asn Asn Tyr Pro Lys
    770                 775

<210> SEQ ID NO 31
<211> LENGTH: 322
```

```
<212> TYPE: PRT
<213> ORGANISM: Bacillus thuringiensis

<400> SEQUENCE: 31

Met Asn Phe Leu Tyr Asn Phe Val Thr Leu Asp Met Leu Ile Leu Asn
 1               5                  10                  15

Arg Leu Glu Gly Ser Asp Phe Lys Met Lys Lys Lys Ala Ile Val Cys
            20                  25                  30

Gly Leu Leu Ala Ser Thr Leu Leu Gly Gly Gly Thr Phe Val Asp Ala
        35                  40                  45

Val Ser Ala Ala Glu Ile Gln Lys Thr Asn His Leu Asn Lys Tyr Asp
    50                  55                  60

Ser Ala Gln Glu Lys Ala Leu Gln Asp Ile Asn Gln Glu Ala Leu Gln
65                  70                  75                  80

Asp Ile Asp Gln Lys Val Asn Lys Met Ile Asp Ser Ile Pro Pro Ile
                85                  90                  95

Phe Gly Ser Lys Tyr Thr Arg Thr Asp Arg Tyr Gly Glu Ser Leu Thr
            100                 105                 110

Tyr Ser Gly Ile Asn Leu Lys Glu Asn Asn Ser Thr Asn Val Glu Pro
        115                 120                 125

Met Tyr Phe Gly Ser Asn Thr Phe Tyr Asn Asp Thr Glu Leu Glu Gln
    130                 135                 140

Ser Tyr Asn Thr Thr Ser Phe Ser Glu Ala Val Thr Lys Ser Thr Thr
145                 150                 155                 160

Thr Gln Thr Gln Asn Gly Phe Lys Ser Gly Val Thr Thr Gly Gly Lys
                165                 170                 175

Val Gly Ile Pro Phe Val Ala Glu Gly Glu Val Lys Ile Asn Leu Glu
            180                 185                 190

Tyr Asn Phe Thr His Thr Asn Ser Asn Thr Thr Ser Lys Thr Thr Thr
        195                 200                 205

Leu Thr Ala Pro Pro Gln Pro Val Lys Val Pro Ala Gly Lys Val Tyr
    210                 215                 220

Lys Ala Asp Val Tyr Phe Glu Lys Lys Ser Thr Ser Gly Thr Val Glu
225                 230                 235                 240

Leu Tyr Gly Asp Leu Leu Thr Gly Val Val Ala Glu Gly Arg Thr Ser
                245                 250                 255

Phe Val Gly Asn Val Leu His Lys Ala Thr Asp Thr Gln Gly Leu Ile
            260                 265                 270

Gln Ser Pro Glu Asp Ser Asn Lys Val Arg Ala Val Gly Lys Gly Thr
        275                 280                 285

Phe Thr Thr Glu His Gly Ser Asn Phe Ile Val Lys Thr Tyr Asp Val
    290                 295                 300

Thr Ser Gly Gln Lys Ser Ala Lys Leu Val Asp Thr Arg Val Ile Pro
305                 310                 315                 320

Ile Lys


<210> SEQ ID NO 32
<211> LENGTH: 323
<212> TYPE: PRT
<213> ORGANISM: Bacillus thuringiensis

<400> SEQUENCE: 32

Met Asn Leu Arg Arg Ile Ser Met Arg Val Tyr Lys Lys Leu Ala Thr
 1               5                  10                  15

Leu Ala Pro Ile Ala Ala Leu Ser Thr Ser Ile Leu Cys Ser Pro Ala
            20                  25                  30
```

```
Met Thr Phe Ala Ala Glu Lys Glu Ser Thr Val Lys Gln Thr Thr Gln
        35                  40                  45

Gln Ser Ala Val Gln Gln Gly Arg Ile Ile Gln Gly Tyr Leu Ile Lys
    50                  55                  60

Asn Gly Val Lys Ile Pro Val Tyr Thr Gly Gly Leu Val Thr Asn Lys
65                  70                  75                  80

Ala Glu Gln Gly Ala Ala Ala Phe Pro Gln Leu Ser Ser Asn Pro Asn
                85                  90                  95

Asp Pro Ile Pro Gln Lys Gly Ser Ile Ser Ser Glu Asp Gly Asn Ile
            100                 105                 110

Gly Asp Ile Leu Tyr Phe Ser Lys Thr Pro Met Gly Asp Asn Val Tyr
        115                 120                 125

Ile Lys Lys Leu Glu Asn Asn Asn Ile Glu Ile Gly Lys Tyr Asn Arg
    130                 135                 140

Gly Thr Leu Glu Leu Ser Lys Phe Val Thr Val Asn Gly Asp Pro Gln
145                 150                 155                 160

Gly Pro Ile Met Leu Phe Asp Ala Thr Val Lys Arg Glu Thr Ala Phe
                165                 170                 175

Glu Lys Ile Gly Gly Ala Val Gln Pro Lys Ala Thr Gln Tyr Thr Phe
            180                 185                 190

Ser Gln Ala Val Thr Ser Gly Leu Ser Thr Ser Asp Ala Ile Gly Gly
        195                 200                 205

Ser Leu Thr Leu Gly Tyr Lys Ile Ser Leu Lys Glu Gly Gly Gly Val
    210                 215                 220

Val Pro Ala Glu Ala Thr Gln Glu Phe Ser Thr Gln Leu Ser Ala Thr
225                 230                 235                 240

Tyr Asn His Thr Ile Thr Val Thr Asn Gln Thr Thr Asn Thr Gln Thr
                245                 250                 255

Gln Thr Phe Lys Pro Ile Asp Ser Tyr Gly Gln Ser Thr Tyr Ala Ala
            260                 265                 270

Ala Val Tyr Gln Leu Lys Ser His Tyr Thr Val Ile Pro Gly Ala Gly
        275                 280                 285

Leu Gln Lys Gly Leu Asn Ser Gly Tyr Val Leu Asp Gln Thr Ala Phe
    290                 295                 300

Ser Tyr Ser Asp Ser Asp Leu Tyr Leu Ala Val Thr Pro Gly Ala Gly
305                 310                 315                 320

Ser Asn Val


<210> SEQ ID NO 33
<211> LENGTH: 252
<212> TYPE: PRT
<213> ORGANISM: Bacillus thuringiensis

<400> SEQUENCE: 33

Met Ile Thr Asn Gln Ala Ala Gln Ala Ser Asp Ala Pro Tyr Pro Glu
 1               5                  10                  15

Leu Pro Ser Asn Pro Asn Asp Ala Ile Pro Asn Ala Gly Ala Thr His
            20                  25                  30

Ala Glu Asn Gly Ser Val Gly Ser Val Leu Tyr Phe Lys Gln Ile Asp
        35                  40                  45

Leu Asn Asn Leu Gly Ala Gly Ile Gly Asn Ser Gln Lys Asp Tyr Val
    50                  55                  60

Tyr Val Glu Lys Lys Gly Asp Ser Gly Tyr Glu Leu Gly Asn Tyr Asn
65                  70                  75                  80
```

-continued

Pro Leu Thr Leu Gln Arg Thr Lys Ile Lys Asp Tyr Asp Lys Ser Ser
85 90 95

Glu Leu Ala Glu Lys Met Asp Gly Tyr Phe Lys Ser Thr Ile Thr Arg
100 105 110

Asp Thr Phe Phe Ser Lys Ile Gly Ser Gly Val Val Pro Lys Asn Ala
115 120 125

Ala Tyr Thr Phe Ser Gln Ala Val Thr Ser Gly Leu Thr Thr Ser Asp
130 135 140

Ala Ile Gly Gly Ala Leu Thr Leu Gly Tyr Lys Val Ser Val Thr Glu
145 150 155 160

Gly Gly Gly Ile Phe Pro Ala Ala Ala Ser Glu Glu Phe Ser Ala Gln
165 170 175

Leu Thr Ala Thr Tyr Asn His Thr Ile Thr Val Ser Ser Gln Val Thr
180 185 190

Asn Thr Gln Thr Leu Gly Ile Thr Lys Ala Ala Asp Gly Tyr Gln Tyr
195 200 205

Asp Lys Tyr Val Gly Ala Val Tyr Gln Leu His Ser Lys Tyr Thr Phe
210 215 220

Lys Pro Ser Asp Glu Leu Gln Phe Ala Met Asn Ser Pro Phe Gly Tyr
225 230 235 240

Lys Val Ile Leu Asn Gln Arg Ala Gln Ser Phe Gln
245 250

<210> SEQ ID NO 34
<211> LENGTH: 1441
<212> TYPE: PRT
<213> ORGANISM: Bacillus thuringiensis

<400> SEQUENCE: 34

Met Thr Thr Ile Asn Glu Leu Tyr Pro Ala Val Pro Tyr Asn Val Leu
1 5 10 15

Ala Tyr Ala Pro Pro Leu Asn Leu Ala Asp Ser Thr Pro Trp Gly Gln
20 25 30

Ile Val Val Ala Asp Ala Ile Lys Glu Ala Trp Asp Asn Phe Gln Lys
35 40 45

Tyr Gly Val Leu Asp Leu Thr Ala Ile Asn Gln Gly Phe Asp Asp Ala
50 55 60

Asn Thr Gly Ser Phe Ser Tyr Gln Ala Leu Ile Gln Thr Val Leu Gly
65 70 75 80

Ile Ile Gly Thr Ile Gly Met Thr Val Pro Val Ala Ala Pro Phe Ala
85 90 95

Ala Thr Ala Pro Ile Ile Ser Leu Phe Val Gly Phe Phe Trp Pro Lys
100 105 110

Lys Asp Lys Gly Pro Gln Leu Ile Asp Ile Ile Asp Lys Glu Ile Lys
115 120 125

Lys Leu Leu Asp Lys Glu Leu Gly Glu Gln Lys Arg Asn Asp Leu Val
130 135 140

Ser Ala Leu Asn Glu Met Gln Glu Gly Ala Asn Glu Leu Ser Asp Ile
145 150 155 160

Met Thr Asn Ala Leu Phe Glu Gly Thr Ile Gln Gly Asn Val Val Thr
165 170 175

Asn Asp Asn Pro Gln Gly Lys Arg Arg Thr Pro Lys Ala Pro Thr Val
180 185 190

Ser Asp Tyr Glu Asn Val Tyr Ser Ala Tyr Phe Val Glu His Val Asp
195 200 205

-continued

```
Phe Arg Asn Lys Ile Ser Thr Phe Leu Thr Gly Ser Tyr Asp Leu Ile
    210                 215                 220

Ala Leu Pro Leu Tyr Ala Leu Ala Lys Thr Met Glu Leu Ser Leu Tyr
225                 230                 235                 240

Gln Ser Phe Ile Asn Phe Ala Asn Lys Trp Met Asp Phe Val Tyr Thr
                245                 250                 255

Lys Ala Ile Asn Glu Ser Ala Thr Asp Asp Met Lys Arg Asp Tyr Gln
            260                 265                 270

Ala Arg Tyr Asn Thr Gln Lys Ser Asn Leu Ala Val Gln Lys Thr Gln
        275                 280                 285

Leu Ile Asn Lys Ile Lys Asp Gly Thr Asp Ala Val Met Lys Val Phe
    290                 295                 300

Lys Asp Thr Asn Asn Leu Pro Ser Ile Gly Thr Asn Lys Leu Ala Val
305                 310                 315                 320

Asn Ala Arg Asn Lys Tyr Ile Arg Ala Leu Gln Ile Asn Cys Leu Asp
                325                 330                 335

Leu Val Ala Leu Trp Pro Gly Leu Tyr Pro Asp Glu Tyr Leu Leu Pro
            340                 345                 350

Leu Gln Leu Asp Lys Thr Arg Val Val Phe Ser Asp Thr Met Gly Pro
        355                 360                 365

Asp Glu Thr His Asp Gly Gln Met Lys Val Leu Asn Ile Leu Asp Ser
    370                 375                 380

Thr Thr Ser Tyr Asn His Gln Asp Ile Gly Ile Ser Thr Thr Gln Asp
385                 390                 395                 400

Val Asn Ser Leu Leu Phe Tyr Pro Arg Lys Glu Leu Leu Glu Leu Asp
                405                 410                 415

Phe Ala Lys Tyr Ile Ser Ser Ser Ser Arg Phe Trp Val Tyr Gly Phe
            420                 425                 430

Gly Leu Lys Tyr Ser Asp Asp Asn Phe Tyr Arg Tyr Gly Asp Asn Asp
        435                 440                 445

Pro Ser Ser Asp Phe Lys Pro Ala Tyr Lys Trp Phe Thr Lys Asn Ser
    450                 455                 460

Gln Phe Glu Asn Leu Pro Thr Tyr Gly Asn Pro Thr Pro Ile Thr Asn
465                 470                 475                 480

Leu Asn Ala Lys Thr Gln Val Thr Ser Tyr Leu Asp Ala Leu Ile Tyr
                485                 490                 495

Tyr Ile Asp Gly Gly Thr Asn Leu Tyr Asn Asn Ala Ile Leu His Asp
            500                 505                 510

Thr Gly Gly Tyr Ile Pro Gly Tyr Pro Gly Val Glu Gly Tyr Gly Met
        515                 520                 525

Ser Asn Asn Glu Pro Leu Ala Gly Gln Lys Leu Asn Ala Leu Tyr Pro
    530                 535                 540

Ile Lys Val Glu Asn Val Ser Gly Ser Gln Gly Lys Leu Gly Thr Ile
545                 550                 555                 560

Ala Ala Tyr Val Pro Leu Asn Leu Gln Pro Glu Asn Ile Ile Gly Asp
                565                 570                 575

Ala Asp Pro Asn Thr Gly Phe Pro Leu Asn Val Ile Lys Gly Phe Pro
            580                 585                 590

Phe Glu Lys Tyr Gly Pro Asp Tyr Glu Gly Arg Gly Ile Ser Val Val
        595                 600                 605

Lys Glu Trp Ile Asn Gly Ala Asn Ala Val Lys Leu Ser Pro Gly Gln
    610                 615                 620

Ser Val Gly Val Gln Ile Lys Asn Ile Thr Lys Gln Asn Tyr Gln Ile
625                 630                 635                 640
```

-continued

```
Arg Thr Arg Tyr Ala Ser Asn Asn Ser Asn Gln Val Tyr Phe Asn Val
                645                 650                 655

Asp Pro Gly Gly Ser Pro Leu Phe Ala Gln Ser Val Thr Phe Glu Ser
            660                 665                 670

Thr Thr Asn Val Thr Ser Gly Gln Gln Gly Glu Asn Gly Arg Tyr Thr
        675                 680                 685

Leu Lys Thr Ile Phe Ser Gly Asn Asp Leu Leu Thr Val Glu Ile Pro
    690                 695                 700

Val Gly Asn Phe Tyr Val His Val Thr Asn Lys Gly Ser Ser Asp Ile
705                 710                 715                 720

Phe Leu Asp Arg Leu Glu Phe Ser Thr Val Pro Ser Tyr Val Ile Tyr
                725                 730                 735

Ser Gly Asp Tyr Asp Ala Thr Gly Thr Asp Asp Val Leu Leu Ser Asp
            740                 745                 750

Pro His Glu Tyr Phe Tyr Asp Val Ile Val Asn Gly Thr Ala Ser His
        755                 760                 765

Ser Ser Ala Ala Thr Ser Met Asn Leu Leu Asn Lys Gly Thr Val Val
    770                 775                 780

Arg Ser Ile Asp Ile Pro Gly His Ser Thr Ser Tyr Ser Val Gln Tyr
785                 790                 795                 800

Ser Val Pro Glu Gly Phe Asp Glu Val Arg Ile Leu Ser Ser Leu Pro
                805                 810                 815

Asp Ile Ser Gly Thr Ile Arg Val Glu Ser Ser Lys Pro Pro Val Phe
            820                 825                 830

Lys Asn Asp Gly Asn Ser Gly Asp Gly Gly Asn Thr Glu Tyr Asn Phe
        835                 840                 845

Asn Phe Asp Leu Ser Gly Leu Gln Asp Thr Gly Leu Tyr Ser Gly Lys
    850                 855                 860

Leu Lys Ser Gly Ile Arg Val Gln Gly Asn Tyr Thr Tyr Thr Gly Ala
865                 870                 875                 880

Pro Ser Leu Asn Leu Val Val Tyr Arg Asn Asn Ser Val Val Ser Thr
                885                 890                 895

Phe Pro Val Gly Ser Pro Phe Asp Ile Thr Ile Thr Thr Glu Thr Asp
            900                 905                 910

Lys Val Ile Leu Ser Leu Gln Pro Gln His Gly Leu Ala Thr Val Thr
        915                 920                 925

Gly Thr Gly Thr Ile Thr Ile Pro Asn Asp Lys Leu Ala Ile Val Tyr
    930                 935                 940

Asp Lys Leu Phe Lys Leu Pro His Asp Leu Glu Asn Ile Arg Ile Gln
945                 950                 955                 960

Val Asn Ala Leu Phe Ile Ser Ser Thr Gln Asn Glu Leu Ala Lys Glu
                965                 970                 975

Val Asn Asp His Asp Ile Glu Glu Val Ala Leu Lys Val Asp Ala Leu
            980                 985                 990

Ser Asp Glu Val Phe Gly Lys Glu Lys Lys Glu Leu Arg Lys Leu Val
        995                 1000                1005

Asn Gln Ala Lys Arg Leu Ser Lys Ala Arg Asn Leu Leu Val Gly Gly
    1010                1015                1020

Asn Phe Asp Asn Trp Glu Ala Trp Tyr Lys Gly Lys Glu Val Ala Arg
1025                1030                1035                1040

Val Ser Asp His Glu Leu Leu Lys Ser Asp His Val Leu Leu Pro Pro
                1045                1050                1055

Pro Thr Met Tyr Pro Ser Tyr Ile Tyr Gln Lys Val Glu Glu Thr Lys
```

```
        1060                1065                1070

Leu Lys Pro Asn Thr Arg Tyr Met Ile Ser Gly Phe Ile Ala His Ala
    1075                1080                1085

Glu Asp Leu Glu Ile Val Val Ser Arg Tyr Gly Gln Glu Val Arg Lys
    1090                1095                1100

Ile Val Gln Val Pro Tyr Gly Glu Ala Phe Pro Leu Thr Ser Asn Gly
1105                1110                1115                1120

Ser Ile Cys Cys Thr Pro Ser Phe Arg Arg Asp Gly Lys Leu Ser Asp
                1125                1130                1135

Pro His Phe Phe Ser Tyr Ser Ile Asp Val Gly Glu Leu Asp Met Thr
            1140                1145                1150

Ala Gly Pro Gly Ile Glu Leu Gly Leu Arg Ile Val Asp Arg Leu Gly
        1155                1160                1165

Met Ala Arg Val Ser Asn Leu Glu Ile Arg Glu Asp Arg Ser Leu Thr
    1170                1175                1180

Ala Asn Glu Ile Arg Lys Val Gln Arg Met Ala Arg Asn Trp Arg Thr
1185                1190                1195                1200

Glu Tyr Glu Lys Glu Arg Ala Glu Val Thr Ala Leu Ile Glu Pro Val
                1205                1210                1215

Leu Asn Gln Ile Asn Ala Leu Tyr Glu Asn Gly Asp Trp Asn Gly Ser
            1220                1225                1230

Ile Arg Ser Asp Ile Ser Tyr Tyr Asp Ile Glu Ser Ile Val Leu Pro
        1235                1240                1245

Thr Leu Pro Arg Leu Arg His Trp Phe Val Pro Asp Met Leu Thr Glu
    1250                1255                1260

His Gly Asn Ile Met Asn Arg Phe Glu Glu Ala Leu Asn Arg Ala Tyr
1265                1270                1275                1280

Thr Gln Leu Glu Gly Asn Thr Leu Leu His Asn Gly His Phe Thr Thr
                1285                1290                1295

Asp Ala Val Asn Trp Met Ile Gln Gly Asp Ala His Gln Val Ile Leu
            1300                1305                1310

Glu Asp Gly Arg Arg Val Leu Arg Leu Pro Asp Trp Ser Ser Ser Val
        1315                1320                1325

Ser Gln Thr Ile Glu Ile Glu Lys Phe Asp Pro Asp Lys Glu Tyr Asn
    1330                1335                1340

Leu Val Phe His Ala Gln Gly Glu Gly Thr Val Thr Leu Glu His Gly
1345                1350                1355                1360

Glu Lys Thr Lys Tyr Ile Glu Thr His Thr His His Phe Ala Asn Phe
                1365                1370                1375

Thr Thr Ser Gln Ser Gln Gly Ile Thr Phe Glu Ser Asn Lys Val Thr
            1380                1385                1390

Val Glu Ile Ser Ser Glu Asp Gly Glu Leu Leu Val Asp His Ile Ala
        1395                1400                1405

Leu Val Glu Val Pro Met Phe Asn Lys Asn Gln Met Val Asn Glu Asn
    1410                1415                1420

Arg Asp Val Asn Ile Asn Ser Asn Thr Asn Met Asn Asn Ser Asn Asn
1425                1430                1435                1440

Gln
```

<210> SEQ ID NO 35
<211> LENGTH: 731
<212> TYPE: PRT
<213> ORGANISM: Bacillus thuringiensis

<400> SEQUENCE: 35

-continued

```
Met Thr Thr Ile Asn Glu Leu Tyr Pro Ala Val Pro Tyr Asn Val Leu
1               5                   10                  15

Ala Tyr Ala Pro Pro Leu Asn Leu Ala Asp Ser Thr Pro Trp Gly Gln
            20                  25                  30

Ile Val Val Ala Asp Ala Ile Lys Glu Ala Trp Asp Asn Phe Gln Lys
        35                  40                  45

Tyr Gly Val Leu Asp Leu Thr Ala Ile Asn Gln Gly Phe Asp Asp Ala
    50                  55                  60

Asn Thr Gly Ser Phe Ser Tyr Gln Ala Leu Ile Gln Thr Val Leu Gly
65                  70                  75                  80

Ile Ile Gly Thr Ile Gly Met Thr Val Pro Val Ala Ala Pro Phe Ala
                85                  90                  95

Ala Thr Ala Pro Ile Ile Ser Leu Phe Val Gly Phe Phe Trp Pro Lys
            100                 105                 110

Lys Asp Lys Gly Pro Gln Leu Ile Asp Ile Ile Asp Lys Glu Ile Lys
        115                 120                 125

Lys Leu Leu Asp Lys Glu Leu Gly Glu Gln Lys Arg Asn Asp Leu Val
    130                 135                 140

Ser Ala Leu Asn Glu Met Gln Glu Gly Ala Asn Glu Leu Ser Asp Ile
145                 150                 155                 160

Met Thr Asn Ala Leu Phe Glu Gly Thr Ile Gln Gly Asn Val Val Thr
                165                 170                 175

Asn Asp Asn Pro Gln Gly Lys Arg Arg Thr Pro Lys Ala Pro Thr Val
            180                 185                 190

Ser Asp Tyr Glu Asn Val Tyr Ser Ala Tyr Phe Val Glu His Val Asp
        195                 200                 205

Phe Arg Asn Lys Ile Ser Thr Phe Leu Thr Gly Ser Tyr Asp Leu Ile
    210                 215                 220

Ala Leu Pro Leu Tyr Ala Leu Ala Lys Thr Met Glu Leu Ser Leu Tyr
225                 230                 235                 240

Gln Ser Phe Ile Asn Phe Ala Asn Lys Trp Met Asp Phe Val Tyr Thr
                245                 250                 255

Lys Ala Ile Asn Glu Ser Ala Thr Asp Asp Met Lys Arg Asp Tyr Gln
            260                 265                 270

Ala Arg Tyr Asn Thr Gln Lys Ser Asn Leu Ala Val Gln Lys Thr Gln
        275                 280                 285

Leu Ile Asn Lys Ile Lys Asp Gly Thr Asp Ala Val Met Lys Val Phe
    290                 295                 300

Lys Asp Thr Asn Asn Leu Pro Ser Ile Gly Thr Asn Lys Leu Ala Val
305                 310                 315                 320

Asn Ala Arg Asn Lys Tyr Ile Arg Ala Leu Gln Ile Asn Cys Leu Asp
                325                 330                 335

Leu Val Ala Leu Trp Pro Gly Leu Tyr Pro Asp Glu Tyr Leu Leu Pro
            340                 345                 350

Leu Gln Leu Asp Lys Thr Arg Val Val Phe Ser Asp Thr Met Gly Pro
        355                 360                 365

Asp Glu Thr His Asp Gly Gln Met Lys Val Leu Asn Ile Leu Asp Ser
    370                 375                 380

Thr Thr Ser Tyr Asn His Gln Asp Ile Gly Ile Ser Thr Thr Gln Asp
385                 390                 395                 400

Val Asn Ser Leu Leu Phe Tyr Pro Arg Lys Glu Leu Leu Glu Leu Asp
                405                 410                 415

Phe Ala Lys Tyr Ile Ser Ser Ser Ser Arg Phe Trp Val Tyr Gly Phe
```

```
            420                 425                 430

Gly Leu Lys Tyr Ser Asp Asp Asn Phe Tyr Arg Tyr Gly Asp Asn Asp
        435                 440                 445

Pro Ser Ser Asp Phe Lys Pro Ala Tyr Lys Trp Phe Thr Lys Asn Ser
    450                 455                 460

Gln Phe Glu Asn Leu Pro Thr Tyr Gly Asn Pro Thr Pro Ile Thr Asn
465                 470                 475                 480

Leu Asn Ala Lys Thr Gln Val Thr Ser Tyr Leu Asp Ala Leu Ile Tyr
                485                 490                 495

Tyr Ile Asp Gly Gly Thr Asn Leu Tyr Asn Asn Ala Ile Leu His Asp
            500                 505                 510

Thr Gly Gly Tyr Ile Pro Gly Tyr Pro Gly Val Glu Gly Tyr Gly Met
        515                 520                 525

Ser Asn Asn Glu Pro Leu Ala Gly Gln Lys Leu Asn Ala Leu Tyr Pro
    530                 535                 540

Ile Lys Val Glu Asn Val Ser Gly Ser Gln Gly Lys Leu Gly Thr Ile
545                 550                 555                 560

Ala Ala Tyr Val Pro Leu Asn Leu Gln Pro Glu Asn Ile Ile Gly Asp
                565                 570                 575

Ala Asp Pro Asn Thr Gly Phe Pro Leu Asn Val Ile Lys Gly Phe Pro
            580                 585                 590

Phe Glu Lys Tyr Gly Pro Asp Tyr Glu Gly Arg Gly Ile Ser Val Val
        595                 600                 605

Lys Glu Trp Ile Asn Gly Ala Asn Ala Val Lys Leu Ser Pro Gly Gln
    610                 615                 620

Ser Val Gly Val Gln Ile Lys Asn Ile Thr Lys Gln Asn Tyr Gln Ile
625                 630                 635                 640

Arg Thr Arg Tyr Ala Ser Asn Asn Ser Asn Gln Val Tyr Phe Asn Val
                645                 650                 655

Asp Pro Gly Gly Ser Pro Leu Phe Ala Gln Ser Val Thr Phe Glu Ser
            660                 665                 670

Thr Thr Asn Val Thr Ser Gly Gln Gln Gly Glu Asn Gly Arg Tyr Thr
        675                 680                 685

Leu Lys Thr Ile Phe Ser Gly Asn Asp Leu Leu Thr Val Glu Ile Pro
    690                 695                 700

Val Gly Asn Phe Tyr Val His Val Thr Asn Lys Gly Ser Ser Asp Ile
705                 710                 715                 720

Phe Leu Asp Arg Leu Glu Phe Ser Thr Val Pro
                725                 730
```

<210> SEQ ID NO 36
<211> LENGTH: 364
<212> TYPE: PRT
<213> ORGANISM: Bacillus thuringiensis

<400> SEQUENCE: 36

```
Met Leu Ile Lys Glu Met Gln Tyr Met His Ser Ile Lys Lys Tyr Lys
 1               5                  10                  15

Lys Val Leu Leu Ile Ala Pro Leu Ala Cys Met Leu Thr Gly Ala Ile
            20                  25                  30

Leu Pro Thr Ala Thr Thr Val His Ala Gln Glu Val Glu Asn Lys Lys
        35                  40                  45

Ala Val Ser Met Met Lys Pro Gly Gly Glu Phe Gly Ala Thr Lys Tyr
    50                  55                  60

Ser Lys Glu Asn Leu Val Lys Glu Ile Asn Leu Arg Leu Leu Thr Ala
```

```
65                  70                  75                  80

Leu Asp Arg Ser Thr Ser Leu Arg Glu Lys Phe His Ile Lys Gly Asn
                85                  90                  95

Glu Val Leu Asp Val Ser Gln Leu Asp Asp Thr Ser Lys Gln Leu Met
            100                 105                 110

Glu Lys Leu Gln Leu Thr Ala Glu Gly Ser Ile Asp Val Lys Pro His
        115                 120                 125

Val Asp Ser Tyr Lys Asp Leu Gly Gln Thr Asn Ile Val Thr Tyr Asn
    130                 135                 140

Asn Asp Asn Gly Val Val Gly Gln Thr Tyr Asn Thr Pro Glu Thr Thr
145                 150                 155                 160

Val Lys Glu Ser Glu Thr His Thr Tyr Ser Asn Thr Glu Gly Val Lys
                165                 170                 175

Leu Gly Leu Glu Val Gly Thr Lys Ile Thr Val Gly Ile Pro Phe Ile
            180                 185                 190

Gly Lys Asp Glu Thr Glu Ile Lys Ala Thr Ser Glu Phe Ser Tyr Glu
        195                 200                 205

His Asn Asp Ser Gln Thr Lys Thr Lys Glu Thr Asp Val Thr Phe Lys
    210                 215                 220

Ser Gln Pro Val Val Ala Ala Pro Gly Gly Thr Thr Thr Tyr Tyr Gly
225                 230                 235                 240

Asp Ile Lys Thr Ala Thr Phe Ser Gly Ser Phe Gln Ser Asp Ala Tyr
                245                 250                 255

Val Ala Gly Gly Phe Glu Leu Lys Val Pro Ile Ala His Asp Met Ala
            260                 265                 270

Ser Pro Lys Ile Asp Arg Tyr Glu Thr Ala Thr Leu Thr Ala Ala Asp
        275                 280                 285

Ile Tyr Glu Ile Phe Asn Ala Ser Asn Ala Ile Ala Ala Pro Asn Tyr
    290                 295                 300

Leu Lys Leu Asp Asn Ala Gly Lys Lys Val Leu Leu Thr Asp Lys Ala
305                 310                 315                 320

Thr Phe Asp Ile Asn Gly Gln Gly Gly Phe Tyr Thr Thr Leu Gln Val
                325                 330                 335

Lys Phe Val Pro Lys Asp Ser Asn Lys Lys Pro Gln Met Met Ser Tyr
            340                 345                 350

Lys Glu Tyr Val Gln Lys Met Asn Asn Asn Glu Leu
        355                 360
```

<210> SEQ ID NO 37
<211> LENGTH: 394
<212> TYPE: PRT
<213> ORGANISM: Bacillus thuringiensis

<400> SEQUENCE: 37

```
Met Tyr Ser Ile Lys Arg Tyr Lys Lys Val Ala Ile Val Ala Pro Leu
 1              5                   10                  15

Val Cys Leu Leu Gly Thr Gly Leu Thr Phe Val Asn Lys Pro Ile Pro
            20                  25                  30

Ala Ala Ala Ala Val Thr Thr Asn Tyr Ser Thr Ala Asp Ser Ala Ser
        35                  40                  45

Asn Phe Gln Pro Ile Ser Lys Tyr Thr Leu Ala Gly Asp Leu Tyr Glu
    50                  55                  60

Arg Tyr Met Arg Ala Leu Val Arg His Pro Glu Leu Leu Ser Ser Gly
65                  70                  75                  80

Gly Leu Lys Pro Val Thr Asn Gln Thr Asp Leu Glu Gln Ile Asp Gly
```

85 90 95

Tyr Tyr Lys Val Met Ala Gln Phe Ile Arg Asp Asn Asn Gln Asn Phe
100 105 110

Pro Ser Pro Phe Asn Arg Pro Ser Met Lys Leu Met Thr Gly Val Asn
115 120 125

Pro Phe Phe Asn Trp Ala Pro Gln Tyr Thr Asn Leu Ser Thr Gln Asn
130 135 140

Val Ile Asn Leu Asp Asn Pro Lys Val Asp Asp Tyr Lys Glu Asp Asn
145 150 155 160

Ile Glu Leu Ala Thr Tyr Thr Asn Asn Thr Thr Ser Glu Gln Thr Phe
165 170 175

Ser Thr Pro Ser Lys Ser Glu Lys Val Thr Asp Ser Phe Thr Tyr Ser
180 185 190

Asn Ser Glu Gly Gly Lys Leu Gly Val Ser Ser Thr Thr Thr Ile Arg
195 200 205

Ala Gly Ile Pro Ile Ala Gln Ala Gln Glu Thr Leu Thr Met Ser Phe
210 215 220

Glu Ala Thr Tyr Asn His Thr Ser Ser Asn Thr Ser Ser Thr Glu Lys
225 230 235 240

Thr Val Thr Tyr Pro Ser Gln Val Leu Lys Cys Leu Pro Gly Tyr Arg
245 250 255

Thr Ser Leu Ile Val Lys Val Ser Gln Ala Asn Phe Ser Gly Thr Met
260 265 270

Asp Phe Asp Val Glu Pro Thr Val Ser Ser Leu Ile Asp Gly Ile Glu
275 280 285

Lys Asn Trp Lys Asp Ile Lys Asp Asp Lys Thr Ile Lys Gly Asp Lys
290 295 300

Ser Gly Asp Tyr Thr Val Pro Asn Arg Gln Glu Phe Leu Tyr Asn Val
305 310 315 320

Tyr Lys Tyr Ser Asp Leu Pro Ile Pro Ser Tyr Val Lys Leu Asp Asp
325 330 335

Lys Lys Lys Thr Val Ser Phe Gly Lys Val Thr Thr Pro Tyr Thr Gly
340 345 350

Val Ala Gly His Leu Ser Glu Ala Asn Ala Thr Gln Val Lys Leu Glu
355 360 365

Ser Leu Asp Lys Ala Gln Lys Pro Ile Ile Met Pro Leu Lys Gln Tyr
370 375 380

Gln Gln Lys Ile Gln Asn His Glu Ser Phe
385 390

<210> SEQ ID NO 38
<211> LENGTH: 360
<212> TYPE: PRT
<213> ORGANISM: Bacillus thuringiensis

<400> SEQUENCE: 38

Met His Ser Ile Lys Lys Tyr Lys Lys Ile Leu Leu Val Ala Pro Leu
1 5 10 15

Ala Cys Met Leu Thr Gly Ala Ile Leu Pro Thr Ala Thr Thr Val His
20 25 30

Ala Gln Glu Ile Lys Gly Pro Gly Val Met Lys Pro Asp Val Pro Trp
35 40 45

Asn Gln Glu His Tyr Thr Lys Glu Asn Leu Ala Trp Arg Ala Ala Asp
50 55 60

Arg Leu Ser Tyr Ala Ala Asp Arg Ile Pro Ser Leu Arg Glu Lys Phe

-continued

```
65                  70                  75                  80

Lys Leu Lys Pro Asn Glu His Phe Tyr Cys Ser Asn Asp Thr Arg Tyr
                85                  90                  95

Tyr Met Glu Glu Thr Leu Leu Lys Asn Leu Gln Leu Ser Ala Glu Gly
            100                 105                 110

Pro Ile Asn Val Thr Pro His Val Asp Ser Tyr Thr Asp Leu Gly Gln
        115                 120                 125

Thr Asn Leu Leu Thr Tyr Asn Asn Asp Asp Gly Ile Val Glu Gln Lys
    130                 135                 140

Ala Ser Thr Pro Glu Thr Thr Ile Lys Glu Ser Glu Thr Ser Ser Tyr
145                 150                 155                 160

Ser Asn Lys Glu Gly Val Thr Leu Gly Ala Glu Val Glu Ser Lys Val
                165                 170                 175

Thr Phe Asn Ile Pro Phe Ile Val Ala Gly Glu Thr Lys Val Ile Ala
            180                 185                 190

Lys Ser Glu Phe Ser Tyr Glu His Asp Asp Thr Gln Thr Lys Thr His
        195                 200                 205

Glu Lys Glu Val Thr Phe Lys Ser Gln Glu Ile Val Ala Ala Pro Glu
    210                 215                 220

Gly Thr Thr Thr Tyr Tyr Gly Ser Ile Lys Thr Ala Asn Phe Ser Gly
225                 230                 235                 240

Ser Phe Gln Ser Asp Ala Val Val Gly Gly Gly Val Thr Leu Thr Leu
                245                 250                 255

Pro Ile Gly Val Met Asp Lys Asp Gly Gly Gln Lys Lys Thr His Thr
            260                 265                 270

Glu Thr Ala Thr Leu Thr Ala Glu Asp Met Tyr Glu Ile Phe Lys Ala
        275                 280                 285

Pro Met Pro Trp Asp Met Asn Lys Leu Pro Pro Tyr Leu Lys Leu Asp
    290                 295                 300

Asp Ser Gly Lys Arg Val Leu Leu Ala Glu Lys Ala Thr Phe Asp Ile
305                 310                 315                 320

Lys Gly Gln Gly Gly Phe Tyr Thr Glu Ile Gln Ala Lys Phe Val Pro
                325                 330                 335

Lys Asp Lys Asn Lys Lys Thr Gln Ile Met Pro Tyr Ala Glu Tyr Val
            340                 345                 350

Gln Lys Val Lys Gln Asn Ala Leu
        355                 360


<210> SEQ ID NO 39
<211> LENGTH: 676
<212> TYPE: PRT
<213> ORGANISM: Bacillus thuringiensis

<400> SEQUENCE: 39

Met Lys Ser Met Asn Ser Tyr Gln Asn Lys Asn Glu Tyr Glu Ile Leu
 1               5                  10                  15

Asp Ala Ser Gln Asn Asn Ser Thr Met Ser Thr Arg Tyr Pro Arg Tyr
            20                  25                  30

Pro Leu Ala Lys Asp Pro Gln Ala Ser Met Gln Thr Thr Asn Tyr Lys
        35                  40                  45

Asp Trp Leu Asn Leu Cys Asp Thr Pro Asn Met Glu Asn Pro Glu Phe
    50                  55                  60

Gln Ser Val Gly Arg Ser Ala Leu Ser Ile Leu Ile Asn Leu Ser Ser
65                  70                  75                  80

Arg Ile Leu Ser Leu Leu Gly Ile Pro Phe Ala Ala Gln Ile Gly Gln
```

-continued

```
                85                  90                  95

Leu Trp Ser Tyr Thr Leu Asn Leu Leu Trp Pro Val Ala Asn Asn Ala
            100                 105                 110

Thr Gln Trp Glu Ile Phe Met Arg Thr Ile Glu Glu Leu Ile Asn Ala
        115                 120                 125

Arg Ile Glu Thr Ser Val Arg Asn Arg Ala Leu Ala Glu Leu Ala Gly
    130                 135                 140

Leu Gly Asn Ile Leu Glu Asp Tyr Lys Val Val Leu Gln Arg Trp Asn
145                 150                 155                 160

Leu Asn Pro Thr Asn Pro Thr Leu Gln Arg Asp Val Val Arg Gln Phe
                165                 170                 175

Glu Ile Val His Ala Phe Phe Arg Phe Gln Met Pro Val Phe Ala Val
            180                 185                 190

Asp Gly Phe Glu Val Pro Leu Leu Pro Val Tyr Ala Ser Ala Ala Asn
        195                 200                 205

Leu His Leu Leu Leu Leu Arg Asp Val Val Ile Asn Gly Ala Arg Trp
    210                 215                 220

Gly Leu Glu Ser Asp Val Ile Asn Asp Tyr His Asp Leu Gln Leu Arg
225                 230                 235                 240

Leu Thr Ser Thr Tyr Val Asp His Cys Val Thr Trp Tyr Asn Thr Gly
                245                 250                 255

Leu Asn Arg Leu Ile Gly Thr Asn Ala Arg Gln Trp Val Thr Tyr Asn
            260                 265                 270

Gln Phe Arg Arg Glu Met Thr Ile Ser Val Leu Asp Ile Ile Ser Leu
        275                 280                 285

Phe Ser Asn Tyr Asp Val Arg Arg Tyr Pro Thr Lys Thr Gln Ser Glu
    290                 295                 300

Leu Thr Arg Met Ile Tyr Thr Asp Pro Ile Gly Thr Glu Gly Asn Gln
305                 310                 315                 320

Phe Ile Pro Gly Trp Val Asp Asn Ala Pro Ser Phe Ser Val Ile Glu
                325                 330                 335

Asn Ser Val Val Arg Ser Pro Gly Ala Phe Thr Phe Leu Glu Arg Val
            340                 345                 350

Gly Ile Phe Thr Gly Phe Leu His Gly Trp Ser Ser Arg Ser Glu Phe
        355                 360                 365

Trp Ser Ala His Arg Leu Phe Ser Arg Pro Val Leu Gly Trp Ile Trp
    370                 375                 380

Glu Ser Val Ile Phe Gly Asn Pro Gln Asn Asn Ile Gly Tyr Gln Glu
385                 390                 395                 400

Val Asp Phe Thr Asn Phe Asp Val Phe Ser Ile Asn Ser Arg Ala Thr
                405                 410                 415

Ser His Met Phe Pro Asn Gly Ser Ala Arg Leu Phe Gly Val Pro Arg
            420                 425                 430

Val Thr Phe Asp Leu Ser Asn Val Thr Asn Asn Asn Leu Ala Gln Arg
        435                 440                 445

Thr Tyr Asn Arg Pro Phe Thr Phe Gly Gly Gln Asp Ile Val Ser Arg
    450                 455                 460

Leu Pro Gly Glu Thr Thr Glu Ile Pro Asn Ser Ser Asn Phe Ser His
465                 470                 475                 480

Arg Leu Ala His Ile Ser Ser Phe Pro Val Gly Asn Asn Gly Ser Val
                485                 490                 495

Leu Ser Tyr Gly Trp Thr His Arg Asn Val Asn Arg His Asn Arg Leu
            500                 505                 510
```

```
Asn Pro Asn Ser Ile Thr Gln Ile Pro Ala Ile Lys Phe Ala Ser Gly
        515                 520                 525

Ser Ala Arg Arg Gly Pro Gly His Thr Gly Gly Asp Leu Ala Ile Ala
    530                 535                 540

Gln Gln His Ser Gly Tyr Gln Leu Phe Met Gln Ser Pro Ser Ala Gln
545                 550                 555                 560

Arg Tyr Arg Leu Arg Leu Arg Tyr Ala Gly Ile Ser Gly Gly Ser Ile
                565                 570                 575

Ser Val Ser His Arg Asp Glu Asn Asn Gln Asn Ile Leu His Ser Ala
            580                 585                 590

Thr Phe Asn Val Arg Ala Thr Ser Gly Gln Leu Arg Tyr Ala Asp Phe
        595                 600                 605

Ile Tyr Thr Asp Leu Glu Glu Asn Thr Thr Leu Phe Glu Thr Arg Asn
    610                 615                 620

Gly Val Asn Leu Tyr Arg Leu Met Ile Phe Val Ser Ser Gly Ser Ile
625                 630                 635                 640

Leu Ile Asp Arg Ile Glu Tyr Ile Pro Glu Asn Thr Thr Thr Ile Glu
                645                 650                 655

Tyr Glu Glu Glu Arg Asn Leu Glu Lys Glu Lys Lys Ala Val Asp Asp
            660                 665                 670

Leu Phe Thr Asn
        675


<210> SEQ ID NO 40
<211> LENGTH: 567
<212> TYPE: PRT
<213> ORGANISM: Bacillus thuringiensis

<400> SEQUENCE: 40

Met Asn Asn Met Tyr Thr Asn Asn Met Lys Thr Thr Leu Lys Leu Glu
 1               5                  10                  15

Thr Thr Asp Tyr Glu Ile Asp Gln Ala Ala Ile Ser Ile Glu Cys Met
            20                  25                  30

Ser Asp Glu Gln Asp Leu Gln Glu Lys Met Met Leu Trp Asp Glu Val
        35                  40                  45

Lys Leu Ala Lys Gln Leu Ser Gln Ser Arg Asn Leu Leu Tyr Asn Gly
    50                  55                  60

Asp Phe Glu Asp Ser Ser Asn Gly Trp Lys Thr Ser Asn Asn Ile Thr
65                  70                  75                  80

Ile Gln Leu Glu Asn Pro Ile Leu Lys Gly Lys Tyr Leu Asn Met Pro
                85                  90                  95

Gly Ala Arg Asp Ile Tyr Gly Thr Ile Phe Pro Thr Tyr Val Tyr Gln
            100                 105                 110

Lys Ile Asp Glu Ser Lys Leu Lys Pro Asn Thr Arg Tyr Arg Val Arg
        115                 120                 125

Gly Phe Val Gly Ser Ser Lys Asp Leu Lys Leu Val Val Thr Arg Tyr
    130                 135                 140

Glu Lys Glu Ile Asp Ala Ser Met Asp Val Pro Asn Asp Leu Ser Tyr
145                 150                 155                 160

Met Gln Pro Ser Pro Ser Cys Gly Asp Tyr Gly Cys Asp Ser Ser Ser
                165                 170                 175

Gln Pro Met Met Asn Gln Gly Tyr Pro Thr Pro Tyr Thr Asp Asp Tyr
            180                 185                 190

Ala Ser Asp Met Tyr Ala Cys Ser Ser Asn Leu Gly Lys Lys His Val
        195                 200                 205
```

```
Lys Cys His Asp Arg His Pro Phe Asp Phe His Ile Asp Thr Gly Glu
    210                 215                 220

Leu Asp Thr Asn Thr Asn Leu Gly Ile Cys Ile Leu Phe Lys Ile Ser
225                 230                 235                 240

Asn Pro Asp Gly Tyr Ala Thr Leu Gly Asn Leu Glu Val Ile Glu Glu
                245                 250                 255

Gly Pro Leu Thr Ser Glu Ala Leu Ala His Val Asn Gln Lys Glu Lys
            260                 265                 270

Lys Trp Asn Gln Gln Met Glu Lys Lys Arg Ser Glu Thr Gln Gln Ala
        275                 280                 285

Tyr Asp Pro Ala Lys Gln Ala Val Asp Ala Leu Phe Thr Asn Ser Gln
    290                 295                 300

Gly Glu Glu Leu His Tyr His Ile Thr Leu Asp His Ile Gln Asn Ala
305                 310                 315                 320

Asn Gln Leu Val Gln Ser Ile Pro Tyr Val His His Ala Trp Leu Pro
                325                 330                 335

Asp Ala Pro Gly Met Asn Tyr Asp Leu Tyr Asn Asn Leu Lys Val Arg
            340                 345                 350

Ile Glu Gln Ala Arg Tyr Leu Tyr Asp Ala Arg Asn Val Ile Thr Asn
        355                 360                 365

Gly Asp Phe Ala Gln Gly Leu Thr Gly Trp His Ala Thr Gly Lys Val
    370                 375                 380

Asp Val Gln Gln Met Asp Gly Ala Ser Val Leu Val Leu Ser Asn Trp
385                 390                 395                 400

Ser Ala Gly Val Ser Gln Asn Leu His Ala Gln Asp His His Gly Tyr
                405                 410                 415

Met Leu Arg Val Ile Ala Lys Lys Glu Gly Pro Gly Lys Gly Tyr Val
            420                 425                 430

Thr Met Met Asp Cys Asn Gly His Gln Glu Thr Leu Lys Phe Thr Ser
        435                 440                 445

Cys Glu Glu Gly Tyr Met Thr Lys Thr Val Glu Val Phe Pro Glu Ser
    450                 455                 460

Asp Arg Val Arg Ile Glu Ile Gly Glu Thr Glu Gly Thr Phe Tyr Ile
465                 470                 475                 480

Asp Ser Ile Glu Leu Leu Cys Met Gln Gly Tyr Ala Ser Asn Asn Thr
                485                 490                 495

Pro His Thr Gly Asn Met Tyr Glu Gln Ser Tyr Asn Gly Ile Tyr Asn
            500                 505                 510

Gln Asn Thr Ser Asp Leu Tyr His Gln Gly Tyr Thr Asn Asn Tyr Asn
        515                 520                 525

Gln Glu Ser Ser Ser Met Tyr Asn Gln Asn Tyr Thr Asn Asn Asp Asp
    530                 535                 540

Gln His Ser Gly Cys Thr Cys Asn Gln Gly His Asn Ser Gly Cys Thr
545                 550                 555                 560

Cys Asn Gln Gly Tyr Asn Arg
                565

<210> SEQ ID NO 41
<211> LENGTH: 640
<212> TYPE: PRT
<213> ORGANISM: Bacillus thuringiensis

<400> SEQUENCE: 41

Met Glu Glu Leu Glu Leu Lys Arg Thr Asn Thr Leu Ser Ser Glu Asp
 1               5                  10                  15
```

-continued

```
Val Asn Ile Leu Gln Ile Glu Asn Leu Val Lys Glu Tyr Val Lys Gln
            20                  25                  30

Thr Tyr Gly Asn Ser Ala Glu Ile Lys Lys Leu Ser Leu Asp Gly Leu
        35                  40                  45

Asp Val Leu Tyr Asn Leu Asp Ile Pro Ser Ile Leu Lys Gly Thr Ser
    50                  55                  60

Ser Ser Ser Ala Ile Lys Val Gly Thr Asp Asn Leu Asn Asn Pro Thr
65                  70                  75                  80

Asp Thr Ala Lys Thr Ile Lys Leu Pro Val Lys Asn Val Arg Lys Lys
                85                  90                  95

Glu Phe Lys Val Lys Pro Ile Gln Ala Leu Asn Phe Glu Asn Gly Ala
            100                 105                 110

Thr Ile Thr Lys Lys Ser Ile Thr Ser Ile Pro Ser Ile Asn Ala Thr
        115                 120                 125

Phe Ile Ala Leu Ala Glu Gln Asn Phe Gln Asn Ala His Phe His Ile
    130                 135                 140

Val Asn Asp Ser Gln Ser Tyr Glu Asn Glu Ile Pro Ile Tyr Val Pro
145                 150                 155                 160

Pro His Ser Lys Val Glu Ile Thr Tyr Tyr Val Lys Glu Ile Gln Phe
                165                 170                 175

Asp Ala Ile Ile Gln Ser Thr Ala Thr Ile Gly Gly Ser Ile Ser Phe
            180                 185                 190

Glu Tyr Ile Val His Asp Asn Gly His Glu Gly Ile Asp Phe Leu Thr
        195                 200                 205

Ile Phe Glu Leu Val Asn Ser Leu Asn Leu Asn Asp Phe Glu Ile Gln
    210                 215                 220

Glu Ala Ser Asp Val His Gly Lys Val Val Tyr Lys Gly Lys Ser Gln
225                 230                 235                 240

Phe Gln Gly Thr Val Gly Leu Asn Leu Phe Met Gln Ile Lys Gly Thr
                245                 250                 255

Pro Leu Asp Glu Ser Lys Asn Asn Tyr Glu Phe Thr Lys Val Leu Ser
            260                 265                 270

Glu Asp Val Glu Met Ser Leu Ser Pro Ser Glu Gly Glu Tyr Tyr Ile
        275                 280                 285

Asp Phe Gly Ser Ser Pro Lys Leu Thr Asn Lys Glu Glu Val Ile Val
    290                 295                 300

Lys Phe Thr Arg Asp Tyr Leu Leu Ser Asn Asp Arg Lys Asn Ala Tyr
305                 310                 315                 320

Val Gln Gln Leu Pro Arg Leu Glu Tyr Gly Glu Glu Val Thr Thr Leu
                325                 330                 335

Lys Ser Ile Asp Thr Ala His Glu Arg Lys Glu Ile Ile Ala Ser Thr
            340                 345                 350

Ile Asn Thr Phe Gln Asn Pro Ser Asp Thr Glu Ile Thr Arg Asn Thr
        355                 360                 365

Ile Lys Glu Thr Phe Ser Thr Thr Asp Thr Ile Thr Thr Thr Ala Thr
    370                 375                 380

Thr Asp Lys Phe Leu Glu Leu Gly Gly Ser Ile Glu Thr Ser Ala Lys
385                 390                 395                 400

Gly Lys Val Pro Leu Val Ala Glu Ala Ser Ile Lys Val Thr Gln Ser
                405                 410                 415

Ile Lys Gly Gly Trp Lys Trp Val Ser Thr Lys Thr Asn Thr Arg Thr
            420                 425                 430

Asn Val His Thr Ile Glu Ile Pro Ser Gln Ser Ile Lys Ile Pro Pro
        435                 440                 445
```

His Lys Met Trp Lys Tyr Gln Tyr Ile Leu Thr Lys Phe Glu Ser Ser
    450                 455                 460

Gly Tyr Leu Ser Ser Ala Trp Glu Ile Asn Thr Lys Glu Ser Met Ser
465                 470                 475                 480

Ala Pro Glu Val His Ile Gly Tyr Tyr Asn Lys Asp Leu Gln Asn Pro
                485                 490                 495

Arg Asn Ile Thr Gly Leu Ser Ala Asn Val Glu Ser Gly Asn Val Val
            500                 505                 510

Gly Arg Val Phe Glu Phe Asn Lys Phe Gln Pro Gly Gly Leu His Tyr
        515                 520                 525

Lys Ile Leu Asn Ser Glu Asn Ile Leu Asn Ala Thr Pro Tyr Gln Phe
    530                 535                 540

Phe Lys Glu Leu Ala Lys Arg Val Asn Gln Tyr Pro Leu Ile Gln Asn
545                 550                 555                 560

Asn Pro Arg Tyr Arg Arg Leu Gly Ile Leu Leu Gly Phe Gly Lys Asp
                565                 570                 575

Ile Ser Gln Ile Thr Trp Glu Pro Gln Ile His Tyr Asn Glu His Val
            580                 585                 590

Leu Phe Asp Ala Glu Glu Leu Leu Asn Val Leu Arg Phe Asp Asp Ile
        595                 600                 605

Ala Asn Lys Val Tyr Ala Leu Asp Gly Gly Thr Pro Phe Thr Val Ala
    610                 615                 620

Val Gly His Glu Leu Leu Pro Lys Glu Ser Ile Glu Pro Leu Asn Asn
625                 630                 635                 640

<210> SEQ ID NO 42
<211> LENGTH: 966
<212> TYPE: PRT
<213> ORGANISM: Bacillus thuringiensis

<400> SEQUENCE: 42

Met Met Asn Met Ser Asn Thr Leu Ala Pro Tyr Asn Val Leu Arg Ser
1               5                   10                  15

Met Asp Met Pro Asn Ile Ser Gly Thr Lys Trp Asp Lys Gly Met Phe
            20                  25                  30

Ile Asn Ala Leu Asp Asn Thr Ser Phe Leu Leu Glu Leu Ile Glu Lys
        35                  40                  45

Gly Ile Asn Asp Asp Asp Asp Val Leu Gly Leu Leu Ser Phe Ile Gly
    50                  55                  60

Leu Thr Ala Leu Glu Ala Ile Pro Ile Val Gly Gly Val Met Ser Lys
65                  70                  75                  80

Leu Val Ser Met Ile Phe Phe Pro Thr Lys Ser Ser Ile Asn Phe Gln
                85                  90                  95

Lys Ile Trp Glu Gln Leu Glu Lys Ala Ile Glu Gln Ile Val Asp Lys
            100                 105                 110

Lys Ile Thr Glu Ala Met Met Ser Gln Leu Met Gln Glu Ile Ala Gly
        115                 120                 125

Leu Ala Asp Val Leu Glu Glu Tyr Arg Asn Ala Tyr Asp Leu Tyr Asn
    130                 135                 140

Gly Lys Lys Leu Phe Asn Ile Pro Asp Lys Met Thr Pro Gly Asp Tyr
145                 150                 155                 160

Leu Ile Asn Val Phe Thr Thr Ala Asn Leu Gln Phe Ile Gln Arg Ile
                165                 170                 175

Pro Thr Phe Gln Asn Ser Ile Tyr Asp Val Val Phe Leu Pro Phe Phe
            180                 185                 190

-continued

```
Val His Ala Ala Glu Met His Ile Leu Leu Ile Arg Asp Ala Ala Ile
        195                 200                 205

His Gly Gln Glu Trp Gly Met Asp Glu Thr Val His Gln Lys Phe Lys
    210                 215                 220

Arg Asp Leu Lys Thr Leu Ile Asn Lys Tyr Ser Ser Tyr Leu Leu Ala
225                 230                 235                 240

Thr Tyr Lys Lys Gly Leu Lys Glu Ala Ser Glu Lys Lys Leu Glu Asn
                245                 250                 255

Asn Asp Phe Pro Thr Ser Asn Asn Gln His His Tyr Ile Asn Thr Val
            260                 265                 270

Arg Trp Asn Val Ile Asn Gln Tyr Lys Arg Gly Met Ala Leu Thr Val
        275                 280                 285

Phe Asp Phe Ala Tyr Lys Trp Lys Tyr Tyr Gln Glu Val Tyr Gln Asn
    290                 295                 300

Asn Ile Thr Leu Asn Pro Ala Arg Thr Ile Tyr Ser Asp Ile Ala Gly
305                 310                 315                 320

Ser Val Tyr Pro Tyr Glu Lys Thr Thr Asn Glu Ile Asp Asn Ile Ile
                325                 330                 335

Lys Glu Gln Asn Leu Lys Tyr Arg Gly Leu Leu Lys Glu Leu Leu Ile
            340                 345                 350

Asn His Gly Asp Arg Ile Asp Ser Ile Gln Ser Lys Tyr Ile Arg Asn
        355                 360                 365

Asn Glu Ile Ile Asp Ser Asn Arg Thr Gly Gly Ala Gly Gly Arg Ala
    370                 375                 380

Thr Phe Phe Asp Leu Lys Ser Pro Ile Asn Asn Pro Phe Ile Gln Val
385                 390                 395                 400

Asn Met Trp Ser Glu Leu Val Pro Phe Ser Leu Gly Phe Lys Tyr Tyr
                405                 410                 415

Asn Gly Glu Glu Ser Lys Leu Ile Trp Gly Gly Gly Thr Pro Gly Lys
            420                 425                 430

His Lys Phe Gly Ser Tyr His Tyr Val Gly Asn Lys Val Ser Ser Ile
        435                 440                 445

Ile Gly Phe Gly Lys Asn Gly Thr Gly Gly Phe Asn Ser Leu Asp Ala
    450                 455                 460

Met Val Val Gly Phe Lys Arg Asp Asp Tyr Ile Pro Glu Asn Arg Phe
465                 470                 475                 480

Val Gly Val Asn Lys Asn Gly Glu Pro Val Thr Lys Val Ile Asp Ala
                485                 490                 495

Glu Asn Phe Tyr Gln Glu Lys Phe Gln Ser Asn Ile Lys Met Ile Asp
            500                 505                 510

Glu Pro Met Phe Gly Glu Ala Val Leu Gln Phe Glu Asn Tyr Ser Asn
        515                 520                 525

Asn Leu Asn Lys Asp Ser Tyr Val Thr Tyr Gln Ile Asp Ala Lys Ile
    530                 535                 540

Glu Gly Thr Tyr Glu Leu His Val Ile Ile Gly Ala Lys Lys Gln Lys
545                 550                 555                 560

Asp Lys Ile Ala Phe Lys Met Ala Leu Asn Glu Lys Gln Pro Glu Lys
                565                 570                 575

Phe Ile Thr Glu Pro Phe Asn Ala Gly Asp Ile Trp Glu Gly Ile Ser
            580                 585                 590

Leu Ser Glu Gly Leu Val Tyr Lys Arg Ile Leu Leu Gly Asn Phe Gln
        595                 600                 605

Leu Lys Lys Gly Met Asn Arg Ile Thr Ile His Asn Gly Val Leu Gln
```

```
    610                 615                 620

Thr Ser Ala Asn Ile Lys Thr Trp Asn Leu Ala Lys Leu Glu Leu Thr
625                 630                 635                 640

Leu Thr Ser Asp Ser Leu Lys Asp Pro Asp Ile Thr Thr Leu Tyr Asp
                645                 650                 655

Lys Asp Asn Tyr Ser Gly Thr Lys Lys Phe Ile Phe Glu Asn Thr Ser
            660                 665                 670

Arg Leu Lys Asp Phe Asn Asp Lys Thr Ser Ser Ile Lys Val Glu Ser
        675                 680                 685

His Leu Ala Gly Ile Arg Ile Tyr Gln Asp Tyr Asn Tyr Lys Gly Lys
    690                 695                 700

Ser Met Asp Leu Val Gly Gly Glu Lys Ile Ser Leu Lys Asn His Ser
705                 710                 715                 720

Phe Asn Asn Arg Ala Ser Ser Val Lys Phe Ala Asn Ile Val Leu Tyr
                725                 730                 735

Asn Gln Asp Asn Tyr Gln Gly Ser Arg Lys Leu Val Phe Glu Asp Ile
            740                 745                 750

Pro Asp Leu Gly Lys Gln Ser Phe Asn Asp Lys Thr Ser Ser Ile Val
        755                 760                 765

Val Ser Ser Asn Val Ser Gly Ala Arg Leu Tyr Glu His Ala Tyr Tyr
    770                 775                 780

Lys Gly Lys Tyr Val Asp Val Val Gly Gly Gln Lys Leu Asn Leu Lys
785                 790                 795                 800

Asn His Val Leu Asn Lys Lys Ile Ser Ser Ile Lys Phe Phe Lys Glu
                805                 810                 815

Gly Glu Val Leu Asn Gly Val Tyr Gln Ile Ile Thr Ala Ile Asn Asn
            820                 825                 830

Thr Ser Val Ile Asp Lys His Leu Glu Asn Ser Asn Val His Leu Trp
        835                 840                 845

Glu Asn Ala Glu Asn Lys Asn Gln Lys Trp Arg Ile Glu Tyr Asp Val
    850                 855                 860

Ala Lys Lys Ala Tyr Gln Ile Lys Asn Met Leu Asp Glu Lys Leu Val
865                 870                 875                 880

Leu Ser Thr His Glu Leu Phe Pro Ile Phe Ser Ala Leu Tyr Cys Leu
                885                 890                 895

Pro Asn Lys Gly Tyr Val Ser Gln Tyr Trp Ile Phe Glu Tyr Val Gly
            900                 905                 910

Asn Gly Tyr Tyr Ile Ile Lys Asn Lys Ala Tyr Pro Asp Trp Val Leu
        915                 920                 925

Asp Val Asp Gly Leu Asn Ser Asp Asn Gly Thr Leu Ile Lys Leu His
    930                 935                 940

Ser Gln His Asp Leu Thr Asp Pro Leu Ile Asn Ala Gln Lys Phe Lys
945                 950                 955                 960

Leu Lys Asp Ile Asn Asn
                965


<210> SEQ ID NO 43
<211> LENGTH: 769
<212> TYPE: PRT
<213> ORGANISM: Bacillus thuringiensis

<400> SEQUENCE: 43

Met Met Asn Met Ser Asn Thr Leu Ala Pro Tyr Asn Val Leu Arg Ser
 1               5                  10                  15

Met Asp Met Pro Asn Ile Ser Gly Thr Lys Trp Asp Lys Gly Met Phe
```

-continued

```
            20                  25                  30

Ile Asn Ala Leu Asp Asn Thr Ser Phe Leu Leu Glu Leu Ile Glu Lys
        35                  40                  45

Gly Ile Asn Asp Asp Asp Asp Val Leu Gly Leu Leu Ser Phe Ile Gly
    50                  55                  60

Leu Thr Ala Leu Glu Ala Ile Pro Ile Val Gly Gly Val Met Ser Lys
65                  70                  75                  80

Leu Val Ser Met Ile Phe Phe Pro Thr Lys Ser Ser Ile Asn Phe Gln
                85                  90                  95

Lys Ile Trp Glu Gln Leu Glu Lys Ala Ile Glu Gln Ile Val Asp Lys
            100                 105                 110

Lys Ile Thr Glu Ala Met Met Ser Gln Leu Met Gln Glu Ile Ala Gly
        115                 120                 125

Leu Ala Asp Val Leu Glu Glu Tyr Arg Asn Ala Tyr Asp Leu Tyr Asn
    130                 135                 140

Gly Lys Lys Leu Phe Asn Ile Pro Asp Lys Met Thr Pro Gly Asp Tyr
145                 150                 155                 160

Leu Ile Asn Val Phe Thr Thr Ala Asn Leu Gln Phe Ile Gln Arg Ile
                165                 170                 175

Pro Thr Phe Gln Asn Ser Ile Tyr Asp Val Val Phe Leu Pro Phe Phe
            180                 185                 190

Val His Ala Ala Glu Met His Ile Leu Leu Ile Arg Asp Ala Ala Ile
        195                 200                 205

His Gly Gln Glu Trp Gly Met Asp Glu Thr Val His Gln Lys Phe Lys
    210                 215                 220

Arg Asp Leu Lys Thr Leu Ile Asn Lys Tyr Ser Ser Tyr Leu Leu Ala
225                 230                 235                 240

Thr Tyr Lys Lys Gly Leu Lys Glu Ala Ser Glu Lys Lys Leu Glu Asn
                245                 250                 255

Asn Asp Phe Pro Thr Ser Asn Asn Gln His His Tyr Ile Asn Thr Val
            260                 265                 270

Arg Trp Asn Val Ile Asn Gln Tyr Lys Arg Gly Met Ala Leu Thr Val
        275                 280                 285

Phe Asp Phe Ala Tyr Lys Trp Lys Tyr Tyr Gln Glu Val Tyr Gln Asn
    290                 295                 300

Asn Ile Thr Leu Asn Pro Ala Arg Thr Ile Tyr Ser Asp Ile Ala Gly
305                 310                 315                 320

Ser Val Tyr Pro Tyr Glu Lys Thr Thr Asn Glu Ile Asp Asn Ile Ile
                325                 330                 335

Lys Glu Gln Asn Leu Lys Tyr Arg Gly Leu Leu Lys Glu Leu Leu Ile
            340                 345                 350

Asn His Gly Asp Arg Ile Asp Ser Ile Gln Ser Lys Tyr Ile Arg Asn
        355                 360                 365

Asn Glu Ile Ile Asp Ser Asn Arg Thr Gly Gly Ala Gly Gly Arg Ala
    370                 375                 380

Thr Phe Phe Asp Leu Lys Ser Pro Ile Asn Asn Pro Phe Ile Gln Val
385                 390                 395                 400

Asn Met Trp Ser Glu Leu Val Pro Phe Ser Leu Gly Phe Lys Tyr Tyr
                405                 410                 415

Asn Gly Glu Glu Ser Lys Leu Ile Trp Gly Gly Gly Thr Pro Gly Lys
            420                 425                 430

His Lys Phe Gly Ser Tyr His Tyr Val Gly Asn Lys Val Ser Ser Ile
        435                 440                 445
```

```
Ile Gly Phe Gly Lys Asn Gly Thr Gly Gly Phe Asn Ser Leu Asp Ala
    450                 455                 460

Met Val Val Gly Phe Lys Arg Asp Asp Tyr Ile Pro Glu Asn Arg Phe
465                 470                 475                 480

Val Gly Val Asn Lys Asn Gly Glu Pro Val Thr Lys Val Ile Asp Ala
                485                 490                 495

Glu Asn Phe Tyr Gln Glu Lys Phe Gln Ser Asn Ile Lys Met Ile Asp
            500                 505                 510

Glu Pro Met Phe Gly Glu Ala Val Leu Gln Phe Glu Asn Tyr Ser Asn
        515                 520                 525

Asn Leu Asn Lys Asp Ser Tyr Val Thr Tyr Gln Ile Asp Ala Lys Ile
    530                 535                 540

Glu Gly Thr Tyr Glu Leu His Val Ile Ile Gly Ala Lys Lys Gln Lys
545                 550                 555                 560

Asp Lys Ile Ala Phe Lys Met Ala Leu Asn Glu Lys Gln Pro Glu Lys
                565                 570                 575

Phe Ile Thr Glu Pro Phe Asn Ala Gly Asp Ile Trp Glu Gly Ile Ser
            580                 585                 590

Leu Ser Glu Gly Leu Val Tyr Lys Arg Ile Leu Leu Gly Asn Phe Gln
        595                 600                 605

Leu Lys Lys Gly Met Asn Arg Ile Thr Ile His Asn Gly Val Leu Gln
    610                 615                 620

Thr Ser Ala Asn Ile Lys Thr Trp Asn Leu Ala Lys Leu Glu Leu Thr
625                 630                 635                 640

Leu Thr Ser Asp Ser Leu Lys Asp Pro Asp Ile Thr Thr Leu Tyr Asp
                645                 650                 655

Lys Asp Asn Tyr Ser Gly Thr Lys Lys Phe Ile Phe Glu Asn Thr Ser
            660                 665                 670

Arg Leu Lys Asp Phe Asn Asp Lys Thr Ser Ser Ile Lys Val Glu Ser
        675                 680                 685

His Leu Ala Gly Ile Arg Ile Tyr Gln Asp Tyr Asn Tyr Lys Gly Lys
    690                 695                 700

Ser Met Asp Leu Val Gly Gly Glu Lys Ile Ser Leu Lys Asn His Ser
705                 710                 715                 720

Phe Asn Asn Arg Ala Ser Ser Val Lys Phe Ala Asn Ile Val Leu Tyr
                725                 730                 735

Asn Gln Asp Asn Tyr Gln Gly Ser Arg Lys Leu Val Phe Glu Asp Ile
            740                 745                 750

Pro Asp Leu Gly Lys Gln Ser Phe Asn Asp Lys Thr Ser Ser Ile Val
        755                 760                 765

Val


<210> SEQ ID NO 44
<211> LENGTH: 575
<212> TYPE: PRT
<213> ORGANISM: Bacillus thuringiensis

<400> SEQUENCE: 44

Met Asn Gly Asn Gly Arg His Asp Gly Trp Asn Gln Asn Gln His Ile
 1               5                  10                  15

Glu Asn Gly Gln Met Asn Pro Asn His Ser Gly Ser Cys Lys Cys Gly
            20                  25                  30

Cys Gln Gln Asn Asn Asn Gly Ser Tyr Pro Ser Asn Glu Tyr Asn Ser
        35                  40                  45

Asn Asn Asn Gly Ser Tyr Pro Ser Asn Glu Tyr Asn Ser Asn Asn Asn
```

-continued

```
    50                  55                  60

Gly Ser Tyr Pro Ser Asn Glu Tyr Asn Ser Asn Asn Asn Gly Ser Tyr
65                  70                  75                  80

Pro Ser Asn Glu Tyr Asn Ser Asn Asn Asn Gly Ser Tyr Pro Ser Asn
                85                  90                  95

Glu Tyr Asn Ser Asn Asn Asn Gly Ser Tyr Pro Ser Asn Glu Tyr Asn
            100                 105                 110

Ser Asn Asn Asn Gly Ser Tyr Pro Ser Asn Glu Tyr Asn Ser Asn Asn
        115                 120                 125

Asn Gly Ser Tyr Pro Ser Asn Glu Tyr Asn Ser Asn Asn Asn Gly Ser
    130                 135                 140

Tyr Ser Ser Asn Glu Tyr Asn Ser Asn Asn Asn Gly Ser Tyr Pro Ser
145                 150                 155                 160

Asn Glu Tyr Asn Ser Asn Asn Asn Gly Ser Tyr Pro Ser Asn Glu Tyr
                165                 170                 175

Asn Ser Asn Asn Asn Gly Ser Tyr Pro Ser Asn Glu Tyr Val Gly Gly
            180                 185                 190

Tyr Ser Ile Gln Asp Gly Leu Pro Gln Glu Ser Lys Gln Phe Gln Lys
        195                 200                 205

Ile Ser Asn Met Asn Thr Arg Asp Asn His Arg Val Leu Asp Ala Gln
    210                 215                 220

Asp Thr Tyr Phe Gly Gln Leu Ile Asp Asn Arg Val Gly Asp Thr Cys
225                 230                 235                 240

Lys Tyr Val Glu His Lys Asn Ser Val Ile Tyr Glu Leu Ser Arg Gln
                245                 250                 255

Pro Val Tyr Thr Pro Asp Ser Gln Tyr Phe Ile Phe Tyr Gln Met Asp
            260                 265                 270

Asn Gly Asn Phe Ile Ile Ala Asn Lys Glu Asn Ser Arg Val Leu Glu
        275                 280                 285

Val Ile Phe Ser Ser Val Asn Gly Phe Val Thr Ile Ser Asn Glu Phe
    290                 295                 300

Asn Ala Thr Ser Asp Gln Arg Phe Lys Val Val Arg Ser Lys Asn Asp
305                 310                 315                 320

Thr Phe Arg Leu Val Thr Glu Gly Asn Lys Thr Leu Asn Ile Cys Gly
                325                 330                 335

His Ser Phe Gln Tyr Asn Thr Lys Ile Thr Ala Val Asn Ala Asp Ile
            340                 345                 350

Asp Gly Asp Asn Tyr Leu Phe Gln Lys Ser Met Asp Lys Asp Thr Arg
        355                 360                 365

Asp Leu Tyr Phe Gly Thr Ile Ser Asn Lys Asn Pro Glu Ile Leu Asn
    370                 375                 380

Asp Pro Arg Asn Leu Lys Ser Leu Asp Asp Leu Gly Asp Glu Pro Arg
385                 390                 395                 400

Ala Phe Lys Gly Ala Ala Leu Leu Pro Ala Leu Phe Val Asn Asp Pro
                405                 410                 415

Arg Tyr Ser Val His Arg Arg Val Ser Asn Ser Pro Tyr Tyr Tyr Leu
            420                 425                 430

Glu Tyr Thr Gln Tyr Trp His Arg Ile Trp Thr Asp Val Leu Pro Ile
        435                 440                 445

Asp Gly Tyr Gly Ala Trp Ile Glu Met Ile Gly Val Thr Asn Asp Thr
    450                 455                 460

Gln Val Asn Met Lys Asn Ile Met Asn Ile Thr Ile Thr Gly Lys Asp
465                 470                 475                 480
```

-continued

```
Leu Gly Val Asp Leu Gly Ile Asp Leu Gly Leu Arg Phe Gly Asp Lys
                485                 490                 495

Ser Phe Leu Phe Glu Gln Lys Ile Leu Ser Gly Leu Ser Ile Arg Lys
            500                 505                 510

Thr Asp Tyr Pro Asn Leu Gly Ile Asp Glu Arg Ala Met Tyr Gln Arg
        515                 520                 525

Asn Asn Ser Asn Leu Lys Thr Arg Phe Val Arg Tyr Val Lys Lys His
    530                 535                 540

Glu Phe Val Leu Arg Asp Leu Asn Gly Ser Lys Val Ala Glu Pro Trp
545                 550                 555                 560

Ile Ile Thr Glu Asp Arg Ser Ile Thr Lys Glu Tyr Ser Ser Asn
                565                 570                 575


<210> SEQ ID NO 45
<211> LENGTH: 559
<212> TYPE: PRT
<213> ORGANISM: Bacillus thuringiensis

<400> SEQUENCE: 45

Met Lys Tyr Lys Asn Arg Thr Arg Ala Lys Cys Lys Tyr Lys Gln Ala
 1               5                  10                  15

Leu Leu Val Thr Val Ala Thr Met Thr Leu Gly Val Ser Thr Leu Gly
            20                  25                  30

Ser Asn Ala Ser Ala Phe Ala Asp Glu Lys Glu Lys Asn Val Ile Gln
        35                  40                  45

Gln Lys Ser Pro Gly Thr Tyr Tyr Glu Asp Ala Gln Lys Asn Leu Gly
    50                  55                  60

Ser Leu Ala Arg Phe Asp Thr Trp Ala Gln Asp Leu Gly Lys Thr Thr
65                  70                  75                  80

Gly Ala Gly Asn Tyr Lys Thr Thr Leu Gly Met Ala Glu Lys Leu Leu
                85                  90                  95

Pro Thr Ile Tyr Asn Asp Leu Asn Ser Gly Asn Phe Asn Asn Thr Ala
            100                 105                 110

Arg Ser Ile Thr Met Leu Ser Thr Ala Leu Ile Pro Tyr Gly Gly Ala
        115                 120                 125

Phe Ile Ser Pro Ile Ile Gly Ile Leu Trp Pro Glu Asn Gly Pro Asn
    130                 135                 140

Ile Lys Glu Met Leu Gln Glu Met Glu Asn Lys Leu Val Gly Ile Met
145                 150                 155                 160

Asp Glu Lys Ile Glu Ala Lys Asp Leu Asp Asp Leu Glu Ala Ala Val
                165                 170                 175

Lys Gly Leu Met Val Ser Leu Lys Glu Phe Glu Asn Ser Leu Asn Gly
            180                 185                 190

Asn Ile Gly Gly Glu Tyr Tyr Ser Ala Leu Ala Asp Val Asp Ser Leu
        195                 200                 205

Asn Arg Gly Arg Ile Thr Ala Ile Gln Lys Gly Phe Asn Asp Leu Ile
    210                 215                 220

Ser Ala Thr Ser Lys Pro Lys Phe Lys Ile Thr Glu Leu Pro Leu Tyr
225                 230                 235                 240

Thr Ile Ile Ala Thr Ala His Leu Asn Phe Leu Asn Thr Val Glu Lys
                245                 250                 255

Gln Gly Thr Ser Pro Lys Ile Asn Tyr Thr Glu Ala Ala Leu Lys Asp
            260                 265                 270

Leu Leu Gln Asn Met Lys Lys Asn His Lys Asp Tyr Ala Asp Tyr Ile
        275                 280                 285
```

-continued

```
Glu Lys Thr Tyr Thr Glu Gly Glu Ala Arg Ile Asn Ser Lys Leu Glu
    290                 295                 300

Asp Lys Gln Lys Ile Glu Gln Asp Leu Ala Ala Val Asn Gln Lys Leu
305                 310                 315                 320

Ser Glu Met Pro Arg Lys Pro Lys Asn His Thr His Glu Glu Glu Asn
                325                 330                 335

Lys Phe Ile Ile Gln Lys Glu Lys Leu Tyr Ala Gln Gln Asp Ser Leu
            340                 345                 350

Glu Lys Lys Leu Ser Glu Tyr Asn Asp Leu Met Tyr Gln Lys Ser Asp
        355                 360                 365

Phe Tyr Ser Lys Thr Lys Gly Ser Glu Ala Phe Gln Ile Ala Ser Thr
    370                 375                 380

Gly Lys Thr Ile Pro Thr Pro Ser Trp Val Lys Thr Glu Gly Thr Trp
385                 390                 395                 400

Val Cys Glu Ala Gly Phe Trp Phe Tyr Ile Asp Ala Lys Gly Gln Lys
                405                 410                 415

Lys Ser Asp Trp Phe Asn Asp Lys Thr Pro Asp Gly Lys Asp Arg Trp
            420                 425                 430

Tyr Tyr Leu Ser Thr Glu Thr Pro Arg Leu Asp Asn Val Arg Gly Asn
        435                 440                 445

Ala Tyr Val Gly Lys Gly Thr Met Leu Thr Gly Trp Phe His Asp Thr
    450                 455                 460

Arg Lys Asp Lys Gln Ile Ile Gly Val Asn Thr Lys Thr Thr Tyr Glu
465                 470                 475                 480

Tyr Trp Tyr Tyr Leu Ser Pro Glu Lys Asn Leu Lys Asn Ser Ala Gly
                485                 490                 495

Glu Leu Phe Lys Gln Gly Gln Met Met Thr Lys Trp Val Glu Ile Lys
            500                 505                 510

Asp Thr Lys Thr Gly Glu Pro His Trp Tyr Tyr Phe Asn Pro Asp Asp
        515                 520                 525

Gly Ser Met Thr His Asp Lys Lys Ala Val Gln Ile Gly Asp Lys Lys
    530                 535                 540

Tyr Asp Phe Gly Ser Asn Gly Val Cys Thr Thr Pro Asn Gly Tyr
545                 550                 555
```

<210> SEQ ID NO 46
<211> LENGTH: 1293
<212> TYPE: PRT
<213> ORGANISM: Brevibacillus laterosporus

<400> SEQUENCE: 46

```
Met Asn Gln Asn Gln Asn Lys Asn Glu Met Gln Ile Ile Glu Pro Ser
 1               5                  10                  15

Ser Asp Ser Phe Leu Tyr Ser His Asn Asn Tyr Pro Tyr Ala Thr Asp
            20                  25                  30

Pro Asn Thr Val Leu Glu Gly Arg Asn Tyr Lys Glu Trp Leu Asn Lys
        35                  40                  45

Cys Thr Asp Asn Tyr Thr Asp Ala Leu Gln Ser Pro Glu Ala Thr Ala
    50                  55                  60

Ile Ser Lys Gly Ala Val Ser Ala Ala Ile Ser Ile Ser Thr Lys Val
65                  70                  75                  80

Leu Gly Leu Leu Gly Val Pro Phe Ala Ala Gln Ile Gly Gln Leu Trp
                85                  90                  95

Thr Phe Ile Leu Asn Ala Leu Trp Pro Ser Asp Asn Thr Gln Trp Glu
            100                 105                 110
```

-continued

```
Glu Phe Met Arg His Val Glu Glu Leu Ile Asn Gln Arg Ile Ala Asp
        115                 120                 125

Tyr Ala Arg Asn Lys Ala Leu Ala Glu Leu Thr Gly Leu Gly Asn Asn
    130                 135                 140

Leu Asp Leu Tyr Ile Glu Ala Leu Asp Asp Trp Lys Arg Asn Pro Thr
145                 150                 155                 160

Ser Gln Glu Ala Lys Thr Arg Val Ile Asp Arg Phe Arg Ile Val Asp
                165                 170                 175

Gly Leu Phe Glu Ala Tyr Ile Pro Ser Phe Ala Val Ser Gly Tyr Gln
            180                 185                 190

Val Gln Leu Leu Thr Val Tyr Ala Ala Ala Asn Leu His Leu Leu
        195                 200                 205

Leu Leu Arg Asp Ser Thr Ile Tyr Gly Ile Asp Trp Gly Leu Ser Gln
    210                 215                 220

Thr Asn Val Asn Asp Asn Tyr Asn Arg Gln Ile Arg Leu Thr Ala Thr
225                 230                 235                 240

Tyr Ala Asn His Cys Thr Thr Trp Tyr Gln Thr Gly Leu Glu Arg Leu
                245                 250                 255

Arg Gly Ser Asn Ala Ser Ser Trp Val Thr Tyr Asn Arg Phe Arg Arg
            260                 265                 270

Glu Met Thr Leu Thr Val Leu Asp Ile Cys Ser Leu Phe Ser Asn Tyr
        275                 280                 285

Asp Tyr Arg Ser Tyr Pro Ala Glu Val Arg Gly Glu Ile Thr Arg Glu
    290                 295                 300

Ile Tyr Thr Asp Pro Val Gly Val Gly Trp Val Asp Ser Ala Pro Ser
305                 310                 315                 320

Phe Gly Glu Ile Glu Asn Leu Ala Ile Arg Ala Pro Arg Thr Val Thr
                325                 330                 335

Trp Leu Asn Ser Thr Arg Ile Phe Thr Gly Arg Leu Gln Gly Trp Ser
            340                 345                 350

Gly Thr Asn Asn Tyr Trp Ala Ala His Met Gln Asn Phe Ser Glu Thr
        355                 360                 365

Asn Ser Gly Asn Ile Gln Phe Glu Gly Pro Leu Tyr Gly Ser Thr Val
    370                 375                 380

Gly Thr Ile His Arg Thr Asp Asp Tyr Asp Met Gly Asn Arg Asp Ile
385                 390                 395                 400

Tyr Thr Ile Thr Ser Gln Ala Val Leu Gly Leu Trp Ala Thr Gly Gln
                405                 410                 415

Arg Val Leu Gly Val Ala Ser Ala Arg Phe Thr Leu Arg Asn Leu Phe
            420                 425                 430

Asn Asn Leu Thr Gln Val Leu Val Tyr Glu Asn Pro Ile Ser Ser Thr
        435                 440                 445

Phe Gly Ser Ser Thr Leu Thr His Glu Leu Ser Gly Glu Asn Ser Asp
    450                 455                 460

Arg Pro Thr Ser Ser Asp Tyr Ser His Arg Leu Thr Ser Ile Thr Gly
465                 470                 475                 480

Phe Arg Ala Gly Ala Asn Gly Thr Val Pro Val Phe Gly Trp Thr Ser
                485                 490                 495

Ala Thr Val Asp Arg Asn Asn Ile Ile Glu Arg Asn Lys Ile Thr Gln
            500                 505                 510

Phe Pro Gly Val Lys Ser His Thr Leu Asn Asn Cys Gln Val Val Arg
        515                 520                 525

Gly Thr Gly Phe Thr Gly Gly Asp Trp Leu Arg Pro Asn Asn Asn Gly
    530                 535                 540
```

```
Thr Phe Arg Leu Thr Ile Thr Ser Phe Ser Ser Gln Ser Tyr Arg Ile
545                 550                 555                 560

Arg Leu Arg Tyr Ala Thr Ser Val Gly Asn Thr Ser Leu Val Ile Ser
                565                 570                 575

Ser Ser Asp Ala Gly Ile Ser Ser Thr Thr Ile Pro Leu Thr Ser Thr
            580                 585                 590

Ile Thr Ser Leu Pro Gln Thr Val Pro Tyr Gln Ala Phe Arg Val Val
        595                 600                 605

Asp Leu Pro Ile Thr Phe Thr Thr Pro Thr Thr Gln Arg Asn Tyr Thr
    610                 615                 620

Phe Asp Phe Arg Leu Gln Asn Pro Ser Asn Ala Asn Val Phe Ile Asp
625                 630                 635                 640

Arg Phe Glu Phe Val Pro Ile Gly Gly Ser Leu Ser Glu Tyr Glu Thr
                645                 650                 655

Lys His Gln Leu Glu Lys Ala Arg Lys Ala Val Asn Asp Leu Phe Thr
            660                 665                 670

Asn Glu Ser Lys Asn Val Leu Lys Lys Asp Thr Thr Asp Tyr Asp Ile
        675                 680                 685

Asp Gln Ala Ala Asn Leu Val Glu Cys Val Ser Asp Glu Cys Ala Asn
    690                 695                 700

Ala Lys Met Ile Leu Leu Asp Glu Val Lys Tyr Ala Lys Gln Leu Ser
705                 710                 715                 720

Glu Ala Arg Asn Leu Leu Leu Asn Gly Asn Phe Glu Tyr Gln Asp Arg
                725                 730                 735

Asp Gly Glu Asn Pro Trp Lys Thr Ser Pro Asn Val Thr Ile Gln Glu
            740                 745                 750

Asn Asn Pro Ile Phe Lys Gly Arg Tyr Leu Ser Met Ser Gly Ala Asn
        755                 760                 765

Asn Ile Glu Ala Thr Asn Glu Ile Phe Pro Thr Tyr Val Tyr Gln Lys
    770                 775                 780

Ile Asp Glu Ser Lys Leu Lys Pro Tyr Thr Arg Tyr Lys Val Arg Gly
785                 790                 795                 800

Phe Val Gly Asn Ser Lys Asp Leu Glu Leu Leu Val Thr Arg Tyr Asp
                805                 810                 815

Glu Glu Val Asp Ala Ile Leu Asn Val Pro Asn Asp Ile Pro His Ala
            820                 825                 830

Pro Pro Pro Phe Cys Gly Glu Phe Asp Arg Cys Lys Pro His Ser Tyr
        835                 840                 845

Pro Pro Ile Asn Pro Glu Cys His His Asp Val Ile Asn Asn Ile Glu
    850                 855                 860

Ile Ser Ser Pro Cys Gln His Asn Lys Met Val Asp Asn Ala Asp Ile
865                 870                 875                 880

Ser Tyr Arg His Ser Arg Leu Ser Lys Lys His Gly Ile Cys His Glu
                885                 890                 895

Ser His His Phe Glu Phe His Ile Asp Thr Gly Lys Ile Asp Leu Val
            900                 905                 910

Glu Asn Leu Gly Ile Trp Val Val Phe Lys Ile Cys Ser Thr Asp Gly
        915                 920                 925

Tyr Ala Thr Leu Asp Asn Leu Glu Val Ile Glu Glu Gly Pro Leu Gly
    930                 935                 940

Ala Glu Ser Leu Glu Arg Val Lys Arg Arg Glu Lys Lys Trp Lys His
945                 950                 955                 960

His Met Glu His Lys Cys Ser Glu Thr Lys His Ala Tyr His Ala Ala
```

-continued

```
                965                 970                 975

Lys Gln Ala Val Val Ala Leu Phe Thr Asn Ser Lys Tyr Asp Arg Leu
            980                 985                 990

Lys Phe Glu Thr Thr Ile Ser Asn Ile Leu Phe Ala Asp Tyr Leu Val
        995                 1000                1005

Gln Ser Ile Pro Tyr Val Tyr Asn Lys Trp Leu Pro Gly Val Pro Gly
    1010                1015                1020

Met Asn Tyr Asp Ile Tyr Thr Glu Leu Lys Asn Leu Phe Thr Gly Ala
1025                1030                1035                1040

Phe Asn Leu Tyr Asp Gln Arg Asn Ile Ile Lys Asn Gly Asp Phe Asn
                1045                1050                1055

Arg Gly Leu Met His Trp His Ala Thr Pro His Ala Arg Val Glu Gln
            1060                1065                1070

Ile Ile Asp Asn Arg Ser Val Leu Val Leu Pro Asn Tyr Ala Ala Asn
        1075                1080                1085

Val Ser Gln Glu Val Cys Leu Glu His Asn Arg Gly Tyr Val Leu Arg
    1090                1095                1100

Val Thr Ala Lys Lys Glu Gly Pro Gly Ile Gly Tyr Val Thr Phe Ser
1105                1110                1115                1120

Asp Cys Ala Asn His Ile Glu Lys Leu Thr Phe Thr Ser Cys Asp Tyr
                1125                1130                1135

Gly Thr Asn Val Val Pro Tyr Glu Gln Ser Asn Tyr Pro Thr Asp Gly
            1140                1145                1150

Val Pro Tyr Gly Gln His Gly Cys Asn Ile Asp Gly Val Pro Tyr Glu
        1155                1160                1165

Gln Ser Gly Tyr Arg Thr Asp Gly Val Pro Tyr Glu Gln Ser Gly Tyr
    1170                1175                1180

Arg Thr Asp Gly Val Pro Tyr Glu Gln Ser Gly His Arg Thr Asp Gly
1185                1190                1195                1200

Val Pro Tyr Glu Gln Ser Gly Tyr Arg Thr Asp Gly Val Pro Cys Glu
                1205                1210                1215

Gln His Gly Cys His Thr Asp Gly Leu Pro His Ile Gln His Gly Cys
            1220                1225                1230

Arg Thr Asp Gly Leu Pro His Ile Gln His Gly Cys Arg Thr Asp Arg
        1235                1240                1245

Ser Arg Asp Glu Leu Leu Gly Tyr Val Thr Lys Thr Ile Asp Val Phe
    1250                1255                1260

Pro Asn Thr Asp Lys Val Arg Ile Asp Ile Gly Glu Thr Glu Gly Thr
1265                1270                1275                1280

Phe Lys Val Glu Ser Val Glu Leu Ile Cys Met Glu Glu
                1285                1290


<210> SEQ ID NO 47
<211> LENGTH: 647
<212> TYPE: PRT
<213> ORGANISM: Brevibacillus laterosporus

<400> SEQUENCE: 47

Met Asn Gln Asn Gln Asn Lys Asn Glu Met Gln Ile Ile Glu Pro Ser
 1               5                  10                  15

Ser Asp Ser Phe Leu Tyr Ser His Asn Asn Tyr Pro Tyr Ala Thr Asp
            20                  25                  30

Pro Asn Thr Val Leu Glu Gly Arg Asn Tyr Lys Glu Trp Leu Asn Lys
        35                  40                  45

Cys Thr Asp Asn Tyr Thr Asp Ala Leu Gln Ser Pro Glu Ala Thr Ala
```

```
    50                  55                  60

Ile Ser Lys Gly Ala Val Ser Ala Ala Ile Ser Ile Ser Thr Lys Val
65                  70                  75                  80

Leu Gly Leu Leu Gly Val Pro Phe Ala Ala Gln Ile Gly Gln Leu Trp
                85                  90                  95

Thr Phe Ile Leu Asn Ala Leu Trp Pro Ser Asp Asn Thr Gln Trp Glu
            100                 105                 110

Glu Phe Met Arg His Val Glu Glu Leu Ile Asn Gln Arg Ile Ala Asp
        115                 120                 125

Tyr Ala Arg Asn Lys Ala Leu Ala Glu Leu Thr Gly Leu Gly Asn Asn
    130                 135                 140

Leu Asp Leu Tyr Ile Glu Ala Leu Asp Asp Trp Lys Arg Asn Pro Thr
145                 150                 155                 160

Ser Gln Glu Ala Lys Thr Arg Val Ile Asp Arg Phe Arg Ile Val Asp
                165                 170                 175

Gly Leu Phe Glu Ala Tyr Ile Pro Ser Phe Ala Val Ser Gly Tyr Gln
            180                 185                 190

Val Gln Leu Leu Thr Val Tyr Ala Ala Ala Ala Asn Leu His Leu Leu
        195                 200                 205

Leu Leu Arg Asp Ser Thr Ile Tyr Gly Ile Asp Trp Gly Leu Ser Gln
    210                 215                 220

Thr Asn Val Asn Asp Asn Tyr Asn Arg Gln Ile Arg Leu Thr Ala Thr
225                 230                 235                 240

Tyr Ala Asn His Cys Thr Thr Trp Tyr Gln Thr Gly Leu Glu Arg Leu
                245                 250                 255

Arg Gly Ser Asn Ala Ser Ser Trp Val Thr Tyr Asn Arg Phe Arg Arg
            260                 265                 270

Glu Met Thr Leu Thr Val Leu Asp Ile Cys Ser Leu Phe Ser Asn Tyr
        275                 280                 285

Asp Tyr Arg Ser Tyr Pro Ala Glu Val Arg Gly Glu Ile Thr Arg Glu
    290                 295                 300

Ile Tyr Thr Asp Pro Val Gly Val Gly Trp Val Asp Ser Ala Pro Ser
305                 310                 315                 320

Phe Gly Glu Ile Glu Asn Leu Ala Ile Arg Ala Pro Arg Thr Val Thr
                325                 330                 335

Trp Leu Asn Ser Thr Arg Ile Phe Thr Gly Arg Leu Gln Gly Trp Ser
            340                 345                 350

Gly Thr Asn Asn Tyr Trp Ala Ala His Met Gln Asn Phe Ser Glu Thr
        355                 360                 365

Asn Ser Gly Asn Ile Gln Phe Glu Gly Pro Leu Tyr Gly Ser Thr Val
    370                 375                 380

Gly Thr Ile His Arg Thr Asp Asp Tyr Asp Met Gly Asn Arg Asp Ile
385                 390                 395                 400

Tyr Thr Ile Thr Ser Gln Ala Val Leu Gly Leu Trp Ala Thr Gly Gln
                405                 410                 415

Arg Val Leu Gly Val Ala Ser Ala Arg Phe Thr Leu Arg Asn Leu Phe
            420                 425                 430

Asn Asn Leu Thr Gln Val Leu Val Tyr Glu Asn Pro Ile Ser Ser Thr
        435                 440                 445

Phe Gly Ser Ser Thr Leu Thr His Glu Leu Ser Gly Glu Asn Ser Asp
    450                 455                 460

Arg Pro Thr Ser Ser Asp Tyr Ser His Arg Leu Thr Ser Ile Thr Gly
465                 470                 475                 480
```

-continued

```
Phe Arg Ala Gly Ala Asn Gly Thr Val Pro Val Phe Gly Trp Thr Ser
                485                 490                 495

Ala Thr Val Asp Arg Asn Asn Ile Ile Glu Arg Asn Lys Ile Thr Gln
            500                 505                 510

Phe Pro Gly Val Lys Ser His Thr Leu Asn Asn Cys Gln Val Val Arg
        515                 520                 525

Gly Thr Gly Phe Thr Gly Gly Asp Trp Leu Arg Pro Asn Asn Asn Gly
    530                 535                 540

Thr Phe Arg Leu Thr Ile Thr Ser Phe Ser Ser Gln Ser Tyr Arg Ile
545                 550                 555                 560

Arg Leu Arg Tyr Ala Thr Ser Val Gly Asn Thr Ser Leu Val Ile Ser
                565                 570                 575

Ser Ser Asp Ala Gly Ile Ser Ser Thr Thr Ile Pro Leu Thr Ser Thr
            580                 585                 590

Ile Thr Ser Leu Pro Gln Thr Val Pro Tyr Gln Ala Phe Arg Val Val
        595                 600                 605

Asp Leu Pro Ile Thr Phe Thr Thr Pro Thr Thr Gln Arg Asn Tyr Thr
    610                 615                 620

Phe Asp Phe Arg Leu Gln Asn Pro Ser Asn Ala Asn Val Phe Ile Asp
625                 630                 635                 640

Arg Phe Glu Phe Val Pro Ile
                645


<210> SEQ ID NO 48
<211> LENGTH: 1256
<212> TYPE: PRT
<213> ORGANISM: Brevibacillus laterosporus

<400> SEQUENCE: 48

Met Asn Gln Asn Gln Asn Gln Asn Gln Asn Lys Asn Glu Leu Gln Ile
 1               5                  10                  15

Ile Glu Pro Ser Ser Asp Ser Phe Leu Tyr Ser His Asn Asn Tyr Pro
            20                  25                  30

Tyr Ala Thr Asp Pro Asn Thr Val Leu Gln Gly Arg Asn Tyr Lys Glu
        35                  40                  45

Trp Leu Asn Met Cys Thr Gly Thr Asp Asp Ser Arg Ser Pro Glu Ala
    50                  55                  60

Ala Ser Thr Ala Lys Ser Ala Ile Ser Val Ala Ile Thr Ile Ser Thr
65                  70                  75                  80

Thr Ile Leu Gly Leu Leu Gly Val Pro Phe Ala Ser Gln Ile Gly Ala
                85                  90                  95

Phe Tyr Asn Phe Val Leu Asn Thr Val Trp Pro Gln Gly Asn Asn Gln
            100                 105                 110

Trp Glu Glu Phe Met Arg His Val Glu Asp Leu Ile Asn Glu Arg Ile
        115                 120                 125

Ala Asp Tyr Ala Arg Ser Lys Ala Leu Ala Glu Leu Ala Gly Leu Gly
    130                 135                 140

Asn Asn Leu Asp Leu Tyr Arg Glu Ala Phe Glu Asp Trp Arg Arg Asn
145                 150                 155                 160

Pro Thr Ser Gln Gln Ala Lys Thr Arg Val Ile Glu Arg Phe Arg Ile
                165                 170                 175

Leu Asp Gly Leu Phe Glu Gln Tyr Met Pro Ser Phe Ala Val Gln Gly
            180                 185                 190

Phe Gln Val Gln Leu Leu Thr Val Tyr Ala Ser Ala Ala Asn Ile His
        195                 200                 205
```

```
Leu Phe Leu Leu Arg Asp Ser Ser Ile Tyr Gly Leu Asp Trp Gly Leu
    210                 215                 220

Ser Gln Thr Asn Val Asn Glu Asn Tyr Asn Arg Gln Ile Arg His Ala
225                 230                 235                 240

Ala Thr Tyr Ala Asn His Cys Thr Thr Trp Tyr Gln Thr Gly Leu Gln
                245                 250                 255

Arg Leu Gln Gly Thr Asn Ala Thr Ser Trp Val Ala Tyr Asn Arg Phe
            260                 265                 270

Arg Arg Glu Met Thr Leu Thr Val Leu Asp Ile Ser Ser Leu Phe Ser
        275                 280                 285

Asn Tyr Asp Tyr Arg Ser Tyr Pro Thr Glu Val Arg Gly Glu Leu Thr
    290                 295                 300

Arg Glu Ile Tyr Thr Asp Pro Val Gly Arg Asn Trp Gln Asn Ser Ala
305                 310                 315                 320

Pro Ser Phe Ala Gln Ile Glu Asn Leu Ala Ile Arg Ala Pro Arg Thr
                325                 330                 335

Val Thr Trp Leu Asn Ser Thr Arg Ile Ser Thr Gly Thr Leu Gln Gly
            340                 345                 350

Trp Ser Gly Ser Asn Arg Tyr Trp Ala Ala His Met Gln Asn Phe Ser
        355                 360                 365

Glu Thr Asn Ser Gly Asn Ile Arg Phe Asp Gly Pro Leu Tyr Gly Ser
    370                 375                 380

Thr Val Gly Thr Ile His Arg Thr Asp Asp Tyr Asp Met Gly Asn Arg
385                 390                 395                 400

Asp Ile Tyr Thr Ile Thr Ser Glu Val Val Ala Ser Leu Trp Ala Thr
                405                 410                 415

Gly Gln Thr Val Leu Gly Val Ala Ser Ala Arg Phe Thr Leu Arg Asn
            420                 425                 430

Leu Phe Asn Asn Leu Thr Gln Ala Leu Val Tyr Glu Asn Pro Ile Ser
        435                 440                 445

Ser Ser Phe Asn Arg Ser Thr Leu Thr His Glu Leu Pro Gly Glu Asn
    450                 455                 460

Ser Asp Arg Pro Thr Ser Ser Asp Tyr Ser His Arg Leu Ser Ser Ile
465                 470                 475                 480

Thr Gly Phe Arg Ala Gly Ala Asn Gly Thr Val Pro Val Phe Gly Trp
                485                 490                 495

Thr Ser Ala Thr Val Asp Arg Asn Asn Ile Ile Glu Arg Asn Lys Ile
            500                 505                 510

Thr Gln Phe Pro Gly Val Lys Ser His Thr Leu Asn Asn Cys Gln Val
        515                 520                 525

Val Arg Gly Thr Gly Phe Thr Gly Gly Asp Trp Leu Arg Pro Asn Asn
    530                 535                 540

Asn Gly Thr Phe Arg Leu Thr Ile Thr Ser Phe Ser Ser Gln Ser Tyr
545                 550                 555                 560

Arg Ile Arg Leu Arg Tyr Ala Thr Ser Val Gly Asn Thr Ser Leu Val
                565                 570                 575

Ile Ser Ser Ser Asp Gly Gly Ile Ser Ser Thr Thr Ile Pro Leu Thr
            580                 585                 590

Ser Thr Ile Thr Ser Leu Pro Gln Thr Val Pro Tyr Gln Ala Phe Arg
        595                 600                 605

Val Val Asp Leu Pro Ile Thr Phe Thr Thr Pro Thr Thr Gln Arg Asn
    610                 615                 620

Tyr Thr Phe Asp Phe Arg Leu Gln Asn Pro Ser Asn Ala Asn Val Phe
625                 630                 635                 640
```

```
Ile Asp Arg Ile Glu Phe Val Pro Ile Gly Gly Ser Leu Ser Glu Tyr
                645                 650                 655

Glu Thr Lys His Gln Leu Glu Lys Ala Arg Lys Ala Val Asn Asp Leu
            660                 665                 670

Phe Thr Asn Glu Ser Lys Asn Val Leu Lys Lys Asp Thr Thr Asp Tyr
        675                 680                 685

Asp Ile Asp Gln Ala Ala Asn Leu Val Glu Cys Val Ser Asp Glu Cys
    690                 695                 700

Ala Asn Ala Lys Met Ile Leu Leu Asp Glu Val Lys Tyr Ala Lys Gln
705                 710                 715                 720

Leu Ser Glu Ala Arg Asn Leu Leu Leu Asn Gly Asn Phe Asp Asn Ile
                725                 730                 735

Asp Arg Asp Gly Glu Asn Pro Trp Lys Thr Ser Pro Asn Val Thr Ile
            740                 745                 750

Gln Glu Asn Asn Pro Ile Phe Lys Gly Arg Tyr Leu Ser Met Ser Gly
        755                 760                 765

Ala Asn Asn Ile Glu Ala Thr Asn Glu Ile Phe Pro Thr Tyr Ala Tyr
    770                 775                 780

Gln Lys Ile Asp Glu Ala Lys Leu Lys Pro Tyr Thr Arg Tyr Lys Val
785                 790                 795                 800

Arg Gly Phe Val Gly Asn Ser Lys Asp Leu Glu Leu Leu Val Thr Arg
                805                 810                 815

Tyr Asp Glu Glu Val Asp Ala Ile Leu Asn Val Pro Asn Asp Ile Pro
            820                 825                 830

His Ala Pro Pro Pro Phe Cys Gly Glu Phe Asp Arg Cys Asn Pro His
        835                 840                 845

Ser Tyr Pro Pro Met Asn Pro Glu Cys His His Asp Val Ile Asn Asn
    850                 855                 860

Ile Glu Ile Ser Ser Pro Cys Gln His Asn Lys Met Val Asp Asn Ala
865                 870                 875                 880

Asp Ile Ser Tyr Arg His Ser His Lys Lys His Gly Ile Cys His Glu
                885                 890                 895

Ser His His Phe Glu Phe His Ile Asp Thr Gly Lys Ile Asp Leu Val
            900                 905                 910

Glu Asn Leu Gly Ile Trp Val Ile Phe Lys Ile Cys Ser Thr Asp Gly
        915                 920                 925

Tyr Ala Thr Leu Asp Asn Leu Glu Val Ile Glu Glu Arg Pro Leu Gly
    930                 935                 940

Ala Glu Ser Leu Glu Arg Val Lys Arg Arg Glu Lys Lys Trp Lys His
945                 950                 955                 960

His Met Glu His Lys Cys Ser Glu Thr Lys Leu Ala Tyr His Ala Ala
                965                 970                 975

Lys Gln Ala Leu Val Gly Leu Phe Thr Asn Thr Glu Tyr Asp Arg Leu
            980                 985                 990

Lys Phe Glu Thr Thr Ile Ser Asn Ile Leu Phe Ala Asp Tyr Leu Val
        995                 1000                1005

Gln Ser Ile Pro Tyr Val Tyr Asn Lys Trp Leu Pro Asp Val Pro Gly
    1010                1015                1020

Met Asn Phe Glu Ile Tyr Thr Glu Leu Lys Asn Leu Tyr Thr Gly Ala
1025                1030                1035                1040

Phe Asn Leu Tyr Asp Gln Arg Asn Ile Ile Lys Asn Gly Asp Phe Asn
                1045                1050                1055

Arg Gly Leu Met His Trp His Ala Thr Pro His Ala Arg Val Glu Gln
```

```
            1060                1065                1070

Ile Asp Asn Arg Ser Val Leu Val Leu Pro Asn Tyr Ala Ala Asn Val
        1075                1080                1085

Ser Gln Glu Val Cys Leu Glu His Asn Arg Gly Tyr Val Leu Arg Val
    1090                1095                1100

Thr Ala Lys Lys Glu Gly Pro Gly Ile Gly Tyr Ile Thr Phe Ser Asp
1105                1110                1115                1120

Cys Ala Asn Asn Ile Glu Lys Leu Thr Phe Thr Ser Cys Asp Tyr Gly
                1125                1130                1135

Thr Asn Glu Val Pro Tyr Glu Gln Ser Asn Tyr Pro Thr Asp Gly Val
            1140                1145                1150

Ser Tyr Gly His His Gly Cys Asn Ile Asp Arg Val Arg Tyr Glu Glu
        1155                1160                1165

Ser Gly Tyr Arg Thr Asp Gly Val Pro Tyr Glu Gln Ser Gly Tyr Arg
    1170                1175                1180

Ala Asp Gly Val Ser Tyr Glu Gln His Gly Cys His Thr Asp Gly Val
1185                1190                1195                1200

Pro Tyr Lys Gln His Gly Cys Arg Thr Asp Arg Ser Arg Asp Glu Gln
                1205                1210                1215

Leu Gly Tyr Val Thr Lys Thr Ile Asp Val Phe Pro Asp Thr Asp Lys
            1220                1225                1230

Val Arg Ile Asp Ile Gly Glu Thr Glu Gly Thr Phe Lys Val Glu Ser
        1235                1240                1245

Val Glu Leu Ile Cys Met Glu Glu
    1250                1255


<210> SEQ ID NO 49
<211> LENGTH: 649
<212> TYPE: PRT
<213> ORGANISM: Brevibacillus laterosporus

<400> SEQUENCE: 49

Met Asn Gln Asn Gln Asn Gln Asn Gln Asn Lys Asn Glu Leu Gln Ile
 1               5                  10                  15

Ile Glu Pro Ser Ser Asp Ser Phe Leu Tyr Ser His Asn Asn Tyr Pro
            20                  25                  30

Tyr Ala Thr Asp Pro Asn Thr Val Leu Gln Gly Arg Asn Tyr Lys Glu
        35                  40                  45

Trp Leu Asn Met Cys Thr Gly Thr Asp Asp Ser Arg Ser Pro Glu Ala
    50                  55                  60

Ala Ser Thr Ala Lys Ser Ala Ile Ser Val Ala Ile Thr Ile Ser Thr
65                  70                  75                  80

Thr Ile Leu Gly Leu Leu Gly Val Pro Phe Ala Ser Gln Ile Gly Ala
                85                  90                  95

Phe Tyr Asn Phe Val Leu Asn Thr Val Trp Pro Gln Gly Asn Asn Gln
            100                 105                 110

Trp Glu Glu Phe Met Arg His Val Glu Asp Leu Ile Asn Glu Arg Ile
        115                 120                 125

Ala Asp Tyr Ala Arg Ser Lys Ala Leu Ala Glu Leu Ala Gly Leu Gly
    130                 135                 140

Asn Asn Leu Asp Leu Tyr Arg Glu Ala Phe Glu Asp Trp Arg Arg Asn
145                 150                 155                 160

Pro Thr Ser Gln Gln Ala Lys Thr Arg Val Ile Glu Arg Phe Arg Ile
                165                 170                 175

Leu Asp Gly Leu Phe Glu Gln Tyr Met Pro Ser Phe Ala Val Gln Gly
```

-continued

```
            180                 185                 190

Phe Gln Val Gln Leu Leu Thr Val Tyr Ala Ser Ala Ala Asn Ile His
        195                 200                 205

Leu Phe Leu Leu Arg Asp Ser Ser Ile Tyr Gly Leu Asp Trp Gly Leu
    210                 215                 220

Ser Gln Thr Asn Val Asn Glu Asn Tyr Asn Arg Gln Ile Arg His Ala
225                 230                 235                 240

Ala Thr Tyr Ala Asn His Cys Thr Thr Trp Tyr Gln Thr Gly Leu Gln
                245                 250                 255

Arg Leu Gln Gly Thr Asn Ala Thr Ser Trp Val Ala Tyr Asn Arg Phe
            260                 265                 270

Arg Arg Glu Met Thr Leu Thr Val Leu Asp Ile Ser Ser Leu Phe Ser
        275                 280                 285

Asn Tyr Asp Tyr Arg Ser Tyr Pro Thr Glu Val Arg Gly Glu Leu Thr
    290                 295                 300

Arg Glu Ile Tyr Thr Asp Pro Val Gly Arg Asn Trp Gln Asn Ser Ala
305                 310                 315                 320

Pro Ser Phe Ala Gln Ile Glu Asn Leu Ala Ile Arg Ala Pro Arg Thr
                325                 330                 335

Val Thr Trp Leu Asn Ser Thr Arg Ile Ser Thr Gly Thr Leu Gln Gly
            340                 345                 350

Trp Ser Gly Ser Asn Arg Tyr Trp Ala Ala His Met Gln Asn Phe Ser
        355                 360                 365

Glu Thr Asn Ser Gly Asn Ile Arg Phe Asp Gly Pro Leu Tyr Gly Ser
    370                 375                 380

Thr Val Gly Thr Ile His Arg Thr Asp Asp Tyr Asp Met Gly Asn Arg
385                 390                 395                 400

Asp Ile Tyr Thr Ile Thr Ser Glu Val Val Ala Ser Leu Trp Ala Thr
                405                 410                 415

Gly Gln Thr Val Leu Gly Val Ala Ser Ala Arg Phe Thr Leu Arg Asn
            420                 425                 430

Leu Phe Asn Asn Leu Thr Gln Ala Leu Val Tyr Glu Asn Pro Ile Ser
        435                 440                 445

Ser Ser Phe Asn Arg Ser Thr Leu Thr His Glu Leu Pro Gly Glu Asn
    450                 455                 460

Ser Asp Arg Pro Thr Ser Ser Asp Tyr Ser His Arg Leu Ser Ser Ile
465                 470                 475                 480

Thr Gly Phe Arg Ala Gly Ala Asn Gly Thr Val Pro Val Phe Gly Trp
                485                 490                 495

Thr Ser Ala Thr Val Asp Arg Asn Asn Ile Ile Glu Arg Asn Lys Ile
            500                 505                 510

Thr Gln Phe Pro Gly Val Lys Ser His Thr Leu Asn Asn Cys Gln Val
        515                 520                 525

Val Arg Gly Thr Gly Phe Thr Gly Gly Asp Trp Leu Arg Pro Asn Asn
    530                 535                 540

Asn Gly Thr Phe Arg Leu Thr Ile Thr Ser Phe Ser Ser Gln Ser Tyr
545                 550                 555                 560

Arg Ile Arg Leu Arg Tyr Ala Thr Ser Val Gly Asn Thr Ser Leu Val
                565                 570                 575

Ile Ser Ser Ser Asp Gly Gly Ile Ser Ser Thr Thr Ile Pro Leu Thr
            580                 585                 590

Ser Thr Ile Thr Ser Leu Pro Gln Thr Val Pro Tyr Gln Ala Phe Arg
        595                 600                 605
```

```
Val Val Asp Leu Pro Ile Thr Phe Thr Thr Pro Thr Thr Gln Arg Asn
    610                 615                 620

Tyr Thr Phe Asp Phe Arg Leu Gln Asn Pro Ser Asn Ala Asn Val Phe
625                 630                 635                 640

Ile Asp Arg Ile Glu Phe Val Pro Ile
                645


<210> SEQ ID NO 50
<211> LENGTH: 317
<212> TYPE: PRT
<213> ORGANISM: Brevibacillus laterosporus

<400> SEQUENCE: 50

Met Lys Lys Phe Ala Ser Leu Ile Leu Ile Ser Val Phe Leu Phe Ser
 1               5                  10                  15

Ser Thr Gln Phe Val His Ala Ser Ser Thr Asp Val Gln Glu Arg Leu
            20                  25                  30

Arg Asp Leu Ala Arg Glu Asn Glu Ala Gly Thr Leu Asn Glu Ala Trp
        35                  40                  45

Asn Thr Asn Phe Lys Pro Ser Asp Glu Gln Gln Phe Ser Tyr Ser Pro
    50                  55                  60

Thr Glu Gly Ile Val Phe Leu Thr Pro Pro Lys Asn Val Ile Gly Glu
65                  70                  75                  80

Arg Arg Ile Ser Gln Tyr Lys Val Asn Asn Ala Trp Ala Thr Leu Glu
                85                  90                  95

Gly Ser Pro Thr Glu Val Ser Gly Thr Pro Leu Tyr Val Gly Lys Asn
            100                 105                 110

Val Leu Asp Asn Ser Lys Gly Thr Ser Asp Gln Glu Leu Leu Thr Pro
        115                 120                 125

Glu Phe Asn Tyr Thr Tyr Thr Glu Ser Thr Ser Asn Thr Thr Thr His
    130                 135                 140

Gly Leu Lys Leu Gly Val Lys Thr Thr Ala Thr Met Lys Phe Pro Ile
145                 150                 155                 160

Ala Gln Gly Ser Met Glu Ala Ser Thr Glu Tyr Asn Phe Gln Asp Ser
                165                 170                 175

Ser Thr Asp Thr Thr Thr Lys Thr Val Ser Tyr Lys Ser Pro Ser Gln
            180                 185                 190

Lys Ile Lys Val Pro Ala Gly Lys Thr Phe Arg Val Leu Ala Tyr Leu
        195                 200                 205

Asn Thr Gly Ser Ile Ser Gly Glu Ala Asn Leu Tyr Ala Asn Val Gly
    210                 215                 220

Gly Ile Ala Trp Gly Val Leu Pro Gly Tyr Pro Asn Gly Gly Gly Val
225                 230                 235                 240

Asn Ile Gly Ala Val Leu Thr Lys Cys Gln Gln Lys Gly Trp Gly Asp
                245                 250                 255

Phe Arg Asn Phe Gln Pro Ser Gly Arg Asp Val Ile Val Lys Gly Gln
            260                 265                 270

Gly Thr Phe Lys Ser Asn Tyr Gly Thr Asp Phe Ile Leu Lys Ile Glu
        275                 280                 285

Asp Ile Thr Asp Ser Lys Leu Arg Asn Asn Asn Gly Ser Gly Thr Val
    290                 295                 300

Val Gln Glu Ile Lys Val Pro Leu Ile Arg Thr Glu Ile
305                 310                 315


<210> SEQ ID NO 51
<211> LENGTH: 1154
```

```
<212> TYPE: PRT
<213> ORGANISM: Bacillus thuringiensis

<400> SEQUENCE: 51

Met Asn Phe Leu Phe Leu Val Asn Tyr Glu Lys Asn Lys Phe Lys Tyr
 1               5                  10                  15

Asn Ile Gln Gly Asp Leu Asn Met Asn Gln Lys Asn Tyr Asp Ile Ile
            20                  25                  30

Gly Ser Ser Thr Asn Gly Thr Thr Lys Leu Pro Glu Asp Tyr Asn Ile
        35                  40                  45

Ile Ile Ser Pro Asp Ala Ala Pro Glu Ala Val Thr Ile Ala Ile Ser
    50                  55                  60

Ile Thr Gly Glu Val Leu Ser Leu Phe Gly Val Pro Gly Ala Thr Leu
65                  70                  75                  80

Gly Ser Thr Leu Leu Asn Thr Leu Val Asp Lys Leu Trp Pro Thr Asn
                85                  90                  95

Thr Asn Thr Val Trp Gly Thr Phe Thr Glu Glu Thr Ala Lys Leu Ile
            100                 105                 110

Asn Glu Val Tyr Asn Pro Ser Asp Pro Val Val Lys Asp Ala Asp Ala
        115                 120                 125

Arg Leu Thr Ser Leu His Glu Ser Leu Lys Leu Tyr Gln Leu Ala Phe
    130                 135                 140

Gly Asn Trp Phe Lys Ser Gln Asp Asn Ser Lys Leu Lys Glu Glu Val
145                 150                 155                 160

Arg Arg Gln Phe Asp Ile Thr His Asn Arg Phe Val Thr Ser Met Pro
                165                 170                 175

Phe Phe Lys Val Ser Asp Tyr Glu Ile Arg Leu Leu Thr Asn Tyr Ala
            180                 185                 190

Gln Ala Ala Asn Leu His Leu Thr Phe Leu Arg Asp Ala Ser Ile Tyr
        195                 200                 205

Gly Leu Asp Trp Gly Phe Ser Asp Glu His Ser Asn Asp Leu Tyr Glu
    210                 215                 220

Gln Gln Lys Asn Arg Thr Gly Glu Tyr Thr Asp His Cys Val Lys Trp
225                 230                 235                 240

Tyr Asn Ala Gly Leu Glu Lys Leu Lys Gly Asn Leu Thr Gly Glu Asn
                245                 250                 255

Trp Tyr Thr Tyr Asn Arg Phe Arg Arg Glu Met Thr Leu Met Val Leu
            260                 265                 270

Asp Val Val Ala Leu Phe Pro Asn Tyr Asp Thr Arg Met Tyr Pro Ile
        275                 280                 285

Ala Thr Ser Ser Glu Leu Thr Arg Met Ile Tyr Thr Asp Pro Ile Ala
    290                 295                 300

Tyr Thr Gln Ser Asp Pro Trp Tyr Lys Ile Thr Ser Leu Ser Phe Ser
305                 310                 315                 320

Asn Ile Glu Asn Ser Ala Ile Pro Ser Pro Ser Phe Phe Arg Trp Leu
                325                 330                 335

Lys Ser Val Ser Ile Asn Ser Gln Trp Trp Gly Ser Gly Pro Asn Gln
            340                 345                 350

Thr Tyr Tyr Trp Val Gly His Glu Leu Val Tyr Ser Asn Ser Asn Tyr
        355                 360                 365

Asn Gln Ser Leu Lys Val Lys Tyr Gly Asp Pro Asn Ser Tyr Ile Glu
    370                 375                 380

Pro Pro Asp Ser Phe Ser Phe Ser Ser Thr Asp Val Tyr Arg Thr Ile
385                 390                 395                 400
```

-continued

```
Ser Val Val Arg Asn Ser Ile Ser Asn Tyr Ile Val Ser Glu Val Gln
            405                 410                 415

Phe Asn Ser Ile Ser Asn Thr Asn Gln Ile Ser Glu Glu Ile Tyr Lys
        420                 425                 430

His Gln Ser Asn Trp Asn Arg Arg Glu Thr Lys Asp Ser Ile Thr Glu
    435                 440                 445

Leu Ser Leu Ala Ala Asn Pro Pro Thr Thr Phe Gly Asn Val Ala Glu
    450                 455                 460

Tyr Ser His Arg Leu Ala Tyr Ile Ser Glu Ala Tyr Gln Ser Asn Asn
465                 470                 475                 480

Pro Ser Lys Tyr Pro Ala Tyr Ile Pro Val Phe Gly Trp Thr His Thr
            485                 490                 495

Ser Val Arg Tyr Asp Asn Lys Ile Phe Pro Asp Lys Ile Thr Gln Ile
        500                 505                 510

Pro Ala Val Lys Ser Ser Ser Ala Glu Gly Gly Thr Trp Lys Asn Ile
    515                 520                 525

Ala Lys Gly Pro Gly Phe Thr Gly Gly Asp Val Thr Thr Ala Val Ser
    530                 535                 540

Pro Ala Phe Ile Thr Asp Met Ile Lys Ile His Val Thr Leu Asp Pro
545                 550                 555                 560

Asn Ser Leu Ser Gln Lys Tyr Arg Ala Arg Leu Arg Tyr Ala Ser Asn
            565                 570                 575

Ala Tyr Val Ala Ala Thr Leu Tyr Thr Asn Ser Ser Ser Asn Tyr Asn
        580                 585                 590

Phe Glu Leu Thr Lys Gly Thr Thr Glu Gln Phe Thr Thr Tyr Asn Ser
    595                 600                 605

Tyr Gln Tyr Val Asp Ile Pro Gly Ser Ile Gln Phe Asn Thr Thr Ser
    610                 615                 620

Asp Thr Val Ser Val Tyr Leu His Met Asp Ser Thr Thr Asn Ala Asn
625                 630                 635                 640

Val His Val Asp Arg Ile Glu Phe Ile Pro Val Asp Glu Asn Tyr Asp
            645                 650                 655

Asn Arg Val Thr Leu Glu Lys Ala Gln Lys Ala Val Asn Ala Leu Phe
        660                 665                 670

Thr Ala Gly Arg His Ala Leu Gln Thr Asp Val Thr Asp Phe Lys Val
    675                 680                 685

Asp Gln Val Ser Ile Leu Val Asp Cys Val Ser Gly Glu Leu Tyr Pro
    690                 695                 700

Asn Glu Lys Arg Glu Leu Leu Ser Leu Val Lys Tyr Ala Lys Arg Leu
705                 710                 715                 720

Ser Tyr Ser Arg Asn Leu Leu Leu Asp Pro Thr Phe Asp Ser Ile Asn
            725                 730                 735

Ser Ser Glu Glu Asn Gly Trp His Gly Ser Asn Gly Ile Ala Ile Gly
        740                 745                 750

Asn Gly Asn Phe Val Phe Lys Gly Asn Tyr Leu Ile Phe Ser Gly Thr
    755                 760                 765

Asn Asp Thr Gln Tyr Pro Thr Tyr Leu Tyr Gln Lys Ile Asp Glu Ser
    770                 775                 780

Lys Leu Lys Glu Tyr Thr Arg Tyr Lys Leu Arg Gly Phe Ile Glu Ser
785                 790                 795                 800

Ser Gln Asp Leu Glu Ala Tyr Val Ile Arg Tyr Asp Ala Lys Tyr Glu
            805                 810                 815

Thr Leu Asp Val Ser Asn Asn Leu Tyr Pro Asp Ile Ser Pro Val Asn
        820                 825                 830
```

```
Ala Cys Gly Glu Pro Asn Arg Cys Ala Ala Leu Pro Tyr Leu Asp Glu
        835                 840                 845

Asn Pro Arg Leu Glu Cys Ser Ser Ile Gln Asp Gly Ile Leu Ser Asp
    850                 855                 860

Ser His Ser Phe Ser Leu Asn Ile Asp Thr Gly Ser Ile Asp Ser Asn
865                 870                 875                 880

Glu Asn Val Gly Ile Trp Val Leu Phe Lys Ile Ser Thr Pro Glu Gly
                885                 890                 895

Tyr Ala Lys Phe Gly Asn Leu Glu Val Ile Glu Asp Gly Pro Val Ile
            900                 905                 910

Gly Glu Ala Leu Ala Arg Val Lys Arg Gln Glu Thr Lys Trp Arg Asn
        915                 920                 925

Lys Leu Thr Gln Leu Arg Thr Glu Thr Gln Ala Ile Tyr Thr Arg Ala
    930                 935                 940

Lys Gln Ala Ile Asp Asn Leu Phe Thr Asn Ala Gln Asp Ser His Leu
945                 950                 955                 960

Lys Ile Gly Ala Thr Phe Ala Ser Ile Val Ala Ala Arg Lys Ile Val
                965                 970                 975

Gln Ser Ile Arg Glu Ala Tyr Met Pro Trp Leu Ser Ile Val Pro Gly
            980                 985                 990

Val Asn Tyr Pro Ile Phe Thr Glu Leu Asn Glu Arg Val Gln Gln Ala
        995                 1000                1005

Phe Gln Leu Tyr Asp Val Arg Asn Val Val Arg Asn Gly Arg Phe Leu
    1010                1015                1020

Asn Gly Val Ser Asp Trp Ile Val Thr Ser Asp Val Thr Val Gln Glu
1025                1030                1035                1040

Glu Asn Gly Asn Asn Val Leu Val Leu Ser Asn Trp Asp Ala Gln Val
                1045                1050                1055

Leu Gln Cys Leu Lys Leu Tyr Gln Asp Arg Gly Tyr Ile Leu Arg Val
            1060                1065                1070

Thr Ala Arg Lys Glu Gly Leu Gly Glu Gly Tyr Ile Thr Ile Thr Asp
        1075                1080                1085

Glu Glu Gly Tyr Thr Asp Gln Leu Thr Phe Gly Thr Cys Glu Glu Ile
    1090                1095                1100

Asp Ala Ser Asn Thr Phe Val Ser Thr Gly Tyr Ile Thr Lys Glu Leu
1105                1110                1115                1120

Glu Phe Phe Pro Asp Thr Glu Lys Val Arg Ile Glu Val Gly Glu Thr
                1125                1130                1135

Glu Gly Thr Phe Arg Val Glu Ser Val Glu Leu Phe Leu Met Glu Glu
            1140                1145                1150

His Cys


<210> SEQ ID NO 52
<211> LENGTH: 651
<212> TYPE: PRT
<213> ORGANISM: Bacillus thuringiensis

<400> SEQUENCE: 52

Met Asn Phe Leu Phe Leu Val Asn Tyr Glu Lys Asn Lys Phe Lys Tyr
 1               5                  10                  15

Asn Ile Gln Gly Asp Leu Asn Met Asn Gln Lys Asn Tyr Asp Ile Ile
            20                  25                  30

Gly Ser Ser Thr Asn Gly Thr Thr Lys Leu Pro Glu Asp Tyr Asn Ile
        35                  40                  45
```

-continued

```
Ile Ile Ser Pro Asp Ala Ala Pro Glu Ala Val Thr Ile Ala Ile Ser
    50                  55                  60

Ile Thr Gly Glu Val Leu Ser Leu Phe Gly Val Pro Gly Ala Thr Leu
65                  70                  75                  80

Gly Ser Thr Leu Leu Asn Thr Leu Val Asp Lys Leu Trp Pro Thr Asn
                85                  90                  95

Thr Asn Thr Val Trp Gly Thr Phe Thr Glu Glu Thr Ala Lys Leu Ile
            100                 105                 110

Asn Glu Val Tyr Asn Pro Ser Asp Pro Val Val Lys Asp Ala Asp Ala
        115                 120                 125

Arg Leu Thr Ser Leu His Glu Ser Leu Lys Leu Tyr Gln Leu Ala Phe
    130                 135                 140

Gly Asn Trp Phe Lys Ser Gln Asp Asn Ser Lys Leu Lys Glu Glu Val
145                 150                 155                 160

Arg Arg Gln Phe Asp Ile Thr His Asn Arg Phe Val Thr Ser Met Pro
                165                 170                 175

Phe Phe Lys Val Ser Asp Tyr Glu Ile Arg Leu Leu Thr Asn Tyr Ala
            180                 185                 190

Gln Ala Ala Asn Leu His Leu Thr Phe Leu Arg Asp Ala Ser Ile Tyr
        195                 200                 205

Gly Leu Asp Trp Gly Phe Ser Asp Glu His Ser Asn Asp Leu Tyr Glu
    210                 215                 220

Gln Gln Lys Asn Arg Thr Gly Glu Tyr Thr Asp His Cys Val Lys Trp
225                 230                 235                 240

Tyr Asn Ala Gly Leu Glu Lys Leu Lys Gly Asn Leu Thr Gly Glu Asn
                245                 250                 255

Trp Tyr Thr Tyr Asn Arg Phe Arg Arg Glu Met Thr Leu Met Val Leu
            260                 265                 270

Asp Val Val Ala Leu Phe Pro Asn Tyr Asp Thr Arg Met Tyr Pro Ile
        275                 280                 285

Ala Thr Ser Ser Glu Leu Thr Arg Met Ile Tyr Thr Asp Pro Ile Ala
    290                 295                 300

Tyr Thr Gln Ser Asp Pro Trp Tyr Lys Ile Thr Ser Leu Ser Phe Ser
305                 310                 315                 320

Asn Ile Glu Asn Ser Ala Ile Pro Ser Pro Ser Phe Phe Arg Trp Leu
                325                 330                 335

Lys Ser Val Ser Ile Asn Ser Gln Trp Trp Gly Ser Gly Pro Asn Gln
            340                 345                 350

Thr Tyr Tyr Trp Val Gly His Glu Leu Val Tyr Ser Asn Ser Asn Tyr
        355                 360                 365

Asn Gln Ser Leu Lys Val Lys Tyr Gly Asp Pro Asn Ser Tyr Ile Glu
    370                 375                 380

Pro Pro Asp Ser Phe Ser Phe Ser Ser Thr Asp Val Tyr Arg Thr Ile
385                 390                 395                 400

Ser Val Val Arg Asn Ser Ile Ser Asn Tyr Ile Val Ser Glu Val Gln
                405                 410                 415

Phe Asn Ser Ile Ser Asn Thr Asn Gln Ile Ser Glu Glu Ile Tyr Lys
            420                 425                 430

His Gln Ser Asn Trp Asn Arg Arg Glu Thr Lys Asp Ser Ile Thr Glu
        435                 440                 445

Leu Ser Leu Ala Ala Asn Pro Pro Thr Thr Phe Gly Asn Val Ala Glu
    450                 455                 460

Tyr Ser His Arg Leu Ala Tyr Ile Ser Glu Ala Tyr Gln Ser Asn Asn
465                 470                 475                 480
```

Pro Ser Lys Tyr Pro Ala Tyr Ile Pro Val Phe Gly Trp Thr His Thr
485 490 495

Ser Val Arg Tyr Asp Asn Lys Ile Phe Pro Asp Lys Ile Thr Gln Ile
500 505 510

Pro Ala Val Lys Ser Ser Ser Ala Glu Gly Gly Thr Trp Lys Asn Ile
515 520 525

Ala Lys Gly Pro Gly Phe Thr Gly Gly Asp Val Thr Thr Ala Val Ser
530 535 540

Pro Ala Phe Ile Thr Asp Met Ile Lys Ile His Val Thr Leu Asp Pro
545 550 555 560

Asn Ser Leu Ser Gln Lys Tyr Arg Ala Arg Leu Arg Tyr Ala Ser Asn
565 570 575

Ala Tyr Val Ala Ala Thr Leu Tyr Thr Asn Ser Ser Ser Asn Tyr Asn
580 585 590

Phe Glu Leu Thr Lys Gly Thr Thr Glu Gln Phe Thr Thr Tyr Asn Ser
595 600 605

Tyr Gln Tyr Val Asp Ile Pro Gly Ser Ile Gln Phe Asn Thr Thr Ser
610 615 620

Asp Thr Val Ser Val Tyr Leu His Met Asp Ser Thr Thr Asn Ala Asn
625 630 635 640

Val His Val Asp Arg Ile Glu Phe Ile Pro Val
645 650

<210> SEQ ID NO 53
<211> LENGTH: 1206
<212> TYPE: PRT
<213> ORGANISM: Bacillus thuringiensis

<400> SEQUENCE: 53

Met Arg Leu Lys Lys Leu Leu Val Cys Asn Ile Arg Ile Gly Gly Thr
1 5 10 15

Asn Met Asn Leu Gly Asn Tyr Asn Glu Phe Asp Ile Ile Asp Ile Thr
20 25 30

Glu Asn Asn Gln Thr Lys Thr Ser Arg Tyr Asn Asn Val Asn Arg Gln
35 40 45

Glu Asn Pro Ser Asn Met Ile Ile Ser Asn Pro Ser Ser Asn Tyr Pro
50 55 60

Leu Ala Asn Asn Pro Asn Thr Pro Phe Gln Asn Ile Asn Tyr Lys Asp
65 70 75 80

Phe Leu Asn Met Asn Glu Glu Ile Ala Pro Tyr Ala Ser Ser Lys Asp
85 90 95

Val Ile Phe Ser Ser Met Asn Ile Ile Arg Thr Phe Met Gly Phe Ala
100 105 110

Gly His Gly Thr Ala Gly Gly Ile Val Ala Leu Phe Thr Glu Val Leu
115 120 125

Arg Leu Leu Trp Pro Asn Lys Gln Asp Glu Leu Trp Glu Ser Phe Met
130 135 140

Lys Glu Val Glu Lys Leu Ile Glu Gln Glu Ile Thr Asp Ala Val Val
145 150 155 160

Ser Lys Ala Leu Ala Glu Leu Glu Gly Leu Arg Asn Ala Leu Gln Gly
165 170 175

Tyr Thr Asp Ala Leu Glu Ala Trp Gln Asn Asn Arg Ser Asp Lys Leu
180 185 190

Lys Gln Leu Leu Val Tyr Asp Arg Phe Val Ser Thr Glu Asn Leu Phe
195 200 205

```
Lys Phe Ala Met Pro Ser Phe Arg Val Gly Gly Phe Glu Val Pro Leu
    210                 215                 220

Leu Thr Val Tyr Ala Gln Ala Ala Asn Leu His Leu Leu Leu Leu Lys
225                 230                 235                 240

Asn Ser Glu Leu Phe Gly Ala Glu Trp Gly Met Gln Gln Tyr Glu Ile
                245                 250                 255

Asp Leu Phe Tyr Asn Glu Gln Lys Asp Tyr Val Val Glu Tyr Thr Asp
            260                 265                 270

His Cys Val Lys Trp Tyr Thr Glu Gly Leu Asn Arg Leu Lys Asn Ala
        275                 280                 285

Ser Gly Val Lys Gly Lys Val Trp Glu Glu Tyr Asn Arg Phe Arg Arg
    290                 295                 300

Glu Met Thr Ile Met Val Leu Asp Leu Leu Pro Leu Phe Pro Ile Tyr
305                 310                 315                 320

Asp Val Arg Thr Tyr Pro Thr Glu Thr Val Thr Glu Leu Thr Arg Gln
                325                 330                 335

Ile Phe Thr Asp Pro Ile Gly Leu Arg Gly Ile Asn Glu Ser Lys Tyr
            340                 345                 350

Pro Asp Trp Tyr Gly Ala Ala Ser Asp Ser Phe Ser Leu Ile Glu Asn
        355                 360                 365

Arg Ala Val Pro Gln Pro Ser Leu Phe Gln Trp Leu Thr Glu Phe Lys
    370                 375                 380

Val Tyr Thr Lys Tyr Val Glu Pro Asn Asp Lys Leu Thr Ile Leu Ala
385                 390                 395                 400

Gly His Ser Val Thr Thr Gln Tyr Thr Ser Tyr Tyr Lys Lys Ser Thr
                405                 410                 415

Phe Thr Tyr Gly Asp Thr Ser Ser Ala Asn Ser Ser Arg Thr Phe Asp
            420                 425                 430

Leu Leu Ala Lys Asp Val Tyr Gln Val Asp Ser Val Ala Ala Ala Ser
        435                 440                 445

Lys Ser Ala Thr Trp Tyr Leu Ala Val Pro Glu Met Arg Leu Tyr Ser
    450                 455                 460

Ile Asn Thr Asn Asn Ile Leu Ser Glu Asp Tyr Phe Ser Leu Ser Thr
465                 470                 475                 480

Asn Ile Pro Ser Ser Lys Met Arg Arg Met Tyr Ser Ser Glu Glu Leu
                485                 490                 495

Pro Ile Gly Ile Ser Asp Thr Pro Ile Tyr Gly Asp Leu Glu Glu Tyr
            500                 505                 510

Ser His Arg Leu Ser Phe Ile Ser Glu Ile Met His Asn Ser Gly Ser
        515                 520                 525

Val Thr Gly Ser Asn Asn Ile Lys Gly Ile Ile Pro Val Leu Gly Trp
    530                 535                 540

Thr His Thr Ser Val Ser Pro Glu Asn Tyr Ile His Arg Asp Lys Ile
545                 550                 555                 560

Ser Gln Leu Tyr Ala Val Lys Ala Tyr Thr Thr Ser Asn Val Ser Val
                565                 570                 575

Val Gly Gly Pro Gly Phe Leu Gly Gly Asn Ile Ile Lys Gly Asn Asn
            580                 585                 590

Asp Pro Ala Ser Tyr Thr Gly Ser Val Ser Trp Ala Ile Arg Leu Asp
        595                 600                 605

Gly Ser Thr Val Ser Arg Phe Arg Leu Arg Ile Pro Tyr Ala Ala Glu
    610                 615                 620

Thr Asp Gly Thr Phe Ser Ile Thr Val Arg Asp Asp Leu Gly Pro Phe
```

-continued

```
625                 630                 635                 640

Thr Ile Lys Lys Asp Phe Ile Ala Thr Met Lys Pro Gly Asp Pro Leu
                645                 650                 655

Ser Tyr Gly Lys Phe Glu Tyr Leu Glu Phe Glu Gln Thr Met Ser Leu
            660                 665                 670

Asn Asn Lys His Gly Gln Phe Phe Val His Thr Glu Asn Leu Lys Asp
        675                 680                 685

Arg Asn Ser Ser Val Tyr Trp Asn Arg Val Glu Ile Ile Pro Val Asp
    690                 695                 700

Glu Asn Tyr Asp Asn Arg Val Arg Leu Glu Lys Ala Gln Lys Ala Val
705                 710                 715                 720

Asn Ala Leu Phe Thr Ala Gly Arg His Ala Leu Gln Thr Asn Val Thr
                725                 730                 735

Asp Tyr Lys Val Asp Gln Val Ser Ile Leu Val Asp Ser Val Ser Gly
            740                 745                 750

Glu Leu Tyr Pro Asn Glu Lys Arg Glu Leu Gln Ser Leu Val Lys Tyr
        755                 760                 765

Ala Lys Arg Leu Ser Tyr Ser Arg Asn Leu Leu Leu Asp Pro Thr Phe
    770                 775                 780

Asp Ser Ile Asn Ser Ser Glu Glu Asn Gly Trp Tyr Gly Ser Asn Gly
785                 790                 795                 800

Ile Ala Ile Gly Asn Gly Asn Phe Val Phe Lys Gly Asn Tyr Leu Asn
                805                 810                 815

Phe Ser Gly Thr Asn Asp Thr Gln Tyr Pro Thr Tyr Leu Tyr Gln Lys
            820                 825                 830

Ile Asp Glu Ser Lys Leu Lys Glu Tyr Thr Arg Tyr Lys Leu Arg Gly
        835                 840                 845

Phe Ile Glu Ser Ser Gln Asp Leu Glu Ala Tyr Val Val Arg Tyr Asp
    850                 855                 860

Ala Lys His Glu Thr Leu Asp Val Ser Asn Asn Leu Phe Pro Asp Ile
865                 870                 875                 880

Ser Pro Val Asn Ala Cys Gly Glu Pro Asn Arg Cys Ala Ala Leu Pro
                885                 890                 895

Tyr Leu Asp Lys Asn Pro Arg Leu Glu Cys Ser Leu Ile Gln Asp Gly
            900                 905                 910

Ile Leu Ser Asp Ser His Ser Phe Ser Leu Asn Ile Asp Thr Gly Ser
        915                 920                 925

Ile Asp Ser Thr Glu Asn Val Gly Ile Trp Val Leu Phe Lys Ile Ser
    930                 935                 940

Thr Pro Glu Gly Tyr Ala Lys Phe Gly Asn Leu Glu Val Ile Glu Tyr
945                 950                 955                 960

Gly Pro Val Ile Gly Glu Ala Leu Ala Arg Val Lys Arg Gln Glu Thr
                965                 970                 975

Lys Trp Arg Asn Lys Leu Thr Gln Leu Arg Thr Glu Thr Gln Ala Ile
            980                 985                 990

Tyr Thr Arg Ala Lys Gln Ala Ile Asp Asn Leu Phe Thr Asn Thr Gln
        995                 1000                1005

Asp Ser Tyr Leu Lys Ile Gly Ala Thr Phe Ala Ser Ile Val Ala Ala
    1010                1015                1020

Arg Lys Ile Val Gln Ser Ile Arg Glu Ala Tyr Met Ser Trp Leu Ser
1025                1030                1035                1040

Ile Val Pro Gly Val Asn Tyr Pro Ile Phe Thr Glu Leu Asn Glu Arg
                1045                1050                1055
```

```
Val Gln Arg Ala Phe Gln Leu Tyr Asp Val Arg Asn Val Val Arg Asn
            1060                1065                1070

Gly Arg Phe Leu Ser Gly Val Ser Asp Trp Ile Val Thr Ser Asp Val
        1075                1080                1085

Lys Val Gln Glu Glu Asn Gly Asn Asn Val Leu Val Leu Ser Asn Trp
    1090                1095                1100

Asp Ala Gln Val Leu Gln Cys Leu Lys Leu Tyr Gln Asp Arg Gly Tyr
1105                1110                1115                1120

Ile Leu Arg Val Thr Ala Arg Lys Glu Gly Leu Gly Glu Gly Tyr Ile
                1125                1130                1135

Thr Ile Thr Asp Glu Glu Gly His Thr Asp Gln Leu Thr Phe Gly Thr
            1140                1145                1150

Cys Glu Glu Ile Asp Ala Ser Asn Thr Phe Val Ser Thr Gly Tyr Ile
        1155                1160                1165

Thr Lys Glu Leu Glu Phe Phe Pro Asp Thr Glu Lys Val Arg Ile Glu
    1170                1175                1180

Ile Gly Glu Thr Glu Gly Ile Phe Lys Val Glu Ser Val Glu Leu Phe
1185                1190                1195                1200

Leu Met Glu Asp Leu Cys
                1205
```

<210> SEQ ID NO 54
<211> LENGTH: 703
<212> TYPE: PRT
<213> ORGANISM: Bacillus thuringiensis

<400> SEQUENCE: 54

```
Met Arg Leu Lys Lys Leu Leu Val Cys Asn Ile Arg Ile Gly Gly Thr
 1               5                  10                  15

Asn Met Asn Leu Gly Asn Tyr Asn Glu Phe Asp Ile Ile Asp Ile Thr
            20                  25                  30

Glu Asn Asn Gln Thr Lys Thr Ser Arg Tyr Asn Asn Val Asn Arg Gln
        35                  40                  45

Glu Asn Pro Ser Asn Met Ile Ile Ser Asn Pro Ser Ser Asn Tyr Pro
    50                  55                  60

Leu Ala Asn Asn Pro Asn Thr Pro Phe Gln Asn Ile Asn Tyr Lys Asp
65                  70                  75                  80

Phe Leu Asn Met Asn Glu Glu Ile Ala Pro Tyr Ala Ser Ser Lys Asp
                85                  90                  95

Val Ile Phe Ser Ser Met Asn Ile Ile Arg Thr Phe Met Gly Phe Ala
            100                 105                 110

Gly His Gly Thr Ala Gly Gly Ile Val Ala Leu Phe Thr Glu Val Leu
        115                 120                 125

Arg Leu Leu Trp Pro Asn Lys Gln Asp Glu Leu Trp Glu Ser Phe Met
    130                 135                 140

Lys Glu Val Glu Lys Leu Ile Glu Gln Glu Ile Thr Asp Ala Val Val
145                 150                 155                 160

Ser Lys Ala Leu Ala Glu Leu Glu Gly Leu Arg Asn Ala Leu Gln Gly
                165                 170                 175

Tyr Thr Asp Ala Leu Glu Ala Trp Gln Asn Asn Arg Ser Asp Lys Leu
            180                 185                 190

Lys Gln Leu Leu Val Tyr Asp Arg Phe Val Ser Thr Glu Asn Leu Phe
        195                 200                 205

Lys Phe Ala Met Pro Ser Phe Arg Val Gly Gly Phe Glu Val Pro Leu
    210                 215                 220
```

-continued

```
Leu Thr Val Tyr Ala Gln Ala Ala Asn Leu His Leu Leu Leu Leu Lys
225                 230                 235                 240

Asn Ser Glu Leu Phe Gly Ala Glu Trp Gly Met Gln Gln Tyr Glu Ile
                245                 250                 255

Asp Leu Phe Tyr Asn Glu Gln Lys Asp Tyr Val Val Glu Tyr Thr Asp
            260                 265                 270

His Cys Val Lys Trp Tyr Thr Glu Gly Leu Asn Arg Leu Lys Asn Ala
        275                 280                 285

Ser Gly Val Lys Gly Lys Val Trp Glu Glu Tyr Asn Arg Phe Arg Arg
    290                 295                 300

Glu Met Thr Ile Met Val Leu Asp Leu Leu Pro Leu Phe Pro Ile Tyr
305                 310                 315                 320

Asp Val Arg Thr Tyr Pro Thr Glu Thr Val Thr Glu Leu Thr Arg Gln
                325                 330                 335

Ile Phe Thr Asp Pro Ile Gly Leu Arg Gly Ile Asn Glu Ser Lys Tyr
            340                 345                 350

Pro Asp Trp Tyr Gly Ala Ala Ser Asp Ser Phe Ser Leu Ile Glu Asn
        355                 360                 365

Arg Ala Val Pro Gln Pro Ser Leu Phe Gln Trp Leu Thr Glu Phe Lys
    370                 375                 380

Val Tyr Thr Lys Tyr Val Glu Pro Asn Asp Lys Leu Thr Ile Leu Ala
385                 390                 395                 400

Gly His Ser Val Thr Thr Gln Tyr Thr Ser Tyr Tyr Lys Lys Ser Thr
                405                 410                 415

Phe Thr Tyr Gly Asp Thr Ser Ser Ala Asn Ser Ser Arg Thr Phe Asp
            420                 425                 430

Leu Leu Ala Lys Asp Val Tyr Gln Val Asp Ser Val Ala Ala Ala Ser
        435                 440                 445

Lys Ser Ala Thr Trp Tyr Leu Ala Val Pro Glu Met Arg Leu Tyr Ser
    450                 455                 460

Ile Asn Thr Asn Asn Ile Leu Ser Glu Asp Tyr Phe Ser Leu Ser Thr
465                 470                 475                 480

Asn Ile Pro Ser Ser Lys Met Arg Arg Met Tyr Ser Ser Glu Glu Leu
                485                 490                 495

Pro Ile Gly Ile Ser Asp Thr Pro Ile Tyr Gly Asp Leu Glu Glu Tyr
            500                 505                 510

Ser His Arg Leu Ser Phe Ile Ser Glu Ile Met His Asn Ser Gly Ser
        515                 520                 525

Val Thr Gly Ser Asn Asn Ile Lys Gly Ile Ile Pro Val Leu Gly Trp
    530                 535                 540

Thr His Thr Ser Val Ser Pro Glu Asn Tyr Ile His Arg Asp Lys Ile
545                 550                 555                 560

Ser Gln Leu Tyr Ala Val Lys Ala Tyr Thr Thr Ser Asn Val Ser Val
                565                 570                 575

Val Gly Gly Pro Gly Phe Leu Gly Gly Asn Ile Ile Lys Gly Asn Asn
            580                 585                 590

Asp Pro Ala Ser Tyr Thr Gly Ser Val Ser Trp Ala Ile Arg Leu Asp
        595                 600                 605

Gly Ser Thr Val Ser Arg Phe Arg Leu Arg Ile Pro Tyr Ala Ala Glu
    610                 615                 620

Thr Asp Gly Thr Phe Ser Ile Thr Val Arg Asp Asp Leu Gly Pro Phe
625                 630                 635                 640

Thr Ile Lys Lys Asp Phe Ile Ala Thr Met Lys Pro Gly Asp Pro Leu
                645                 650                 655
```

```
Ser Tyr Gly Lys Phe Glu Tyr Leu Glu Phe Glu Gln Thr Met Ser Leu
            660                 665                 670

Asn Asn Lys His Gly Gln Phe Phe Val His Thr Glu Asn Leu Lys Asp
        675                 680                 685

Arg Asn Ser Ser Val Tyr Trp Asn Arg Val Glu Ile Ile Pro Val
    690                 695                 700
```

<210> SEQ ID NO 55
<211> LENGTH: 772
<212> TYPE: PRT
<213> ORGANISM: Bacillus thuringiensis

<400> SEQUENCE: 55

```
Met Val Asn Glu Asn Met Asp Met Tyr Asn Asn Asn Gly Ser Met Asn
 1               5                  10                  15

Gly Asn Pro Asp Met Tyr Asn Lys Asn Gly Ser Met Asn Gly Asn Thr
            20                  25                  30

Asp Val Tyr Asn Asn Asn Gly Ser Met Asn Gly Asn Pro Asp Met Tyr
        35                  40                  45

Asn Asn Asn Gly Ser Met Asn Gly Asn Thr Asp Val Tyr Asn Asn Asn
    50                  55                  60

Gly Ser Met Asn Gly Asn Pro Asp Val Tyr Asn Lys Asn Gly Ser Met
65                  70                  75                  80

Asp Gly Asn Pro Asp Met Tyr Asn Asn Asn Gly Ser Met Asn Gly Asn
                85                  90                  95

Thr Asp Val Tyr Asn Lys Asn Gly Ser Met Asn Gly Asn Pro Asp Met
            100                 105                 110

Tyr Asn Asn Asn Gly Ser Met Asn Gly Asn Thr Asp Val Tyr Asn Asn
        115                 120                 125

Asn Gly Ser Met Asn Gly Asn Thr Asp Asn Gln Val Pro Ala Tyr Asn
    130                 135                 140

Ile Leu Ser Ala Glu Asn Pro Ser Asn Ile Leu Glu Ser Asp Thr Arg
145                 150                 155                 160

Cys Thr Leu Asn Val Lys Asn Val Gln Asp Glu Ala Ile Cys Thr Gly
                165                 170                 175

Ser Asn Leu Thr Asn Glu Ile Gly Pro Leu Val Val Pro Ile Ala Phe
            180                 185                 190

Thr Pro Ile Ile Leu Thr Pro Ala Leu Ile Glu Val Gly Lys Trp Leu
        195                 200                 205

Gly Val Gln Ile Gly Lys Trp Ala Leu Ser Thr Ala Leu Lys Glu Leu
    210                 215                 220

Lys Ser Phe Leu Phe Pro Asn Ser Asp Pro Gln Arg Glu Met Glu Lys
225                 230                 235                 240

Leu Arg Ile Glu Leu Glu Asn Ser Phe Asn Lys Lys Leu Thr Glu Asp
                245                 250                 255

Lys Leu Asn Phe Leu Thr Ala Ala Tyr Thr Gly Phe Asn Asn Leu Ser
            260                 265                 270

Asn Ser Phe Ile Ser Ala Thr Glu Arg Val Lys Ala Ala Glu Ile Thr
        275                 280                 285

Leu Ala Thr Ala Pro Ser Gln Glu Asn Gln Asp Ile Leu Asp Glu Ala
    290                 295                 300

Arg Thr Leu Ala Arg Asp Tyr Phe Val Ser Leu His Ser Gln Met Ile
305                 310                 315                 320

Val Trp Leu Pro Gln Phe Glu Ile Ser Gly Tyr Glu Glu Ile Ser Leu
                325                 330                 335
```

-continued

```
Pro Leu Phe Thr Gln Met Cys Thr Leu His Leu Thr His Leu Lys Asp
            340                 345                 350

Gly Val Leu Met Gly Gln Asn Trp Gly Leu Ser Thr Asp Asp Ile Lys
        355                 360                 365

His Phe Lys Gly Glu Phe Tyr Arg Leu Ser Asn Asp Tyr Thr Ser Arg
    370                 375                 380

Ala Phe Asp Ser Phe His Arg Gly Phe Asn Arg Leu Arg Thr Gln Gln
385                 390                 395                 400

Gly Thr Ala Gly Val Ile Lys Phe Arg Thr Ala Met Asn Ala Tyr Ala
                405                 410                 415

Phe Asp Asn Ile Tyr Lys Trp Ser Leu Leu Arg Tyr Glu Gly Ile Asn
            420                 425                 430

Pro Arg Ile Thr Arg Ser Leu Trp His Tyr Ile Gly Tyr Asn Ser Ser
        435                 440                 445

Leu Gly Ser Asn Asp Phe Asn Thr Leu Tyr Lys Leu Met Val Gly Ile
    450                 455                 460

Pro His Glu Arg Phe Arg Thr Val Ala Ile Gly Tyr Arg Ala Lys Thr
465                 470                 475                 480

Gly Glu Asp Trp Lys Val Thr Gly Ala Lys Ser Thr Phe Tyr Ser Gly
                485                 490                 495

Gly Gly Glu Trp Val Gly Asn Val Ser Lys Ala Thr Arg Ile Pro Val
            500                 505                 510

Tyr Thr Thr Lys Thr Asp Trp Arg Gln Phe Glu Arg Arg Ile His Gly
        515                 520                 525

Arg Leu Gly Thr Glu Gln Tyr Thr Arg Trp His Leu Thr Ile Gln Asp
    530                 535                 540

Thr Asn Ile Ile Gly Asn Ser Tyr Leu Thr Gly Leu Pro Phe Asp Ile
545                 550                 555                 560

Ser Tyr Pro Asp Tyr Phe Ile Arg Thr Ile Ser Ala Lys Pro Glu Ala
                565                 570                 575

Tyr Pro Ile Tyr Lys Ser Leu Ser Leu Gly Asp Asn Pro Gly Tyr Val
            580                 585                 590

Val Asp Asn Pro Gly Asn Asn Leu Ile Ile Gly Phe Ser Pro Asp Asn
        595                 600                 605

Leu Lys Thr Phe Met Thr Asp Gly Asn Arg Tyr His Ser Ile Glu Ser
    610                 615                 620

Gly Tyr Pro Thr Asn Pro Ser Cys Thr Ile Pro Ala Val Leu Tyr Asn
625                 630                 635                 640

Ser Val Ser Asn Pro Phe Gln Ala Tyr Phe Asn Asp Glu Leu Gly Asn
                645                 650                 655

Gly Ser Asp Gly Ser Ile Thr Leu Ile Arg Arg Gly Gly Ala His Tyr
            660                 665                 670

Leu Val Asp Ser Arg Ser Ala Ser Tyr Asp Arg Ser Phe Arg Leu Ile
        675                 680                 685

Ile Arg Ile Gln Ala Gly Ser Ser Ala Phe Lys Val Thr Val Arg Ser
    690                 695                 700

Arg His Thr Ser Glu Ser Phe Glu Leu Asn Phe Thr Leu Leu Ser Asp
705                 710                 715                 720

Gln Asp Ile Asn Tyr Tyr Tyr Asp Tyr Ile Ser Gln Pro Phe Asn Leu
                725                 730                 735

Ser Ser Thr Tyr Tyr Tyr Ile Asp Val Glu Arg Val Val Ser Asp Asp
            740                 745                 750

Ile Arg Ala Leu Thr Phe Asn Gln Met Ile Ile Val Pro Thr Thr Glu
```

```
        755                 760                 765

Phe Gln Ile Leu
    770


<210> SEQ ID NO 56
<211> LENGTH: 289
<212> TYPE: PRT
<213> ORGANISM: Bacillus thuringiensis

<400> SEQUENCE: 56

Met Ala Ile Tyr Asp Ile Ala Ala Asp Leu Phe Asp Leu Thr Arg Trp
 1               5                  10                  15

Tyr Ala Glu Gln Asn Tyr Asn Ala Asn Pro Thr Thr Phe Arg Gly Ala
            20                  25                  30

Lys Val Tyr Asp Arg Ile Val Ser Asp Val Gln Ser Ile Pro Glu Lys
        35                  40                  45

Val Asp Phe Asn Leu Ile Pro Gly Leu Ala Tyr Thr Val Lys Asn Glu
    50                  55                  60

Ile Val Asn Asp Thr Asn Thr Glu Gln Ser Met Ser Thr Lys Leu Met
65                  70                  75                  80

His Thr Leu Ile Glu Ser Asn Ser Val Thr Thr Thr Lys Gly Tyr Lys
                85                  90                  95

Ile Gly Ser Ser Ile Lys Asn Thr Phe Ser Val Asn Ile Glu Gly Ser
            100                 105                 110

Phe Phe Val Gly Gly Gly Ser Thr Glu His Ser Ile Glu Val Ser Val
        115                 120                 125

Ser Gly Glu Tyr Asn His Ser Ser Ser Glu Thr Lys Thr Asn Thr Ser
    130                 135                 140

Gln Lys Thr Trp Glu Tyr Asn Ser Pro Ile Leu Val Pro Ala Lys Thr
145                 150                 155                 160

Lys Val Thr Ala Thr Leu Asp Ile Tyr Ala Gly Pro Val Val Val Pro
                165                 170                 175

Val Thr Leu Lys Ser Thr Val Thr Gly Thr Gly Ile Val Asn Asn Phe
            180                 185                 190

Pro Asn Val Leu Thr Ser Leu Ser Tyr Ile Asp Arg Asn Asn Lys Leu
        195                 200                 205

Trp Thr Asp Ser Leu Pro Thr Ala Leu Leu Tyr Asp Tyr Arg Asn Gln
    210                 215                 220

Trp Pro Gly Ser Gln Ser Ile Tyr Val Gly Lys Asn Gly Gly Gly Val
225                 230                 235                 240

Gln Val Glu Gly Lys Ala Glu Ile Gln Leu Glu Leu Gly Leu Tyr Ser
                245                 250                 255

Ile Ala Thr Phe Asp Ser Gln Pro Leu Ser Gly Asn Thr Thr Gly Lys
            260                 265                 270

Glu Ala Val Tyr Ser Lys Ala Ile Leu Arg Asp Gly Ser Ile Ile Asp
        275                 280                 285

Ile


<210> SEQ ID NO 57
<211> LENGTH: 295
<212> TYPE: PRT
<213> ORGANISM: Bacillus thuringiensis

<400> SEQUENCE: 57

Met Ala Ile His Asp Val Gly Thr Asp Leu Leu Glu Phe Ala Lys Trp
 1               5                  10                  15
```

```
Tyr Ala Thr Thr Asn Tyr Asn Ala Asn Pro Asn Thr Phe Arg Asn Pro
            20                  25                  30

Gln Ile Phe Glu Ser Val Val Gly Glu Ser Glu Ile Ile Pro Lys Asn
        35                  40                  45

Asp Thr Phe Glu Thr Ile Pro Lys Leu Thr Thr Val Val Thr Asp Val
    50                  55                  60

Ile Ile Asn Asp Thr Ser Val Pro Gln Ser Ile Thr Pro Lys Ile Met
65                  70                  75                  80

Gln Lys Thr Ser Glu Thr Ile Thr Thr Thr Thr Thr Gln Gly Phe Lys
                85                  90                  95

Val Gly Ser Glu Ile Lys Tyr Thr Asn Thr Met Lys Val Asn Leu Leu
            100                 105                 110

Leu Val Gly Gly Val Ser Asn Ser Ile Ala Val Ser Ile Ser Ala Glu
        115                 120                 125

Tyr Asn Tyr Ser Ser Ser Glu Thr Glu Thr Asn Ile Thr Glu Lys Ala
    130                 135                 140

Trp Glu Tyr Asn Arg Pro Val Leu Val Leu Pro Arg Thr Lys Val Thr
145                 150                 155                 160

Ala Thr Leu Ser Ile Tyr Ser Gly Ser Phe Thr Ile Pro Val Thr Leu
                165                 170                 175

Lys Ser Thr Ile Ser Gly Asn His Ile Ser Asn Ser Gly Tyr Gly Tyr
            180                 185                 190

Ala Leu Ser Ser Ile Gly Tyr Thr Asp Tyr Asn Asn Arg Ser Trp Thr
        195                 200                 205

Asp Ile Tyr Arg Thr Asn Phe Leu Tyr Asp Tyr Arg Asn Glu Trp Pro
    210                 215                 220

Gly Arg Lys Pro Ile Tyr Val Gly Arg Asp Asn Ile Gly Val Lys Val
225                 230                 235                 240

Glu Gly Glu Ser Arg Val Asp Ala Glu Leu Gly Leu Tyr Ser Ile Val
                245                 250                 255

Thr Phe Lys Glu Glu Pro Leu Pro Gly Asn Asn Leu Ile Gly Asn Gly
            260                 265                 270

Arg Thr Tyr Ser Met Ala Ile Leu Arg Asp Gly Ser Thr Met Asp Ile
        275                 280                 285

Ser Ile Pro Lys Asn Asn Asn
    290                 295


<210> SEQ ID NO 58
<211> LENGTH: 1333
<212> TYPE: PRT
<213> ORGANISM: Bacillus thuringiensis

<400> SEQUENCE: 58

Met Ala Gln Leu Asn Glu Ile Tyr Pro Ser Tyr Tyr Asn Val Leu Ala
 1               5                  10                  15

Tyr Pro Pro Leu Ile Leu Asp Asp Lys Ser Leu Tyr Asp Gln Tyr Thr
            20                  25                  30

Glu Trp Lys Lys Lys Ile Asp Lys Thr Trp Lys Gln Tyr Asp Lys Asp
        35                  40                  45

Phe Leu Pro Lys Pro Leu Met Asp Leu Gly Lys Ser Leu Ala Glu Ala
    50                  55                  60

Tyr Lys Gly Asp Pro Asp Gly Tyr Leu His Ile Ala Asn Thr Ala Ile
65                  70                  75                  80

Arg Ile Ala Phe Leu Leu Ile Pro Gly Gly Gln Thr Ala Ala Phe Gly
                85                  90                  95
```

-continued

```
Val Asn Leu Val Leu Asn Lys Ala Ile Gly Ile Phe Tyr Pro Pro Gln
            100                 105                 110

Asn Lys Ser Leu Phe Asp Gln Ile Lys Asp Ala Val Ser Asn Leu Val
        115                 120                 125

Asp Gln Lys Leu Ile Asp Gln Glu Ile Ser Gly Val Leu Ile Lys Leu
    130                 135                 140

Asn Ser Leu Gln Gln Pro Leu Ser Arg Phe Ser Asn Ser Ile Gln Arg
145                 150                 155                 160

Ala Val Gly Lys Pro Gln Asp Phe Asp Asp Gln Thr Thr Ser Ser Asn
                165                 170                 175

Ala Ile Ile Leu Asp Glu Thr Gln Asp Cys Ser Lys Asp Asp Ser Cys
            180                 185                 190

Ser Cys Ser Asn Thr Gln Pro Arg Pro Ser Asp Ala Pro Leu Cys Thr
        195                 200                 205

Pro Cys Ile Cys Arg Met Lys Glu Val Gln Gln Thr Phe Asn Asn Ser
    210                 215                 220

Ser Thr Asp Val Asn Arg Ala Leu Thr Asp Met Lys Thr Thr Leu Lys
225                 230                 235                 240

Asp Val Val Gly Ala Asp Gln Leu Arg Ser Tyr Met Gln Ile Tyr Leu
                245                 250                 255

Pro Leu Tyr Val Thr Ala Ala Thr Met Glu Leu Gln Met Tyr Lys Thr
            260                 265                 270

Tyr Ile Asp Phe Thr Gln Lys Phe Asp Phe Asp Val Thr Gly Thr Thr
        275                 280                 285

Lys Glu His Val Asn Glu Leu Arg Gln Lys Ile Lys Thr His Ser Glu
    290                 295                 300

Tyr Ile Met Gly Leu Phe Lys Lys Ser Leu Pro Glu Ile Ser Asn Asn
305                 310                 315                 320

Thr Lys Glu Gln Leu Asn Ala Tyr Ile Lys Tyr Thr Arg Asn Ile Thr
                325                 330                 335

Leu Asn Ala Leu Asp Met Val Ser Thr Trp Lys Phe Leu Asp Pro Val
            340                 345                 350

Asp Tyr Pro Thr Thr Ala Thr Phe Asn Pro Thr Arg Ile Ile Phe Asn
        355                 360                 365

Asp Leu Ala Gly Pro Val Glu Cys Leu Asn Ser Thr Gln Asp Ser Asn
    370                 375                 380

Lys Leu His Phe Asn Phe Phe Asp Met Asn Gly Gln Ser Met Pro Asn
385                 390                 395                 400

Asn Asp Ile Phe Asn Tyr Phe Tyr Arg Gly Met Gln Val Lys Gly Leu
                405                 410                 415

Gln Ile Gln Thr Tyr Thr Ser Ser Asp Thr Lys Asn Pro Gln His Phe
            420                 425                 430

Pro Val Gly Phe Leu Ser Ser Tyr Tyr Gly Ser Asn Gly Asp Phe Pro
        435                 440                 445

Phe Asp Lys Arg Val Asp Pro Asn Lys Phe Thr Gly Gly Ser Lys Ser
    450                 455                 460

Val Lys Leu Gly Asp Asp Val Tyr Glu Ser Arg Ser Ala Leu Ser Val
465                 470                 475                 480

Ile Asn Ala Val Ser Asn Gln Leu Gln Val Phe Leu Asn Tyr Ile Asp
                485                 490                 495

Thr Glu Asp Leu Tyr Phe Asp Gln Ser Val Ser Pro Gly Gly Thr Ala
            500                 505                 510

Cys Gly Ser Gly Asn Ser Thr Ile Trp Pro Asp Gln Lys Ile Gln Ala
        515                 520                 525
```

```
Ile Tyr Pro Ile Gln Pro Asp Asn Ser Gln Thr Tyr Pro Ser Tyr Tyr
    530                 535                 540

Ser Thr Ser Lys Ile Gly Phe Val Thr Thr Leu Val Pro Asn Asp Thr
545                 550                 555                 560

Thr Pro Trp Ile Thr Phe Thr Asp Asn Gly Asn Asn Ser Ile Tyr Thr
                565                 570                 575

Phe Ser Ala Glu Asn Thr Arg Thr Leu Thr Gly Ser Ala Gly Pro Val
            580                 585                 590

Arg Glu Phe Ile Thr Gly Ser Ala Pro Leu Gly Leu Ser Pro Gly Gly
        595                 600                 605

Gly Ala Gln Tyr Ser Ile Asn Thr Ser Asp Ala Pro Ser Gly Asp Tyr
    610                 615                 620

Gln Val Arg Val His Val Ala Thr Pro Gly Ser Gly Gly Ser Leu Ala
625                 630                 635                 640

Ile Ser Val Asp Gly Lys Thr Gln Thr Leu Gln Leu Pro Asp Thr Asn
                645                 650                 655

Val Asn Asp Thr Asn His Ile Ala Gly Phe Ala Gly Thr Tyr Thr Leu
            660                 665                 670

Ala Pro Ala Thr Gln Val Asp Ala Ala Thr Leu Lys Pro Lys Ala Pro
        675                 680                 685

Thr Glu Asn Ile Phe Pro Val Arg Gln Thr Ser Ser Leu Pro Val Ser
    690                 695                 700

Ile Thr Asn Asn Ser Ser Thr Val Ile Asn Ile Asp Arg Ile Glu Phe
705                 710                 715                 720

Val Pro Val Ser Ala Pro Ala Pro Asp Pro Ser Pro Asp Ser Gly Lys
                725                 730                 735

Pro Ile His Lys Ser Val Pro Lys Thr Val Thr Gln Leu Ser Thr Thr
            740                 745                 750

Lys Glu Ile Trp Ser Ser Thr Ser Glu Tyr Ala Thr Thr Ile Ser Phe
        755                 760                 765

Thr Gly Asn Val Tyr Asn Asp Ala Ser Ile Thr Phe Gln Leu Leu Ser
    770                 775                 780

Ser Gly Gln Val Val Lys Glu Phe Pro Phe Thr Gly Asn Gly Val Ala
785                 790                 795                 800

Ser Lys Pro Gly Phe His Gly Ser Ser Pro Ser Cys Tyr Asp Thr Pro
                805                 810                 815

Tyr Pro Phe Ser Gln Pro Asp Leu Ser Val Pro Lys Tyr Asn Lys Leu
            820                 825                 830

Gln Val Val Met Lys Ser Asp Gly Tyr Ser Lys Pro Cys Asp Leu Gly
        835                 840                 845

Asp Ser Phe Pro Asn Thr Phe Asp Ala Glu Ile Asp Ile Lys Phe Asn
    850                 855                 860

Leu Ser Asp Thr Ala Asp Leu Ala Gln Ile Thr Ala Gln Val Gln Gly
865                 870                 875                 880

Leu Phe Thr Ser Ser Ser Ser Thr Glu Leu Ser Pro Asn Val Ser Gly
                885                 890                 895

Tyr Gln Ile Asp Gln Ile Ala Leu Lys Val Asn Ala Leu Ser Asp Glu
            900                 905                 910

Val Phe Cys Lys Glu Lys Ile Val Leu Arg Lys Leu Val Asn Lys Ala
        915                 920                 925

Lys Gln Phe Met Lys Thr Arg Asn Leu Leu Ile Gly Gly Asp Phe Glu
    930                 935                 940

Ile Leu Asp Lys Trp Ala Leu Gly Thr Gln Ala Thr Ile Lys Asp Asn
```

-continued

```
945                 950                 955                 960

Ser Ser Leu Phe Lys Gly Asn His Leu Phe Leu Gln Pro Thr Asn Gly
                965                 970                 975

Ile Ser Ser Ser Tyr Ala Tyr Gln Lys Ile Asp Glu Ser Lys Leu Lys
            980                 985                 990

Pro Tyr Thr Arg Tyr Asn Val Ser Gly Phe Val Ala Gln Ser Glu His
        995                 1000                1005

Leu Glu Ile Val Val Ser Arg Tyr Gly Lys Glu Ile Asp Lys Ile Leu
    1010                1015                1020

Asn Val Pro Tyr Glu Glu Ala Leu Pro Val Ser Ser Gly Asn Gln Ser
1025                1030                1035                1040

Thr Cys Cys Lys Pro Ser Ser Cys Ser Cys Ser Ala Cys Thr Gly Gly
                1045                1050                1055

Pro His Pro His Phe Phe Ser Tyr Ser Ile Asp Val Gly Lys Leu Tyr
            1060                1065                1070

Pro Asp Leu Asn Pro Gly Ile Glu Phe Gly Leu Arg Leu Ala His Pro
        1075                1080                1085

Ser Gly Tyr Ala Lys Val Gly Asn Leu Glu Ile Val Glu Glu Arg Pro
    1090                1095                1100

Leu Thr Asn Thr Glu Ile Arg Lys Ile Gln Arg Lys Glu Glu Lys Trp
1105                1110                1115                1120

Lys Lys Ala Trp Asp Thr Glu Arg Ala Glu Ile Asn Ala Ile Leu Gln
                1125                1130                1135

Pro Val Ile Asn Gln Ile Asn Ala Phe Tyr Thr Asn Gly Asp Trp Asn
            1140                1145                1150

Gly Ser Ile Leu Pro His Val Thr Tyr Gln Asp Leu Tyr Asn Ile Val
        1155                1160                1165

Leu Pro Glu Leu Ser Lys Leu Arg His Trp Phe Met Lys Asp Arg Pro
    1170                1175                1180

Gly Glu His Tyr Thr Ile Leu Gln Gln Phe Lys Gln Ala Leu Glu Arg
1185                1190                1195                1200

Val Phe Asn Gln Leu Glu Glu Arg Asn Leu Ile His Asn Gly Ser Phe
                1205                1210                1215

Thr Asn Gly Leu Ala Asn Trp Leu Val Asp Gly Asp Thr Gln Ile Thr
            1220                1225                1230

Thr Leu Glu Asn Gly Asn Leu Ala Leu Gln Leu Ser Asp Trp Asp Ala
        1235                1240                1245

Ser Ala Ser Gln Ser Ile Asp Ile Ser Asp Phe Asp Glu Asp Lys Glu
    1250                1255                1260

Tyr Thr Val Arg Val Tyr Ala Lys Gly Lys Gly Thr Ile Arg Thr Val
1265                1270                1275                1280

Asn Cys Glu Asn Glu Pro Leu Ser Phe Asn Thr Asn Thr Phe Thr Ile
                1285                1290                1295

Leu Glu Gln Arg Leu Tyr Phe Asp Asn Pro Ser Val Leu Leu His Ile
            1300                1305                1310

Gln Ser Glu Gly Ser Glu Phe Val Ile Gly Ser Val Glu Leu Ile Glu
        1315                1320                1325

Leu Ser Asp Asp Glu
    1330
```

<210> SEQ ID NO 59
<211> LENGTH: 723
<212> TYPE: PRT
<213> ORGANISM: Bacillus thuringiensis

<400> SEQUENCE: 59

```
Met Ala Gln Leu Asn Glu Ile Tyr Pro Ser Tyr Tyr Asn Val Leu Ala
 1               5                  10                  15

Tyr Pro Pro Leu Ile Leu Asp Asp Lys Ser Leu Tyr Asp Gln Tyr Thr
            20                  25                  30

Glu Trp Lys Lys Lys Ile Asp Lys Thr Trp Lys Gln Tyr Asp Lys Asp
        35                  40                  45

Phe Leu Pro Lys Pro Leu Met Asp Leu Gly Lys Ser Leu Ala Glu Ala
    50                  55                  60

Tyr Lys Gly Asp Pro Asp Gly Tyr Leu His Ile Ala Asn Thr Ala Ile
65                  70                  75                  80

Arg Ile Ala Phe Leu Leu Ile Pro Gly Gly Gln Thr Ala Ala Phe Gly
                85                  90                  95

Val Asn Leu Val Leu Asn Lys Ala Ile Gly Ile Phe Tyr Pro Pro Gln
            100                 105                 110

Asn Lys Ser Leu Phe Asp Gln Ile Lys Asp Ala Val Ser Asn Leu Val
        115                 120                 125

Asp Gln Lys Leu Ile Asp Gln Glu Ile Ser Gly Val Leu Ile Lys Leu
    130                 135                 140

Asn Ser Leu Gln Gln Pro Leu Ser Arg Phe Ser Asn Ser Ile Gln Arg
145                 150                 155                 160

Ala Val Gly Lys Pro Gln Asp Phe Asp Asp Gln Thr Thr Ser Ser Asn
                165                 170                 175

Ala Ile Ile Leu Asp Glu Thr Gln Asp Cys Ser Lys Asp Asp Ser Cys
            180                 185                 190

Ser Cys Ser Asn Thr Gln Pro Arg Pro Ser Asp Ala Pro Leu Cys Thr
        195                 200                 205

Pro Cys Ile Cys Arg Met Lys Glu Val Gln Gln Thr Phe Asn Asn Ser
    210                 215                 220

Ser Thr Asp Val Asn Arg Ala Leu Thr Asp Met Lys Thr Thr Leu Lys
225                 230                 235                 240

Asp Val Val Gly Ala Asp Gln Leu Arg Ser Tyr Met Gln Ile Tyr Leu
                245                 250                 255

Pro Leu Tyr Val Thr Ala Ala Thr Met Glu Leu Gln Met Tyr Lys Thr
            260                 265                 270

Tyr Ile Asp Phe Thr Gln Lys Phe Asp Phe Asp Val Thr Gly Thr Thr
        275                 280                 285

Lys Glu His Val Asn Glu Leu Arg Gln Lys Ile Lys Thr His Ser Glu
    290                 295                 300

Tyr Ile Met Gly Leu Phe Lys Lys Ser Leu Pro Glu Ile Ser Asn Asn
305                 310                 315                 320

Thr Lys Glu Gln Leu Asn Ala Tyr Ile Lys Tyr Thr Arg Asn Ile Thr
                325                 330                 335

Leu Asn Ala Leu Asp Met Val Ser Thr Trp Lys Phe Leu Asp Pro Val
            340                 345                 350

Asp Tyr Pro Thr Thr Ala Thr Phe Asn Pro Thr Arg Ile Ile Phe Asn
        355                 360                 365

Asp Leu Ala Gly Pro Val Glu Cys Leu Asn Ser Thr Gln Asp Ser Asn
    370                 375                 380

Lys Leu His Phe Asn Phe Phe Asp Met Asn Gly Gln Ser Met Pro Asn
385                 390                 395                 400

Asn Asp Ile Phe Asn Tyr Phe Tyr Arg Gly Met Gln Val Lys Gly Leu
                405                 410                 415
```

```
Gln Ile Gln Thr Tyr Thr Ser Ser Asp Thr Lys Asn Pro Gln His Phe
            420                 425                 430

Pro Val Gly Phe Leu Ser Ser Tyr Tyr Gly Ser Asn Gly Asp Phe Pro
        435                 440                 445

Phe Asp Lys Arg Val Asp Pro Asn Lys Phe Thr Gly Gly Ser Lys Ser
    450                 455                 460

Val Lys Leu Gly Asp Asp Val Tyr Glu Ser Arg Ser Ala Leu Ser Val
465                 470                 475                 480

Ile Asn Ala Val Ser Asn Gln Leu Gln Val Phe Leu Asn Tyr Ile Asp
                485                 490                 495

Thr Glu Asp Leu Tyr Phe Asp Gln Ser Val Ser Pro Gly Gly Thr Ala
            500                 505                 510

Cys Gly Ser Gly Asn Ser Thr Ile Trp Pro Asp Gln Lys Ile Gln Ala
        515                 520                 525

Ile Tyr Pro Ile Gln Pro Asp Asn Ser Gln Thr Tyr Pro Ser Tyr Tyr
    530                 535                 540

Ser Thr Ser Lys Ile Gly Phe Val Thr Thr Leu Val Pro Asn Asp Thr
545                 550                 555                 560

Thr Pro Trp Ile Thr Phe Thr Asp Asn Gly Asn Asn Ser Ile Tyr Thr
                565                 570                 575

Phe Ser Ala Glu Asn Thr Arg Thr Leu Thr Gly Ser Ala Gly Pro Val
            580                 585                 590

Arg Glu Phe Ile Thr Gly Ser Ala Pro Leu Gly Leu Ser Pro Gly Gly
        595                 600                 605

Gly Ala Gln Tyr Ser Ile Asn Thr Ser Asp Ala Pro Ser Gly Asp Tyr
    610                 615                 620

Gln Val Arg Val His Val Ala Thr Pro Gly Ser Gly Gly Ser Leu Ala
625                 630                 635                 640

Ile Ser Val Asp Gly Lys Thr Gln Thr Leu Gln Leu Pro Asp Thr Asn
                645                 650                 655

Val Asn Asp Thr Asn His Ile Ala Gly Phe Ala Gly Thr Tyr Thr Leu
            660                 665                 670

Ala Pro Ala Thr Gln Val Asp Ala Ala Thr Leu Lys Pro Lys Ala Pro
        675                 680                 685

Thr Glu Asn Ile Phe Pro Val Arg Gln Thr Ser Ser Leu Pro Val Ser
    690                 695                 700

Ile Thr Asn Asn Ser Ser Thr Val Ile Asn Ile Asp Arg Ile Glu Phe
705                 710                 715                 720

Val Pro Val


<210> SEQ ID NO 60
<211> LENGTH: 378
<212> TYPE: PRT
<213> ORGANISM: Bacillus thuringiensis

<400> SEQUENCE: 60

Met Tyr Cys Asn Thr Ile Leu Arg Lys Arg Tyr Lys Lys Leu Ala Thr
 1               5                  10                  15

Ile Ile Pro Leu Thr Ser Met Ser Ala Val Ala Ile Ala Pro Ala Thr
            20                  25                  30

Ser Phe Ala Val Glu Thr Gln Lys Ala Asp Val Ser Ser Gln Glu Gly
        35                  40                  45

Pro Ile Gln Gly Tyr Gln Met Glu Asn Gly Lys Ile Thr Pro Val Tyr
    50                  55                  60

Lys Asn Lys Leu Thr Gln Phe Asn Thr Ala Asp Asp Ile Asp Pro Gly
```

```
65                  70                  75                  80

Leu Pro Leu Leu Pro Glu Asn Pro Tyr Asn Pro Ile Pro Asp His Gly
                85                  90                  95

Thr Ala Tyr Val Glu Ser Thr Asp Ile Gly Asp Thr Val Tyr Phe Lys
            100                 105                 110

Pro Phe Glu Pro Pro Lys Asn Asn Val Leu Glu Leu Gly Asp Cys Asp
        115                 120                 125

Asp Asn Thr Tyr Gln Trp Ser Val Phe Val Asp Ser Gln Lys Tyr Lys
    130                 135                 140

Ser Val Gly Tyr Phe Val Gln Lys Gln Ala Asp Gly Gln Ile Arg Val
145                 150                 155                 160

Gly Tyr Tyr Asn Pro Glu Asp Leu Ser Leu Ile Thr Asp Ser Asn His
                165                 170                 175

Ala Phe Ala Gly Val Pro Gly Phe Lys Leu Thr Ala Glu Glu Lys Ala
            180                 185                 190

Glu Met Gln Arg Asp Leu Asn Arg Glu Tyr Gly Asp Ile Trp Asp Gly
        195                 200                 205

Thr Ser Lys Leu Lys Arg Glu Thr Asn Tyr Lys Leu Leu Pro Asn Ala
    210                 215                 220

Ser Gly Leu Gln Asp Asp Ala Ser Gly Phe Gly Tyr Asn Gln Thr Leu
225                 230                 235                 240

Thr Ser Gly Val Ser Thr Thr Asn Met Phe Gly Ile Ala Thr Thr Val
                245                 250                 255

Gly Trp Lys Met Gly Ile Lys Val Ser Val Val Pro Leu Val Ala Asp
            260                 265                 270

Val Thr Ser Glu Ile Ser Ala Ser Leu Thr Ala Ser Tyr Gln His Thr
        275                 280                 285

Val Asn Val Thr Asn Gln Thr Ser Ser Gln Val Lys Phe Asp Val Ser
    290                 295                 300

Arg Val Asp Asn Pro Asp Tyr Lys Tyr Asn Asp Tyr Ala Ala Ala Val
305                 310                 315                 320

Tyr Lys Ile Tyr Thr Asp Tyr Thr Leu Glu Pro Gly Lys Gly Leu Ser
                325                 330                 335

Arg Phe Leu Ala Lys Gln Asp Leu Lys Asp Pro Val Arg Thr Ala Ala
            340                 345                 350

Leu Ala Asn Thr Asn Tyr Ala Tyr Glu Gly Ser Lys Tyr Tyr Phe Thr
        355                 360                 365

Val Thr Pro Gly Ser His Lys Lys Ile Val
    370                 375


<210> SEQ ID NO 61
<211> LENGTH: 383
<212> TYPE: PRT
<213> ORGANISM: Bacillus thuringiensis

<400> SEQUENCE: 61

Met Asp Phe Leu Asn Tyr Tyr Asn Lys Leu Lys Asn Glu Leu Asp Asp
 1               5                  10                  15

Val Asn Ser Lys Lys Tyr Ser Leu Glu Tyr Thr Ser Asp Gly Leu Met
            20                  25                  30

Val Gln Pro Thr Asp Asp Pro Leu Asn Thr Met Pro Leu Pro Asp Arg
        35                  40                  45

Pro Val Leu Ser Gly Asn Pro Asn Asp Pro Ile Pro Ser Glu Gly Thr
    50                  55                  60

Thr Arg Thr Asp Ile Gln Lys Gln Asn Pro Pro Phe Phe Thr Phe Lys
```

-continued

```
65                  70                  75                  80

Val Val Ala Lys Leu Ala Tyr Ser Gly Lys Gly Glu Asn Cys Gln Lys
                85                  90                  95

Ala Arg Ala Ala Ser Val Tyr Gly Ala Val Leu Glu Leu Glu Lys Val
            100                 105                 110

Lys Gln Leu Pro Glu Tyr Ser Asn Val Tyr Leu Tyr Ser Glu Thr Gly
        115                 120                 125

Ile Lys Thr Asp Arg Ser Asn Ile Arg Tyr Asn Thr Asp Gly Ile Ile
    130                 135                 140

Gln Phe Leu Asn Pro Ser Phe Ile Asn Thr Phe Ser Ser Asn Pro Ile
145                 150                 155                 160

Lys Tyr Gly Asp Thr Val Gly Tyr Ile Ser Tyr Pro Tyr Asp Thr Leu
                165                 170                 175

Lys Phe Pro Ser Thr Thr Gln Leu Glu Arg Leu Val Tyr Phe Asn Leu
            180                 185                 190

Leu Asp Ser Asn Ile Leu Asp Lys His Ile Gly Phe Asp Trp Ser Lys
        195                 200                 205

Ser Val Thr Asn Gly Thr Glu Asp Thr Glu Met Trp Thr His Ser Ser
    210                 215                 220

Thr Val Gly Ala Glu Leu Asn Leu Lys Asp Ile Leu Gln Ile Asn Ala
225                 230                 235                 240

Ser Tyr Glu His Thr Phe Ser Thr Ser His Met Glu Lys Lys Glu Asn
                245                 250                 255

Thr Val Ser Lys Thr Ala His Phe Asn Ser Pro Leu Pro Pro Tyr Asn
            260                 265                 270

Tyr Ala Thr Trp Val Ala Ala Ile Tyr Gln Leu Ser Ile Arg Tyr Gln
        275                 280                 285

Arg Thr Asn Ala Gln Pro Ile Leu Asp Thr Ile Asn Ala Val Asn Ser
    290                 295                 300

Gly Leu Thr Ala Ser Glu Thr Asp Ile Tyr Leu Lys Ala Leu Tyr Gly
305                 310                 315                 320

Ala Gly Lys Asn Gly Lys Pro Ala Val Gly Asp Pro Ser Ile Leu His
                325                 330                 335

Lys Leu Ser Asn Val Ile Glu Asp Ala Tyr Glu Tyr Leu Tyr Tyr Ser
            340                 345                 350

Asp Thr Leu Tyr Phe Thr Gln Thr Pro Ser Gly Asn Ser Pro Thr Pro
        355                 360                 365

Asn Ser Pro Asn Arg Ile Gln Phe Ile Ala Thr Asp Pro Gln Ser
    370                 375                 380


<210> SEQ ID NO 62
<211> LENGTH: 634
<212> TYPE: PRT
<213> ORGANISM: Artificial Sequence
<220> FEATURE:
<223> OTHER INFORMATION: truncated variant Axmi207

<400> SEQUENCE: 62

Met Pro Ser Ser Asp Ser Phe Leu Tyr Ser His Asn Asn Tyr Pro Tyr
 1               5                  10                  15

Ala Thr Asp Pro Asn Thr Val Leu Glu Gly Arg Asn Tyr Lys Glu Trp
            20                  25                  30

Leu Asn Lys Cys Thr Asp Asn Tyr Thr Asp Ala Leu Gln Ser Pro Glu
        35                  40                  45

Ala Thr Ala Ile Ser Lys Gly Ala Val Ser Ala Ala Ile Ser Ile Ser
    50                  55                  60
```

-continued

```
Thr Lys Val Leu Gly Leu Leu Gly Val Pro Phe Ala Ala Gln Ile Gly
65                  70                  75                  80

Gln Leu Trp Thr Phe Ile Leu Asn Ala Leu Trp Pro Ser Asp Asn Thr
                85                  90                  95

Gln Trp Glu Glu Phe Met Arg His Val Glu Glu Leu Ile Asn Gln Arg
            100                 105                 110

Ile Ala Asp Tyr Ala Arg Asn Lys Ala Leu Ala Glu Leu Thr Gly Leu
        115                 120                 125

Gly Asn Asn Leu Asp Leu Tyr Ile Glu Ala Leu Asp Asp Trp Lys Arg
    130                 135                 140

Asn Pro Thr Ser Gln Glu Ala Lys Thr Arg Val Ile Asp Arg Phe Arg
145                 150                 155                 160

Ile Val Asp Gly Leu Phe Glu Ala Tyr Ile Pro Ser Phe Ala Val Ser
                165                 170                 175

Gly Tyr Gln Val Gln Leu Leu Thr Val Tyr Ala Ala Ala Ala Asn Leu
            180                 185                 190

His Leu Leu Leu Leu Arg Asp Ser Thr Ile Tyr Gly Ile Asp Trp Gly
        195                 200                 205

Leu Ser Gln Thr Asn Val Asn Asp Asn Tyr Asn Arg Gln Ile Arg Leu
    210                 215                 220

Thr Ala Thr Tyr Ala Asn His Cys Thr Thr Trp Tyr Gln Thr Gly Leu
225                 230                 235                 240

Glu Arg Leu Arg Gly Ser Asn Ala Ser Ser Trp Val Thr Tyr Asn Arg
                245                 250                 255

Phe Arg Arg Glu Met Thr Leu Thr Val Leu Asp Ile Cys Ser Leu Phe
            260                 265                 270

Ser Asn Tyr Asp Tyr Arg Ser Tyr Pro Ala Glu Val Arg Gly Glu Ile
        275                 280                 285

Thr Arg Glu Ile Tyr Thr Asp Pro Val Gly Val Gly Trp Val Asp Ser
    290                 295                 300

Ala Pro Ser Phe Gly Glu Ile Glu Asn Leu Ala Ile Arg Ala Pro Arg
305                 310                 315                 320

Thr Val Thr Trp Leu Asn Ser Thr Arg Ile Phe Thr Gly Arg Leu Gln
                325                 330                 335

Gly Trp Ser Gly Thr Asn Asn Tyr Trp Ala Ala His Met Gln Asn Phe
            340                 345                 350

Ser Glu Thr Asn Ser Gly Asn Ile Gln Phe Glu Gly Pro Leu Tyr Gly
        355                 360                 365

Ser Thr Val Gly Thr Ile His Arg Thr Asp Asp Tyr Asp Met Gly Asn
    370                 375                 380

Arg Asp Ile Tyr Thr Ile Thr Ser Gln Ala Val Leu Gly Leu Trp Ala
385                 390                 395                 400

Thr Gly Gln Arg Val Leu Gly Val Ala Ser Ala Arg Phe Thr Leu Arg
                405                 410                 415

Asn Leu Phe Asn Asn Leu Thr Gln Val Leu Val Tyr Glu Asn Pro Ile
            420                 425                 430

Ser Ser Thr Phe Gly Ser Ser Thr Leu Thr His Glu Leu Ser Gly Glu
        435                 440                 445

Asn Ser Asp Arg Pro Thr Ser Ser Asp Tyr Ser His Arg Leu Thr Ser
    450                 455                 460

Ile Thr Gly Phe Arg Ala Gly Ala Asn Gly Thr Val Pro Val Phe Gly
465                 470                 475                 480

Trp Thr Ser Ala Thr Val Asp Arg Asn Asn Ile Ile Glu Arg Asn Lys
```

-continued

```
                485                 490                 495

Ile Thr Gln Phe Pro Gly Val Lys Ser His Thr Leu Asn Asn Cys Gln
            500                 505                 510

Val Val Arg Gly Thr Gly Phe Thr Gly Gly Asp Trp Leu Arg Pro Asn
        515                 520                 525

Asn Asn Gly Thr Phe Arg Leu Thr Ile Thr Ser Phe Ser Ser Gln Ser
    530                 535                 540

Tyr Arg Ile Arg Leu Arg Tyr Ala Thr Ser Val Gly Asn Thr Ser Leu
545                 550                 555                 560

Val Ile Ser Ser Ser Asp Ala Gly Ile Ser Ser Thr Thr Ile Pro Leu
                565                 570                 575

Thr Ser Thr Ile Thr Ser Leu Pro Gln Thr Val Pro Tyr Gln Ala Phe
            580                 585                 590

Arg Val Val Asp Leu Pro Ile Thr Phe Thr Thr Pro Thr Thr Gln Arg
        595                 600                 605

Asn Tyr Thr Phe Asp Phe Arg Leu Gln Asn Pro Ser Asn Ala Asn Val
    610                 615                 620

Phe Ile Asp Arg Phe Glu Phe Val Pro Ile
625                 630


<210> SEQ ID NO 63
<211> LENGTH: 306
<212> TYPE: DNA
<213> ORGANISM: Bacillus thuringiensis

<400> SEQUENCE: 63

atgacaacaa taaatgaatt atatccggct gtaccttata atgtactggc atatgctcca     60

ccacttaatt tagctgattc gacaccatgg ggtcaaatag ttgttgctga tgcaattaaa    120

gaagcttggg ataattttca aaaatatggt gtattagatt taacagctat aaatcaaggg    180

tttgatgatg caaatacagg ttcttttagt tatcaagctt taatacaaac tgttttgggt    240

attataggta caatttggta tgacagttcc tgtggctgct ccatttgcag ctacagcgcc    300

tattat                                                               306


<210> SEQ ID NO 64
<211> LENGTH: 4065
<212> TYPE: DNA
<213> ORGANISM: Bacillus thuringiensis

<400> SEQUENCE: 64

atgacagttc ctgtggctgc tccatttgca gctacagcgc ctattattag tttatttgta     60

ggattttttt ggcctaaaaa agataaggga ccacaattaa tcgatataat tgataaagaa    120

attaaaaaat tattagataa ggaattagga gagcaaaaac gtaatgattt agttagtgct    180

ttaaatgaga tgcaagaggg agcaaatgag ttaagtgata ttatgactaa tgcacttttt    240

gaaggtacta tacagggaaa tgttgttact aatgataacc ctcaaggtaa aaggcgaact    300

cctaaagctc caacagttag tgattatgag aatgtttatt cggcatattt tgtggaacat    360

gtggatttta gaaacaaaat atctacgttt cttactggtt cttatgatct tatagcactc    420

ccattatatg cattagcaaa aacaatggag ctttcattgt atcaatcatt tattaatttt    480

gctaataaat ggatggattt tgtatataca aaagcaatta atgaatcagc aactgatgat    540

atgaaaagag attatcaagc gagatacaat actcaaaaaa gtaatttagc tgtacaaaaa    600

acacaattga ttaacaaaat taaagatggt acagatgctg ttatgaaagt ttttaaagat    660

accaataatt taccttcaat aggtactaat aaattagcag taaatgctcg taataagtat    720
```

-continued

```
attagggcct tacaaataaa ttgtttagat ttagttgctt tgtggcctgg cttatatcca    780
gatgaatatc ttttaccatt acaattagat aaaacacgtg ttgtattttc tgatacaatg    840
ggacctgatg aaacacatga tggtcaaatg aaagttttaa atatattaga ctcaactaca    900
agttataacc atcaagatat aggaataagt acaactcaag atgtaaattc tttattattt    960
tatccaagaa aagaactgtt agaattagat tttgctaaat atatttcatc tagtagtcgt   1020
ttttgggttt atggatttgg cttaaaatat tcagatgata acttttatag atatggtgat   1080
aacgatccaa gcagtgattt taaacctgca tataagtggt ttacgaaaaa ttcccagttc   1140
gaaaaccttc ctacttatgg aaatcctact cctattacta atttaaatgc taaaactcaa   1200
gtaacttctt atcttgatgc attaatatat tatatagacg gaggaactaa tctatataat   1260
aatgcgattc ttcatgatac agggggttat attccgggat atccaggtgt agaaggatat   1320
ggtatgagta ataatgaacc tttagcagga caaaaattaa atgctttata tcctataaaa   1380
gtggaaaatg taagtggttc acaaggaaaa ttaggaacaa tagcagctta tgttccttta   1440
aatttacaac cagaaaatat tattggtgat gctgatccga atacaggttt tccccttaat   1500
gtaattaaag gatttccatt tgaaaaatat ggacctgatt atgagggacg aggaatttcg   1560
gttgtaaaag aatggataaa tggtgcaaat gctgtaaaat tgtctccagg tcaatcagtt   1620
ggggtacaaa ttaaaaatat aacaaaacaa aattatcaaa ttcgtactcg ttatgcaagt   1680
aataacagta atcaagtata ttttaatgta gatccaggtg gatcaccatt atttgcacaa   1740
tcagtaacat ttgaatctac aacaaatgtt acaagtggcc aacaaggcga aaatggtaga   1800
tatacattaa aaactatttt ttctggtaat gatctactta cagtagaaat ccctgttgga   1860
aatttttatg tgcatgttac gaataaagga tcttctgata tctttttaga tcgtcttgag   1920
ttttctacag ttccttcata tgttatatat tcaggtgatt atgatgctac aggtacagat   1980
gatgtcttat tgtcagatcc acatgagtat ttttatgatg tcatagtgaa tggtactgct   2040
agtcattcta gtgcagctac ttctatgaat ttgctcaata aaggaaccgt agtaagaagc   2100
attgatattc caggtcactc aacgtcttat tctgtacagt attcagttcc agaaggattt   2160
gatgaagtta gaattctcag ttctcttccg gatattagtg gaactataag agtagaatct   2220
agtaaaccac ctgtatttaa gaatgatggt aatagtggtg atggtggtaa tactgaatat   2280
aattttaatt ttgatttatc aggattgcaa gatactgggc tttattctgg taaacttaaa   2340
tctggtattc gtgtgcaagg taattacact tacacaggtg ctccatcttt aaatctggtt   2400
gtttacagaa ataatagtgt tgtatccact tttccagtag gttctccttt tgatatcact   2460
ataacaacag aaactgataa ggttatcctt tcattacaac ctcaacatgg gttggcaaca   2520
gttactggta ctggcacaat aacaattcct aatgataaat tagcaattgt ttatgataag   2580
ttatttaaat taccacatga tttagaaaat ataagaatac aagtaaatgc attattcata   2640
tcgagtacac aaaatgaatt agctaaagaa gtaaatgacc atgatattga agaagttgca   2700
ttgaaagtag atgcattatc ggatgaagta tttggaaaag agaaaaaaga attacgtaaa   2760
ctggtcaatc aagcgaaacg tttaagtaaa gcacgaaacc ttctggtagg aggcaatttt   2820
gataattggg aagcttggta taaaggaaaa gaagttgcaa gagtatctga tcatgaatta   2880
ttgaagagtg atcatgtatt attaccgcct ccaactatgt atccatccta tatatatcaa   2940
aaagtagaag aaacaaaatt aaagccaaat actcgttata tgatttctgg tttcatcgca   3000
catgcggaag atttagaaat tgtggtttct cgttatgggc aagaagtaag gaaaatagtg   3060
caagttccat atggagaagc tttcccatta acatccaatg gatcaatttg ttgtacacca   3120
```

-continued

```
agttttagac gtgatggaaa actatcagat ccacatttct ttagttatag tattgatgta   3180
ggtgaactgg atatgacggc aggtccaggt attgaattgg gacttcgtat tgtagatcga   3240
ttaggaatgg cccgtgtaag taatttagaa attcgtgaag atcgttcttt aacagcaaat   3300
gaaatacgaa aagtgcaacg tatggcaaga aattggagaa ccgaatatga gaaagaacgt   3360
gcagaagtaa cagcattaat tgaacctgta ttaaaccaaa tcaatgcgtt atatgaaaat   3420
ggagattgga atggttctat tcgttcagat atttcgtact acgatataga atctattgta   3480
ttaccaacat taccaagatt acgtcattgg tttgttcctg atatgttaac tgaacatgga   3540
aatatcatga atcgattcga agaagcatta aatcgtgctt atacacagct ggaaggaaat   3600
acactattgc ataacggtca ttttacaaca gatgcggtaa attggatgat acaaggagat   3660
gcacatcagg taatattaga agatggtaga cgtgtattac gattaccaga ctggtcttcg   3720
agtgtatccc aaacaattga aatcgagaaa tttgatccag ataaagaata caacttagta   3780
tttcatgcgc aaggagaagg aacggttacg ttggagcatg gagaaaaaac aaaatatata   3840
gaaacgcata cacatcattt tgcgaatttt acaacatcac aaagtcaagg aattacgttt   3900
gaatcgaata aggtgaccgt ggaaatttct tcagaagatg ggaattattt ggtagatcat   3960
atcgcacttg tggaagttcc tatgtttaac aagaatcaaa tggtcaatga aaatagagat   4020
gtaaatataa atagcaatac aaatatgaat aatagcaata atcaa                   4065
```

<210> SEQ ID NO 65
<211> LENGTH: 4772
<212> TYPE: DNA
<213> ORGANISM: Bacillus thuringiensis

<400> SEQUENCE: 65

```
taccettcat atagtataaa gggacaacct cctatttata tatatattat tgtaattaca     60
ttatagaaga tcaaacagaa aaaagttttt tgaattggtt caatatacca actatatagc    120
ataaactatc tttgtattta tttataataa ttttttaagg agtgaaataa tgacaacaat    180
aaatgaatta tatccggctg taccttataa tgtactggca tatgctccac cacttaattt    240
agctgattcg acaccatggg gtcaaatagt tgttgctgat gcaattaaag aagcttggga    300
taattttcaa aaatatggtg tattagattt aacagctata aatcaagggt ttgatgatgc    360
aaatacaggt tcttttagtt atcaagcttt aatacaaact gttttgggta ttataggtac    420
aatttggtat gacagttcct gtggctgctc catttgcagc tacagcgcct attattagtt    480
tatttgtagg atttttttgg cctaaaaaag ataagggacc acaattaatc gatataattg    540
ataaagaaat taaaaaatta ttagataagg aattaggaga gcaaaaacgt aatgatttag    600
ttagtgcttt aaatgagatg caagagggag caaatgagtt aagtgatatt atgactaatg    660
cactttttga aggtactata cagggaaatg ttgttactaa tgataaccct caaggtaaaa    720
ggcgaactcc taaagctcca acagttagtg attatgagaa tgtttattcg gcatattttg    780
tggaacatgt ggattttaga aacaaaatat ctacgtttct tactggttct tatgatctta    840
tagcactccc attatatgca ttagcaaaaa caatggagct ttcattgtat caatcattta    900
ttaattttgc taataaatgg atggattttg tatatacaaa agcaattaat gaatcagcaa    960
ctgatgatat gaaaagagat tatcaagcga gatacaatac tcaaaaaagt aatttagctg   1020
tacaaaaaac acaattgatt aacaaaatta aagatggtac agatgctgtt atgaaagttt   1080
ttaaagatac caataattta ccttcaatag gtactaataa attagcagta aatgctcgta   1140
ataagtatat tagggcctta caaataaatt gtttagattt agttgctttg tggcctggct   1200
```

```
tatatccaga tgaatatctt ttaccattac aattagataa aacacgtgtt gtattttctg   1260
atacaatggg acctgatgaa acacatgatg gtcaaatgaa agttttaaat atattagact   1320
caactacaag ttataaccat caagatatag gaataagtac aactcaagat gtaaattctt   1380
tattatttta tccaagaaaa gaactgttag aattagattt tgctaaatat atttcatcta   1440
gtagtcgttt ttgggtttat ggatttggct taaaatattc agatgataac ttttatagat   1500
atggtgataa cgatccaagc agtgatttta aacctgcata taagtggttt acgaaaaatt   1560
cccagttcga aaaccttcct acttatggaa atcctactcc tattactaat ttaaatgcta   1620
aaactcaagt aacttcttat cttgatgcat taatatatta tatagacgga ggaactaatc   1680
tatataataa tgcgattctt catgatacag gggttatat tccgggatat ccaggtgtag   1740
aaggatatgg tatgagtaat aatgaacctt tagcaggaca aaaattaaat gctttatatc   1800
ctataaaagt ggaaaatgta agtggttcac aaggaaaatt aggaacaata gcagcttatg   1860
ttcctttaaa tttacaacca gaaaatatta ttggtgatgc tgatccgaat acaggttttc   1920
cccttaatgt aattaaagga tttccatttg aaaaatatgg acctgattat gagggacgag   1980
gaatttcggt tgtaaaagaa tggataaatg gtgcaaatgc tgtaaaattg tctccaggtc   2040
aatcagttgg ggtacaaatt aaaaatataa caaaacaaaa ttatcaaatt cgtactcgtt   2100
atgcaagtaa taacagtaat caagtatatt ttaatgtaga tccaggtgga tcaccattat   2160
ttgcacaatc agtaacattt gaatctacaa caaatgttac aagtggccaa caaggcgaaa   2220
atggtagata tacattaaaa actatttttt ctggtaatga tctacttaca gtagaaatcc   2280
ctgttggaaa tttttatgtg catgttacga ataaaggatc ttctgatatc tttttagatc   2340
gtcttgagtt ttctacagtt ccttcatatg ttatatattc aggtgattat gatgctacag   2400
gtacagatga tgtcttattg tcagatccac atgagtattt ttatgatgtc atagtgaatg   2460
gtactgctag tcattctagt gcagctactt ctatgaattt gctcaataaa ggaaccgtag   2520
taagaagcat tgatattcca ggtcactcaa cgtcttattc tgtacagtat tcagttccag   2580
aaggatttga tgaagttaga attctcagtt ctcttccgga tattagtgga actataagag   2640
tagaatctag taaaccacct gtatttaaga atgatggtaa tagtggtgat ggtggtaata   2700
ctgaatataa ttttaatttt gatttatcag gattgcaaga tactgggctt tattctggta   2760
aacttaaatc tggtattcgt gtgcaaggta attacactta cacaggtgct ccatctttaa   2820
atctggttgt ttacagaaat aatagtgttg tatccacttt tccagtaggt tctcctttttg   2880
atatcactat aacaacagaa actgataagg ttatcctttc attacaacct caacatgggt   2940
tggcaacagt tactggtact ggcacaataa caattcctaa tgataaatta gcaattgttt   3000
atgataagtt atttaaatta ccacatgatt tagaaaatat aagaatacaa gtaaatgcat   3060
tattcatatc gagtacacaa aatgaattag ctaaagaagt aaatgaccat gatattgaag   3120
aagttgcatt gaaagtagat gcattatcgg atgaagtatt tggaaaagag aaaaaagaat   3180
tacgtaaact ggtcaatcaa gcgaaacgtt taagtaaagc acgaaacctt ctggtaggag   3240
gcaattttga taattgggaa gcttggtata aaggaaaaga agttgcaaga gtatctgatc   3300
atgaattatt gaagagtgat catgtattat taccgcctcc aactatgtat ccatcctata   3360
tatatcaaaa agtagaagaa acaaaattaa agccaaatac tcgttatatg atttctggtt   3420
tcatcgcaca tgcggaagat ttagaaattg tggtttctcg ttatgggcaa gaagtaagga   3480
aaatagtgca agttccatat ggagaagctt tcccattaac atccaatgga tcaatttgtt   3540
gtacaccaag ttttagacgt gatggaaaac tatcagatcc acatttcttt agttatagta   3600
```

```
ttgatgtagg tgaactggat atgacggcag gtccaggtat tgaattggga cttcgtattg   3660
tagatcgatt aggaatggcc cgtgtaagta atttagaaat tcgtgaagat cgttctttaa   3720
cagcaaatga aatacgaaaa gtgcaacgta tggcaagaaa ttggagaacc gaatatgaga   3780
aagaacgtgc agaagtaaca gcattaattg aacctgtatt aaaccaaatc aatgcgttat   3840
atgaaaatgg agattggaat ggttctattc gttcagatat ttcgtactac gatatagaat   3900
ctattgtatt accaacatta ccaagattac gtcattggtt tgttcctgat atgttaactg   3960
aacatggaaa tatcatgaat cgattcgaag aagcattaaa tcgtgcttat acacagctgg   4020
aaggaaatac actattgcat aacggtcatt ttacaacaga tgcggtaaat tggatgatac   4080
aaggagatgc acatcaggta atattagaag atggtagacg tgtattacga ttaccagact   4140
ggtcttcgag tgtatcccaa acaattgaaa tcgagaaatt tgatccagat aaagaataca   4200
acttagtatt tcatgcgcaa ggagaaggaa cggttacgtt ggagcatgga gaaaaaacaa   4260
aatatataga aacgcataca catcattttg cgaattttac aacatcacaa agtcaaggaa   4320
ttacgtttga atcgaataag gtgaccgtgg aaatttcttc agaagatggg gaattattgg   4380
tagatcatat cgcacttgtg gaagttccta tgtttaacaa gaatcaaatg gtcaatgaaa   4440
atagagatgt aaatataaat agcaatacaa atatgaataa tagcaataat caataacttt   4500
tatatgtaaa caggtgcaag tgtttgttgc acctgttttt tcaccctgtt tctaaaaaaa   4560
tgaggaggtt agatgtatgc aaaagaaatc aaaagtaata gaaccaacaa ataatagtat   4620
gtcagtaaat aataatattt cattaaaaac accgatgcca attgggtata gaaaaaaatc   4680
aggttgtggt tgtgggaaac gtcgttaagt ggaaaatgaa tctgtggaat ggataaaaac   4740
aagtgtgaaa gttgaacgtt catccaattt ac                                  4772
```

<210> SEQ ID NO 66
<211> LENGTH: 723
<212> TYPE: DNA
<213> ORGANISM: Bacillus thuringiensis

<400> SEQUENCE: 66

```
atggccgata tgcctgtaaa taatactcat atatcacaaa atgattttcc aatctgtaca     60
actgaagaag aacgtttaat tccattttgt tgtttggttc agctaccaca tgattttcaa    120
cttgttcctt attgcaaacc acgtcttgta tacaacattg gatgccttgg aacgactaaa    180
gaaacgtgta aaaaaaccat acaagtagag gattgtggac aaacggaaat tgatttgcag    240
atattaaagg caaaaggatg catcaccttt cttgtgaata tagatgtaga acctgtctgt    300
gaagaagaga tttgctcgag tgttccgcac acaaaggaca tgattttgtg ttgtaaagga    360
accgtatgtg tagacaaaat tttaaaatgc agtgttgact gtttacctga tattcattta    420
gattgtgaga atgtaaaagt ttgtgattta caagtaaaat cactctgcga ggaagattgt    480
cattctgtaa agattacagg gtattttcag atttgtattg attaaataaa gatttttaaa    540
tgcatacttt tttacatcca ctcaaataga gagagtgttg caaggttaaa aagcaatatg    600
tttttataaa tatttattta tttcttttgt cctggtgcag aaaaataaaa taatttcaaa    660
atgatttttc taactttgcc ataatactac taaaaaggtg atagagagac taagaatgat    720
aag                                                                  723
```

<210> SEQ ID NO 67
<211> LENGTH: 174
<212> TYPE: PRT
<213> ORGANISM: Bacillus thuringiensis

<400> SEQUENCE: 67

```
Met Ala Asp Met Pro Val Asn Asn Thr His Ile Ser Gln Asn Asp Phe
 1               5                  10                  15

Pro Ile Cys Thr Thr Glu Glu Glu Arg Leu Ile Pro Phe Cys Cys Leu
            20                  25                  30

Val Gln Leu Pro His Asp Phe Gln Leu Val Pro Tyr Cys Lys Pro Arg
        35                  40                  45

Leu Val Tyr Asn Ile Gly Cys Leu Gly Thr Thr Lys Glu Thr Cys Lys
    50                  55                  60

Lys Thr Ile Gln Val Glu Asp Cys Gly Gln Thr Glu Ile Asp Leu Gln
65                  70                  75                  80

Ile Leu Lys Ala Lys Gly Cys Ile Thr Phe Leu Val Asn Ile Asp Val
                85                  90                  95

Glu Pro Val Cys Glu Glu Glu Ile Cys Ser Ser Val Pro His Thr Lys
            100                 105                 110

Asp Met Ile Leu Cys Cys Lys Gly Thr Val Cys Val Asp Lys Ile Leu
        115                 120                 125

Lys Cys Ser Val Asp Cys Leu Pro Asp Ile His Leu Asp Cys Glu Asn
    130                 135                 140

Val Lys Val Cys Asp Leu Gln Val Lys Ser Leu Cys Glu Glu Asp Cys
145                 150                 155                 160

His Ser Val Lys Ile Thr Gly Tyr Phe Gln Ile Cys Ile Asp
                165                 170
```

<210> SEQ ID NO 68
<211> LENGTH: 589
<212> TYPE: DNA
<213> ORGANISM: Bacillus thuringiensis

<400> SEQUENCE: 68

```
atgacatttg attacgagga agaagaaagg gatttgtccc aactccgacc atctgattct      60

tcaagatcaa caggtgaacc aagaacggat tgtgacctaa ccacaaattg tgaagttcct     120

ttttgttgcg tcgtcacgct cccacatgga tttcagtacg aatcccgaaa acaaacaaag     180

cttgtatacg atattagttg tcttaccttt gcacacgaga tgtgtcaacg atctatcaac     240

gtggatcagt gtggtacagt tgatgtagat ttacaagtct taaaaataaa gggctgtgtg     300

tcactgtata tcaacgttcc gattctaccc attcgtgagg agacgatgtg tacgttacac     360

agacagccga catctctcta tacctgttgt caggataccc tttgtgtaga tcatattgtg     420

aaatgtagtg tgggaagtct cccttactac gtgttggatg gcaatcatat acaagtgtgt     480

gacttacagg tacgtcctgt atcagaagta catccacacg tattacaagt atccggtcgt     540

tttgagtttt tatatacgta agtatctata tgaggagtga gataaagat                 589
```

<210> SEQ ID NO 69
<211> LENGTH: 186
<212> TYPE: PRT
<213> ORGANISM: Bacillus thuringiensis

<400> SEQUENCE: 69

```
Met Thr Phe Asp Tyr Glu Glu Glu Glu Arg Asp Leu Ser Gln Leu Arg
 1               5                  10                  15

Pro Ser Asp Ser Ser Arg Ser Thr Gly Glu Pro Arg Thr Asp Cys Asp
            20                  25                  30

Leu Thr Thr Asn Cys Glu Val Pro Phe Cys Cys Val Val Thr Leu Pro
        35                  40                  45
```

-continued

```
His Gly Phe Gln Tyr Glu Ser Arg Lys Gln Thr Lys Leu Val Tyr Asp
    50                  55                  60

Ile Ser Cys Leu Thr Phe Ala His Glu Met Cys Gln Arg Ser Ile Asn
65                  70                  75                  80

Val Asp Gln Cys Gly Thr Val Asp Val Asp Leu Gln Val Leu Lys Ile
                85                  90                  95

Lys Gly Cys Val Ser Leu Tyr Ile Asn Val Pro Ile Leu Pro Ile Arg
            100                 105                 110

Glu Glu Thr Met Cys Thr Leu His Arg Gln Pro Thr Ser Leu Tyr Thr
        115                 120                 125

Cys Cys Gln Asp Thr Leu Cys Val Asp His Ile Val Lys Cys Ser Val
    130                 135                 140

Gly Ser Leu Pro Tyr Tyr Val Leu Asp Gly Asn His Ile Gln Val Cys
145                 150                 155                 160

Asp Leu Gln Val Arg Pro Val Ser Glu Val His Pro His Val Leu Gln
                165                 170                 175

Val Ser Gly Arg Phe Glu Phe Leu Tyr Thr
            180                 185


<210> SEQ ID NO 70
<211> LENGTH: 4
<212> TYPE: PRT
<213> ORGANISM: Artificial Sequence
<220> FEATURE:
<223> OTHER INFORMATION: ER targeting peptide

<400> SEQUENCE: 70

Lys Asp Glu Leu
 1
```